United States Patent
Togawa et al.

(10) Patent No.: US 12,258,622 B2
(45) Date of Patent: Mar. 25, 2025

(54) METHOD FOR ESTIMATING INFLAMMATION AREA OF PERIODONTAL POCKETS

(71) Applicant: GC CORPORATION, Sunto-gun (JP)

(72) Inventors: Naoyuki Togawa, Chiyoda-ku (JP); Ai Hara, Chiyoda-ku (JP); Shinya Murakami, Suita (JP); Takenori Nozaki, Suita (JP)

(73) Assignee: GC CORPORATION, Sunto-gun (JP)

( * ) Notice: Subject to any disclaimer, the term of this patent is extended or adjusted under 35 U.S.C. 154(b) by 1252 days.

(21) Appl. No.: 16/760,199

(22) PCT Filed: Nov. 2, 2018

(86) PCT No.: PCT/JP2018/040916
§ 371 (c)(1),
(2) Date: Jul. 20, 2020

(87) PCT Pub. No.: WO2019/088271
PCT Pub. Date: May 9, 2019

(65) Prior Publication Data
US 2021/0164028 A1 Jun. 3, 2021

(30) Foreign Application Priority Data
Nov. 2, 2017 (JP) ................................. 2017-212403

(51) Int. Cl.
| | | |
|---|---|---|
| C12Q 1/6837 | (2018.01) | |
| C12Q 1/689 | (2018.01) | |
| G16B 20/20 | (2019.01) | |
| G16B 40/20 | (2019.01) | |
| G16B 30/10 | (2019.01) | |
| G16H 10/40 | (2018.01) | |
| G16H 50/20 | (2018.01) | |
| G16H 50/30 | (2018.01) | |

(52) U.S. Cl.
CPC ........... *C12Q 1/6837* (2013.01); *C12Q 1/689* (2013.01); *G16B 20/20* (2019.02); *G16B 40/20* (2019.02); *G16B 30/10* (2019.02); *G16H 10/40* (2018.01); *G16H 50/20* (2018.01); *G16H 50/30* (2018.01)

(58) Field of Classification Search
CPC ...... C12Q 1/6837; C12Q 1/689; G16B 20/20; G16B 40/20
See application file for complete search history.

(56) References Cited

U.S. PATENT DOCUMENTS

| | | |
|---|---|---|
| 2007/0269813 A1 | 11/2007 | Dewhirst et al. |
| 2017/0211131 A1 | 7/2017 | Cheng et al. |
| 2019/0153518 A1 | 5/2019 | Hara et al. |

FOREIGN PATENT DOCUMENTS

| | | |
|---|---|---|
| EP | 3 483 266 A1 | 5/2019 |
| JP | 2004-51536 A | 2/2004 |
| JP | 4917815 82 | 4/2012 |
| JP | 5869323 B2 | 2/2016 |
| JP | 2017-23093 A | 2/2017 |
| JP | 2017-85944 A | 5/2017 |
| WO | WO 2018/012011 A1 | 1/2018 |

OTHER PUBLICATIONS

Notice of Reasons for Rejection issued Jul. 12, 2022 in Japanese Patent Application No. 2019-550508 (with English machine translation), 16 pages.
Chinese Office Action issued Mar. 2, 2023 in Chinese Patent Application No. 201880084885.4 (with unedited computer-generated English Translation), 7 pages.
International Search Report issued Jan. 29, 2019 in PCT/JP2018/040916, 2 pages.
Extended European Search Report Issued Dec. 18, 2020 in European Patent Application No. 18872517.0, 6 pages.
Nesse, W., et al., "Periodontal inflamed surface area: quantifying inflammatory burden", Journal of Clinical Periodontal, Aug. 2008, 35(8)pp. 868-673.
Minabe, M., et al., "Clinical Significance of Evaluation Method of Periodontal Pocket Inflammation Area as Systemic Disease-Related Test Marker for Periodontal Disease", Journal of Japanese Society for Evidence and the Dental Professional: JJSEDP, vol. 1, No. 1, pp. 7-12, 2009 (with English translation).
Park, S.-Y., et al., "Periodontal inflamed surface area as a novel numerical variable describing periodontal conditions", Journal of Periodontal Implant Society, Oct. 30, 2017, vol. 47, pp. 328-338.
Maruyama, N., et al., "Intraindividual variation in core microbiota in peri-implantitis and periodontitis", Scientific Reports, 2014, vol. 4, pp. 1-10, XP 55747713.
Kozlovsky, A., et al.. "Effect of Aggregatibacter actinomycetemcomitans from Aggressive Periodontitis patients on *Streptococcus* mutans", Oral Diseases, 2015. 21, pp. 955-961, XP 55755354.

(Continued)

*Primary Examiner* — Jerry Lin
(74) *Attorney, Agent, or Firm* — Oblon, McClelland, Maier & Neustadt, L.L.P.

(57) ABSTRACT

A method for simply predicting the degree of inflammation of periodontal tissue such as an inflamed area (PISA or CAPRS value), and a device (e.g., a DNA chip) used for the method are provided. The method is a method for estimating a periodontal pocket inflammation area by detecting bacterial loads of two or more types of bacteria in saliva and using the obtained detection results as indexes, wherein bacteria to be detected include: a bacterium having a positive correlation between the bacterial load of the bacterium and the periodontal pocket inflammation area and a bacterium having a negative correlation between the bacterial load of the bacterium and the periodontal pocket inflammation area.

7 Claims, 14 Drawing Sheets
Specification includes a Sequence Listing.

(56) References Cited

OTHER PUBLICATIONS

Chinese Office Action issued on Jan. 4, 2024 in Chinese Patent Application No. 201880084885.4 (with unedited computer-generated English translation), 10 pages.
Preliminary Office Action issued on Jun. 11, 2024, in corresponding Brazilian Patent Application No. BR112020008566-9 with English Translation.
Examination report No. 1 for standard patent application dated Jun. 11, 2024, issued in corresponding Australian patent application No. 2018361590.
Office Action dated Sep. 23, 2024, issued to the corresponding Canadian Patent Application No. 3,084,010, 7 pages total.
Akito Sakanaka et al. "Distinct signatures of dental plaque metabolic byproducts dictated by periodontal inflammatory status" Scientific Reports, 7:42818, Feb. 21, 2017, 10 pages total.

METHOD FOR ESTIMATING INFLAMMATION AREA OF PERIODONTAL POCKETS

TECHNICAL FIELD

The present invention relates to a method for estimating a periodontal pocket inflammation area.

BACKGROUND ART

Diagnosis of periodontal disease is performed by measuring the periodontal pocket, attachment level, X-ray image diagnosis, and the like. However, these diagnostic methods place a heavy burden on a subject, and require a considerable amount of time, especially when performed in a large number of people. Further, these periodontal disease diagnosis methods have complicated operation procedures, and there is a problem that there are individual differences in judgment criteria because they are based on the experience and skills of dentists.

Therefore, simple methods for diagnosing periodontal disease have been proposed so far. For example, Patent Literature 1 discloses a method for diagnosing periodontal disease using a protein contained in gingival crevicular fluid as a marker for periodontal disease. In addition, Patent Literature 2 discloses a method for predicting the periodontal pocket depth (PPD) and gingival bleeding index (GBI) by analyzing a plurality of proteins in saliva. However, in general, for PPD and GBI, since there are 168 measurement points (28 teeth×6-point method), it is unknown which point is actually predicted.

Meanwhile, more generally, as disclosed in Patent Literature 3, the periodontal disease bacteria present in gingival crevicular fluid and the periodontal disease bacteria in saliva are measured. The periodontal inflamed surface area (PISA) value calculated from the periodontal pocket depth (PPD) and gingival bleeding index (GBI) is proposed as an index corresponding to periodontal disease bacteria present in saliva (Non Patent Literature 1). The PISA value is calculated by multiplying the periodontal epithelial surface area (PESA) value calculated from the periodontal pocket depth (PPD) by the gingival bleeding index (GBI).

In addition to this, the CAPRS value is proposed by Takizawa et al. (Non Patent Literature 2). As described in the literature, this value is calculated by obtaining the clinical area of tooth root surface (CARS), i.e., total surface area of roots located on the apex side of the gingival margin, from the attachment level, and then, subtracting the effective area of tooth root surface from the obtained value. In fact, the value is calculated by replacing it with the case where the position of gingival margin coincides with the anatomical cervical line, and it is considered to be the same as the value of PESA shown in FIG. 1 (b) of Non Patent Literature 1. Although the gingival bleeding index (GBI) is not included in the calculation of the concealed area in periodontal pocket of tooth root surface (CAPRS) value, the area itself should be approximated to the inflammation area on the inner surface of the pocket as described in the literature, and should be considered as the "periodontal pocket inflammation area" together with the PISA value.

Up to now, in order to easily evaluate the "periodontal pocket inflammation area," the relationship with the number of periodontal disease bacteria in saliva has been examined. However, there is no correlation between the bacterial count of a P.g bacterium (*Porphyromonas gingivalis*) and the CAPRS value and between the bacterial count of a red-complex bacterium (a P.g bacterium, a T.d bacterium (*Treponema denticola*), or a T.f bacterium (*Tannerella forsythensis*)) and the CAPRS value (Non Patent Literature 2, FIGS. 3a 3b). Thus, a method for simply predicting the "periodontal pocket inflammation area" from a saliva sample has been unknown.

CITATION LIST

Patent Literature

Patent Literature 1: JP Patent Publication (Kokai) No. 2004-51536 A
Patent Literature 2: JP Patent No. 5869323
Patent Literature 3: JP Patent No. 4917815

Non Patent Literature

Non Patent Literature 1: Periodontal inflamed surface area: quantifying inflammatory burden. J Clin Periodontol. 2008 August; 35(8):668-73.
Non Patent Literature 2: "Clinical Significance of Periodontal Pocket Inflammation Area Evaluation Method as Systemic Disease-Related Test Marker for Periodontal Disease (in Japanese)," Journal of Japanese Society for Evidence and the Dental Professional: JJSEDP, vol. 1: 7-12, 2009

SUMMARY OF INVENTION

Technical Problem

Under such circumstances, it has been desired to provide a method for estimating a periodontal pocket inflammation area based on the detection results of the bacterial load in saliva.

Further, under such circumstances, it has been desired to provide a method for simply predicting the degree of inflammation of periodontal tissue such as the periodontal inflamed surface area (PISA value) based on the detection results of the bacterial load in saliva.

Solution to Problem

The present invention has been made in consideration of the above situation, and provides the following methods for estimating a periodontal pocket inflammation area and comprehensively estimating the degree of inflammation of periodontal tissue.

[1] A method for estimating a periodontal pocket inflammation area by detecting bacterial loads of two or more types of bacteria in saliva and using the obtained detection results as indexes, wherein bacteria to be detected include:
 a bacterium having a positive correlation between a bacterial load of the bacterium and the periodontal pocket inflammation area; and
 a bacterium having a negative correlation between a bacterial load of the bacterium and the periodontal pocket inflammation area.

[2] The method according to [1], wherein the periodontal pocket inflammation area is represented by a PISA or CAPRS value.

[3] The method according to [1] or [2], wherein the bacterium having the positive correlation is at least one selected from the group consisting of *Treponema denticola*, *Tannerella forsythia*, *Fusobacterium nucleatum* subsp. *animalis*, *Porphyromonas gingivalis*, *Campylobacter rectus*,

*Fusobacterium nucleatum* subsp. *nucleatum*, *Selenomonas noxia*, *Veillonella parvula*, *Streptococcus gordonii*, *Fusobacterium nucleatum* subsp. *vincentii*, *Streptococcus intermedius*, *Capnocytophaga ochracea*, *Capnocytophaga sputigena*, *Aggregatibacter actinomycetemcomitans*, *Fusobacterium nucleatum* subsp. *polymorphum*, *Fusobacterium periodonticum*, SR1 sp. OT 345, *Porphyromonas catoniae*, *Selenomonas sputigena*, *Neisseria flavescens*, *Streptococcus sobrinus*, *Parvimonas micra*, *Peptostreptococcus stomatis*, *Treponema socranskii*, *Eubacterium saphenum*, *Eubacterium nodatum*, *Treponema medium*, *Filifactor alocis*, and *Porphyromonas endodontalis*.

[4] The method according to any one of [1] to [3], wherein the bacterium having the negative correlation is at least one selected from the group consisting of *Streptococcus mutans*, *Actinomyces odontolyticus*, *Streptococcus mitis* bv 2, *Streptococcus mitis*, *Campylobacter concisus*, *Capnocytophaga gingivalis*, *Prevotella pallens*, *Streptococcus salivarius*, *Eubacterium sulci*, *Rothia mucilaginosa*, *Prevotella denticola*, *Veillonella atypica*, *Prevotella histicola*, *Megasphaera micronuciformis*, and *Streptococcus parasanguinis*.

[5] The method according to claim 1, which comprises the following steps (1) to (4):
(1) a step of detecting the bacterial load of each bacterium in saliva from a saliva sample of a subject with a known periodontal pocket inflammation area;
(2) a step of obtaining a correlation coefficient of the bacterial load of each bacterium with a periodontal pocket inflammation area unique to each bacterium and constructing a relational expression between the bacterial load of each bacterium and the periodontal pocket inflammation area, thereby creating a prediction model;
(3) a step of detecting the bacterial load of each bacterium in saliva from a saliva sample of a subject with an unknown periodontal pocket inflammation area; and
(4) a step of inserting the bacterial load of each bacterium obtained in (3) into the relational expression obtained in (2), thereby estimating the periodontal pocket inflammation area.

[6] The method according to [5], wherein a method for creating the prediction model is a method using one selected from among machine learning algorithms of linear regression, regression tree, model tree, neural network, support vector machine, bagging, boosting, and random forest.

[7] A method for comprehensively estimating the degree of inflammation of periodontal tissue by detecting a bacterial load of at least one type of bacterium in saliva and using the obtained detection results as indexes.

[8] The method according to [7], wherein the degree of inflammation of periodontal tissue is represented by a PISA or CAPRS value.

[9] The method according to [7] or [8], wherein the bacterial load of the bacterium detected is a copy number of the bacterium in saliva.

[10] The method according to any one of [7] and [8], wherein the bacterial load of the bacterium detected is based on 16S rRNA sequence information of the bacterium in saliva.

[11] The method according to any one of [7] to [10], wherein the bacterium detected is a bacterium belonging to at least one genus selected from among the genera *Porphyromonas*, *Tannerella*, *Treponema*, *Prevotella*, *Campylobacter*, *Fusobacterium*, *Streptococcus*, *Aggregatibacter*, *Capnocytophaga*, *Eikenella*, *Actinomyces*, *Veillonella*, and *Selenomonas*.

[12] The method according to any one of [7] to [11], wherein the bacterium detected is a bacterium belonging to at least one selected from among *Streptococcus mutans*, *Actinomyces odontolyticus*, *Streptococcus mitis* bv 2, *Streptococcus mitis*, *Campylobacter concisus*, *Prevotella intermedia*, *Campylobacter showae*, *Prevotella nigrescens*, *Eikenella corrodens*, *Capnocytophaga gingivalis*, *Actinomyces naeslundii* II, *Streptococcus constellatus*, *Campylobacter gracilis*, *Fusobacterium periodonticum*, *Fusobacterium nucleatum* subsp. *polymorphum*, *Aggregatibacter actinomycetemcomitans*, *Capnocytophaga sputigena*, *Capnocytophaga ochracea*, *Streptococcus intermedius*, *Fusobacterium nucleatum* subsp. *vincentii*, *Streptococcus gordonii*, *Veillonella parvula*, *Selenomonas noxia*, *Fusobacterium nucleatum* subsp. *nucleatum*, *Campylobacter rectus*, *Porphyromonas gingivalis*, *Fusobacterium nucleatum* subsp. *animalis*, *Tannerella forsythia*, and *Treponema denticola*.

[13] The method according to any one of [7] to [12], wherein the bacterium detected includes a bacterium that can have a positive correlation between the bacterial load of the bacterium and the degree of inflammation of periodontal tissue.

[14] The method according to [13], wherein the bacterium that can have the positive correlation is at least one selected from among *Fusobacterium periodonticum*, *Fusobacterium nucleatum* subsp. *polymorphum*, *Aggregatibacter actinomycetemcomitans*, *Capnocytophaga sputigena*, *Capnocytophaga ochracea*, *Streptococcus intermedius*, *Fusobacterium nucleatum* subsp. *vincentii*, *Streptococcus gordonii*, *Veillonella parvula*, *Selenomonas noxia*, *Fusobacterium nucleatum* subsp. *nucleatum*, *Campylobacter rectus*, *Porphyromonas gingivalis*, *Fusobacterium nucleatum* subsp. *animalis*, *Tannerella forsythia*, and *Treponema denticola*.

[15] The method according to any one of [7] to [12], wherein the bacterium detected includes a bacterium that can have a negative correlation between the bacterial load of the bacterium and the degree of inflammation of periodontal tissue.

[16] The method according to [15], wherein the bacterium that can have the negative correlation is at least one selected from among *Streptococcus mutans*, *Actinomyces odontolyticus*, *Streptococcus mitis* bv 2, *Streptococcus mitis*, *Campylobacter concisus*, *Prevotella intermedia*, *Campylobacter showae*, *Prevotella nigrescens*, *Eikenella corrodens*, *Capnocytophaga gingivalis*, *Actinomyces naeslundii* II, *Streptococcus constellatus*, and *Campylobacter gracilis*.

Advantageous Effects of Invention

According to the present invention, it is possible to simply predict the periodontal pocket inflammation area based on the detection results of bacterial loads in saliva. In other words, it is possible to simply estimate the degree of inflammation of the entire oral cavity by using saliva collected, without performing precise periodontal disease examination (pocket measurement or imaging).

In addition, according to the present invention, it is possible to simply predict the degree of inflammation of periodontal tissue such as an inflamed area (PISA or CAPRS value) based on the detection results of bacterial loads in saliva. In other words, it is possible to simply estimate the degree of inflammation (inflammation index value) of the entire oral cavity by using saliva collected, without performing precise periodontal disease examination (pocket measurement or imaging).

BRIEF DESCRIPTION OF DRAWINGS

FIG. 1-2 is a figure showing a model tree of PISA prediction calculated from the SN ratio of each bacterial load (continuation of FIG. 1-1; number 1 surrounded by a square in FIG. 1-1 is connected to number 21 in FIG. 1-2).

FIG. 2 is a figure showing a scatter diagram of PISA values (horizontal axis) predicted from the model tree in FIG. 1 and PISA measurement values (vertical axis).

FIG. 4-1 is a figure showing a model tree of PISA prediction calculated from the SN ratio of each bacterial load after interchip correction using 34 data out of 46 data in total.

FIG. 4-1 is a figure showing a model tree of PISA prediction calculated from the SN ratio of each bacterial load after interchip correction using 34 data out of 46 data in total (continuation of FIG. 4-1; number 1 surrounded by a square in FIG. 4-1 is connected to number 11 in FIG. 4-2, and number 13 surrounded by a square in FIG. 4-1 is connected to number 12 in FIG. 4-2).

DESCRIPTION OF EMBODIMENTS

Figure 1:
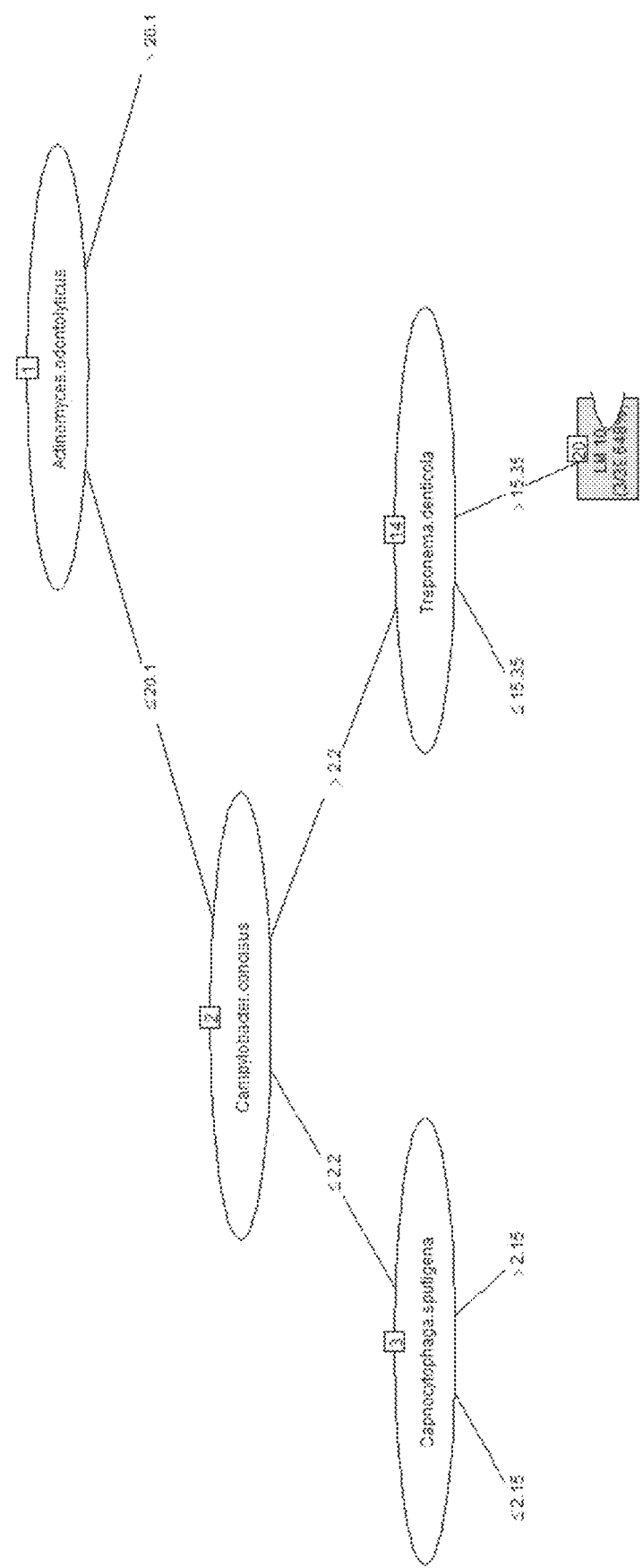
FIG. 1-1 is a figure showing a model tree of PISA prediction calculated from the SN ratio of each bacterial load.
Figure 1:
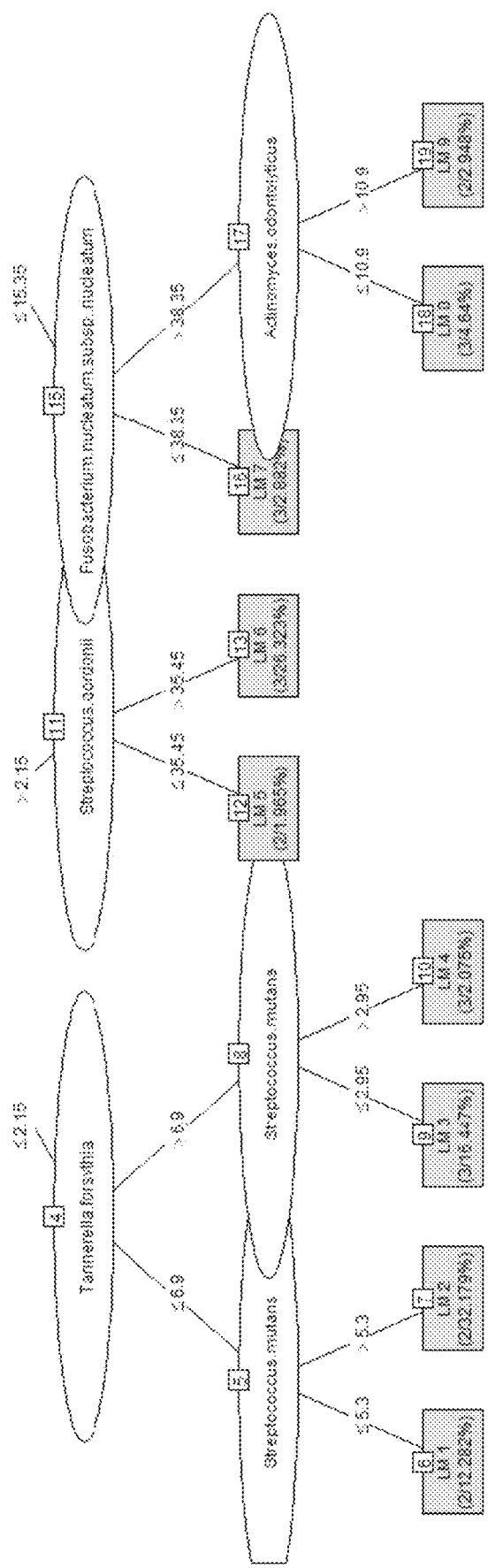

Hereinafter, the present invention will be described in detail. The scope of the present invention is not limited to these descriptions, and other than the following examples, the scope of the present invention can be appropriately modified and implemented within a range not impairing the gist of the present invention. All publications cited in the present specification, for example, prior art literature, publications, patent publications, and other patent literature are incorporated herein by reference.

The invention of the method for estimating the periodontal pocket inflammation area (hereinafter, also referred to as "first invention group"), which is a first aspect of the present invention, includes the following steps: i) a step of detecting bacterial loads of two or more types of bacteria in saliva; and ii) a step of estimating a periodontal pocket inflammation area by using the obtained detection results as indexes.

The invention of the method for comprehensively estimating the degree of inflammation of periodontal tissue (hereinafter, also referred to as "second invention group"), which is a second aspect of the present invention, includes the following steps: i) a step of detecting a bacterial load of at least one type of bacterium in saliva (i.e., saliva of a subject, especially a human); and ii) a step of comprehensively estimating the degree of inflammation of periodontal tissue by using the obtained detection results as indexes.

1. Oligonucleotide Probes for Detecting Bacterial Loads of Bacteria in Saliva

In the method of the present invention, a DNA chip can be used when measuring the load of bacteria in the oral cavity from saliva collected from a subject. For example, the following probe (a) (bacterium-specific probe) can be mounted on the DNA chip, and further, the probe (b) (total load index probe) and the probe (c) (absolute load index probe) can be mounted thereon.

(a) Bacterial-specific probe: A probe consisting of a nucleic acid that specifically hybridizes with a detection target bacterial gene (or part thereof)
(b) Total load index probe: A probe consisting of nucleic acids that hybridize with all bacterial genes
(c) Absolute load index probe: A probe consisting of nucleic acids that specifically and separately hybridize with one or more types of absolute load indexes In addition, in general, a DNA chip is a general term for a substrate on which probes are arranged. Further, names such as DNA chip and DNA microarray are not distinguished from each other and are synonymous.

(1) Detection Target Bacteria in Saliva

In the method of the present invention, detection target bacteria in saliva (targets for measuring the bacterial load) are not limited, but are preferably bacteria that belong to the genera listed as follows, i.e., bacteria that belong to at least one genus selected from: the genera *Porphyromonas, Tannerella, Treponema, Prevotella, Campylobacter, Fusobacterium, Streptococcus, Aggregatibacter, Capnocytophaga, Eikenella, Actinomyces, Veillonella, Selenomonas, Eubacterium, Parvimonas, Filifactor, Haemophilus, Alloprevotella, Solobacterium, Rothia, Peptostreptococcus, Gemella, Corynebacterium, Neisseria, Granulicatella*, and *Megasphaera*; and the genera of the phylum SR1.

More specifically, it is more preferable to detect at least one type or two or more types selected from various bacteria listed below.

*Porphyromonas gingivalis*
*Tannerella forsythia*
*Treponema denticola*
*Campylobacter gracilis*
*Campylobacter rectus*
*Campylobacter showae*
*Fusobacterium nucleatum* subsp. *vincentii*
*Fusobacterium nucleatum* subsp. *polymorphum*
*Fusobacterium nucleatum* subsp. *animalis*
*Fusobacterium nucleatum* subsp. *nucleatum*
*Fusobacterium periodonticum*
*Prevotella intermedia*
*Prevotella nigrescens*
*Streptococcus constellatus*
*Aggregatibacter actinomycetemcomitans*
*Campylobacter concisus*
*Capnocytophaga gingivalis*
*Capnocytophaga ochracea*
*Capnocytophaga sputigena*
*Eikenella corrodens*
*Streptococcus gordonii*

*Streptococcus intermedius*
*Streptococcus mitis*
*Streptococcus mitis* bv 2
*Actinomyces odontolyticus*
*Veillonella parvula*
*Actinomyces naeslundii* II
*Selenomonas noxia*
*Streptococcus mutans*
*Eubacterium nodatum*
*Parvimonas micra*
*Filifactor alocis*
*Streptococcus sobrinus*
*Porphyromonas pasteri*
*Veillonella atypica*
*Haemophilus parainfluenzae*
*Alloprevotella* spp. (*A. rava,* OT 308)
*Streptococcus parasanguinis*
*Actinomyces israelii*
*Prevotella pallens*
*Prevotella loescheii*
*Prevotella histicola*
*Solobacterium moorei*
*Prevotella melaninogenica*
*Selenomonas sputigena*
*Rothia dentocariosa*
*Rothia mucilaginosa*
*Veillonella rogosae*
*Peptostreptococcus stomatis*
*Prevotella denticola*
*Porphyromonas endodontalis*
*Streptococcus salivarius*
*Actinomyces graevenitzii*
*Treponema medium*
*Treponema socranskii*
*Gemella sanguinis*
*Porphyromonas catoniae*
*Corynebacterium matruchotii*
*Eubacterium saphenum*
*Neisseria flavescens*
*Granulicatella adiacens*
*Eubacterium sulci*
*Megasphaera micronuciformis*
*Prevotella shahii*
SR1 sp. OT 345

In the "first invention group", a bacterium having a positive correlation between the bacterial load of the bacterium and the periodontal pocket inflammation area (a relationship in which the periodontal pocket inflammation area increases when the bacterial load increases) (hereinafter sometimes abbreviated as "bacterium having a positive correlation"), and a bacterium having a negative correlation between the bacterial load of the bacterium and the periodontal pocket inflammation area (a relationship in which the periodontal pocket inflammation area decreases when the bacterial load increases) (hereinafter sometimes abbreviated as "bacterium having a negative correlation") are used.

The periodontal pocket inflammation area is the area of inflammation, which includes the periodontal inflamed surface area (PISA) and/or the concealed area in periodontal pocket of tooth root surface (CAPRS). If there is an index of a similar concept, the index is also included.

The PISA value indicates the area of inflammation of the periodontal tissue of the entire oral cavity in square millimeters ($mm^2$). It can be calculated from the periodontal epithelial surface area (PESA) and the presence or absence of bleeding on probing (BOP) during probing. The periodontal epithelial surface area (PESA) can be calculated from the area defined in advance for each tooth type and the periodontal pocket depth (PPD). An automatic calculation spreadsheet (Excel file) for the 6-point method is distributed as additional information in Non Patent Literature 1. A person skilled in the art can confirm the above calculation method by looking at the calculation formula described in the Excel file.

As described in the literature, the CAPRS value is calculated by obtaining the clinical area of tooth root surface (CARS), i.e., total surface area of roots located on the apex side of the gingival margin, from the attachment level, and then, subtracting the effective area of tooth root surface from the obtained value. In fact, the value is calculated by replacing it with the case where the position of gingival margin coincides with the anatomical cervical line, and it is considered to be the same as the value of PESA shown in FIG. 1 (*b*) of Non Patent Literature 1. Although the gingival bleeding index (GBI) is not included in the calculation of the CAPRS value, the area itself should be approximated to the inflammation area on the inner surface of the pocket as described in the literature, and should be considered as the "periodontal pocket inflammation area" together with the PISA value.

The periodontal pocket inflammation area is preferably represented by the PISA or CAPRS value.

A bacterium having a positive correlation and a bacterium having a negative correlation can be confirmed by a tool capable of measuring the bacterial load (or a measured amount proportional to the bacterial load such as SN ratio). The tool is not particularly limited, and for example, a DNA chip can be used.

When a DNA chip is used for confirmation, an oral sample is measured with the DNA chip, and then, a correlation coefficient between the periodontal pocket inflammation area and the bacterial load of each bacterium or the measured amount such as the SN ratio is calculated. Thus, the bacteria can be classified and identified as a bacterial group having a positive correlation coefficient and a bacterial group having a negative correlation coefficient. The absolute value of the correlation coefficient for these bacteria is preferably 0.02 or more, more preferably 0.1 or more, still more preferably 0.2 or more, particularly preferably 0.4 or more, and most preferably 0.6 or more when the number of measurements is 40 or more.

When using the experimental error-corrected data to create a prediction model for estimating the periodontal pocket inflammation area, which will be described later, the experimental error-corrected data are used for classification of bacterial groups as well.

Preferable examples of a bacterium having a positive correlation include the bacteria listed below. It is more preferable to detect at least one, preferably two or more of these bacteria.

*Treponema denticola*
*Tannerella forsythia*
*Fusobacterium nucleatum* subsp. *animalis*
*Porphyromonas gingivalis*
*Campylobacter rectus*
*Fusobacterium nucleatum* subsp. *nucleatum*
*Selenomonas noxia*
*Veillonella parvula*
*Streptococcus gordonii*
*Fusobacterium nucleatum* subsp. *vincentii*
*Streptococcus intermedius*
*Capnocytophaga ochracea*
*Capnocytophaga sputigena*

*Aggregatibacter actinomycetemcomitans*
*Fusobacterium nucleatum* subsp. *polymorphum*
*Fusobacterium periodonticum*
SR1 sp. OT 345
*Porphyromonas catoniae*
*Selenomonas sputigena*
*Neisseria flavescens*
*Streptococcus sobrinus*
*Parvimonas micra*
*Peptostreptococcus stomatis*
*Treponema socranskii*
*Eubacterium saphenum*
*Eubacterium nodatum*
*Treponema medium*
*Filifactor alocis*
*Porphyromonas endodontalis*

Preferable examples of a bacterium having a negative correlation include the bacteria listed below. It is more preferable to detect at least one, preferably two or more of these bacteria.
*Streptococcus mutans*
*Actinomyces odontolyticus*
*Streptococcus mitis* bv 2
*Streptococcus mitis*
*Campylobacter concisus*
*Capnocytophaga gingivalis*
*Prevotella pallens*
*Streptococcus salivarius*
*Eubacterium sulci*
*Rothia mucilaginosa*
*Prevotella denticola*
*Veillonella atypica*
*Prevotella histicola*
*Megasphaera micronuciformis*
*Streptococcus parasanguinis*

In the "second invention group," a bacterium having a positive correlation between the bacterial load of the bacterium and the degree of inflammation of periodontal tissue (PISA value or CAPRS value) and a bacterium having a negative correlation therebetween are preferably exemplified.

Preferable examples of the bacterium having a positive correlation include, for example, the bacteria listed below. It is more preferable to detect at least one, preferably two or more of these bacteria.
*Treponema denticola*
*Tannerella forsythia*
*Fusobacterium nucleatum* subsp. *animalis*
*Porphyromonas gingivalis*
*Campylobacter rectus*
*Fusobacterium nucleatum* subsp. *nucleatum*
*Selenomonas noxia*
*Veillonella parvula*
*Streptococcus gordonii*
*Fusobacterium nucleatum* subsp. *vincentii*
*Streptococcus intermedius*
*Capnocytophaga ochracea*
*Capnocytophaga sputigena*
*Aggregatibacter actinomycetemcomitans*
*Fusobacterium nucleatum* subsp. *polymorphum*
*Fusobacterium periodonticum*

In addition, preferable examples of the bacterium having a negative correlation include, for example, the bacteria listed below. It is more preferable to detect at least one, preferably two or more of these bacteria.
*Streptococcus mutans*
*Actinomyces odontolyticus*
*Streptococcus mitis* bv 2
*Streptococcus mitis*
*Campylobacter concisus*
*Capnocytophaga gingivalis*

(2) Bacterial-Specific Probe

In the present invention, an oligo DNA that can be used as a bacterial-specific probe is one that can hybridize with a base sequence in a specific region of a base sequence of a nucleic acid from a bacterium in saliva. Here, the nucleic acid may be any of DNA and RNA including chromosomal DNA and plasmid DNA, and is not limited, but chromosomal DNA is preferable. Specifically, an oligonucleotide used as a probe in the present invention is capable of hybridizing with the base sequence of the 16S rRNA gene in the bacterial chromosomal DNA.

It is preferable that probes that can be used in the present invention are designed by selecting a region having a base sequence specific to each of bacteria to be detected and designing a base sequence of the region. In general, in designing a probe, in addition to selecting a specific region, it is necessary that the melting temperature (Tm) is uniform and that a secondary structure is difficult to form.

The specific base sequence corresponding to each bacterial species in saliva can be found by means of, for example, performing multiple alignment and designing probes in different regions between species. The algorithm for alignment is not particularly limited, but as a more specific analysis program, for example, a program such as ClustalX1.8 can be used. The parameters used for the alignment may be executed in the default state of each program, but can be adjusted as appropriate according to the type of program.

The probe specificity probe may be a specificity that collectively detects bacteria of the same genus based on the genus-level specificity or may be a specificity that can be detected at the individual species level. Probes can be appropriately selected and designed according to the detection purpose.

Examples of bacterial-specific probes that can be used in the present invention are shown in Table A below (SEQ ID NOS: 1 to 29).

(3) Total Load Index Probe

A total load index probe is a probe for capturing all bacteria in a specimen (in saliva) that can be amplified with a specific primer pair. In detecting bacteria, it is also important to detect the total bacterial load from the viewpoints of the proportion of detection target bacteria with respect to the entire bacteria including non-detection target bacteria and the overall abundance of bacteria present in a specimen.

The non-detection target bacteria can be understood as the sum (total) of bacteria of known types which are known to be present but may not be detected, and bacteria of unknown types which are unknown to be present.

In order to detect the total bacterial load, for example, it is possible to measure the total bacterial load independently of a DNA chip. Meanwhile, the simplicity of the operation is improved by mounting a probe, which is an index of the total bacterial load, in the DNA chip. Regarding probes, a base sequence common to many types of bacterial species may be used from the base sequences amplified by the primer pair. When such a sequence cannot be found, a plurality of relatively common sequences may be designed and comprehensively judged to be used as the total load index probe. The total load index probe is preferably a probe that hybridizes with a nucleic acid from a bacterium contained in a specimen, specifically, a probe that includes a base sequence common in a plurality of types of detection target bacteria from the base sequence amplified by the specific primer pair. Examples of the total load index probe are shown in Table A below (SEQ ID NO: 31).

The total load index usually increases because it represents the total amount of amplification products specific to individual species. Therefore, the signal intensity of interest may exceed the range of detectable signal intensities.

In order to prevent such a situation, it is desirable to limit the amount of a specimen used for hybridization. Alternatively, when designing a probe, for example, the Tm value of the probe is lowered. Specifically, it is conceivable to reduce the GC content or shorten the probe sequence length itself.

Further, at the time of hybridization, it is possible to reduce the signal intensity by adding a nucleic acid that competitively acts on the hybridization between the amplified nucleic acid and the total load index probe. Examples of such a nucleic acid include a nucleic acid having a sequence which is wholly or partially the same as that of the total load index probe, or a nucleic acid which wholly or partially has a complementary sequence of the total load index probe.

(4) Absolute Load Index Probe

An absolute load index probe is a probe that hybridizes only with an nucleic acid corresponding to an absolute load index.

In the present specification, the absolute load index refers to a nucleic acid that is added to a specimen in a fixed amount before an amplification reaction or a hybridization reaction. The absolute load index refers to a nucleic acid that can be surely amplified by a normal amplification reaction, and serves as a so-called positive control.

Therefore, when a probe specific to the absolute load index is mounted on a DNA chip, it can be confirmed from the detection results whether the amplification reaction, hybridization, or the like has been appropriately performed. Further, when one type of absolute load index is set, if the amplification efficiency or hybridization efficiency is slightly increased or decreased, the correction coefficient can be calculated by comparing the signal intensities of the absolute load index. The corrected signal intensity can be compared among a plurality of DNA chips.

Examples of the absolute load index probe are shown in Table A below (SEQ ID NO: 30).
In addition, an example of the absolute load index is set forth in SEQ ID NO: 74 below.

Absolute Load Index Probe:

(SEQ ID NO: 30)
CTATTCGACCAGCGATATCACTACGTAGGC

Absolute Load Index:

(SEQ ID NO: 74)
GTGAGAAGCCTACACAAACGTAACGTCAGGGCTAAGACAAACGCTAACGG

TACACCCTAGATGGGAGCTTGTAGCTAGATCGCTAAGTCCTACCGACATG

TAGGCATACTCACGAAGGCAATTCCCTGAAAGCCTCGTCTTATCCCGAAC

TTGGCATCTGCTGATACGTCAGGTTGAACGCGTACATTTACCTGTCATGC

GTGGGCCTTCTCCGAATAGCCTACGTAGTGATATCGCTGGTCGAATAGGC

GGATTGCTCATAAATGCACATTGGCTAAGGCCCACGGAACACGAATCACG

TGAGATCACTTACTATTCGACGGAACTACTATACGCACCGGGACATGCAA

GTAGCGTCCCACAAGCATAAGGAACTCTATACTCGCCATCTACGCAGCTA

-continued

CAGGGGATACACGTATGAGCGGTTACGAAGTAAAGCCGAGATAGAGCGGT

CTTTAGAGAAAAAACAGGATTAGATACCCTGGTAGTCC

In a case in which the absolute load index is added before an amplification reaction, it needs to be a nucleic acid that is amplified by a specific primer pair, that is, it needs to have a base sequence complementary to the primer pair. In addition, in order to detect the absolute load index by hybridization, it needs to have a nucleotide sequence that neither detection target bacteria nor non-detection target bacteria have.

The specific primer means that the sequence to be amplified is limited, and the primer pair does not necessarily have to be one pair. A multiplex method using two or more pairs of primers can also be applied as necessary. Examples of primer pairs are shown in Table B below. A pair of primers for bacterial amplification (SEQ ID NOS: 32 and 33) and a pair of absolute load index primers (SEQ ID NOS: 34 and 35) can be used.

As the absolute load index, for example, a nucleic acid standard substance for quantitative analysis developed by the National Institute of Advanced Industrial Science and Technology (AIST) may be used or it may be newly designed. When designing the absolute load index, for example, it is possible to use the RNDBETWEEN function of software "EXCEL" (manufactured by MICROSOFT), randomly generate X integers from 1 to 4 (X is an arbitrary number), connect them to create a numerical value of X digits consisting only of numerical values 1 to 4, and replace 1 with A, 2 with T, 3 with C, and 4 with G, thereby obtaining a large number of random sequences based on the X bases of ATGC.

Of these sequences, only the sequences in which the sum of G and T is the same as the sum of A and T are extracted, and the extracted sequences are searched by BLAST against a database such as NCBI's GenBank to select a sequence including few similar sequences to a biologically-derived nucleic acid, and primer sequences are added to both ends of the sequence. Thus, the absolute load index can be designed. Further, the designed sequence can be appropriately linked to increase the length, or can be partially removed to shorten the length.

In order to make the reaction efficiency during the amplification reaction as constant as possible, it is desirable that the base length amplified in a detection target bacterium and the amplified base length of the absolute load index do not have a large difference. For example, if the amplification product of the detection target bacterium is about 500 bp, the amplification product of the absolute load index is preferably about 300 bp to 1000 bp.

Meanwhile, in a case in which the amplified chain length is confirmed by electrophoresis after amplification, it is also possible to design an amplification product with a length different from that of the detection target bacterium and detect the amplification product from the absolute load index at a position different from the band of the detection target bacterium, thereby confirming the success or failure of the amplification reaction before hybridization.

Lastly, if the absolute load index in the specimen is excessively high in terms of concentration, competition with detection target bacteria in an amplification reaction may become intense, and there is a possibility that detection target bacteria, which should be detected, may not be detected. Therefore, it is necessary to properly adjust the concentration according to the application.

TABLE A

| SEQ ID NO | Sequence | Probe name |
|---|---|---|
| 1 | TTCAATGCAATACTCGTATC | Porphyromonas gingivalis |
| 2 | CACGTATCTCATTTTATTCCCCTGT | Tannerella forsythia |
| 3 | CCTCTTCTTCTTATTCTTCATCTGC | Treponema denticola |
| 4 | GCCTTCGCAATAGGTATT | Campylobacter gracilis |
| 5 | GTCATAATTCTTTCCCAAGA | Campylobacter rectus |
| 6 | CAATGGGTATTCTTCTTGAT | Campylobacter showae |
| 7 | TAGTTATACAGTTTCCAACG | Fusobacterium nucleatum subsp. vincentii |
| 8 | CCAGTACTCTAGTTACACA | Fusobacterium nucleatum subsp. polymorphum |
| 9 | TTTCTTTCTTCCCAACTGAA | Fusobacterium nucleatum subsp. animalis |
| 10 | TACATTCCGAAAAACGTCAT | Fusobacterium nucleatum subsp. nucleatum |
| 11 | TATGCAGTTTCCAACGCAA | Fusobacterium periodonticum |
| 12 | CGAAGGGTAAATGCAAAAAGGC | Prevotella intermedia |
| 13 | CTTTATTCCCACATAAAAGC | Prevotella nigrescens |
| 14 | AAGTACCGTCACTGTGTG | Streptococcus constellatus |
| 15 | GTCAATTTGGCATGCTATTAACACACC | Aggregatibacter actinomycetemcomitans |
| 16 | CCCAAGCAGTTCTATGGT | Campylobacter concisus |
| 17 | TACACGTACACCTTATTCTT | Capnocytophaga gingivalis |
| 18 | CAACCATTCAAGACCAACA | Capnocytophaga ochracea |
| 19 | TCAAAGGCAGTTGCTTAGT | Capnocytophaga sputigena |
| 20 | CTCTAGCTATCCAGTTCAG | Eikenella corrodens |
| 21 | CACCCGTTCTTCTCTTACA | Streptococcus gordonii |
| 22 | ACAGTATGAACTTTCCATTCT | Streptococcus intermedius |
| 23 | TCTCCCCTCTTGCACTCA | Streptococcus mitis |
| 24 | TCCCCTCTTGCACTCAAGT | Streptococcus mitis bv 2 |
| 25 | AAGTCAGCCCGTACCCA | Actinomyces odontolyticus |
| 26 | TCCTTCTAACTGTTCGC | Veillonella parvula |
| 27 | CCACCCACAAGGAGCAG | Actinomyces naeslundii II |
| 28 | TTCGCATTAGGCACGTTC | Selenomonas noxia |
| 29 | CACACGTTCTTGACTTAC | Streptococcus mutans |
| 30 | CTATTCGACCAGCGATATCACTACGTAGGC | Control DNA |
| 31 | CGTATTACCGCGGCTGCTGGCAC | Total bacteria |

TABLE B

| SEQ ID NO | Role | Sequence (5'→3') |
|---|---|---|
| 32 | Forward primer (for bacterial amplification) | TCCTACGGGAGGCAGCAGT |
| 33 | Reverse primer (for bacterial amplification) | CAGGGTATCTAATCCTGTTTGCTACC |
| 34 | Forward primer (for absolute load index amplification) | GAGAAGCCTACACAAACGTAACGTC |
| 35 | Reverse primer (for absolute load index amplification) | CTCTAAAGACCGCTCTATCTCGG |

When designing probes used in the present invention, it is preferable to consider stringency in hybridization. By setting the stringency to a dense degree to a certain extent, even if there are similar nucleotide sequence regions between specific regions in each nucleic acid in various bacteria, other different regions can be distinguished and hybridized. When the base sequences between the specific regions are almost different, the stringency can be set to a mild level.

Such stringency conditions include, for example, hybridization at 50° C. to 60° C. under the dense conditions and hybridization at 30° C. to 40° C. under the mild conditions. For hybridization conditions, examples of stringent conditions include, for example, "0.24 M Tris.HCl/0.24M NaCl/0.05% Tween-20, 40° C.," "0.24 M Tris.HCl/0.24M NaCl/0.05% Tween-20, 37° C.," and "0.24 M Tris.HCl/0.24 M NaCl/0.05% Tween-20, 30° C.," and examples of more stringent conditions include, for example, "0.24M Tris.HCl/0.24 M NaCl/0.05% Tween-20, 50° C.," "0.24 M Tris.HCl/0.24 M NaCl/0.05% Tween-20, 55° C.," and "0.06M Tris.HCl/0.06M NaCl/0.05% Tween-20, 60° C." More specifically, there is also a method in which hybridization is performed by adding a probe and keeping it at 50° C. for 1 hour or more, and then washing it in 0.24 M Tris.HCl/0.24 M NaCl/0.05% Tween-20 four times for 20 minutes at 50° C., and washing it once with 0.24 M Tris.HCl/0.24 M NaCl at 50° C. for 10 minutes at the end. By increasing the temperature during hybridization or washing, more stringent conditions can be set. A person skilled in the art can set the conditions by considering various conditions such as the probe concentration, the probe length, and the reaction time, in addition to the conditions such as the salt concentration of buffer and the temperature. For the detailed procedure of the hybridization method, "Molecular Cloning, A Laboratory Manual 4th ed." (Cold Spring Harbor Press (2012), "Current Protocols in Molecular Biology" (John Wiley & Sons (1987-1997)), and the like can be referred to.

The length of a probe used in the present invention is not limited, but is preferably 10 bases or more, more preferably 16 to 50 bases, and still more preferably 18 to 35 bases. As long as the length of a probe is appropriate (within the above range), nonspecific hybridization (mismatch) can be suppressed and such a probe can be used for specific detection.

It is preferable to confirm Tm when designing a probe used in the present invention. Tm means the temperature at which 50% of any nucleic acid strand hybridizes with its complementary strand. In order for the template DNA or RNA and the probe to form a double strand and hybridize with each other, the temperature of hybridization needs to be optimized. Meanwhile, if the temperature is excessively lowered, a nonspecific reaction is likely to occur, and therefore, the temperature is preferably as high as possible. Accordingly, the Tm of a nucleic acid fragment to be designed is an important factor for hybridization. Known probe design software can be used for confirmation of Tm, and examples of software usable in the present invention include Probe Quest (registered trademark; DYNACOM Co., Ltd.). The confirmation of Tm can also be performed by manually calculating without using software. In that case, a calculation formula based on the nearest neighbor method, the Wallance method, the GC % method, or the like can be used. In the probe of the present invention, the average Tm is preferably, but not limited to, about 35° C. to 70° C. or 45° C. to 60° C. Note that other conditions that allow the probe to achieve specific hybridization include the GC content and the like, and the conditions are well known to those skilled in the art.

In addition, the nucleotide constituting the probe used in the present invention may be any of DNA, RNA, or PNA, and may be a hybrid of two or more types of DNA, RNA and PNA.

Specifically, preferable examples of the probe used in the present invention include those containing the base sequence of the following DNAs (d) or (e). For example, when amplification is performed using the primers (SEQ ID NOS: 32 to 35) shown in Table B, the sequences shown in Table A (SEQ ID NOS: 1 to 31) above can be used as a probe. It is preferable to use at least two sequences selected from the base sequences set forth in SEQ ID NOS: 1 to 31. Further, such sequences may be sequences complementary to at least two sequences selected from the base sequences set forth in SEQ ID NOS: 1 to 31, and may be sequences substantially identical to at least two sequences selected from the base sequences set forth in SEQ ID NOS: 1 to 31 or sequences substantially identical to sequences complementary to at least two sequences selected from the base sequences set forth in SEQ ID NOS: 1 to 31.

Here, the sequences "substantially identical" refers to those that specifically hybridize with the sequences set forth in SEQ ID NOS: 1 to 31 or their complementary sequences under stringent conditions.

(d) DNAs consisting of the base sequences set forth in SEQ ID NOS: 1-31

(e) DNAs each capable of hybridizing with a DNA having a base sequence complementary to DNA of (d) above under stringent conditions and detecting at least a part of the base sequence of a nucleic acid from a bacterium in saliva Regarding the various DNAs of (d) above, the description of Table A above can be referred to for their specific base sequences, probe names, and oral bacteria to be detected.

The DNAs of (e) above are can be obtained from a cDNA library or a genomic library by carrying out known hybridization methods such as colony hybridization, plaque hybridization, and Southern blotting using the various DNAs (d) above or DNAs consisting of complementary nucleotide sequences thereof, or fragments thereof as probes. As the library, a library prepared by a known method may be used, or a commercially available cDNA library or genomic library may be used without any limitation. For the detailed procedure of the hybridization method, the same one as described above can be referred to. Regarding the DNAs of (e) above, the "stringent conditions" are the conditions during hybridization, which means conditions in which the salt concentration of buffer is 24 to 390 mM and the temperature is 40° C. to 65° C., and preferably, the salt concentration is preferably 48.8 to 195 mM and the temperature is 45° C. to 60° C. Specifically, for example, conditions in which the salt concentration is 97.5 mM and the temperature is 50° C. can be mentioned. Furthermore, in addition to such conditions of the salt concentration and temperature, various conditions such as the probe concentration, probe length, reaction time, and the like are also taken into consideration, and the conditions for obtaining DNA of (e) above can be set as appropriate. DNA that hybridizes has a base sequence that is preferably at least 60%, more preferably 80% or more, still more preferably 90% or more, even more preferably 95% or more, particularly preferably 98% or more, and most preferably 99% or more homologous to the base sequence of DNA of (d) above.

The probe used in the present invention can be prepared by, for example, chemical synthesis based on a usual oligonucleotide synthesis method (purification is carried out by HPLC or the like). Such a probe can be designed by, for example, Probe Quest (registered trademark; DYNACOM Co., Ltd.). In addition, the probe of the present invention may include an additional sequence such as a tag sequence.

According to the method of the present invention, the base sequence of the nucleic acid possessed by the bacterium in saliva to be detected does not need to be the base sequence itself, and a part of the base sequence may be mutated by deletion, substitution, insertion, or the like. Therefore, a mutated gene that hybridizes with a sequence complementary to the base sequence under stringent conditions and has a function or activity derived from each base sequence may also have the base sequence of the nucleic acid to be detected. The probe can also be designed based on the base sequence of such mutated gene. Here, as the "stringent conditions," the same conditions as described above can be applied.

2. DNA Chip

As described above, according to the method of the present invention, a DNA chip can be used for detecting/ measuring the bacterial load in saliva. The DNA chip is used for the purpose of comprehensively estimating the degree of inflammation of periodontal tissue, and a plurality of the various oligonucleotide probes described in Item 1. above are arranged on a substrate serving as a support.

As the form of the substrate serving as a support, any form such as a flat plate (e.g., a glass plate, resin plate, or silicon plate), a rod shape, beads, or the like can be used. When a flat plate is used as the support, predetermined probes can be fixed on the flat plate at predetermined intervals by type (e.g., the spotting method; see Science 270, 467-470 (1995), etc.). It is also possible to successively synthesize predetermined probes by type at specific positions on a flat plate (e.g., the photolithography method; see Science 251, 767-773 (1991), etc.). Other preferable support forms include those using hollow fibers. When using hollow fibers as the support, a DNA chip obtained by fixing a predetermined probe to each hollow fiber by type, bundling and fixing all the hollow fibers, and then repeating cutting in the longitudinal direction of the fibers (hereinafter, referred to as "fiber type DNA chip") can be preferably exemplified. This microarray can be described as a type of microarray prepared by immobilizing nucleic acids on a through-hole substrate, and is also called a so-called "through-hole type DNA chip" (see JP Patent No. 3510882).

The method of fixing the probes to the support is not limited, and any binding mode may be used. Further, fixation of the probes is not limited to direct fixation to the support. For example, the support may be coated in advance with a polymer such as polylysine and the probes may be fixed to the treated support. Furthermore, when a tubular body such as a hollow fiber is used as the support, the tubular body can be configured to hold a gel-like material and a probe can be fixed to the gel-like material.

Hereinafter, a fiber type DNA chip, which is one aspect of the DNA chip, will be described in detail. This DNA chip can be produced through, for example, the following steps (i) to (iv).

(i) A step of producing an array by three-dimensionally arranging a plurality of hollow fibers such that the longitudinal directions of the hollow fibers are the same direction (ii) A step of producing a block body by embedding the array (iii) A step of introducing a gel precursor polymerizable solution containing an oligonucleotide probe into the hollow portion of each hollow fiber of the block body to carry out a polymerization reaction and holding the gel-like material containing the probe in the hollow portion (iv) A step of thinning the block body by cutting it in the direction intersecting the longitudinal direction of the hollow fiber The material used for the hollow fiber is not limited, but for example, materials described in JP Patent Publication (Kokai) No. 2004-163211 A and the like are preferable.

The hollow fibers are three-dimensionally arranged such that their lengths in the longitudinal direction are the same (step (i)). Examples of the arrangement method include a method for arranging a plurality of hollow fibers in parallel on a sheet-like material such as an adhesive sheet at predetermined intervals to form a sheet and winding the sheet in a spiral shape (see JP Patent Publication (Kokai) No. 11-108928 A (1999)) and a method in which two perforated plates provided with a plurality of holes at predetermined intervals are overlapped such that the holes match, hollow fibers are allowed to pass through those holes, and the two perforated plates are opened with an interval and temporarily fixed, and then, a curable resin material is filled around each hollow fiber between the two porous plates for curing (see JP Patent Publication (Kokai) No. 2001-133453 A).

The produced array is embedded such that the arrangement is not disturbed (step (ii)). Preferable examples of the embedding method include a method in which a polyurethane resin, an epoxy resin, or the like is poured into a gap between fibers and a method in which fibers are bonded to each other by heat fusion.

In the embedded array, a gel precursor polymerizable solution (gel forming solution) containing an oligonucleotide probe is filled in the hollow part of each hollow fiber, and a polymerization reaction is carried out in the hollow part (step (iii)). As a result, the gel-like material to which the probe is fixed can be held in the hollow portion of each hollow fiber.

The gel precursor polymerizable solution is a solution containing a reactive substance such as a gel-forming polymerizable monomer, and the solution can be a gel-like material by polymerizing and crosslinking the monomer or the like. Examples of such a monomer include acrylamide, dimethylacrylamide, vinylpyrrolidone, and methylenebisacrylamide. In this case, the solution may contain a polymerization initiator or the like.

After fixing the probe in the hollow fiber, the block body is cut into thin sections in a direction intersecting the longitudinal direction of the hollow fiber (preferably in a direction orthogonal thereto) (step (iv)). The thin sections thus obtained can be used as a DNA chip. The thickness of the DNA chip is preferably about 0.01 mm to 1 mm. The block body can be cut with, for example, a microtome, a laser, or the like.

Preferable examples of the fiber type DNA chip described above include a DNA chip (Genopal (trademark)) manufactured by Mitsubishi Chemical Corporation.

In the fiber type DNA chip, the probes can be arranged three-dimensionally in the gel as described above such that the three-dimensional structure can be maintained. Therefore, as compared with a flat DNA chip in which a probe is bound to a surface-coated slide glass, the detection efficiency is increased, and an extremely sensitive and reproducible test can be performed.

Further, the number of types of probes arranged on a DNA chip is preferably 500 types or less, preferably 250 types or less, and more preferably 100 types or less on a single DNA chip. By limiting the number (type) of probes arranged in this way to some extent, it becomes possible to detect oral bacteria of interest with higher sensitivity. The type of probe is distinguished by the base sequence. Therefore, even if probes originate from the same gene, they are specified as different types unless there is no difference between their base sequences.

3. Detection of Bacteria in Saliva (Measurement of Bacterial Load)

According to the method of the present invention, the method for detecting a bacterium to measure the bacterial load thereof in saliva is, for example, a method including the following steps.

(i) A step of using saliva as a specimen serving as an oral sample collected from a subject and extracting nucleic acids in the specimen (in saliva)

(ii) A step of bringing the extracted nucleic acids into contact with the aforementioned oligonucleotide probe of the present invention or the DNA chip of the present invention (iii) A step of calculating the bacterial load from the signal intensity obtained from the DNA chip Hereinafter, the details of the detection method will be described step by step.

(1) Step (i)

In this step, saliva is used as a specimen serving as an oral sample collected from a subject, and nucleic acids of bacteria contained in the specimen (in saliva) are extracted. The method for collecting saliva is not particularly limited, and examples thereof include a method using a commercially available saliva collecting kit, a method for collecting saliva with a swab in the mouth, and a method for collecting saliva directly into a container.

A subject whose saliva is collected is not particularly limited, but for example, in addition to a patient suffering from oral inflammation such as periodontal disease, the subject may be a person who is unaware of oral inflammation such as periodontal disease, a patient with a systemic disease such as heart disease or a pregnant woman who is possibly associated with periodontal disease, or a healthy subject with no suspicion of periodontal disease.

Next, extraction of nucleic acids from the bacteria present in the obtained saliva is performed. The extraction method is not limited, and a known method can be used. For example, an automatic extraction method using a device, a method using a commercially available nucleic acid extraction kit, a method for extraction with phenol after proteinase K treatment, a method using chloroform, or a simple extraction method including a method for heating and dissolving a sample can be exemplified. In addition, it is not particularly necessary to extract nucleic acids from the specimen, and the process may proceed to the next step.

The nucleic acids obtained from the specimen may be directly brought into contact with a DNA chip or the like, or a desired base sequence region may be amplified by PCR or the like, and the amplified fragment may be brought into contact with the DNA chip or the like, without any limitation. The region to be amplified using the obtained nucleic acid as a template is a region encoding the nucleic acid region including the base sequence of the probe used in the present invention or the oligonucleotide arranged on the DNA chip. The desired region to be amplified is not limited and can be obtained by using the base sequence of a highly conserved region regardless of species of bacteria and amplifying a mixture of many kinds at once. The sequence for such amplification may be experimentally isolated and purified, and the base sequence of the isolated polynucleotide may be analyzed and determined based on the sequence. Alternatively, the sequence may be determined by in silico by searching a known base sequence in various databases and obtaining an alignment. The database of nucleic acids or amino acids is not particularly limited, but, for example, a Taxonomy database or the like is available at DDBJ (DNA Data Bank of Japan), EMBL (European Molecular Biology Laboratory, EMBL nucleic acid sequence data library), GenBank (Genetic sequence data bank), and NCBI (National Center for Biotechnology Information).

Specifically, the desired site to be amplified is preferably the ribosomal RNA (16S rRNA) gene in chromosomal DNA of an bacterium. Preferable examples of PCR primers that can be used for amplification of the region include SEQ ID NOS: 32 and 33 shown in Table B above. Amplification of nucleic acids by the PCR method can be performed according to a standard method.

The nucleic acid extracted in this step and an amplified fragment thereof can be labeled appropriately and used in the detection process after hybridization. Specifically, a method for labeling an end of a PCR primer with various reporter dyes, a method for incorporating a reactive nucleotide analog in a reverse transcription reaction, a method for incorporating a biotin-labeled nucleotide, and the like can be considered. Furthermore, it is also possible to label the nucleic acid or a fragment thereof by reacting it with a fluorescent labeling reagent after preparation. As the fluorescent reagent, for example, various reporter dyes (e.g., Cy5, Cy3, VIC, FAM, HEX, TET, fluorescein, FITC, TAMRA, Texas red, and Yakima Yellow) can be used.

(2) Step (ii)

In this step, the nucleic acid or an amplified fragment thereof obtained in step (i) is brought into contact with the probe or DNA chip used in the present invention. Specifically, a hybridization solution containing the nucleic acid or the like is prepared, and the nucleic acid or the like therein is bound (hybridized) to an oligonucleotide probe mounted on the DNA chip. The hybridization solution can be appropriately prepared by using a buffer solution such as SDS or SSC according to a standard method.

The hybridization reaction can be performed by appropriately setting the reaction conditions (e.g., type of buffer solution, pH, and temperature) such that the nucleic acid or the like in the hybridization solution can hybridize with the oligonucleotide probe mounted on the DNA chip under stringent conditions. The term "stringent conditions" as used herein refers to conditions in which cross-hybridization due to similar sequences is unlikely to occur or nucleic acids cross-hybridized by similar sequences are dissociated. Specifically, it means the conditions of washing the DNA chip during the hybridization reaction or after hybridization.

For example, as for the conditions during the hybridization reaction, the reaction temperature is preferably 35° C. to 70° C., more preferably 40° C. to 65° C., and the hybridization time is preferably about 1 minute to 16 hours.

As for the conditions of washing the DNA chip after hybridization, the washing solution composition comprises preferably 0.24 M Tris.HCl/0.24 M NaCl/0.05% Tween-20, and the temperature during washing is preferably 35° C. to 80° C. or 40° C. to 65° C., more preferably 45° C. to 60° C. More specifically, the conditions in which the salt (sodium) concentration is 48 to 780 mM and the temperature is 37° C. to 80° C. are preferable, and the conditions in which the salt concentration is 97.5 to 390 mM and the temperature is 45° C. to 60° C. are more preferable.

After washing, the detection intensity is measured for each spot with an apparatus capable of detecting a label such as a nucleic acid bound to a probe. For example, in a case in which the nucleic acid or the like is fluorescently labeled, the fluorescence intensity can be measured by using various fluorescence detection devices such as CRBIO (manufactured by Hitachi Software Engineering Co., Ltd.), array-WoRx (manufactured by GE Healthcare), Affymetrix 428 Array Scanner (manufactured by Affymetrix, Inc.), GenePix, (Axon Instruments), ScanArray (PerkinElmer), and Genopal Reader (Mitsubishi Chemical Corporation). With respect to these devices, in the case of a fluorescence scanner, scanning can be performed by, for example, appropriately adjusting the laser output and the sensitivity of the detection unit. In the case of a CCD camera type scanner, scanning can be performed by appropriately adjusting the exposure time. The quantification method based on the scan result is performed by quantification software. The quantification software is not particularly limited, and quantification can be performed using the average, median, or the like of the fluorescence intensities of spots. Further, upon quantification, it is preferable to make adjustments in consideration of the dimensional accuracy of the spot range of a DNA fragment or the like, using the fluorescence intensity of a spot without a probe as the background.

(3) Step (iii)

In this step, the bacterial load of a detection target bacterium is calculated from the signal intensity obtained by the above procedure. For example, there is a method for expressing the bacterial load as the SN ratio from the signal intensity of a probe for detecting a detection target bacterium and the signal intensity of the background. Alternatively, preferable methods include a method in which detection is performed under a plurality of conditions by changing the chromosomal DNA concentration of each bacterium in advance, the conversion factor (calibration curve) is obtained to calculate the chromosomal DNA concentration for each bacterium based on the signal intensity obtained under each concentration condition, and the chromosomal DNA concentration is calculated from the signal intensity obtained under each condition. In the present invention, for example, the bacterial load is preferably calculated from the signal intensity based on the 16S rRNA sequence information of a detection target bacterium. Further, it is also preferable to adopt the genome copy number of the detection target bacterium as the bacterial load. The genome copy number can be calculated by multiplying the signal intensity detected by the DNA chip by a previously determined calculation coefficient of each bacterial load (and, if necessary, by multiplying the dilution ratio of the detected specimen). The calculation coefficient for each bacterial load can be obtained as a coefficient for back-calculating each bacterial load from the signal intensity of each bacterium by measuring the signal intensity when detecting the genomic DNA from each bacterium and creating a calibration curve.

In any case, it is preferable to consider the correction coefficient for the signal intensity of each detection target bacterium on the DNA chip.

4. Estimation of Degree of Periodontal Tissue Inflammation

The method of the present invention is a method for estimating the periodontal pocket inflammation area using the detection results of the bacterial load of a bacterium in saliva as indexes. The method of the present invention is a method for comprehensively estimating the degree of inflammation of periodontal tissue using the detection results as indexes.

Any tool can be used for detecting the bacterial load of a bacterium in saliva. As described in Item 3. above, a method using a DNA chip and other methods such as a method for confirming the presence of bacteria by enzyme activity, a method for measuring the electrical resistance to determine the total bacterial load, a method for counting bacteria by a phase contrast microscope and staining, a method for culturing cells and measuring the viable cell count, and a method for quantifying individual bacterial counts by real-time PCR can be exemplified.

In the estimation, the periodontal pocket inflammation area and the degree of inflammation of periodontal tissue are estimated based on, as the bacterial load or a measured amount proportional to the bacterial load, the SN ratio of fluorescence intensity and signal intensity of the DNA chip, the Ct value of real-time PCR, the enzyme activity value, the resistance value upon electrical measurement, or the visually counted value.

Specific methods for estimating the periodontal pocket inflammation area include the following methods.

(1) The bacterial load of each bacterium in saliva from a saliva sample of a subject with a known periodontal pocket inflammation area (e.g., a PISA or CAPRS value) (which can be calculated from the actually measured PPD or the like) is detected.

(2) A correlation coefficient of the bacterial load of each bacterium with a periodontal pocket inflammation area unique to each bacterium is obtained, and a relational expression between the bacterial load of each bacterium and the periodontal pocket inflammation area is constructed, thereby creating a prediction model.

(3) The bacterial load of each bacterium in saliva from a saliva sample of a subject with an unknown periodontal pocket inflammation area is detected.

(4) The bacterial load of each bacterium obtained in (3) is inserted into the relational expression obtained in (2), thereby estimating the periodontal pocket inflammation area.

The method for creating a prediction model is not particularly limited. However, examples of the method include methods using various statistical analysis techniques such as machine learning algorithms of linear regression, regression tree, model tree, neural network, support vector machine, bagging, boosting, and random forest. Of these, in the model tree shown in the Examples described later, it is not necessary to specify the model in advance. Specifically, optimization by the "M5" method using the "caret" package of the statistical software "R" (R Development Core Team) is preferably exemplified.

The number of saliva samples of subjects whose periodontal pocket inflammation areas are actually measured (the number of data used for creating the prediction model) to be used herein is preferably a number equal to or more than the bacterial count (variable) that is used for creating the prediction model. The prediction model may be updated every time the number of data is accumulated.

In the "first invention group," as bacteria to be detected which are used for creating the prediction model, both a bacterium having a positive correlation between the bacterial load of the bacterium and the periodontal pocket inflammation area and a bacterium having a negative correlation between the bacterial load of the bacterium and the periodontal pocket inflammation area are used. This is because in healthy people without the progression of periodontal disease, bacteria having a positive correlation with the periodontal pocket inflammation area are often not detected (the bacterial count becomes 0), and therefore, a predictive model for a range of small periodontal pocket inflammation areas cannot be created only with the bacteria having a positive correlation.

Examples of bacteria used for creating a prediction model are described in Item 1. above. However, in order to improve the prediction accuracy in the end, bacteria are selected in consideration of not only the magnitude of the correlation coefficient of a bacterium alone, but also the accuracy of the amount of change of the bacterium in response to a change in the periodontal pocket inflammation area and the correlation coefficient of bacterial load between bacteria (avoiding a multicollinear relation).

Preferable examples of a bacterium having a positive correlation include the following bacteria:
Porphyromonas_gingivalis, Tannerella_forsythia, Treponema_denticola, Campylobacter_rectus, Fusobacterium_nucleatum_subsp._vincentii, Fusobacterium_nucleatum_subsp._polymorphum,
Fusobacterium_nucleatum_subsp._animalis, Fusobacterium_nucleatum_subsp._nucleatum, Fusobacterium_periodonticum, Aggregatibacter_actinomycetemcomitans, Capnocytophaga_ochracea, Capnocytophaga_sputigena,

*Streptococcus_gordonii, Streptococcus_intermedius, Veillonella_parvula, Selenomonas_noxia, Solobacterium moorei, Prevotella loescheii, Veillonella rogosae, Actinomyces israelii, Corynebacterium matruchotii*, SR1 sp. OT 345, *Porphyromonas catoniae, Selenomonas sputigena, Neisseria flavescens, Streptococcus sobrinus, Parvimonas micra, Peptostreptococcus stomatis, Treponema socranskii, Eubacterium saphenum, Eubacterium nodatum, Treponema medium, Filifactor alocis*, and *Porphyromonas endodontalis*.

More preferable examples of a bacterium having a positive correlation include the following bacteria:
*Porphyromonas_gingivalis, Tannerella_forsythia, Treponema_denticola, Campylobacter_rectus, Fusobacterium_nucleatum_*subsp._*animalis, Fusobacterium_nucleatum_*subsp._*nucleatum, Veillonella_parvula, Selenomonas_noxia, Eubacterium saphenum, Eubacterium nodatum, Treponema medium, Filifactor alocis*, and *Porphyromonas endodontalis*.

As the bacterium having a positive correlation, it is preferable to use 1 or more species, more preferably 4 or more species, still more preferably 8 or more species, and particularly preferably 12 or more species. Further, it is preferable to use 100 or less species, more preferably 75 or less species, still more preferably 50 or less species, and particularly preferably 25 or less species.

Preferable examples of a bacterium having a negative correlation include the following bacteria:
*Streptococcus_mitis, Streptococcus_mitis_*bv_2, *Actinomyces_odontolyticus, Streptococcus_mutans, Campylobacter-_concisus, Capnocytophaga_gingivalis, Prevotella pallens, Streptococcus salivarius, Eubacterium sulci, Rothia mucilaginosa, Prevotella denticola, Veillonella atypica, Prevotella histicola, Megasphaera micronuciformis, Streptococcus parasanguinis, Gemella sanguinis, Alloprevotella* spp. (*A. rava*, OT 308), *Prevotella melaninogenica, Actinomyces graevenitzii, Prevotella shahii, Rothia dentocariosa, Granulicatella adiacens, Porphyromonas pasteri*, and *Haemophilus parainfluenzae*.

More preferable examples of a bacterium having a negative correlation include the following bacteria:
*Actinomyces_odontolyticus, Streptococcus_mutans*, and *Prevotella pallens*.

As the bacterium having a negative correlation, it is preferable to use 1 or more species, more preferably e or more species, still more preferably 4 or more species, and particularly preferably 8 or more species. Further, it is preferable to use 100 or less species, more preferably 75 or less species, still more preferably 50 or less species, and particularly preferably 25 or less species.

As an aside, according to the present invention, statistical analysis processing is performed on a predetermined number of subjects (primary sample population) and stored in the database. From the analysis results of the correlation between the degree of inflammation of periodontal tissue and the bacterial load in saliva, it is possible to estimate what degree of inflammation of periodontal tissue or how much concealed area in periodontal pocket of tooth root surface each of the subjects has. Therefore, when testing an individual subject (one person), by using the data from a plurality of subjects as a sample population to examine where the data of the individual subject is located or applies to the data of the sample population stored in the database, it is possible to estimate the degree of inflammation of periodontal tissue or the concealed area in periodontal pocket of tooth root surface for the individual subject. It is also possible to incorporate the data of the individual subject into the values of the sample population, perform statistical analysis processing again, and then examine where the individual subject is located in the sample population.

According to the method of the present invention, the degree of inflammation of periodontal tissue (the PISA value or CAPRS value) can be estimated and predicted based on the bacterial species in saliva and the bacterial load thereof. Therefore, compared with the case where the PISA value or CAPRS value was actually measured in the past, it is possible to calculate the degree of inflammation of periodontal tissue based on a certain calculation standard even for a large number of subjects in a significantly convenient manner. Further, in the present invention, the degree of inflammation of periodontal tissue includes not only the positive degree but also the negative degree in the range of estimation/prediction. Accordingly, when focusing on bacterial species (indigenous bacteria) with a bacterial load that is inversely correlated with the degree of inflammation of periodontal tissue, it is also possible to estimate/predict whether or not the healthy state of the oral cavity of the subject is maintained. Moreover, the ratio of the bacterial species correlated with the bacterial load or the bacterial species inversely correlated with the degree of inflammation of periodontal tissue may be used as an index.

Hereinafter, the present invention will be described in more detail with reference to the Examples below, but the present invention is not limited thereto.

EXAMPLES

Example 1

Saliva Sample Collection

At the Osaka University Dental Hospital, 46 samples of 1 ml of saliva were collected from a total of 46 male and female subjects in their 20s to 70s undergoing periodontal disease treatment. The saliva collected was frozen and stored at −20° C. before use.

Calculation of PISA Values Associated with Saliva Samples
<Acquisition of Clinical Information>

The following clinical information was recorded for all samples. The following two items are indexes that are widely used in dentistry.

(i) Periodontal pocket depth (PPD): PPD refers to the distance from the gingival margin to the tip of a periodontal probe when the probe is inserted into the pocket. The buccal mesial, buccal center, buccal distal, lingual mesial, lingual central, and lingual centrifugal were measured by the 6-point method, and numerical values were calculated in units of 1 mm.

(ii) Bleeding on probing (BOP): BOP refers to the presence or absence of bleeding when a periodontal probe is inserted into the pocket. The case in which there was no bleeding at the positions corresponding to the above 6-point method was set to 0, and the case in which there was bleeding was set to 1.

Table 1 summarizes (i) periodontal pocket depth (PPD) and (ii) bleeding on probing (BOP).

TABLE 1

| Subject No. | First visit/R | Sample No. | | | | DCM 7 | DCM 6 | DCM 5 | DCM 4 | DCM 3 | DCM 2 | DCM 1 | MCD 1 | MCD 2 | MCD 3 | MCD 4 | MCD 5 | MCD 6 | MCD 7 |
|---|---|---|---|---|---|---|---|---|---|---|---|---|---|---|---|---|---|---|---|
| 21 | First visit | 1 | Upper jaw | Upper jaw mobility | | 1 | 1 | 1 | | 1 | 1 | | 3 | | | | 0 | 0 | 0 |
| 21 | First visit | | Upper jaw | Buccal side | BOP | 1 0 0 | 0 0 0 | 0 0 1 | | 0 0 0 | 0 0 0 | | 0 0 0 | 0 0 0 | | | 1 0 0 | 0 0 1 | 0 1 0 |
| 21 | First visit | | Upper jaw | Buccal side | PD | 4 6 4 | 4 3 3 | 3 2 3 | | 3 2 3 | 4 2 3 | | 4 3 2 | | | | 4 2 3 | 3 4 3 | 3 8 4 |
| 21 | First visit | | Upper jaw | Palatial side | PD | 5 4 3 | 4 4 8 | 4 4 7 | | 4 5 4 | 6 7 5 | | 5 5 4 | | | | 6 6 6 | 3 4 4 | 4 4 7 |
| 21 | First visit | | Upper jaw | Palatial side | BOP | 1 0 0 | 1 0 1 | 0 0 1 | | 0 0 1 | 0 0 0 | | 0 0 0 | | | | 0 0 1 | 0 0 0 | 0 0 1 |
| 21 | First visit | | Lower jaw | Lingual side | BOP | | | 1 0 0 | 0 0 0 | 0 0 1 | 1 0 1 | 1 0 1 | 1 0 0 | 0 0 0 | 0 0 1 | 1 0 1 | | | |
| 21 | First visit | | Lower jaw | Lingual side | PD | | | 4 6 5 | 4 3 4 | 4 3 4 | 3 3 5 | 3 3 5 | 6 5 4 | 4 3 4 | 6 5 4 | 5 3 3 | | | |
| 21 | First visit | | Lower jaw | Lip side | PD | | | 4 3 4 | 4 3 4 | 4 3 4 | 6 4 4 | 6 4 6 | 6 3 6 | 3 3 4 | 5 4 4 | 5 4 3 | | | |
| 21 | First visit | | Lower jaw | Lip side | BOP | | | 1 0 1 | 0 0 0 | 0 0 1 | 1 0 0 | 0 0 1 | 1 0 1 | 1 0 0 | 0 0 0 | 1 0 0 | | | |
| 21 | First visit | | Lower jaw | Lower jaw mobility | | | | 0 | 0 | 1 | 0 | 0 | 0 | 0 | 0 | 0 | | | |
| 21 | R | 2 | Upper jaw | Upper jaw mobility | | 0 | 0 | 1 | 0 | 1 | 1 | 0 | 0 | | | | 0 | 0 | 0 |
| 21 | R | | Upper jaw | Buccal side | BOP | 0 0 0 | 0 0 0 | 0 0 1 | 0 0 0 | 0 0 0 | 0 0 0 | | 0 0 0 | | | | 0 0 0 | 0 0 0 | 0 0 0 |
| 21 | R | | Upper jaw | Buccal side | PD | 3 3 3 | 4 4 3 | 3 2 5 | 2 1 2 | 2 2 3 | 3 2 2 | | 4 1 2 | | | | 2 2 2 | 3 3 3 | 3 4 6 |
| 21 | R | | Upper jaw | Palatial side | PD | 3 2 2 | 3 3 4 | 5 2 6 | 3 2 3 | 3 2 3 | 3 2 3 | | 4 2 4 | | | | 4 2 3 | 3 2 3 | 3 2 3 |
| 21 | R | | Upper jaw | Palatial side | BOP | 0 0 0 | 0 0 0 | 0 0 0 | 0 0 0 | 0 0 0 | 0 0 0 | | 0 0 0 | | | | 0 0 0 | 0 0 0 | 0 0 0 |
| 21 | R | | Lower jaw | Lingual side | BOP | | | 3 2 3 | 2 1 2 | 2 1 2 | 3 2 2 | 3 2 3 | 4 1 2 | 2 1 2 | 2 2 2 | 3 2 2 | | | |
| 21 | R | | Lower jaw | Lingual side | PD | | | 2 2 2 | 3 2 3 | 3 2 3 | 2 2 2 | 3 2 3 | 4 2 4 | 2 2 2 | 3 2 2 | 2 2 2 | | | |
| 21 | R | | Lower jaw | Lip side | PD | | | 0 0 0 | 0 0 0 | 0 0 0 | 0 0 0 | 0 0 0 | 0 0 0 | 0 0 1 | 0 0 0 | 0 0 0 | | | |
| 21 | R | | Lower jaw | Lip side | BOP | | | | | | | | | | | | | | |
| 21 | R | | Lower jaw | Lower jaw mobility | | | | 1 | 0 | 0 | 0 | 0 | 0 | 0 | 0 | 0 | | | |
| 22 | First visit | 3 | Upper jaw | Upper jaw mobility | | 0 | 0 | 0 | 0 | 0 | 0 | 0 | 0 | | | | 0 | 0 | |
| 22 | First visit | | Upper jaw | Buccal side | BOP | 0 0 0 | 0 0 0 | 0 0 0 | 0 0 0 | 0 0 0 | 0 0 0 | 1 0 0 | 0 0 1 | | | | 0 0 0 | 0 0 0 | |
| 22 | First visit | | Upper jaw | Buccal side | PD | 6 3 4 | 4 4 4 | 6 2 4 | 5 3 4 | 3 3 4 | 4 3 4 | 10 7 4 | 3 4 5 | | | | 3 4 4 | | |
| 22 | First visit | | Upper jaw | Palatial side | PD | 7 3 7 | 7 2 6 | 6 4 5 | 6 3 9 | 4 3 4 | 5 3 5 | 6 8 7 | 4 4 7 | | | | 6 3 5 | | |
| 22 | First visit | | Upper jaw | Palatial side | BOP | 0 0 0 | 0 0 0 | 0 0 0 | 0 0 1 | 0 0 0 | 0 0 1 | 0 1 0 | 0 0 1 | | | | 0 0 1 | | |
| 22 | First visit | | Lower jaw | Lingual side | BOP | | | 0 0 0 | 0 0 1 | 0 0 0 | 0 0 0 | 0 0 0 | 0 0 1 | 0 0 0 | 0 0 0 | 0 0 0 | | | |
| 22 | First visit | | Lower jaw | Lingual side | PD | | | | 4 4 5 | 4 3 3 | 3 3 3 | 3 4 3 | 5 4 5 | 4 4 8 | 4 3 4 | 5 6 7 | | | |
| 22 | First visit | | Lower jaw | Lip side | PD | | | | 4 3 6 | 6 5 3 | 8 7 5 | 4 3 4 | 4 3 5 | 4 3 6 | 5 3 6 | 7 3 4 | | | |
| 22 | First visit | | Lower jaw | Lip side | BOP | | | | 0 0 0 | 1 0 0 | 1 0 0 | 0 0 0 | 0 0 1 | 0 0 1 | 1 0 0 | 0 0 0 | | | |
| 22 | First visit | | Lower jaw | Lower jaw mobility | | | | | 0 | 0 | 2 | 2 | 2 | 2 | 1 | 1 | | | |
| 22 | R | 4 | Upper jaw | Upper jaw mobility | | 0 | 0 | 0 | 0 | 0 | 1 | 1 | 2 | 2 | 1 | 0 | 0 | 0 | 0 |
| 22 | R | | Upper jaw | Buccal side | BOP | 1 0 0 | 0 0 0 | 0 0 0 | 0 0 0 | 0 0 0 | 0 0 0 | 0 1 0 | 0 0 1 | 0 0 0 | 1 0 0 | 1 0 0 | 0 0 0 | 0 0 0 | 0 0 0 |
| 22 | R | | Upper jaw | Buccal side | PD | 4 3 3 | 3 3 3 | 4 2 3 | 4 3 3 | 3 2 3 | 3 2 3 | 6 5 5 | 3 3 5 | 4 4 3 | 4 3 3 | 3 3 5 | 3 3 5 | 3 4 4 | 4 4 9 |
| 22 | R | | Upper jaw | Palatial side | PD | 4 3 6 | 6 3 3 | 6 5 6 | 3 2 7 | 3 3 3 | 3 3 4 | 6 5 7 | 3 3 6 | 4 3 3 | 3 3 3 | 6 6 7 | | | |
| 22 | R | | Upper jaw | Palatial side | BOP | 0 0 1 | 0 0 0 | 0 1 0 | 0 0 1 | 0 0 0 | 0 0 0 | 0 0 0 | 0 0 0 | 0 0 0 | 0 0 0 | 1 1 1 | 0 0 0 | 0 0 0 | 0 0 1 |
| 22 | R | | Lower jaw | Lingual side | BOP | | | 0 0 0 | 0 0 1 | 0 0 0 | 0 0 0 | 0 0 0 | 1 0 1 | 0 0 0 | 0 0 0 | 0 0 0 | | | |
| 22 | R | | Lower jaw | Lingual side | PD | | | | 3 4 4 | 4 3 3 | 3 2 2 | 3 2 2 | 4 4 6 | 3 2 6 | 5 6 7 | 6 3 3 | | | |
| 22 | R | | Lower jaw | Lip side | PD | | | | 3 4 4 | 4 3 3 | 6 7 4 | 3 2 3 | 3 2 3 | 3 3 6 | 7 3 4 | 5 2 3 | | | |
| 22 | R | | Lower jaw | Lip side | BOP | | | | 0 1 0 | 0 0 0 | 0 1 0 | 0 0 0 | 1 0 0 | 0 0 0 | 0 0 0 | 0 0 0 | | | |
| 22 | R | | Lower jaw | Lower jaw mobility | | | | | 1 | 0 | 2 | 2 | 2 | 1 | 1 | 0 | | | |
| 23 | First visit | 5 | Upper jaw | Upper jaw mobility | | 0 | 0 | 0 | 0 | 0 | 0 | 0 | 0 | 0 | 0 | 0 | 0 | 0 | 0 |
| 23 | First visit | | Upper jaw | Buccal side | BOP | 1 0 0 | 0 0 0 | 0 0 0 | 0 0 0 | 0 0 0 | 0 0 0 | 0 0 0 | 0 0 1 | 0 0 0 | 0 0 0 | 0 0 0 | 0 0 0 | 0 0 0 | 0 0 0 |
| 23 | First visit | | Upper jaw | Buccal side | PD | 8 4 3 | 3 2 3 | 3 3 3 | 3 3 3 | 2 3 3 | 3 3 3 | 3 4 3 | 2 3 2 | 2 2 3 | 2 3 3 | 3 3 5 | 3 4 4 | 3 4 4 | 4 4 9 |
| 23 | First visit | | Upper jaw | Palatial side | PD | 5 4 3 | 4 3 4 | 4 3 4 | 4 3 4 | 3 3 3 | 3 3 3 | 3 2 3 | 3 2 3 | 3 3 3 | 4 3 3 | 3 3 4 | 4 3 4 | 4 3 4 | 4 3 4 |
| 23 | First visit | | Upper jaw | Palatial side | BOP | 1 0 0 | 0 0 0 | 0 0 0 | 0 0 1 | 0 0 0 | 0 0 0 | 2 2 3 | 1 0 1 | 0 0 0 | 0 0 0 | 0 0 0 | 0 0 0 | 0 0 1 | 0 0 1 |
| 23 | First visit | | Lower jaw | Lingual side | BOP | | | | | | | | | | | | | | |
| 23 | First visit | | Lower jaw | Lingual side | PD | 6 4 3 | 3 3 3 | 3 2 3 | 3 2 3 | 3 2 3 | 3 2 3 | 2 2 3 | 3 2 3 | 3 2 3 | 3 3 3 | 3 3 4 | 4 3 4 | 4 3 4 | 4 3 6 |

TABLE 1-continued

| Subject No. | First visit/R | Sample No. | | | DCM 7 | DCM 6 | DCM 5 | DCM 4 | DCM 3 | DCM 2 | DCM 1 | MCD 1 | MCD 2 | MCD 3 | MCD 4 | MCD 5 | MCD 6 | MCD 7 |
|---|---|---|---|---|---|---|---|---|---|---|---|---|---|---|---|---|---|---|
| 23 | First visit | | Lower jaw | Lip side | PD | 544 | 433 | 323 | 323 | 323 | 423 | 423 | 334 | 333 | 333 | 433 | 333 | 433 | 434 |
| 23 | First visit | | Lower jaw | Lip side | BOP | 000 | 000 | 000 | 000 | 000 | 000 | 000 | 001 | 000 | 000 | 000 | 000 | 001 | 001 |
| 23 | First visit | | Lower jaw | Lower jaw mobility | | 0 | 0 | 0 | 0 | 0 | 0 | 0 | 0 | 0 | 0 | 0 | 0 | 0 | 0 |
| 23 | R | 6 | Upper jaw | Upper jaw mobility | | 0 | 0 | 0 | 0 | 0 | 0 | 0 | 0 | 0 | 0 | 0 | 0 | 0 | 0 |
| 23 | R | | Upper jaw | Buccal side | BOP | 000 | 000 | 000 | 000 | 000 | 000 | 000 | 000 | 000 | 000 | 000 | 000 | 000 | 000 |
| 23 | R | | Upper jaw | Buccal side | PD | 433 | 332 | 323 | 323 | 322 | 222 | 223 | 222 | 222 | 222 | 323 | 323 | 323 | 334 |
| 23 | R | | Upper jaw | Palatial side | PD | 323 | 323 | 323 | 323 | 323 | 222 | 223 | 222 | 222 | 222 | 223 | 323 | 323 | 324 |
| 23 | R | | Upper jaw | Palatial side | BOP | 000 | 001 | 001 | 000 | 000 | 000 | 000 | 000 | 000 | 000 | 000 | 000 | 000 | 001 |
| 23 | R | | Lower jaw | Lingual side | BOP | 000 | 000 | 000 | 000 | 000 | 000 | 000 | 000 | 000 | 000 | 000 | 101 | 000 | 100 |
| 23 | R | | Lower jaw | Lingual side | PD | 433 | 323 | 323 | 323 | 322 | 222 | 222 | 222 | 222 | 222 | 323 | 323 | 333 | 323 |
| 23 | R | | Lower jaw | Lip side | PD | 333 | 323 | 323 | 323 | 323 | 222 | 222 | 222 | 222 | 323 | 323 | 323 | 323 | 323 |
| 23 | R | | Lower jaw | Lip side | BOP | 000 | 000 | 000 | 000 | 000 | 000 | 000 | 000 | 000 | 100 | 000 | 000 | 100 | 000 |
| 23 | R | | Lower jaw | Lower jaw mobility | | 0 | 0 | 0 | 0 | 0 | 0 | 0 | 0 | 0 | 0 | 0 | 0 | 0 | 0 |
| 24 | R | 7 | Upper jaw | Upper jaw mobility | | 0 | 0 | 0 | 0 | 0 | 0 | 0 | 0 | 1 | 0 | 0 | 0 | 0 | 0 |
| 24 | R | | Upper jaw | Buccal side | BOP | 001 | 000 | 000 | 000 | 000 | 000 | 000 | 000 | 000 | 000 | 000 | 000 | 000 | 000 |
| 24 | R | | Upper jaw | Buccal side | PD | 334 | 433 | 333 | 433 | 423 | 423 | 323 | 323 | 334 | 423 | 335 | 323 | 336 | 433 |
| 24 | R | | Upper jaw | Palatial side | PD | 336 | 333 | 334 | 324 | 334 | 333 | 333 | 323 | 323 | 323 | 323 | 323 | 323 | 433 |
| 24 | R | | Upper jaw | Palatial side | BOP | 001 | 010 | 001 | 001 | 001 | 000 | 001 | 000 | 000 | 000 | 100 | 000 | 000 | 001 |
| 24 | R | | Lower jaw | Lingual side | BOP | 000 | 000 | 000 | 000 | 000 | 000 | 000 | 000 | 000 | 000 | 000 | 000 | 000 | 000 |
| 24 | R | | Lower jaw | Lingual side | PD | 333 | 433 | 335 | 323 | 333 | 222 | 222 | 224 | 323 | 323 | 324 | 324 | 333 | 537 |
| 24 | R | | Lower jaw | Lip side | PD | 333 | 633 | 335 | 323 | 323 | 323 | 222 | 222 | 323 | 323 | 323 | 333 | 523 | 336 |
| 24 | R | | Lower jaw | Lip side | BOP | 000 | 000 | 000 | 001 | 000 | 000 | 000 | 000 | 000 | 000 | 000 | 000 | 000 | 001 |
| 24 | First visit | | Lower jaw | Lower jaw mobility | | 0 | 0 | 0 | 0 | 0 | 0 | 0 | 0 | 0 | 0 | 0 | 0 | 0 | 3 |
| 25 | First visit | 8 | Upper jaw | Upper jaw mobility | | 0 | 0 | 0 | 0 | 0 | 0 | 0 | 0 | 0 | 0 | 0 | 0 | 0 | 0 |
| 25 | First visit | | Upper jaw | Buccal side | BOP | 000 | 000 | 000 | 000 | 000 | 000 | 000 | 000 | 000 | 000 | 000 | 000 | 000 | 000 |
| 25 | First visit | | Upper jaw | Buccal side | PD | 644 | 454 | 544 | 656 | 445 | 445 | 555 | 677 | 735 | 325 | 634 | 334 | 433 | 333 |
| 25 | First visit | | Upper jaw | Palatial side | PD | 547 | 447 | 434 | 645 | 445 | 454 | 647 | 777 | 776 | 876 | 456 | 446 | 744 | 444 |
| 25 | First visit | | Upper jaw | Palatial side | BOP | 000 | 000 | 000 | 000 | 000 | 000 | 000 | 000 | 000 | 000 | 000 | 000 | 000 | 000 |
| 25 | R | | Lower jaw | Lingual side | BOP | 000 | 000 | 000 | 000 | 000 | 000 | 000 | 000 | 000 | 000 | 000 | 000 | 000 | 000 |
| 25 | R | | Lower jaw | Lingual side | PD | 323 | 333 | 544 | 544 | 434 | 334 | 444 | 544 | 444 | 434 | 445 | 445 | 894 | 548 |
| 25 | R | | Lower jaw | Lip side | PD | 325 | 426 | 434 | 523 | 445 | 434 | 434 | 444 | 444 | 433 | 444 | 445 | 1078 | 545 |
| 25 | R | | Lower jaw | Lip side | BOP | 001 | 000 | 000 | 000 | 000 | 000 | 000 | 000 | 000 | 000 | 000 | 000 | 101 | 100 |
| 25 | First visit | | Lower jaw | Lower jaw mobility | | 0 | 0 | 0 | 0 | 0 | 0 | 1 | 0 | 0 | 0 | 0 | 0 | 3 | 0 |
| 27 | First visit | 9 | Upper jaw | Upper jaw mobility | | 0 | 0 | 0 | 0 | 0 | 0 | 0 | 0 | 0 | 0 | 1 | 0 | 0 | 0 |
| 27 | First visit | | Upper jaw | Buccal side | BOP | 000 | 000 | 101 | 000 | 000 | 001 | 001 | 100 | 000 | 000 | 100 | 000 | 000 | 000 |
| 27 | First visit | | Upper jaw | Buccal side | PD | 323 | 333 | 101 | 101 | 000 | 000 | 235 | 534 | 523 | 313 | 613 | 312 | 312 | 223 |
| 27 | First visit | | Upper jaw | Palatial side | PD | 325 | 426 | 323 | 523 | 213 | 313 | 325 | 523 | 522 | 333 | 424 | 424 | 323 | 433 |
| 27 | First visit | | Upper jaw | Palatial side | BOP | 001 | 101 | 313 | 000 | 333 | 323 | 001 | 100 | 000 | 000 | 000 | 000 | 000 | 000 |
| 27 | First visit | | Lower jaw | Lingual side | BOP | | 010 | 324 | 323 | 322 | 212 | 213 | 312 | 212 | 212 | 213 | 223 | 323 | 333 |
| 27 | First visit | | Lower jaw | Lingual side | PD | | 010 | 313 | 223 | 324 | 312 | 213 | 312 | 213 | 212 | 213 | 223 | 336 | 336 |
| 27 | First visit | | Lower jaw | Lip side | PD | | 010 | 313 | 223 | 324 | 312 | 213 | 312 | 213 | 212 | 213 | 223 | 336 | 336 |
| 27 | First visit | | Lower jaw | Lip side | BOP | | 000 | 000 | 000 | 000 | 000 | 000 | 100 | 000 | 000 | 000 | 000 | 101 | 001 |
| 27 | First visit | 10 | Lower jaw | Lower jaw mobility | | 1 | 0 | 0 | 0 | 0 | 1 | 2 | 0 | 2 | 0 | 2 | 2 | 1 | 0 |
| 27 | First visit | | Upper jaw | Buccal side | BOP | 100 | 544 | 101 | 000 | 001 | 001 | 010 | 001 | 000 | 001 | 101 | 101 | 101 | 001 |
| 27 | First visit | | Upper jaw | Buccal side | PD | 444 | 544 | 436 | 445 | 439 | 648 | 764 | 749 | 937 | 434 | 8311 | 469 | 748 | 796 |
| 27 | First visit | | Upper jaw | Palatial side | PD | 445 | 644 | 674 | 434 | 556 | 644 | 676 | 647 | 767 | 867 | 10710 | 5510 | 647 | 10811 |
| 27 | First visit | | Upper jaw | Palatial side | BOP | 101 | 101 | 101 | 100 | 001 | 001 | 100 | 001 | 000 | 000 | 101 | 101 | 101 | 101 |
| 27 | First visit | | Lower jaw | Lingual side | BOP | 110 | 001 | 101 | 101 | 100 | 000 | 100 | 000 | 100 | 000 | 000 | 000 | 100 | 000 |

TABLE 1-continued

| Subject No. | First visit/R | Sample No. | | | | DCM 7 | DCM 6 | DCM 5 | DCM 4 | DCM 3 | DCM 2 | DCM 1 | MCD 1 | MCD 2 | MCD 3 | MCD 4 | MCD 5 | MCD 6 | MCD 7 |
|---|---|---|---|---|---|---|---|---|---|---|---|---|---|---|---|---|---|---|---|
| 27 | First visit | | Lower jaw | Lingual side | PD | 764 | | 444 | 546 | 846 | 444 | 643 | 339 | 347 | 644 | 445 | | | 448 |
| 27 | First visit | | Lower jaw | Lip side | PD | 444 | | 434 | 434 | 1037 | 446 | 597 | 459 | 644 | 978 | 644 | | | 4410 |
| 27 | First visit | | Lower jaw | Lip side | BOP | 000 | | 000 | 000 | 000 | 000 | 110 | 001 | 000 | 000 | 000 | | | 000 |
| 27 | First visit | | Lower jaw | Lower jaw mobility | | 0 | | 0 | 0 | 0 | 1 | 2 | 1 | 0 | 0 | 0 | 0 | 0 | 0 |
| 28 | First visit | 11 | Upper jaw | Upper jaw mobility | | 0 | | 0 | 0 | 2 | 0 | 2 | 1 | 0 | 0 | 0 | 0 | 0 | 0 |
| 28 | R | | Upper jaw | Buccal side | BOP | 000 | 000 | 000 | 000 | 000 | 000 | 000 | 000 | 000 | 000 | 000 | 000 | 000 | 000 |
| 28 | R | | Upper jaw | Buccal side | PD | 213 | 222 | 212 | 213 | 312 | 213 | 212 | 212 | 212 | 212 | 313 | 333 | 213 | 312 |
| 28 | R | | Upper jaw | Palatial side | PD | 213 | 213 | 312 | 214 | 312 | 222 | 212 | 212 | 212 | 213 | 324 | 322 | 312 | 333 |
| 28 | R | | Upper jaw | Palatial side | BOP | 000 | 000 | 000 | 000 | 000 | 000 | 000 | 000 | 000 | 000 | 001 | 000 | 000 | 000 |
| 28 | R | | Lower jaw | Lingual side | BOP | 000 | 000 | 000 | 000 | 000 | 100 | 100 | 100 | 111 | 100 | 100 | 000 | 000 | 100 |
| 28 | R | | Lower jaw | Lingual side | PD | 323 | 325 | 412 | 213 | 312 | 213 | 212 | 213 | 325 | 212 | 224 | 212 | 323 | 426 |
| 28 | R | | Lower jaw | Lip side | PD | 324 | 323 | 323 | 313 | 313 | 313 | 322 | 213 | 314 | 313 | 312 | 313 | 325 | 526 |
| 28 | R | | Lower jaw | Lip side | BOP | 011 | 101 | 100 | 001 | 000 | 000 | 000 | 000 | 001 | 000 | 000 | 001 | 001 | 101 |
| 28 | First visit | | Lower jaw | Lower jaw mobility | | 1 | 2 | 1 | 1 | 0 | 1 | 2 | 1 | 2 | 0 | 0 | 0 | 0 | 0 |
| 29 | First visit | 12 | Upper jaw | Upper jaw mobility | | 1 | 0 | 1 | 1 | 0 | 0 | 0 | 1 | 0 | 0 | 0 | 1 | 0 | 0 |
| 29 | R | | Upper jaw | Buccal side | BOP | 100 | 000 | 100 | 100 | 000 | 000 | 001 | 100 | 001 | 001 | 000 | 101 | 001 | 001 |
| 29 | R | | Upper jaw | Buccal side | PD | 934 | 435 | 724 | 1133 | 334 | 346 | 727 | 433 | 436 | 534 | 334 | 526 | 734 | 424 |
| 29 | R | | Upper jaw | Palatial side | PD | 775 | 538 | 765 | 1198 | 434 | 637 | 544 | 433 | 337 | 645 | 445 | 654 | 434 | 335 |
| 29 | R | | Upper jaw | Palatial side | BOP | 000 | 001 | 000 | 100 | 000 | 100 | 100 | 000 | 100 | 100 | 101 | 101 | 101 | 101 |
| 29 | R | | Lower jaw | Lingual side | BOP | 000 | | 000 | 000 | 000 | 011 | 000 | 000 | 000 | 000 | 101 | 100 | 000 | 000 |
| 29 | R | | Lower jaw | Lingual side | PD | 323 | | 433 | 334 | 343 | 769 | 423 | 334 | 443 | 336 | 455 | 334 | 447 | 344 |
| 29 | R | | Lower jaw | Lip side | PD | 324 | | 434 | 333 | 334 | 634 | 433 | 334 | 433 | 336 | 633 | 654 | 658 | 334 |
| 29 | R | | Lower jaw | Lip side | BOP | 011 | | 000 | 001 | 000 | 000 | 000 | 000 | 000 | 000 | 000 | 110 | 111 | 000 |
| 29 | First visit | | Lower jaw | Lower jaw mobility | | 1 | | 0 | 1 | 0 | 1 | 0 | 1 | 2 | 0 | 1 | 0 | 0 | 0 |
| 30 | First visit | 13 | Upper jaw | Upper jaw mobility | | 1 | 1 | 1 | 0 | 0 | 1 | 0 | 0 | 0 | 0 | 0 | 1 | 1 | 1 |
| 30 | R | | Upper jaw | Buccal side | BOP | 111 | 101 | 101 | 000 | 000 | 100 | 001 | 100 | 000 | 000 | 101 | 011 | 101 | 111 |
| 30 | R | | Upper jaw | Buccal side | PD | 664 | 539 | 624 | 423 | 323 | 623 | 512 | 223 | 324 | 223 | 423 | 365 | 835 | 766 |
| 30 | R | | Upper jaw | Palatial side | PD | 435 | 627 | 526 | 423 | 324 | 433 | 323 | 423 | 323 | 633 | 423 | 4711 | 833 | 663 |
| 30 | R | | Upper jaw | Palatial side | BOP | 101 | 101 | 101 | 100 | 101 | 101 | 100 | 100 | 100 | 100 | 100 | 111 | 100 | 110 |
| 30 | R | | Lower jaw | Lingual side | BOP | | | 000 | 000 | 000 | 000 | 000 | 000 | 000 | 000 | 000 | 101 | 111 | 111 |
| 30 | R | | Lower jaw | Lingual side | PD | | | 323 | 334 | 324 | 323 | 312 | 213 | 312 | 324 | 324 | 101 | 447 | 646 |
| 30 | R | | Lower jaw | Lip side | PD | | | 323 | 322 | 222 | 222 | 323 | 223 | 213 | 223 | 333 | 534 | 658 | 636 |
| 30 | R | | Lower jaw | Lip side | BOP | | | 000 | 000 | 000 | 000 | 000 | 000 | 000 | 000 | 000 | 110 | 111 | 101 |
| 30 | First visit | | Lower jaw | Lower jaw mobility | | | | 0 | 1 | 0 | 0 | 0 | 1 | 0 | 0 | 0 | 3 | 0 | 0 |
| 31 | First visit | 14 | Upper jaw | Upper jaw mobility | | 0 | 1 | 1 | 0 | 1 | 0 | 0 | 0 | 0 | 0 | 0 | 1 | 1 | 1 |
| 31 | First visit | | Upper jaw | Buccal side | BOP | 100 | 100 | 100 | 101 | 100 | 000 | 000 | 001 | 000 | 100 | 001 | 100 | 100 | 010 |
| 31 | First visit | | Upper jaw | Buccal side | PD | 333 | 624 | 323 | 323 | 323 | 323 | 323 | 223 | 322 | 223 | 323 | 2810 | 936 | 666 |
| 31 | First visit | | Upper jaw | Palatial side | PD | 433 | 626 | 322 | 433 | 324 | 634 | 333 | 333 | 425 | 423 | 334 | 1069 | 849 | 663 |
| 31 | First visit | | Upper jaw | Palatial side | BOP | 110 | 111 | 000 | 100 | 101 | 101 | 010 | 000 | 000 | 001 | 011 | 111 | 101 | 110 |
| 31 | R | | Lower jaw | Lingual side | BOP | | | 000 | 000 | 000 | 101 | 000 | 000 | 000 | 000 | 001 | 101 | 111 | 111 |
| 31 | R | | Lower jaw | Lingual side | PD | | | 323 | 322 | 424 | 424 | 312 | 324 | 324 | 324 | 324 | 534 | 447 | 646 |
| 31 | R | | Lower jaw | Lip side | PD | | | 322 | 222 | 222 | 222 | 322 | 322 | 222 | 222 | 333 | 553 | 658 | 443 |
| 31 | R | | Lower jaw | Lip side | BOP | | | 000 | 000 | 000 | 000 | 000 | 000 | 000 | 000 | 000 | 101 | 111 | 101 |
| 31 | First visit | | Lower jaw | Lowerjaw mobility | | | | 0 | 1 | 0 | 1 | 0 | 1 | 0 | 0 | 1 | 0 | 1 | 0 |
| 31 | First visit | 15 | Upper jaw | Upper jaw mobility | | 0 | 1 | 1 | 0 | 0 | 0 | 0 | 0 | 0 | | 0 | 0 | 0 | 0 |
| 31 | First visit | | Upper jaw | Buccal side | BOP | 100 | 100 | 100 | 101 | 100 | 000 | 000 | 001 | 000 | | 001 | 000 | 010 | 010 |
| 31 | First visit | | Upper jaw | Buccal side | PD | 333 | 333 | 323 | 323 | 323 | 323 | 333 | 333 | 322 | | 323 | 323 | 334 | 333 |
| 31 | First visit | | Upper jaw | Palatial side | PD | 433 | | 323 | 433 | 434 | 324 | 333 | 333 | 222 | | 333 | 334 | 434 | 434 |
| 31 | First visit | | Upper jaw | Palatial side | BOP | 010 | | 000 | 000 | 000 | 000 | 010 | 000 | 001 | | 011 | 110 | 100 | 001 |

TABLE 1-continued

| Subject No. | First visit/R | Sample No. | | | | DCM 7 | DCM 6 | DCM 5 | DCM 4 | DCM 3 | DCM 2 | DCM 1 | MCD 1 | MCD 2 | MCD 3 | MCD 4 | MCD 5 | MCD 6 | MCD 7 |
|---|---|---|---|---|---|---|---|---|---|---|---|---|---|---|---|---|---|---|---|
| 31 | First visit | | Lower jaw | Lingual side | BOP | 0 0 0 | | 0 0 0 | 0 1 1 | 1 0 1 | 0 0 0 | 0 0 1 | 1 0 0 | 0 0 0 | 1 0 0 | 0 0 0 | 0 0 0 | | 0 0 0 |
| 31 | First visit | | Lower jaw | Lingual side | PD | 5 4 4 | 1 1 0 | 4 4 4 | 5 4 4 | 5 3 4 | 4 4 4 | 4 4 4 | 4 3 4 | 4 3 4 | 4 3 4 | 4 4 4 | 5 4 4 | 4 4 4 |
| 31 | First visit | | Lower jaw | Lip side | PD | 4 4 3 | 7 4 6 | 3 3 3 | 3 3 3 | 3 4 4 | 4 4 4 | 6 4 5 | 4 3 4 | 4 3 4 | 3 3 3 | 4 3 4 | 4 3 3 | 4 3 4 |
| 31 | First visit | | Lower jaw | Lip side | BOP | 0 0 0 | | 0 0 0 | 0 0 1 | 0 0 1 | 0 1 | 1 0 1 | 1 0 0 | 0 0 0 | 0 0 0 | 0 0 0 | 0 0 0 | 1 0 0 |
| 31 | First visit | | Lower jaw | Lower jaw mobility | | 0 | 0 | 0 | 0 | 0 | 0 | 0 | 0 | 0 | 0 | 0 | 0 | 0 |
| 32 | First visit | 16 | Upper jaw | Upper jaw mobility | | | | | | | | | | | | | | |
| 32 | First visit | | Upper jaw | Buccal side | BOP | 1 0 1 | 1 1 1 | 0 0 1 | 0 0 0 | 0 0 1 | 1 1 1 | 1 1 1 | 1 0 0 | 0 0 0 | 0 0 1 | 1 1 1 | 0 0 0 | 0 0 1 |
| 32 | First visit | | Upper jaw | Buccal side | PD | 10 9 5 | 7 4 6 | 7 4 4 | 6 3 4 | 4 3 4 | 7 5 6 | 5 6 7 | 7 10 4 | 10 6 9 | 4 3 10 | 8 3 4 | 4 3 3 | 5 4 4 | 5 4 10 |
| 32 | First visit | | Upper jaw | Palatial side | PD | 6 4 6 | 5 4 6 | 5 3 4 | 5 3 4 | 4 3 4 | 9 5 6 | 6 7 7 | 6 4 4 | 6 9 9 | 4 3 7 | 7 7 7 | 4 4 6 | 9 4 8 | 7 11 11 |
| 32 | First visit | | Upper jaw | Palatial side | BOP | 1 1 1 | 1 1 1 | 1 1 1 | 1 0 0 | 1 0 1 | 1 1 1 | 1 1 1 | 1 1 1 | 1 0 1 | 0 0 1 | 1 1 1 | 1 0 1 | 1 1 1 | 1 1 1 |
| 32 | First visit | | Lower jaw | Lingual side | BOP | 0 1 1 | 1 1 1 | 1 1 1 | 0 1 1 | 0 1 1 | 1 1 1 | 1 1 1 | 9 9 6 | 1 0 1 | 1 0 0 | 1 0 0 | 0 0 1 | 1 1 0 | 1 0 1 |
| 32 | First visit | | Lower jaw | Lingual side | PD | 10 4 4 | 11 9 8 | 10 9 4 | 6 7 6 | 6 6 7 | 7 4 5 | 10 10 10 | 9 9 6 | 4 4 9 | 9 8 7 | 4 3 4 | 7 6 5 | 5 4 7 | 7 4 6 |
| 32 | First visit | | Lower jaw | Lip side | PD | 11 11 5 | 9 4 5 | 4 2 4 | 6 4 6 | 6 3 6 | 10 10 11 | 10 10 11 | 9 4 11 | 7 4 7 | 9 4 10 | 6 3 3 | 4 4 5 | 4 5 7 | 6 4 7 |
| 32 | First visit | | Lower jaw | Lip side | BOP | 1 0 1 | 0 0 1 | 1 0 0 | 0 0 0 | 1 0 1 | 1 1 1 | 1 1 1 | 1 1 1 | 1 1 1 | 1 0 1 | 1 0 0 | 0 0 1 | 1 0 1 | 1 0 0 |
| 32 | First visit | | Lower jaw | Lower jaw mobility | | 0 | | 0 | 0 | 1 | 2 | 1 | 2 | 1 | 1 | 0 | 0 | 0 | 1 |
| 33 | First visit | 17 | Upper jaw | Upper jaw mobility | | 0 | 1 | 1 | 2 | 1 | 2 | 3 | 2 | 1 | 1 | 0 | 0 | 1 | 1 |
| 33 | First visit | | Upper jaw | Buccal side | BOP | 0 0 0 | 0 0 0 | 1 1 1 | 0 0 1 | 0 0 0 | 0 0 0 | 0 0 0 | 1 0 0 | 0 0 0 | 0 0 0 | 0 0 0 | 0 0 0 | 0 0 0 | 0 0 0 |
| 33 | First visit | | Upper jaw | Buccal side | PD | 4 4 5 | 4 7 8 | 6 6 6 | 7 4 7 | 7 3 4 | 4 4 4 | 9 4 9 | 6 7 9 | 4 3 4 | 6 6 7 | 7 3 4 | 5 3 4 | 8 4 4 | 4 8 4 |
| 33 | First visit | | Upper jaw | Palatial side | PD | 4 4 3 | 5 4 8 | 5 3 4 | 7 5 6 | 7 7 5 | 5 4 6 | 11 11 11 | 11 11 11 | 4 4 4 | 6 6 7 | 7 7 7 | 4 4 4 | 9 9 4 | 4 4 4 |
| 33 | First visit | | Upper jaw | Palatial side | BOP | 0 0 0 | 0 0 1 | 0 0 1 | 1 0 1 | 1 0 1 | 1 0 1 | 1 1 1 | 1 1 1 | 0 0 1 | 1 0 1 | 1 0 1 | 0 0 0 | 1 1 0 | 0 0 0 |
| 33 | First visit | | Lower jaw | Lingual side | BOP | | | 0 0 0 | 0 0 0 | 0 0 0 | 0 0 0 | 0 0 0 | | 0 0 0 | 0 0 0 | 0 0 0 | 0 0 0 | 0 0 0 | 0 0 0 |
| 33 | First visit | | Lower jaw | Lingual side | PD | 5 4 8 | 5 4 8 | 7 6 7 | 5 6 7 | 7 6 7 | 8 6 7 | 7 6 8 | 5 5 7 | 6 6 7 | 8 5 5 | 6 7 7 | 4 4 9 | 10 4 4 | 5 4 4 |
| 33 | First visit | | Lower jaw | Lip side | PD | 7 4 6 | 7 4 6 | 5 6 5 | 5 4 6 | 5 3 7 | 9 3 4 | 8 3 4 | 4 3 6 | 7 3 7 | 7 3 6 | 9 4 5 | 6 6 7 | 10 3 4 | 7 4 6 |
| 33 | First visit | | Lower jaw | Lip side | BOP | 1 0 1 | 0 0 0 | 1 0 0 | 0 0 0 | 1 1 1 | 1 1 1 | 1 1 1 | 1 1 1 | 1 1 1 | 0 0 0 | 1 0 1 | 1 1 1 | 1 1 1 | 1 0 1 |
| 33 | First visit | | Lower jaw | Lower jaw mobility | | 0 | 1 | 1 | 1 | 1 | 1 | 2 | 2 | 1 | 1 | 1 | 2 | 1 | 1 |
| 33 | R | 18 | Upper jaw | Upper jaw mobility | | 0 | 0 | 1 | 1 | 2 | 2 | 2 | | 2 | 1 | 1 | 0 | 0 | 0 |
| 33 | R | | Upper jaw | Buccal side | BOP | 0 0 0 | 0 0 0 | 0 0 1 | 0 0 1 | 0 0 0 | 0 0 0 | 0 0 1 | 0 0 0 | 0 0 0 | 0 0 0 | 0 0 0 | 0 0 0 | 0 0 0 | 0 0 1 |
| 33 | R | | Upper jaw | Buccal side | PD | 3 3 3 | 3 3 3 | 4 3 3 | 3 3 4 | 3 3 3 | 4 3 4 | 4 3 3 | 3 3 3 | 3 3 3 | 3 3 3 | 4 3 3 | 3 2 4 | 8 4 4 | 4 9 4 |
| 33 | R | | Upper jaw | Palatial side | PD | 3 3 4 | 4 3 4 | 3 3 3 | 3 3 3 | 5 3 3 | 3 3 3 | 11 11 11 | 11 11 11 | 4 3 5 | 3 4 4 | 4 3 3 | 3 3 3 | 9 9 4 | 4 3 3 |
| 33 | R | | Upper jaw | Palatial side | BOP | 0 0 0 | 1 0 0 | 0 0 0 | 0 0 0 | 1 0 0 | 0 0 0 | 0 0 0 | | 0 0 1 | 0 0 1 | 1 0 0 | 0 0 0 | 1 1 0 | 4 3 3 |
| 33 | R | | Lower jaw | Lingual side | BOP | 0 0 0 | 0 0 0 | 0 0 0 | 0 0 0 | 0 0 0 | 0 0 0 | 0 0 1 | | 0 0 0 | 0 0 0 | 0 0 0 | 0 0 0 | 0 0 0 | 0 0 0 |
| 33 | R | | Lower jaw | Lingual side | PD | 4 3 6 | 4 3 5 | 4 3 4 | 3 3 4 | 3 3 3 | 3 2 4 | 4 3 3 | 3 3 3 | 3 3 3 | 4 3 3 | 4 2 4 | 4 3 5 | 5 3 3 | 4 3 4 |
| 33 | R | | Lower jaw | Lip side | PD | 3 3 4 | 3 3 3 | 3 3 3 | 3 2 3 | 3 2 4 | 3 3 4 | 2 3 3 | 3 3 3 | 4 3 3 | 3 3 4 | 4 2 4 | 4 3 3 | 6 3 3 | 4 3 4 |
| 33 | R | | Lower jaw | Lip side | BOP | 0 0 0 | 1 0 0 | 0 0 0 | 0 0 0 | 1 0 1 | 0 0 0 | 0 0 0 | | 0 0 1 | 0 0 0 | 1 0 0 | 0 0 0 | 0 0 0 | 0 0 0 |
| 33 | R | | Lower jaw | Lower jaw mobility | | 0 | 1 | 1 | 1 | 1 | 1 | 2 | 1 | 2 | 1 | 1 | 2 | 1 | 0 |
| 34 | First visit | 19 | Upper jaw | Upper jaw mobility | | 0 | 1 | 0 | 0 | 0 | 0 | 1 | 0 | 0 | 0 | 0 | 1 | 0 | 0 |
| 34 | First visit | | Upper jaw | Buccal side | BOP | 1 0 1 | 1 1 1 | 1 0 0 | 0 0 0 | 0 0 0 | 0 0 1 | 1 0 1 | 1 0 0 | 1 0 0 | 0 0 0 | 0 0 1 | 0 0 0 | 1 0 0 | 0 0 0 |
| 34 | First visit | | Upper jaw | Buccal side | PD | 4 3 6 | 6 3 6 | 4 2 4 | 3 3 6 | 3 3 3 | 4 3 4 | 5 4 6 | 6 3 4 | 6 3 3 | 3 2 3 | 4 2 5 | 4 2 5 | 3 3 6 | 6 3 6 |
| 34 | First visit | | Upper jaw | Palatial side | PD | 6 3 4 | 6 3 8 | 6 5 3 | 3 3 6 | 4 3 3 | 4 3 4 | 7 3 6 | 7 6 6 | 6 5 3 | 7 6 4 | 4 3 6 | 3 4 7 | 7 3 7 | 5 3 6 |
| 34 | First visit | | Upper jaw | Palatial side | BOP | 1 0 1 | 1 0 1 | 1 0 1 | 1 0 1 | 1 0 0 | 0 0 1 | 1 1 0 | 1 0 0 | 1 0 0 | 1 0 0 | 0 1 1 | 0 0 1 | 0 0 1 | 1 0 0 |
| 34 | First visit | | Lower jaw | Lingual side | BOP | 1 0 1 | 1 0 1 | 1 1 1 | 1 0 1 | 1 0 1 | 1 0 0 | 1 1 0 | 1 1 1 | 1 1 1 | 1 0 0 | 0 1 1 | 1 0 0 | 0 1 1 | 1 1 1 |
| 34 | First visit | | Lower jaw | Lingual side | PD | 6 3 7 | 6 3 6 | 4 3 4 | 8 3 3 | 6 3 3 | 4 3 4 | 6 6 3 | 6 3 6 | 4 3 3 | 4 3 6 | 4 2 4 | 5 3 5 | 8 3 8 | 5 4 6 |
| 34 | First visit | | Lower jaw | Lip side | PD | 5 3 8 | 9 3 5 | 6 3 6 | 6 3 6 | 6 3 3 | 5 5 8 | 4 3 4 | 10 3 3 | 5 3 7 | 4 3 6 | 7 3 5 | 6 3 5 | 10 3 8 | 6 5 6 |
| 34 | First visit | | Lower jaw | Lip side | BOP | 1 0 1 | 1 0 1 | 1 0 1 | 1 0 1 | 1 0 1 | 0 0 0 | 0 0 1 | 1 1 1 | 0 0 1 | 0 0 1 | 1 0 1 | 1 0 1 | 1 0 1 | 1 0 1 |
| 34 | First visit | | Lower jaw | Lower jaw mobility | | 0 | 1 | 0 | 0 | 0 | 0 | 1 | 1 | 1 | 1 | 1 | 1 | 1 | 0 |
| 35 | First visit | 20 | Upper jaw | Upper jaw mobility | | 2 | 1 | 0 | 0 | 0 | 0 | 2 | 0 | 0 | 0 | 0 | 0 | 0 | 0 |
| 35 | First visit | | Upper jaw | Buccal side | PD | 11 9 10 | 9 3 3 | 2 2 4 | 3 3 4 | 3 2 4 | 5 5 5 | 7 3 3 | 3 3 3 | 3 3 3 | 3 2 5 | 4 3 4 | 3 3 4 | 4 9 6 | 7 7 7 |
| 35 | First visit | | Upper jaw | Palatial side | PD | 11 5 4 | 7 3 4 | 4 3 4 | 4 3 3 | 3 3 4 | 7 4 6 | 7 6 4 | 4 3 3 | 3 3 3 | 3 3 7 | 5 3 4 | 4 3 4 | 4 3 5 | 4 7 11 |

TABLE 1-continued

| Subject No. | First visit/R | Sample No. | | | DCM 7 | DCM 6 | DCM 5 | DCM 4 | DCM 3 | DCM 2 | DCM 1 | MCD 1 | MCD 2 | MCD 3 | MCD 4 | MCD 5 | MCD 6 | MCD 7 |
|---|---|---|---|---|---|---|---|---|---|---|---|---|---|---|---|---|---|---|
| 35 | First visit | | Upper jaw | Palatial side | BOP | 0 0 1 | 0 0 0 | 0 0 0 | 0 0 0 | 0 0 0 | 1 0 1 | 1 1 0 | 0 0 0 | 0 0 0 | 0 0 1 | 1 0 0 | 0 0 0 | 0 0 1 | 1 1 1 |
| 35 | First visit | | Lower jaw | Lingual side | BOP | 1 0 1 | 0 0 0 | 0 0 0 | 0 0 0 | 0 0 0 | 0 0 0 | 0 0 0 | 0 0 0 | 0 0 0 | 0 0 1 | 0 0 0 | 0 0 0 | 0 0 0 | 0 1 1 |
| 35 | First visit | | Lower jaw | Lingual side | PD | 10 4 4 | 5 4 7 | 4 3 4 | 4 3 4 | 3 2 2 | 2 2 3 | 3 2 3 | 3 3 3 | 3 3 4 | 5 4 6 | 4 3 4 | 3 3 4 | 5 4 5 | 4 8 11 |
| 35 | First visit | | Lower jaw | Lip side | PD | 11 6 5 | 4 4 4 | 4 3 4 | 4 3 4 | 3 3 3 | 4 3 4 | 3 3 3 | 3 3 3 | 3 2 3 | 6 3 5 | 4 3 4 | 4 3 4 | 7 4 4 | 4 6 10 |
| 35 | First visit | | Lower jaw | Lip side | BOP | 1 1 1 | 0 0 0 | 0 0 0 | 0 0 0 | 0 0 0 | 0 0 0 | 0 0 0 | 0 0 0 | 0 0 0 | 0 0 1 | 1 0 0 | 0 0 0 | 1 0 0 | 0 0 1 |
| 35 | R | 21 | Lower jaw | Lower jaw mobility | | 3 | | | | | | | | | | | | | 2 |
| 35 | R | | Upper jaw | Upper jaw mobility | | | | | | | | | | | | | | | 1 |
| 35 | R | | Upper jaw | Buccal side | BOP | 0 0 0 | 0 0 0 | 0 0 0 | 0 0 0 | 0 0 0 | 0 0 0 | 0 0 0 | 0 0 0 | 0 0 1 | 0 0 0 | 0 0 0 | 0 0 0 | 0 0 1 | 1 0 1 |
| 35 | R | | Upper jaw | Buccal side | PD | 3 3 3 | 4 2 2 | 3 2 3 | 3 2 2 | 3 3 4 | 3 3 4 | 4 2 3 | 2 2 2 | 2 2 2 | 2 2 2 | 3 2 2 | 2 2 3 | 2 6 3 | 3 3 5 |
| 35 | R | | Upper jaw | Palatial side | PD | 4 3 3 | 4 3 3 | 2 2 3 | 3 2 2 | 3 2 3 | 3 2 3 | 4 2 3 | 3 2 3 | 3 2 2 | 3 2 3 | 2 2 3 | 3 2 3 | 3 2 4 | 3 3 5 |
| 35 | R | | Upper jaw | Palatial side | BOP | 0 0 0 | 0 0 0 | 0 0 0 | 0 0 0 | 0 0 0 | 0 0 1 | 0 0 1 | 0 0 0 | 0 0 0 | 0 0 0 | 0 0 0 | 0 0 0 | 0 0 1 | 1 0 1 |
| 35 | R | | Lower jaw | Lingual side | BOP | 0 0 0 | 0 0 0 | 0 0 0 | 0 0 0 | 0 0 0 | 0 1 0 | 1 0 0 | 0 0 0 | 0 0 0 | 0 0 0 | 0 0 0 | 0 0 0 | 1 0 0 | |
| 35 | R | | Lower jaw | Lingual side | PD | 3 3 3 | 3 3 2 | 3 2 2 | 2 2 2 | 2 2 2 | 2 2 2 | 2 2 2 | 2 2 2 | 2 2 3 | 4 2 4 | 4 2 2 | 2 2 3 | 5 3 2 | |
| 35 | R | | Lower jaw | Lip side | PD | 3 3 3 | 3 2 2 | 3 2 3 | 3 2 2 | 2 2 3 | 3 2 3 | 2 2 2 | 2 2 2 | 2 2 3 | 3 2 4 | 3 2 2 | 3 2 3 | 5 2 2 | |
| 35 | R | | Lower jaw | Lip side | BOP | 0 0 0 | 0 0 0 | 0 0 0 | 0 0 0 | 0 0 0 | 0 0 0 | 1 0 0 | 0 0 0 | 0 0 0 | 0 0 0 | 0 0 0 | 0 0 0 | 0 0 0 | 1 0 1 |
| 35 | R | | Lower jaw | Lower jaw mobility | | 0 | | | | | | | 1 | | | | | 0 | | |
| 36 | First visit | 22 | Upper jaw | Upper jaw mobility | | 0 | | | | | | | | | | | | | 0 |
| 36 | First visit | | Upper jaw | Buccal side | BOP | 1 0 1 | 1 0 1 | 1 0 1 | 0 0 1 | 0 0 1 | 1 0 1 | 1 0 0 | 1 0 1 | 1 0 1 | 0 0 0 | 0 0 0 | 1 0 0 | 1 0 1 | 1 0 0 |
| 36 | First visit | | Upper jaw | Buccal side | PD | 4 5 7 | 7 4 7 | 5 2 4 | 3 3 8 | 4 3 5 | 7 2 7 | 6 3 2 | 2 2 8 | 6 3 5 | 3 2 4 | 4 3 3 | 2 2 4 | 7 3 4 | 6 4 3 |
| 36 | First visit | | Upper jaw | Palatial side | PD | 5 3 5 | 5 3 6 | 4 4 3 | 3 3 5 | 4 4 4 | 7 6 6 | 6 6 5 | 4 6 7 | 6 4 5 | 4 6 6 | 4 3 4 | 3 3 4 | 7 2 4 | 5 4 4 |
| 36 | First visit | | Upper jaw | Palatial side | BOP | 0 0 1 | 1 0 1 | 1 0 0 | 0 0 1 | 1 0 1 | 0 1 1 | 1 1 0 | 0 1 1 | 1 0 1 | 1 0 1 | 1 0 1 | 0 0 0 | 1 0 1 | 1 0 1 |
| 36 | First visit | | Lower jaw | Lingual side | BOP | 0 1 1 | 1 0 1 | 1 0 0 | 1 0 0 | 0 0 0 | 0 0 1 | 1 1 0 | 0 0 1 | 1 0 1 | 1 0 1 | 0 0 0 | 0 0 1 | 0 0 1 | 0 0 1 |
| 36 | First visit | | Lower jaw | Lingual side | PD | 4 4 6 | 6 5 7 | 5 5 5 | 5 3 5 | 3 2 3 | 3 2 3 | 3 2 2 | 2 2 6 | 3 3 4 | 3 3 7 | 5 3 4 | 4 6 7 | 4 4 9 | 4 4 5 |
| 36 | First visit | | Lower jaw | Lip side | PD | 7 4 6 | 4 9 6 | 4 2 3 | 4 3 6 | 4 3 4 | 6 2 4 | 6 2 2 | 3 3 7 | 4 3 6 | 3 3 4 | 5 3 4 | 3 3 6 | 5 3 7 | 5 4 4 |
| 36 | First visit | | Lower jaw | Lip side | BOP | 0 0 1 | 1 0 1 | 0 0 0 | 0 0 1 | 0 0 1 | 1 0 0 | 1 0 0 | 0 0 1 | 0 0 1 | 1 0 0 | 1 0 0 | 0 0 1 | 1 0 1 | 1 0 0 |
| 36 | First visit | | Lower jaw | Lower jaw mobility | | 0 | | | | | | | 1 | | | | | 0 | | 0 |
| 37 | First visit | 23 | Upper jaw | Upper jaw mobility | | 0 | | | | | | | 1 | | | | | 0 | | 0 |
| 37 | First visit | | Upper jaw | Buccal side | BOP | 0 0 0 | 0 0 1 | 1 0 1 | 1 0 0 | 0 0 1 | 1 0 0 | 0 0 0 | 0 0 1 | 0 0 1 | 0 0 0 | 0 0 0 | 0 0 1 | 0 0 0 | 0 0 1 |
| 37 | First visit | | Upper jaw | Buccal side | PD | 4 4 4 | 5 5 7 | 5 4 6 | 6 3 4 | 4 3 5 | 6 4 6 | 6 4 4 | 3 4 4 | 5 3 6 | 4 2 6 | 9 3 4 | 4 3 6 | 7 3 4 | 5 3 3 |
| 37 | First visit | | Upper jaw | Palatial side | PD | 4 4 5 | 4 6 7 | 4 4 5 | 5 4 5 | 4 4 4 | 4 3 6 | 6 4 4 | 4 4 5 | 5 4 5 | 4 4 4 | 7 4 4 | 4 7 6 | 7 2 4 | 5 4 4 |
| 37 | First visit | | Upper jaw | Palatial side | BOP | 1 0 1 | 1 0 1 | 1 0 0 | 1 0 0 | 0 0 0 | 0 0 0 | 1 0 0 | 0 0 0 | 1 0 0 | 0 0 1 | 1 0 1 | 0 1 1 | 1 0 1 | 1 0 1 |
| 37 | First visit | | Lower jaw | Lingual side | BOP | 1 0 1 | 1 0 1 | 0 0 0 | 0 0 0 | 1 0 1 | 0 0 0 | 1 0 0 | 0 0 0 | 1 0 0 | 0 0 1 | 1 0 0 | 0 1 1 | 1 0 1 | 1 0 1 |
| 37 | First visit | | Lower jaw | Lingual side | PD | 7 4 6 | 4 9 6 | 4 4 4 | 4 3 4 | 4 3 4 | 4 3 4 | 4 2 3 | 3 3 4 | 5 4 4 | 4 4 4 | 6 4 5 | 4 6 7 | 3 6 3 | 5 5 6 |
| 37 | First visit | | Lower jaw | Lip side | PD | 4 4 6 | 6 5 7 | 5 4 4 | 6 4 4 | 4 4 4 | 4 3 4 | 6 2 2 | 2 3 7 | 4 4 6 | 6 5 7 | 6 4 4 | 3 3 6 | 4 4 9 | 4 4 4 |
| 37 | First visit | | Lower jaw | Lip side | BOP | 0 0 1 | 1 0 1 | 0 0 1 | 1 0 1 | 1 0 0 | 1 0 0 | 1 0 0 | 0 0 1 | 0 0 1 | 1 0 1 | 1 0 0 | 0 0 1 | 1 0 1 | 1 0 1 |
| 37 | First visit | | Lower jaw | Lower jaw mobility | | 0 | | | | | | | | | | | | 1 0 | | |
| 37 | R | 24 | Upper jaw | Upper jaw mobility | | 0 | | | | | | | | | | | | 0 | | 0 |
| 37 | R | | Upper jaw | Buccal side | BOP | 0 0 0 | 0 0 1 | 0 0 0 | 0 0 0 | 0 0 0 | 0 0 0 | 0 0 0 | 0 0 1 | 0 0 1 | 0 0 0 | 0 0 0 | 1 0 0 | 0 0 0 | 0 0 0 |
| 37 | R | | Upper jaw | Buccal side | PD | 4 3 3 | 2 3 4 | 3 3 6 | 5 2 3 | 3 2 4 | 5 2 5 | 5 4 3 | 3 3 5 | 4 2 5 | 3 3 4 | 6 2 2 | 2 2 4 | 6 6 4 | 3 3 3 |
| 37 | R | | Upper jaw | Palatial side | PD | 3 3 4 | 3 2 5 | 3 3 4 | 3 3 4 | 4 3 4 | 4 3 3 | 3 3 3 | 3 3 4 | 5 3 4 | 3 2 3 | 3 2 2 | 3 6 5 | 3 2 3 | 3 3 3 |
| 37 | R | | Upper jaw | Palatial side | BOP | 0 0 0 | 0 0 0 | 0 0 0 | 0 0 0 | 0 0 0 | 0 1 0 | 0 0 0 | 0 0 1 | 0 0 1 | 0 0 0 | 0 0 0 | 0 0 1 | 0 0 1 | 0 0 0 |
| 37 | R | | Lower jaw | Lingual side | BOP | 1 0 0 | 1 0 0 | 0 0 0 | 0 0 0 | 0 0 0 | 0 0 0 | 1 0 0 | 0 0 0 | 0 0 0 | 0 0 0 | 0 0 0 | 0 0 0 | 0 0 0 | 0 0 0 |
| 37 | R | | Lower jaw | Lingual side | PD | 9 3 5 | 6 5 5 | 3 3 3 | 3 3 5 | 5 2 2 | 3 3 3 | 3 3 3 | 3 3 4 | 2 2 3 | 2 3 3 | 3 3 3 | 3 6 5 | 3 4 4 | 3 3 3 |
| 37 | R | | Lower jaw | Lip side | PD | 6 6 3 | 4 9 4 | 3 4 3 | 3 3 5 | 5 3 3 | 3 3 3 | 3 3 3 | 2 3 3 | 2 2 3 | 2 3 6 | 3 3 3 | 3 6 5 | 3 2 3 | 2 2 3 |
| 37 | R | | Lower jaw | Lip side | BOP | 0 1 0 | 0 1 0 | 0 1 0 | 0 1 0 | 0 0 0 | 0 0 0 | 0 0 0 | 0 1 1 | 0 0 1 | 0 1 1 | 0 0 1 | | 0 0 1 | 0 0 0 |
| 37 | R | | Lower jaw | Lower jaw mobility | | 0 | | | | | | | 0 | | | | | 0 | | 0 |
| 38 | First visit | 25 | Upper jaw | Upper jaw mobility | | 0 | | | | | | | 0 | | | | | 0 | | 1 |
| 38 | First visit | | Upper jaw | Buccal side | BOP | 0 0 1 | 1 1 0 | 0 0 0 | 0 0 0 | 0 0 0 | 0 0 0 | 0 0 0 | 0 0 0 | 0 0 0 | 0 0 0 | 0 0 0 | 0 0 0 | 0 0 1 | 1 0 1 |
| 38 | First visit | | Upper jaw | Buccal side | PD | 4 4 6 | 9 6 3 | 3 2 3 | 3 2 3 | 3 2 3 | 3 2 3 | 3 2 2 | 2 3 3 | 3 2 3 | 3 3 3 | 3 3 4 | 4 3 5 | 4 3 5 | 4 9 9 |

TABLE 1-continued

| Subject No. | First visit/R | Sample No. | | | | DCM 7 | DCM 6 | DCM 5 | DCM 4 | DCM 3 | DCM 2 | DCM 1 | MCD 1 | MCD 2 | MCD 3 | MCD 4 | MCD 5 | MCD 6 | MCD 7 |
|---|---|---|---|---|---|---|---|---|---|---|---|---|---|---|---|---|---|---|---|
| 38 | First visit | | Upper jaw | Palatial side | PD | 3 4 4 | 7 3 7 | 4 3 3 | 3 3 3 | 3 3 3 | 3 2 3 | 3 2 3 | 3 2 2 | 3 2 3 | 3 2 3 | 3 2 3 | 3 3 3 | 3 2 5 | 4 3 9 |
| 38 | First visit | | Upper jaw | Palatial side | BOP | 1 0 1 | 1 0 0 | 0 0 0 | 0 0 0 | 0 0 0 | 0 0 0 | 0 0 0 | 0 0 0 | 0 0 0 | 0 0 0 | 0 0 0 | 0 0 1 | 1 0 1 | 1 0 1 |
| 38 | First visit | | Lower jaw | Lingual side | BOP | 0 0 1 | 1 1 1 | 1 0 0 | 0 0 0 | 0 0 0 | 0 0 0 | 3 3 4 | 3 3 3 | 3 2 3 | 3 3 3 | 0 0 1 | | 1 0 0 | 0 0 1 |
| 38 | First visit | | Lower jaw | Lingual side | PD | 4 3 4 | 4 4 7 | 5 2 3 | 4 3 4 | 5 2 3 | 4 3 3 | 3 3 4 | 3 2 3 | 3 2 3 | 3 2 3 | 3 4 7 | 4 3 4 | 4 3 4 | 4 4 4 |
| 38 | First visit | | Lower jaw | Lip side | PD | 3 3 3 | 3 3 4 | 3 3 3 | 3 2 3 | 3 3 3 | 4 3 3 | 3 3 3 | 3 2 3 | 3 2 3 | 3 2 3 | 3 3 3 | 3 3 3 | 3 3 3 | 3 3 4 |
| 38 | First visit | | Lower jaw | Lip side | BOP | 0 0 0 | 0 0 1 | 0 0 0 | 0 0 0 | 0 0 1 | 0 0 0 | 1 0 0 | 0 0 0 | 0 0 0 | 0 0 0 | 0 0 0 | 0 0 0 | 1 0 0 | 0 0 0 |
| 38 | R | 26 | Lower jaw mobility | | | 0 | 0 | 0 | 0 | 0 | 0 | 1 | 0 | 0 | 0 | 0 | 1 | 0 | 0 |
| 38 | R | | Upper jaw mobility | | | 1 | 1 | 1 | 0 | 0 | 0 | 1 | 0 | 0 | 0 | 0 | 0 | 0 | 1 |
| 38 | R | | Upper jaw | Buccal side | PD | 0 0 0 | 0 0 0 | 0 0 0 | 0 0 0 | 0 0 0 | 0 0 0 | 0 0 0 | 2 2 3 | 2 2 2 | 2 2 2 | 3 2 2 | 0 0 0 | 0 0 0 | 0 0 0 |
| 38 | R | | Upper jaw | Palatial side | PD | 3 3 3 | 5 4 3 | 3 2 2 | 3 2 3 | 3 2 2 | 2 2 2 | 2 2 2 | 2 2 3 | 2 2 2 | 2 2 2 | 2 2 3 | 3 2 3 | 3 2 3 | 2 3 5 |
| 38 | R | | Upper jaw | Palatial side | BOP | 3 3 3 | 5 2 7 | 3 2 2 | 3 2 3 | 3 2 2 | 2 2 3 | 3 2 2 | 2 2 3 | 3 2 3 | 3 2 2 | 2 2 3 | 3 2 3 | 2 2 4 | 8 3 6 |
| 38 | R | | Lower jaw | Lingual side | PD | 0 0 0 | 0 0 0 | 0 0 0 | 0 0 0 | 0 0 0 | 0 0 0 | 0 0 0 | 0 0 0 | 0 0 0 | 0 0 0 | 0 0 0 | 0 0 0 | 0 0 0 | 1 0 1 |
| 38 | R | | Lower jaw | Lingual side | PD | 0 0 0 | 4 3 6 | 3 2 3 | 3 3 3 | 3 3 3 | 2 2 2 | 2 2 3 | 2 2 3 | 2 2 2 | 2 2 2 | 3 3 8 | | 1 0 0 | 0 0 0 |
| 38 | R | | Lower jaw | Lip side | PD | 3 3 3 | 3 3 4 | 3 2 3 | 3 2 3 | 3 2 3 | 3 2 3 | 3 2 2 | 2 2 3 | 2 2 2 | 2 2 2 | 3 3 3 | 3 3 3 | 3 3 3 | 4 3 4 |
| 38 | R | | Lower jaw | Lip side | BOP | 0 0 0 | 0 0 0 | 0 0 0 | 0 0 0 | 0 0 0 | 0 0 0 | 0 0 0 | 0 0 0 | 0 0 0 | 0 0 0 | 0 0 0 | 0 0 0 | 0 0 0 | 3 3 3 |
| 38 | R | | Lower jaw mobility | | | 0 | 0 | 0 | 1 | 0 | 0 | 0 | 0 | | | | | 0 | 0 |
| 38 | R | | Upper jaw mobility | | | 3 | 0 | 1 | 1 | 0 | 0 | 1 | 0 | 1 | 0 | 1 | 1 | 0 | 0 |
| 39 | First visit | 27 | Upper jaw | Buccal side | BOP | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 |
| 39 | First visit | | Upper jaw | Buccal side | PD | 6 5 5 | 7 4 6 | 6 4 4 | 6 4 5 | 5 4 8 | 7 3 5 | 7 4 8 | 7 4 7 | 7 4 8 | 7 3 5 | 6 3 5 | 6 3 5 | 5 4 5 | 6 4 4 |
| 39 | First visit | | Upper jaw | Palatial side | PD | 7 10 10 | 9 11 11 | 5 4 7 | 6 4 7 | 7 4 6 | 7 3 9 | 7 4 7 | 6 4 6 | 5 4 5 | 5 4 5 | 5 4 6 | 5 4 5 | 5 4 5 | 9 7 8 |
| 39 | First visit | | Upper jaw | Palatial side | BOP | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 |
| 39 | First visit | | Lower jaw | Lingual side | BOP | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 |
| 39 | First visit | | Lower jaw | Lingual side | PD | 5 6 8 | 8 5 8 | 9 7 7 | 7 3 4 | 6 4 6 | 1 1 4 7 | 5 3 5 | 5 4 5 | 6 3 9 | 4 3 4 | 4 4 6 | 5 5 6 | 5 5 6 | 6 6 7 |
| 39 | First visit | | Lower jaw | Lip side | PD | 6 5 7 | 7 4 7 | 8 4 6 | 7 3 4 | 7 3 10 | 1 1 1 | 7 4 5 | 5 4 5 | 6 3 9 | 5 3 5 | 5 3 5 | 4 6 5 | 4 6 5 | 6 5 7 |
| 39 | First visit | | Lower jaw | Lip side | BOP | 1 1 1 | 1 1 1 | 1 1 1 | 1 1 1 | 1 1 1 | 1 1 1 | 1 0 1 | 1 0 1 | 1 0 1 | 1 1 1 | 1 1 1 | 1 1 1 | 1 1 1 | 1 1 1 |
| 39 | First visit | | Lower jaw mobility | | | 0 | 0 | 1 | 0 | 0 | 1 | 1 | 1 | 1 | 1 | 0 | 0 | 1 | 1 |
| 39 | First visit | | Upper jaw mobility | | | 0 | 0 | 1 | 3 | 1 | 0 | 1 | 1 | 1 | 1 | 1 | 0 | 1 | 1 |
| 41 | First visit | 28 | Upper jaw | Buccal side | BOP | | | 0 0 1 | 1 0 1 | 0 1 1 | | 1 1 0 | 0 0 0 | 0 0 0 | 0 0 0 | 0 0 0 | 0 0 0 | 0 0 1 | 1 0 1 |
| 41 | First visit | | Upper jaw | Buccal side | PD | | | 4 3 9 | 10 4 9 | 3 4 6 | | 5 3 3 | 5 3 3 | 0 0 0 | 3 3 3 | 0 0 0 | 3 3 3 | 3 3 4 | 6 6 7 |
| 41 | First visit | | Upper jaw | Palatial side | PD | 3 4 3 | 4 2 3 | 5 6 8 | 9 8 9 | 4 6 6 | | 5 4 5 | 7 3 4 | 4 4 3 | 3 3 4 | 5 4 6 | 4 3 5 | 4 3 5 | 6 4 9 |
| 41 | First visit | | Upper jaw | Palatial side | BOP | | | 1 1 1 | 1 1 1 | 1 1 1 | | 1 1 1 | 1 1 1 | 0 0 1 | 0 0 0 | 0 0 1 | 0 0 1 | 1 1 1 | 1 1 1 |
| 41 | First visit | | Lower jaw | Lingual side | BOP | 1 1 1 | | 1 0 1 | 1 0 1 | 1 1 1 | 1 1 1 | 1 1 1 | 1 1 1 | 1 1 1 | 1 1 1 | 1 1 1 | 1 1 1 | 1 1 1 | 1 1 1 |
| 41 | First visit | | Lower jaw | Lingual side | PD | 6 3 7 | 5 4 9 | 5 4 5 | 6 6 6 | 5 4 5 | 4 4 5 | 4 4 4 | 4 4 4 | 6 3 6 | 4 3 4 | 4 4 4 | 6 4 9 | 6 4 9 | 7 4 3 |
| 41 | First visit | | Lower jaw | Lip side | PD | 6 6 6 | 6 4 7 | 6 3 4 | 6 3 6 | 5 4 5 | 3 4 5 | 6 6 6 | 4 3 3 | 6 3 3 | 4 3 4 | 5 3 5 | 5 5 6 | 9 8 10 | 6 3 4 |
| 41 | First visit | | Lower jaw | Lip side | BOP | 1 1 1 | 1 1 1 | 1 1 1 | 1 1 1 | 1 0 1 | 1 0 1 | 1 1 1 | 1 0 1 | 1 0 1 | 1 0 1 | 1 1 1 | 1 1 1 | 1 1 1 | 1 1 1 |
| 41 | First visit | | Lower jaw mobility | | | 1 | 0 | 0 | 0 | 0 | 0 | 2 | 2 | 1 | 0 | 0 | 0 | 0 | 1 |
| 41 | First visit | | Upper jaw mobility | | | | | 1 | 2 | 1 | | 1 | 1 | 1 | 1 | 0 | 0 | 0 | 0 |
| 42 | First visit | 29 | Upper jaw | Buccal side | BOP | 0 1 1 | 0 1 1 | 0 0 1 | 0 0 0 | 0 0 0 | 0 0 0 | 0 0 0 | 0 0 0 | 0 0 0 | 0 0 0 | 0 0 0 | 0 0 0 | 0 0 1 | 0 0 0 |
| 42 | First visit | | Upper jaw | Buccal side | PD | 3 4 3 | 5 4 9 | 5 4 5 | 10 4 9 | 3 4 6 | 4 4 5 | 5 3 3 | 5 3 3 | 4 4 3 | 3 3 4 | 3 2 3 | 3 2 3 | 3 3 3 | 3 3 3 |
| 42 | First visit | | Upper jaw | Palatial side | PD | 5 3 3 | 4 2 3 | 6 3 4 | 9 8 9 | 4 6 6 | 4 3 3 | 5 4 5 | 7 3 4 | 6 2 3 | 6 2 3 | 4 3 3 | 4 3 5 | 3 7 6 | 4 4 6 |
| 42 | First visit | | Upper jaw | Palatial side | BOP | 1 0 0 | 0 0 0 | 1 0 1 | 1 0 0 | 1 0 0 | 0 0 0 | 1 1 1 | 1 0 0 | 1 0 0 | 1 0 0 | 0 0 0 | 1 0 0 | 1 0 0 | 1 0 0 |
| 42 | First visit | | Lower jaw | Lingual side | BOP | 0 1 1 | 0 0 1 | 1 0 1 | 1 0 0 | 0 0 0 | 0 0 0 | 0 0 0 | 0 0 0 | 0 0 0 | 0 0 0 | 0 0 0 | 0 0 0 | 0 0 0 | 1 0 0 |
| 42 | First visit | | Lower jaw | Lingual side | PD | 8 8 5 | 6 3 5 | 5 3 4 | 3 2 3 | 3 2 3 | 3 2 3 | 3 2 3 | 2 1 2 | 2 1 2 | 3 2 4 | 5 3 5 | 3 2 3 | 3 2 3 | 4 3 3 |
| 42 | First visit | | Lower jaw | Lip side | PD | 4 3 4 | 7 3 4 | 6 3 4 | 3 2 3 | 3 2 3 | 3 2 3 | 3 2 3 | 3 2 3 | 2 1 2 | 3 2 4 | 4 2 3 | 3 2 3 | 3 3 3 | 4 2 4 |
| 42 | First visit | | Lower jaw | Lip side | BOP | 1 0 0 | 1 0 0 | 0 0 0 | 0 0 1 | 1 0 1 | 0 0 0 | 0 0 0 | 0 0 0 | 0 0 0 | 0 0 0 | 1 1 0 | 0 1 1 | 0 1 1 | 1 0 1 |
| 42 | First visit | | Lower jaw mobility | | | 1 | 1 | 0 | 0 | 0 | 0 | 0 | 0 | 0 | 0 | 0 | 0 | 0 | 0 |
| 43 | First visit | 30 | Upper jaw mobility | | | 0 | 0 | 0 | 0 | 0 | 0 | 0 | 0 | 0 | 0 | 0 | 0 | 0 | 0 |
| 43 | First visit | | Upper jaw | Buccal side | BOP | 0 1 0 | 0 0 1 | 0 0 0 | 0 0 0 | 0 0 0 | 0 0 0 | 0 0 0 | 1 0 0 | 1 0 0 | 0 0 0 | 0 0 0 | 1 0 0 | 1 0 0 | 1 0 1 |

TABLE 1-continued

| Subject No. | First visit/R | Sample No. | | | | DCM 7 | DCM 6 | DCM 5 | DCM 4 | DCM 3 | DCM 2 | DCM 1 | MCD 1 | MCD 2 | MCD 3 | MCD 4 | MCD 5 | MCD 6 | MCD 7 |
|---|---|---|---|---|---|---|---|---|---|---|---|---|---|---|---|---|---|---|---|
| 43 | First visit | | Upperjaw | Buccal side | PD | 4 4 5 | 4 5 3 | 3 2 3 | 3 2 7 | 3 3 4 | 5 4 4 | 3 2 3 | 4 3 3 | 2 2 3 | 3 2 3 | 5 2 3 | 3 2 4 | 6 5 4 | 4 5 6 |
| 43 | First visit | | Upperjaw | Palatial side | PD | 5 3 5 | 6 4 6 | 3 3 3 | 3 3 6 | 3 2 3 | 3 2 3 | 3 2 4 | 5 3 3 | 3 2 3 | 5 4 4 | 4 3 3 | 3 2 3 | 5 2 5 | 5 5 6 |
| 43 | First visit | | Upperjaw | Palatial side | BOP | 1 0 1 | 1 0 1 | 0 0 0 | 1 0 1 | 0 0 1 | 0 0 1 | 1 0 1 | 1 0 1 | 0 0 0 | 1 0 0 | 1 0 1 | 1 0 1 | 1 0 1 | 1 0 1 |
| 43 | First visit | | Lowerjaw | Lingual side | BOP | 0 0 0 | 0 0 0 | 3 2 3 | 3 2 3 | 3 2 3 | 0 0 1 | 1 1 1 | 3 2 4 | 4 1 2 | 2 2 3 | 4 2 3 | 1 0 0 | 0 0 0 | 1 0 0 |
| 43 | First visit | | Lowerjaw | Lingual side | PD | 3 4 3 | 3 2 3 | 3 2 3 | 3 3 3 | 3 2 3 | 3 2 4 | 4 4 4 | 3 2 4 | 4 1 2 | 2 2 3 | 4 2 3 | 4 2 3 | 4 6 5 | 4 2 3 |
| 43 | First visit | | Lowerjaw | Lip side | PD | 4 4 6 | 5 5 4 | 3 2 3 | 3 3 3 | 3 2 3 | 4 3 4 | 4 4 4 | 4 3 4 | 5 2 3 | 3 1 3 | 3 1 3 | 3 2 3 | 4 6 5 | 3 6 5 |
| 43 | First visit | | Lowerjaw | Lip side | BOP | 0 1 1 | 1 1 1 | 0 0 1 | 0 0 1 | 0 0 0 | 1 0 1 | 1 0 1 | 1 0 1 | 1 0 0 | 0 0 0 | 0 0 0 | 0 0 1 | 0 0 1 | 0 1 0 |
| 43 | First visit | | Lowerjaw mobility | | | 0 | 0 | 0 | 0 | 0 | 0 | 0 | 0 | 0 | 0 | 0 | 0 | 0 | 0 |
| 46 | First visit | 31 | Upper jaw mobility | | | 0 | 0 | 0 | 1 | 1 | 0 | 1 | 1 | 0 | 0 | 2 | 1 | 1 | 1 |
| 46 | First visit | | Upper jaw | Buccal side | BOP | 0 0 1 | 1 0 0 | 1 0 1 | 0 0 0 | 1 1 0 | 1 0 1 | 0 0 0 | 0 0 0 | 0 0 0 | 0 0 0 | 0 0 0 | 0 0 0 | 0 0 0 | 0 0 0 |
| 46 | First visit | | Upper jaw | Buccal side | PD | 3 3 5 | 6 3 3 | 4 3 7 | 3 2 4 | 1 1 6 3 | 2 1 2 | 2 2 3 | 3 2 3 | 3 2 3 | 2 2 7 | 6 3 2 | 2 1 2 | 2 3 5 | 3 3 3 |
| 46 | First visit | | Upper jaw | Palatial side | PD | 3 2 4 | 6 2 6 | 9 6 7 | 5 5 8 | 10 9 3 | 3 2 3 | 2 2 3 | 3 2 3 | 3 2 3 | 3 2 6 | 10 3 3 | 3 2 3 | 3 2 6 | 10 3 3 |
| 46 | First visit | | Upper jaw | Palatial side | BOP | 0 0 1 | 1 0 1 | 1 1 0 | 1 0 1 | 1 1 0 | 0 0 0 | 0 0 0 | 0 0 0 | 0 0 0 | 0 0 0 | 1 1 0 | 0 0 0 | 0 0 1 | 1 0 0 |
| 46 | First visit | | Lower jaw | Lingual side | BOP | 0 0 1 | 1 0 1 | 1 1 0 | 0 0 1 | 1 1 0 | 0 0 0 | 0 0 0 | 0 0 0 | 0 0 0 | 0 0 0 | 0 0 0 | 0 0 0 | 0 0 1 | 1 0 0 |
| 46 | First visit | | Lower jaw | Lingual side | PD | 7 2 3 | 9 2 3 | 10 6 3 | 3 2 3 | 3 2 3 | 3 2 2 | 3 2 2 | 2 2 2 | 2 1 2 | 3 2 3 | 3 2 3 | 2 1 3 | 3 3 7 | 7 2 3 |
| 46 | First visit | | Lower jaw | Lip side | PD | 11 4 3 | 9 3 3 | 8 2 3 | 3 2 3 | 3 2 3 | 4 2 2 | 3 2 2 | 2 1 2 | 2 1 2 | 2 1 2 | 2 1 2 | 2 1 3 | 3 2 11 | 11 2 3 |
| 46 | First visit | | Lower jaw | Lip side | BOP | 0 0 1 | 1 1 0 | 1 0 0 | 0 0 1 | 0 1 1 | 0 0 0 | 0 0 0 | 0 0 0 | 0 0 0 | 0 0 0 | 0 0 0 | 0 0 0 | 0 0 1 | 1 0 0 |
| 46 | First visit | | Lower jaw mobility | | | 0 | 0 | 1 | 2 | 2 | 0 | 1 | 0 | 1 | 0 | 0 | 0 | 1 | 1 |
| 47 | First visit | 32 | Upper jaw mobility | | | 0 | 1 | 1 | 0 | 0 | 1 | 0 | 0 | 1 | 0 | 0 | 0 | 0 | 0 |
| 47 | First visit | | Upper jaw | Buccal side | BOP | 1 0 0 | 0 0 0 | 0 0 1 | 1 1 1 | 0 0 0 | 1 0 1 | 1 0 0 | 1 0 0 | 1 0 0 | 1 0 0 | 0 0 0 | 0 0 0 | 0 0 0 | 0 0 0 |
| 47 | First visit | | Upper jaw | Buccal side | PD | 5 4 4 | 4 3 7 | 4 3 5 | 3 3 5 | 3 3 3 | 7 3 5 | 4 3 7 | 4 2 4 | 7 3 3 | 3 2 3 | 3 3 4 | 3 3 3 | 3 3 5 | 4 3 3 |
| 47 | First visit | | Upper jaw | Palatial side | PD | 5 4 3 | 3 3 7 | 4 3 7 | 6 4 4 | 4 3 3 | 7 4 6 | 3 3 6 | 7 3 3 | 4 3 4 | 4 3 4 | 3 2 3 | 3 3 3 | 4 3 4 | 4 4 5 |
| 47 | First visit | | Upper jaw | Palatial side | BOP | 1 0 0 | 0 0 1 | 0 0 1 | 1 0 1 | 0 0 0 | 1 0 1 | 0 0 1 | 1 0 1 | 0 0 0 | 0 0 1 | 0 0 0 | 0 0 0 | 0 0 1 | 0 0 1 |
| 47 | First visit | | Lower jaw | Lingual side | BOP | 1 0 1 | 1 0 1 | 1 0 1 | 0 0 1 | 1 0 1 | 1 0 1 | 1 0 1 | 1 0 1 | 0 0 0 | 1 0 0 | 0 0 1 | 1 0 0 | 0 0 1 | 0 0 1 |
| 47 | First visit | | Lower jaw | Lingual side | PD | 4 4 7 | 6 3 6 | 4 3 4 | 4 3 4 | 4 3 5 | 5 3 5 | 6 4 6 | 4 3 6 | 4 3 4 | 3 3 4 | 4 3 4 | 4 3 4 | 3 3 7 | 6 4 5 |
| 47 | First visit | | Lower jaw | Lip side | PD | 4 4 5 | 5 4 6 | 3 3 3 | 3 2 3 | 4 5 6 | 3 3 6 | 6 3 6 | 8 3 7 | 6 3 5 | 1 0 1 | 4 3 4 | 4 3 4 | 3 2 11 | 4 3 5 |
| 47 | First visit | | Lower jaw | Lip side | BOP | 1 0 1 | 1 1 1 | 0 0 0 | 0 0 0 | 0 1 1 | 0 0 0 | 0 0 1 | 1 0 1 | 1 0 1 | 1 0 1 | 0 0 0 | 0 0 0 | 3 2 11 | 1 0 1 |
| 47 | First visit | | Lower jaw mobility | | | 0 | 0 | 0 | 2 | 2 | 2 | 1 | 0 | 1 | 1 | 0 | 0 | 0 | 0 |
| 48 | First visit | 33 | Upper jaw mobility | | | 1 | 0 | 0 | 1 | 2 | 1 | 3 | 3 | 3 | 1 | 1 | 2 | 0 | 0 |
| 48 | First visit | | Upper jaw | Buccal side | BOP | 1 1 1 | 1 1 1 | 1 1 1 | 1 1 1 | 1 1 | 1 1 1 | 1 1 1 | 1 1 1 | 1 1 1 1 | 9 4 6 | 6 3 10 | 9 4 5 | 0 | 1 1 1 |
| 48 | First visit | | Upper jaw | Buccal side | PD | 6 6 6 | 6 6 4 | 8 4 4 | 3 4 9 | 6 3 9 | 7 3 5 | 9 9 5 | 4 9 9 | 6 6 9 | 9 4 6 | 9 6 6 | 1 1 1 | 6 6 4 | 4 4 4 |
| 48 | First visit | | Upper jaw | Palatial side | PD | 5 3 3 | 3 3 6 | 6 6 5 | 5 5 8 | 8 9 9 | 8 8 8 | 9 6 6 | 6 6 6 | 6 6 9 | 6 6 6 | 9 6 6 | 1 1 1 | 6 3 5 | 4 4 5 |
| 48 | First visit | | Upper jaw | Palatial side | BOP | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 |
| 48 | First visit | | Lower jaw | Lingual side | BOP | 1 1 1 | 1 1 1 | 6 6 6 | 9 9 9 | 6 6 9 | 5 5 5 | 6 6 6 | 6 6 6 | 9 9 9 | 6 6 6 | 6 6 6 | 6 6 9 | 1 0 1 | 1 1 1 |
| 48 | First visit | | Lower jaw | Lingual side | PD | 4 4 4 | 4 4 4 | 6 6 6 | 6 6 3 | 6 6 9 | 5 5 5 | 6 6 9 | 9 9 9 | 9 9 9 | 9 9 9 | 6 6 6 | 6 6 9 | 6 1 1 7 | 5 3 6 |
| 48 | First visit | | Lower jaw | Lip side | PD | 6 4 3 | 3 3 6 | 4 3 4 | 6 3 4 | 7 2 4 | 6 4 5 | 6 3 6 | 8 3 7 | 5 4 7 | 6 7 8 | 7 4 3 | 6 6 9 | 7 1 1 7 | 4 3 6 |
| 48 | First visit | | Lower jaw | Lip side | BOP | 1 1 1 | 1 1 1 | 1 1 1 | 0 0 1 | 1 0 0 | 1 0 0 | 1 0 1 | 1 1 1 | 1 1 1 | 1 1 1 | 1 1 | 1 1 1 | 1 1 1 | 1 1 1 |
| 48 | First visit | | Lower jaw mobility | | | 0 | 2 | 0 | 2 | 2 | 1 | 3 | 3 | 2 | 2 | 1 | 2 | 0 | 1 |
| 49 | First visit | 34 | Upper jaw mobility | | | 1 | 2 | 1 | 1 | 2 | 0 | 0 | 0 | 0 | 0 | 0 | 2 | | |
| 49 | First visit | | Upper jaw | Buccal side | BOP | 1 1 1 | 1 1 1 | 1 0 0 | 6 3 4 | 1 0 1 | 6 4 5 | 0 1 1 | 1 0 1 | 1 1 1 | 4 3 4 | 7 4 7 | 1 1 | 1 1 1 | 1 1 1 |
| 49 | First visit | | Upper jaw | Buccal side | PD | 7 8 9 | 6 7 9 | 7 10 7 | 6 3 4 | 7 2 4 | 6 4 5 | 8 4 9 | 5 4 5 | 5 4 7 | 4 7 9 | 7 8 7 | 8 5 6 | 8 5 6 | 6 3 5 |
| 49 | First visit | | Upper jaw | Palatial side | PD | 1 1 1 | 1 1 1 | 1 1 1 | 4 3 5 | 9 7 4 | 4 4 5 | 10 10 9 | 9 9 9 | 6 7 8 | 4 7 9 | 4 4 6 | 4 4 6 | 7 1 1 7 | 5 3 6 |
| 49 | First visit | | Upper jaw | Palatial side | BOP | 1 1 1 | 1 1 1 | 1 0 1 | 0 0 1 | 1 0 0 | 1 0 0 | 1 0 1 | 1 0 1 | 1 0 1 | 1 0 1 | 1 0 1 | 1 0 1 | 1 1 1 | 1 1 1 |
| 49 | First visit | | Lower jaw | Lingual side | BOP | 2 1 | 2 1 | 1 0 | 1 0 | 1 0 0 | 1 0 0 | 1 0 1 | 1 0 1 | 1 0 1 | 1 0 1 | 1 0 1 | 1 0 1 | 0 | 1 |
| 49 | First visit | | Lower jaw mobility | | | 0 | 0 | 0 | 0 | 0 | 0 | 0 | 0 | | | | | | |
| 50 | First visit | 35 | Upper jaw mobility | | | 2 | | | | | | | | | | | | | 2 |

TABLE 1-continued

| Subject No. | First visit/R | Sample No. | | | DCM 7 | DCM 6 | DCM 5 | DCM 4 | DCM 3 | DCM 2 | DCM 1 | MCD 1 | MCD 2 | MCD 3 | MCD 4 | MCD 5 | MCD 6 | MCD 7 |
|---|---|---|---|---|---|---|---|---|---|---|---|---|---|---|---|---|---|---|
| 50 | First visit | | Upper jaw | Buccal side | BOP | 1 0 0 | | 0 0 0 | 0 0 0 | 0 0 0 | 1 0 0 | 0 0 0 | 0 0 0 | 0 0 0 | 0 0 0 | 0 0 0 | 0 0 0 | 0 0 1 | 1 0 1 |
| 50 | First visit | | Upper jaw | Buccal side | PD | 6 3 3 | | 3 2 3 | 3 2 3 | 3 2 3 | 3 2 3 | 3 2 3 | 2 2 3 | 3 2 3 | 3 2 3 | 4 2 3 | 3 2 3 | 3 3 6 | 7 6 5 |
| 50 | First visit | | Upper jaw | Palatial side | PD | 5 2 3 | | 3 2 3 | 3 2 3 | 3 2 3 | 3 2 3 | 3 2 3 | 2 2 3 | 3 2 3 | 3 2 3 | 3 2 3 | 3 2 3 | 3 2 4 | 3 8 7 |
| 50 | First visit | | Upper jaw | Palatial side | BOP | 1 0 0 | | 0 0 0 | 0 0 0 | 0 0 0 | 0 0 1 | 0 0 1 | 0 0 0 | 0 0 0 | 0 0 0 | 0 0 0 | 0 0 0 | 0 0 1 | 1 1 1 |
| 50 | First visit | | Lower jaw | Lingual side | BOP | | | | | | | | | | | | 1 0 0 | | 1 0 0 |
| 50 | First visit | | Lower jaw | Lingual side | PD | | | 3 2 3 | 3 2 3 | 3 2 3 | 3 2 3 | 3 1 2 | 3 2 3 | 3 1 2 | 3 2 3 | 3 2 3 | 4 3 6 | | 3 2 3 |
| 50 | First visit | | Lower jaw | Lip side | PD | | | 3 2 3 | 3 2 3 | 3 2 3 | 4 2 3 | 3 2 3 | 3 2 3 | 3 2 3 | 3 2 3 | 3 2 3 | 4 3 5 | | 5 2 3 |
| 50 | First visit | | Lower jaw | Lip side | BOP | | | 0 0 0 | 0 0 0 | 0 0 0 | 1 0 1 | 1 0 0 | 0 0 0 | 0 0 0 | 0 0 0 | 0 0 0 | 1 0 1 | 0 0 1 | 1 0 0 |
| 50 | First visit | | Lower jaw | Lower jaw mobility | | | | | | | 0 | 0 | 0 | 0 | 0 | 0 | 0 | | 0 |
| 51 | | 36 | Upper jaw | Upper jaw mobility | | 2 | 3 | 0 | 1 | 0 | 2 | 0 | 2 | 2 | 1 | 0 | 2 | 3 | 0 |
| 51 | First visit | | Upper jaw | Buccal side | BOP | 1 1 1 | 1 1 1 | 1 0 1 | 1 0 1 | 0 0 1 | 1 0 1 | 0 0 1 | 0 0 1 | 1 1 0 | 1 1 1 | 0 0 1 | 1 1 1 | 1 1 0 | 0 0 1 |
| 51 | First visit | | Upper jaw | Buccal side | PD | 10 6 4 | 7 7 11 | 11 8 7 | 5 5 10 | 4 4 5 | 7 4 9 | 9 4 9 | 9 5 9 | 9 5 4 | 9 4 3 | 3 3 4 | 8 7 10 | 11 6 5 | 4 4 9 |
| 51 | First visit | | Upper jaw | Palatial side | PD | 10 7 7 | 7 8 11 | 10 10 7 | 7 5 10 | 4 4 4 | 7 7 9 | 8 7 8 | 8 9 9 | 7 8 8 | 8 7 5 | 4 3 4 | 9 8 9 | 11 10 9 | 4 4 8 |
| 51 | First visit | | Upper jaw | Palatial side | BOP | 1 1 1 | 1 1 1 | 1 1 1 | 1 1 1 | 1 0 0 | 1 0 1 | 1 0 1 | 1 1 1 | 1 1 1 | 1 1 1 | 1 0 1 | 1 1 1 | 1 1 1 | 1 1 1 |
| 51 | First visit | | Lower jaw | Lingual side | PD | 1 0 1 | 1 1 1 | 1 1 1 | 1 1 1 | 1 0 1 | 1 0 1 | 1 0 1 | 1 0 0 | 1 1 1 | 1 0 1 | 1 0 1 | 1 0 1 | 1 1 1 | 1 1 1 |
| 51 | First visit | | Lower jaw | Lingual side | PD | 6 4 4 | 7 7 7 | 7 5 7 | 9 4 7 | 4 7 9 | 6 4 5 | 4 4 5 | 4 4 4 | 7 4 4 | 10 11 11 | 7 4 9 | 5 3 8 | 7 6 5 | 7 4 7 |
| 51 | First visit | | Lower jaw | Lip side | PD | 11 7 4 | 7 8 7 | 5 4 6 | 4 4 5 | 4 3 11 | 7 3 4 | 4 4 5 | 5 4 4 | 8 6 4 | 11 9 11 | 4 3 7 | 1 0 1 | 4 3 4 | 7 4 7 |
| 51 | First visit | | Lower jaw | Lip side | BOP | 1 0 1 | 1 1 1 | 1 1 1 | 1 0 1 | 1 0 1 | 0 0 1 | 1 0 0 | 1 0 0 | 1 0 0 | 1 1 1 | 1 0 1 | 1 0 1 | 1 0 1 | 1 0 1 |
| 51 | First visit | | Lower jaw | Lower jaw mobility | | 1 | 2 | 0 | 1 | 0 | 2 | 2 | 2 | 1 | 0 | 2 | 0 | 1 | 0 |
| 52 | R | 37 | Upper jaw | Upper jaw mobility | | 0 | 0 | 0 | 0 | 0 | 2 | 2 | 1 | 1 | 1 | 1 | 0 | 0 | 1 |
| 52 | R | | Upper jaw | Buccal side | BOP | 0 0 1 | 1 0 1 | 1 0 1 | 1 0 1 | 1 0 1 | 1 0 1 | 0 0 1 | 1 0 1 | 1 0 0 | 0 0 1 | 1 1 1 | 1 0 1 | 1 0 1 | 1 0 1 |
| 52 | R | | Upper jaw | Buccal side | PD | 4 3 5 | 4 2 3 | 3 2 4 | 4 2 3 | 3 2 3 | 4 4 6 | 5 2 3 | 2 2 3 | 2 2 3 | 3 2 3 | 6 4 6 | 3 2 4 | 2 3 9 | 9 5 3 |
| 52 | R | | Upper jaw | Palatial side | PD | 6 3 4 | 5 2 4 | 3 2 4 | 3 2 3 | 3 4 6 | 4 5 7 | 7 4 4 | 3 3 3 | 4 2 3 | 3 4 6 | 3 3 4 | 3 2 3 | 3 4 6 | 9 3 9 |
| 52 | R | | Upper jaw | Palatial side | BOP | 1 0 1 | 1 1 1 | 1 1 1 | 1 1 1 | 1 0 1 | 1 1 1 | 1 1 1 | 1 0 1 | 1 0 1 | 1 0 1 | 1 1 1 | 1 1 1 | 1 1 1 | 1 1 1 |
| 52 | R | | Lower jaw | Lingual side | BOP | 0 1 1 | 1 0 0 | 1 1 1 | 1 1 1 | 1 0 1 | 1 0 1 | 0 0 1 | 1 0 1 | 1 0 1 | 1 0 1 | 1 0 0 | 0 1 1 | 0 1 1 | 1 1 0 |
| 52 | R | | Lower jaw | Lingual side | PD | 2 3 4 | 3 4 4 | 3 2 3 | 3 2 7 | 8 2 3 | 3 2 3 | 4 3 3 | 2 1 2 | 3 2 4 | 4 2 2 | 3 2 3 | 3 2 4 | 3 6 6 | 6 3 3 |
| 52 | R | | Lower jaw | Lip side | PD | 4 3 6 | 6 3 3 | 3 2 3 | 3 2 5 | 4 3 3 | 3 2 4 | 4 3 3 | 3 2 3 | 3 2 4 | 3 2 3 | 3 6 5 | 3 2 3 | 2 2 4 | 7 3 3 |
| 52 | R | | Lower jaw | Lip side | BOP | 0 1 0 | 1 0 1 | 1 0 0 | 0 1 1 | 1 0 1 | 1 0 1 | 1 0 1 | 1 0 1 | 1 0 0 | 1 0 1 | 0 0 1 | 1 1 0 | 1 0 1 | 1 0 1 |
| 52 | R | | Lower jaw | Lower jaw mobility | | 0 | 0 | 0 | 1 | 0 | 0 | 0 | 0 | 0 | 0 | 2 | 0 | 0 | 0 |
| 56 | First visit | 38 | Upper jaw | Upper jaw mobility | | 0 | 0 | 0 | 1 | 0 | 1 | 1 | 0 | 1 | 1 | 1 | 0 | 0 | 0 |
| 56 | First visit | | Upper jaw | Buccal side | BOP | 0 0 1 | 1 0 1 | 0 0 0 | 1 0 1 | 0 0 0 | 1 0 1 | 1 0 0 | 0 0 0 | 0 0 0 | 1 0 0 | 1 0 0 | 0 0 0 | 0 0 0 | 0 1 0 |
| 56 | First visit | | Upper jaw | Buccal side | PD | 3 3 6 | 4 2 6 | 3 1 2 | 3 2 3 | 0 0 0 | 0 0 0 | 0 0 0 | 0 0 0 | 0 0 0 | 0 0 0 | 4 2 3 | 2 2 3 | 2 3 9 | 4 3 3 |
| 56 | First visit | | Upper jaw | Palatial side | PD | 3 2 5 | 5 2 5 | 3 2 4 | 3 2 3 | 0 0 0 | 0 0 0 | 0 0 0 | 0 0 0 | 0 0 0 | 0 0 0 | 5 2 3 | 3 2 3 | 4 2 4 | 3 3 4 |
| 56 | First visit | | Upper jaw | Palatial side | BOP | 0 0 1 | 1 0 0 | 1 0 0 | 1 1 0 | 1 0 1 | 1 0 1 | 1 0 1 | 1 1 1 | 1 1 1 | 1 1 1 | 0 0 1 | 1 1 1 | 0 0 0 | 0 0 1 |
| 56 | First visit | | Lower jaw | Lingual side | BOP | 0 0 0 | 1 0 0 | 0 0 0 | 0 0 0 | 0 0 0 | 0 0 0 | 0 0 0 | 0 0 0 | 0 0 0 | 0 0 0 | 1 0 0 | 1 0 1 | 0 0 0 | 0 0 1 |
| 56 | First visit | | Lower jaw | Lingual side | PD | 2 3 4 | 5 3 4 | 3 2 3 | 3 2 7 | 8 2 3 | 3 1 3 | 3 1 2 | 2 1 2 | 3 2 4 | 4 2 2 | 3 2 3 | 5 3 4 | 3 6 6 | 6 3 3 |
| 56 | First visit | | Lower jaw | Lip side | PD | 7 2 6 | 6 3 3 | 3 2 4 | 3 2 5 | 8 2 3 | 3 2 4 | 4 3 3 | 2 1 2 | 2 2 3 | 3 2 3 | 3 6 5 | 6 3 5 | 3 6 6 | 6 3 4 |
| 56 | First visit | | Lower jaw | Lip side | BOP | 6 5 5 | 4 2 3 | 0 0 0 | 0 1 1 | 0 1 1 | 0 0 0 | 0 0 0 | 2 1 2 | 2 2 3 | 0 0 0 | 0 0 1 | 1 0 0 | 1 0 0 | 1 0 0 |
| 56 | First visit | | Lower jaw | Lower jaw mobility | | 0 | 0 | 0 | 0 | 0 | 0 | 0 | 0 | 0 | 0 | 0 | 0 | 0 | 0 |
| 58 | First visit | 39 | Upper jaw | Upper jaw mobility | | 1 | 0 | 0 | 1 | 1 | 0 | 1 | 1 | 1 | 1 | 1 | 0 | 0 | 0 |
| 58 | First visit | | Upper jaw | Buccal side | BOP | 1 1 1 | 1 1 1 | 1 0 1 | 1 0 1 | 1 0 1 | 1 0 1 | 0 1 0 | 0 0 0 | 1 0 1 | 1 0 0 | 1 0 0 | 1 0 0 | 0 0 1 | 0 0 0 |
| 58 | First visit | | Upper jaw | Buccal side | PD | 3 3 5 | 4 3 3 | 3 2 3 | 3 3 3 | 3 2 3 | 2 2 2 | 2 2 3 | 2 2 2 | 3 2 2 | 3 2 3 | 2 2 3 | 2 2 3 | 3 2 3 | 3 3 3 |
| 58 | First visit | | Upper jaw | Palatial side | PD | 3 6 6 | 5 4 5 | 4 5 4 | 3 3 3 | 3 2 3 | 2 2 3 | 2 3 3 | 3 2 3 | 3 2 3 | 3 2 3 | 3 2 3 | 3 2 3 | 3 3 3 | 4 3 3 |
| 58 | First visit | | Upper jaw | Palatial side | BOP | 1 0 1 | 1 1 1 | 1 1 1 | 1 1 1 | 1 0 1 | 1 0 0 | 0 1 0 | 1 0 1 | 1 0 0 | 1 0 1 | 1 1 1 | 1 1 1 | 0 1 0 | 0 0 1 |
| 58 | First visit | | Lower jaw | Lingual side | BOP | 0 1 1 | 1 1 1 | 1 1 1 | 1 1 1 | 0 0 0 | 1 0 1 | 2 3 3 | 3 2 3 | 3 3 3 | 3 3 3 | 1 1 1 | 3 6 6 | 3 6 6 | 6 3 3 |
| 58 | First visit | | Lower jaw | Lingual side | PD | 6 6 5 | 5 3 4 | 3 2 3 | 3 2 3 | 3 1 3 | 2 2 3 | 2 2 3 | 3 2 3 | 3 2 3 | 3 3 3 | 4 5 4 | 4 3 4 | 4 2 5 | 6 3 4 |
| 58 | First visit | | Lower jaw | Lip side | PD | 3 9 3 | 4 2 3 | 3 2 3 | 3 2 3 | 3 2 3 | 3 2 3 | 2 2 3 | 3 2 3 | 3 2 3 | 3 2 3 | 3 2 3 | 4 3 5 | 4 3 5 | 6 3 4 |
| 58 | First visit | | Lower jaw | Lip side | BOP | 0 1 0 | 1 1 1 | 1 0 0 | 0 0 1 | 0 0 1 | 1 0 1 | 0 0 0 | 0 0 0 | 0 0 1 | 0 0 0 | 0 0 1 | 1 0 0 | 1 0 0 | 1 0 0 |
| 58 | First visit | | Lower jaw | Lower jaw mobility | | 0 | 0 | 0 | 1 | 0 | 2 | 0 | 0 | 1 | 1 | 0 | 1 | 0 | 0 |

TABLE 1-continued

| Subject No. | First visit/R | Sample No. | | | | DCM 7 | DCM 6 | DCM 5 | DCM 4 | DCM 3 | DCM 2 | DCM 1 | MCD 1 | MCD 2 | MCD 3 | MCD 4 | MCD 5 | MCD 6 | MCD 7 |
|---|---|---|---|---|---|---|---|---|---|---|---|---|---|---|---|---|---|---|---|
| 59 | First visit | 40 | Upper jaw | Upper jaw mobility | | 1 | 1 | 0 | 0 | 0 | 0 | 0 | 0 | 0 | 0 | 0 | 0 | 1 | 1 |
| 59 | First visit | | Upper jaw | Buccal side | BOP | 0 0 0 | 1 0 0 | 0 0 1 | 0 0 0 | 0 0 0 | 0 0 0 | 0 0 0 | 0 0 0 | 0 0 0 | 0 0 0 | 0 0 0 | 0 0 0 | 0 0 0 | 0 0 1 |
| 59 | First visit | | Upper jaw | Buccal side | PD | 3 3 3 | 9 2 5 | 5 2 6 | 2 1 2 | 2 1 2 | 3 1 2 | 2 1 2 | 2 1 2 | 3 1 2 | 2 1 2 | 2 1 2 | 2 1 3 | 2 2 2 | 2 3 9 |
| 59 | First visit | | Upper jaw | Palatial side | PD | 3 2 4 | 10 9 3 | 3 2 3 | 3 2 3 | 3 2 2 | 3 2 2 | 2 1 3 | 2 1 3 | 2 1 3 | 2 1 2 | 3 2 3 | 3 2 4 | 3 3 9 |
| 59 | First visit | | Lower jaw | Lingual side | BOP | 0 0 1 | 1 1 0 | 0 0 1 | 0 0 0 | 0 0 0 | 0 0 0 | 0 0 0 | 0 0 0 | 0 0 0 | 0 0 0 | 0 0 0 | 0 0 0 | 0 0 0 | 0 0 1 |
| 59 | First visit | | Lower jaw | Lingual side | PD | 5 2 6 | 6 2 3 | 3 2 3 | 3 2 2 | 2 1 2 | 2 1 2 | 2 1 2 | 2 1 2 | 2 1 2 | 3 1 2 | 3 1 3 | 3 1 3 | 3 3 3 | 4 3 6 |
| 59 | First visit | | Lower jaw | Lip side | PD | 3 3 6 | 3 5 3 | 3 1 3 | 2 1 2 | 3 1 2 | 3 1 2 | 3 1 2 | 2 1 2 | 2 1 2 | 2 1 2 | 3 2 3 | 3 3 3 | 3 4 9 |
| 59 | First visit | | Lower jaw | Lip side | BOP | 0 0 1 | 0 0 1 | 1 1 0 | 0 0 0 | 0 0 0 | 0 0 0 | 0 0 0 | 0 0 0 | 0 0 0 | 0 0 0 | 0 0 0 | 0 0 1 | 0 0 1 |
| 59 | First visit | | Lower jaw | Lower jaw mobility | | 0 | 0 | 0 | 0 | 0 | 0 | 0 | 0 | 0 | 0 | 0 | 0 | 0 | 0 |
| 59 | R | 41 | Upper jaw | Upper jaw mobility | | 0 | 0 | 0 | 0 | 0 | 0 | 0 | 0 | 0 | 0 | 0 | 0 | 0 | 1 |
| 59 | R | | Upper jaw | Buccal side | BOP | 1 0 0 | 0 1 0 | 0 0 0 | 0 0 0 | 0 0 0 | 0 0 0 | 0 0 0 | 0 0 0 | 0 0 0 | 0 0 0 | 0 0 0 | 0 0 0 | 0 0 0 |
| 59 | R | | Upper jaw | Buccal side | PD | 6 3 3 | 5 3 4 | 2 1 2 | 2 1 2 | 2 1 2 | 2 1 2 | 2 1 2 | 2 1 2 | 3 1 2 | 2 1 2 | 2 2 2 | 2 2 3 | 3 2 3 | 3 3 6 |
| 59 | R | | Upper jaw | Palatial side | PD | 6 3 3 | 3 2 2 | 2 1 2 | 2 1 2 | 2 1 2 | 2 1 2 | 2 1 2 | 2 1 3 | 2 1 2 | 2 1 2 | 3 2 3 | 3 2 5 | 3 2 7 |
| 59 | R | | Lower jaw | Lingual side | BOP | 1 0 1 | 1 0 0 | 0 0 0 | 0 0 0 | 0 0 0 | 0 0 0 | 0 0 0 | 0 0 0 | 0 0 0 | 0 0 0 | 0 0 0 | 0 0 1 | 0 0 1 |
| 59 | R | | Lower jaw | Lingual side | PD | 0 0 1 | 0 1 1 | 0 0 0 | 0 0 0 | 0 0 0 | 0 0 0 | 0 0 0 | 0 0 0 | 0 0 0 | 0 0 0 | 0 0 0 | 0 1 1 | 0 0 0 |
| 59 | R | | Lower jaw | Lip side | PD | 3 3 4 | 5 3 4 | 4 3 3 | 3 2 3 | 3 2 3 | 3 2 3 | 2 1 2 | 2 1 2 | 2 1 3 | 2 1 2 | 3 2 3 | 3 3 3 | 3 3 6 |
| 59 | R | | Lower jaw | Lip side | BOP | 3 3 4 | 6 4 2 | 3 1 2 | 2 1 2 | 3 2 3 | 3 1 2 | 2 1 2 | 2 1 2 | 2 1 2 | 3 2 3 | 2 3 4 | 4 3 3 | 3 3 6 |
| 59 | R | | Lower jaw | Lower jaw mobility | | 0 0 1 | 0 1 0 | 1 1 0 | 0 0 0 | 0 0 0 | 0 0 0 | 0 0 0 | 0 0 0 | 0 0 0 | 0 0 0 | 0 0 0 | 1 0 0 | 1 0 0 |
| 60 | First visit | 42 | Upper jaw | Upper jaw mobility | | 0 | 1 | 1 | 0 | 1 | 1 | 1 | 0 | 0 | 0 | 0 | 0 | 0 | 0 |
| 60 | First visit | | Upper jaw | Buccal side | BOP | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 1 1 1 |
| 60 | First visit | | Upper jaw | Buccal side | PD | 6 10 10 | 8 7 9 | 7 7 8 | 8 6 10 | 7 6 7 | 6 4 7 | 8 5 8 | 9 4 10 | 8 5 7 | 8 9 5 | 8 6 6 | 7 5 5 | 6 7 7 |
| 60 | First visit | | Upper jaw | Palatial side | PD | 7 5 6 | 6 5 6 | 6 5 6 | 10 3 7 | 6 5 6 | 6 5 6 | 7 5 6 | 6 5 7 | 7 5 8 | 8 5 4 | 6 5 5 | 9 6 10 | 7 3 7 |
| 60 | First visit | | Lower jaw | Lingual side | BOP | 1 1 1 | 1 0 1 | 1 1 1 | 1 0 1 | 1 1 1 | 1 1 1 | 1 0 1 | 1 0 1 | 1 1 1 | 1 1 1 | 1 1 1 | 1 0 1 | 1 1 1 |
| 60 | First visit | | Lower jaw | Lingual side | PD | 8 7 9 | 6 5 10 | 7 5 6 | 8 6 8 | 9 8 9 | 5 4 4 | 3 5 6 | 6 3 5 | 5 3 5 | 7 5 6 | 8 7 7 | 7 5 5 | 6 5 5 | 4 4 7 |
| 60 | First visit | | Lower jaw | Lip side | PD | 10 11 8 | 8 6 9 | 7 5 6 | 6 4 8 | 7 4 8 | 7 4 5 | 5 5 6 | 6 6 6 | 6 4 7 | 10 6 7 | 6 4 9 | 9 6 10 | 7 3 7 |
| 60 | First visit | | Lower jaw | Lip side | BOP | 1 1 1 | 1 1 1 | 1 1 1 | 1 1 1 | 1 1 1 | 1 1 1 | 1 1 1 | 1 1 1 | 1 1 1 | 1 1 1 | 1 1 1 | 10 3 8 | 1 0 1 |
| 60 | First visit | | Lower jaw | Lower jaw mobility | | 3 | 2 | 1 | 1 | 1 | 1 | 2 | 2 | 1 | 1 | 1 | 1 | 1 | 1 |
| 60 | R | 43 | Upper jaw | Upper jaw mobility | | 0 | 1 | 0 | 0 | 0 | 1 | 2 | 2 | 1 | 1 | 0 | 1 | 2 | 2 |
| 60 | R | | Upper jaw | Buccal side | BOP | 0 0 1 | 1 0 0 | 0 0 0 | 0 0 0 | 0 0 1 | 0 0 0 | 0 0 0 | 0 0 0 | 1 0 0 | 0 0 0 | 0 0 0 | 0 0 0 | 0 0 0 |
| 60 | R | | Upper jaw | Buccal side | PD | 3 2 4 | 5 2 2 | 2 1 3 | 3 1 3 | 3 1 3 | 3 1 2 | 2 1 3 | 2 1 2 | 2 1 2 | 2 1 2 | 3 1 2 | 2 2 2 | 2 1 2 |
| 60 | R | | Upper jaw | Palatial side | PD | 3 2 3 | 4 2 3 | 2 1 2 | 2 1 3 | 2 2 3 | 3 2 2 | 2 1 3 | 2 1 2 | 2 1 2 | 3 1 3 | 2 1 2 | 3 2 3 | 2 1 3 |
| 60 | R | | Lower jaw | Lingual side | BOP | 0 0 0 | 1 0 0 | 0 0 0 | 0 0 1 | 0 0 0 | 0 0 0 | 0 0 0 | 0 0 0 | 0 0 0 | 0 0 0 | 0 0 0 | 0 0 0 | 0 0 0 |
| 60 | R | | Lower jaw | Lingual side | PD | 2 2 3 | 3 3 2 | 2 1 2 | 2 2 7 | 3 1 3 | 3 1 2 | 3 1 2 | 2 1 2 | 2 1 2 | 3 1 3 | 2 1 2 | 3 3 3 | 3 2 3 |
| 60 | R | | Lower jaw | Lip side | PD | 3 2 3 | 3 1 2 | 2 1 2 | 2 2 6 | 3 1 3 | 2 1 2 | 3 1 2 | 2 1 3 | 2 1 3 | 2 1 3 | 2 1 3 | 2 2 3 | 2 2 2 |
| 60 | R | | Lower jaw | Lip side | BOP | 0 0 0 | 0 0 0 | 0 0 0 | 0 0 1 | 0 0 0 | 0 0 0 | 0 0 0 | 0 0 0 | 0 0 0 | 0 0 0 | 0 0 0 | 0 0 0 | 0 0 0 |
| 72 | R | 44 | Upper jaw | Upper jaw mobility | | 0 | 0 | 0 | 0 | 0 | 0 | 0 | 0 | 0 | 0 | 0 | 0 | 0 | 0 |
| 72 | R | | Upper jaw | Buccal side | BOP | 0 0 0 | 0 0 0 | 0 0 0 | 0 0 0 | 0 0 0 | 0 0 0 | 0 0 0 | 0 0 0 | 0 0 0 | 0 0 0 | 0 0 0 | 0 0 0 | 0 0 0 |
| 72 | R | | Upper jaw | Buccal side | PD | 2 3 3 | 3 2 3 | 4 2 3 | 2 1 2 | 2 2 2 | 2 2 2 | 2 2 2 | 2 2 2 | 2 2 2 | 3 2 2 | 3 2 2 | 2 2 3 | 3 2 3 |
| 72 | R | | Upper jaw | Palatial side | PD | 3 3 3 | 3 2 3 | 6 2 2 | 2 2 6 | 3 2 3 | 2 2 2 | 2 2 2 | 2 2 2 | 2 2 2 | 3 2 2 | 3 2 2 | 3 2 3 | 3 3 3 |
| 72 | R | | Lower jaw | Lingual side | BOP | 0 0 0 | 0 0 0 | 1 0 0 | 0 0 1 | 1 0 1 | 0 0 0 | 0 0 0 | 0 0 0 | 0 0 0 | 0 0 0 | 0 0 0 | 0 0 0 | 0 0 1 |

TABLE 1-continued

| Subject No. | First visit/R | Sample No. | | | | DCM 7 | DCM 6 | DCM 5 | DCM 4 | DCM 3 | DCM 2 | DCM 1 | MCD 1 | MCD 2 | MCD 3 | MCD 4 | MCD 5 | MCD 6 | MCD 7 |
|---|---|---|---|---|---|---|---|---|---|---|---|---|---|---|---|---|---|---|---|
| 73 | R | | Lower jaw | Lingual side | BOP | 000 | 000 | 000 | 000 | 000 | 000 | 000 | 000 | 000 | 000 | 000 | 000 | 000 | 000 |
| 73 | R | | Lower jaw | Lingual side | PD | 433 | 333 | 323 | 323 | 323 | 222 | 222 | 322 | 323 | 323 | 223 | 323 | 323 | 334 |
| 73 | R | | Lower jaw | Lip side | PD | 833 | 333 | 323 | 323 | 323 | 223 | 222 | 222 | 223 | 323 | 322 | 223 | 333 | 334 |
| 73 | R | | Lower jaw | Lip side | BOP | 100 | 000 | 000 | 000 | 000 | 000 | 000 | 000 | 000 | 000 | 000 | 0 | 0 | 000 |
| 73 | R | | Lower jaw | Lower jaw mobility | | 0 | 0 | 0 | 1 | 0 | 0 | 0 | 0 | 0 | 0 | 0 | 0 | 0 | 1 |
| 74 | First visit | 45 | Upper jaw | Buccal side | BOP | 001 | 000 | 000 | 001 | 000 | 000 | 001 | 000 | 000 | 000 | 001 | 100 | 001 | 010 |
| 74 | First visit | | Upper jaw | Buccal side | PD | 633 | 333 | 323 | 326 | 324 | 323 | 323 | 323 | 323 | 323 | 223 | 323 | 336 | 633 |
| 74 | First visit | | Upper jaw | Palatial side | PD | 333 | 435 | 333 | 333 | 533 | 333 | 323 | 323 | 323 | 323 | 323 | 223 | 324 | 555 |
| 74 | First visit | | Upper jaw | Palatial side | BOP | 101 | 000 | 101 | 001 | 000 | 100 | 101 | 101 | 100 | 011 | 011 | 000 | 100 | 101 |
| 74 | First visit | | Lower jaw | Lingual side | BOP | 111 | 110 | 010 | 001 | 000 | 000 | 101 | 000 | 010 | 000 | 100 | 000 | 110 | 000 |
| 74 | First visit | | Lower jaw | Lingual side | PD | 468 | 333 | 325 | 323 | 323 | 323 | 323 | 323 | 323 | 323 | 323 | 323 | 333 | 334 |
| 74 | First visit | | Lower jaw | Lip side | PD | 369 | 333 | 335 | 333 | 324 | 424 | 323 | 423 | 323 | 323 | 323 | 323 | 333 | 333 |
| 74 | First visit | | Lower jaw | Lip side | BOP | 010 | 101 | 001 | 001 | 001 | 001 | 101 | 100 | 000 | 000 | 000 | 000 | 000 | 000 |
| 74 | First visit | | Lower jaw | Lower jaw mobility | | 2 | 0 | 1 | 0 | 0 | 0 | 0 | 0 | 0 | 0 | 0 | 0 | 0 | 0 |
| 74 | R | 46 | Upper jaw | Upper jaw mobility | | 1 | 0 | 1 | 1 | 0 | 0 | 0 | 0 | 0 | 0 | 0 | 0 | 0 | 1 |
| 74 | R | | Upper jaw | Buccal side | BOP | 001 | 000 | 000 | 000 | 000 | 001 | 000 | 000 | 000 | 000 | 100 | 001 | 001 | 000 |
| 74 | R | | Upper jaw | Buccal side | PD | 333 | 312 | 212 | 213 | 312 | 212 | 212 | 212 | 212 | 212 | 223 | 424 | 423 |
| 74 | R | | Upper jaw | Palatial side | PD | 333 | 333 | 212 | 323 | 422 | 222 | 222 | 312 | 212 | 213 | 323 | 334 | 344 |
| 74 | R | | Upper jaw | Palatial side | BOP | 101 | 101 | 110 | 101 | 101 | 000 | 000 | 110 | 000 | 010 | 001 | 101 | 101 | 101 |
| 74 | R | | Lower jaw | Lingual side | BOP | 011 | 000 | 010 | 010 | 110 | 010 | 011 | 111 | 101 | 000 | 001 | 010 | 100 | 111 |
| 74 | R | | Lower jaw | Lingual side | PD | 357 | 323 | 324 | 323 | 323 | 212 | 212 | 212 | 212 | 212 | 222 | 323 | 333 | 533 |
| 74 | R | | Lower jaw | Lip side | PD | 467 | 443 | 323 | 322 | 312 | 212 | 212 | 212 | 212 | 212 | 222 | 323 | 323 | 533 |
| 74 | R | | Lower jaw | Lip side | BOP | 110 | 001 | 100 | 110 | 000 | 000 | 001 | 100 | 000 | 000 | 110 | 101 | 000 | 000 |
| 74 | R | | Lower jaw | Lower jaw mobility | | 1 | 0 | 0 | 0 | 0 | 0 | 0 | 0 | 0 | 0 | 0 | 0 | 0 | 1 |

<Calculation of PISA Value>

Next, from the recorded 6-point periodontal disease test results, PISA (periodontal inflamed surface area) was calculated as shown in Table 2 by referring to known literature (Nesse, W., Abbas, F., van der Ploeg, I., Spijkervet, F. K., Dijkstra, P. U., Vissink, A.: Periodontal inflamed surface area: quantifying inflammatory burden. Journal of Clinical Periodontology, 35: 668-673, 2008.). The PISA value indicates the area of inflammation of the periodontal tissue of the entire oral cavity in square millimeters (mm$^2$).
Table 3 collectively shows the PISA values of 46 subjects.

| PPD | tooth | 18 | 17 | 16 | 15 | 14 | 13 | 12 | 11 |
|---|---|---|---|---|---|---|---|---|---|
| | buccal | | 3 3 3 | 3 1 2 | 2 1 2 | 2 1 3 | 3 1 2 | 2 1 2 | 2 1 2 |
| | palatinal | | 3 3 3 | 3 3 3 | 3 2 3 | 3 2 3 | 4 2 2 | 2 2 2 | 2 1 2 |

| PPD | tooth | 21 | 22 | 23 | 24 | 25 | 26 | 27 | 28 |
|---|---|---|---|---|---|---|---|---|---|
| | buccal | 2 1 2 | 3 1 2 | 2 1 | 2 2 3 | | 4 2 4 | 4 2 3 | |
| | palatinal | 3 1 2 | 2 1 2 | 2 1 3 | 3 2 3 | | 3 3 4 | 3 4 4 | |

| PPD | tooth | 48 | 47 | 46 | 45 | 44 | 43 | 42 | 41 |
|---|---|---|---|---|---|---|---|---|---|
| | lingual | | 3 5 7 | 3 2 3 | 3 2 4 | 3 2 3 | 3 2 3 | 2 1 2 | 2 1 2 |
| | buccal | | 4 6 7 | 4 4 3 | 3 2 3 | 3 2 2 | 3 1 2 | 2 1 2 | 2 1 2 |

| PPD | tooth | 31 | 32 | 33 | 34 | 35 | 36 | 37 | 38 |
|---|---|---|---|---|---|---|---|---|---|
| | lingual | 2 1 2 | 2 1 2 | 2 1 2 | 2 2 3 | 3 2 3 | 3 3 3 | 5 3 3 | |
| | buccal | 2 1 2 | 2 1 2 | 2 1 2 | 2 2 2 | 3 2 3 | 3 2 3 | 5 3 3 | |

| tooth | 18 | 17 | 16 | 15 | 14 | 13 | 12 | 11 |
|---|---|---|---|---|---|---|---|---|
| surface area (mm2) | 0 | 88.7854 | 59.0216 | 60.9088 | 44.0797 | 44.4681 | 31.3144 | 23.1588 |

| tooth | 21 | 22 | 23 | 24 | 25 | 26 | 27 | 28 |
|---|---|---|---|---|---|---|---|---|
| surface area (mm2) | 25.8961 | 31.3144 | 34.2884 | 47.0599 | 0.0000 | 94.3231 | 101.0040 | 0 |

| tooth | 48 | 47 | 46 | 45 | 44 | 43 | 42 | 41 |
|---|---|---|---|---|---|---|---|---|
| surface area (mm2) | 0 | 158.2769 | 49.6619 | 59.2711 | 47.1632 | 45.2822 | 26.0392 | 25.9141 |

| tooth | 31 | 32 | 33 | 34 | 35 | 36 | 37 | 38 |
|---|---|---|---|---|---|---|---|---|
| surface area (mm2) | 25.9141 | 26.0392 | 33.9744 | 41.4358 | 55.3020 | 40.0679 | 64.7415 | 0 |

| tooth | PESA | nr of sites with BOP | PISA (mm2) |
|---|---|---|---|
| 18 | 0 | | 0.00 |
| 17 | 88.79 | 3 | 44.39 |
| 16 | 59.02 | 2 | 19.67 |
| 15 | 60.91 | 2 | 20.30 |
| 14 | 44.08 | 2 | 14.69 |
| 13 | 44.47 | 2 | 14.82 |
| 12 | 31.31 | 1 | 5.22 |
| 11 | 23.16 | 1 | 3.86 |
| 21 | 25.9 | 2 | 8.63 |
| 22 | 31.31 | 1 | 5.22 |
| 23 | 34.29 | 1 | 5.71 |
| 24 | 47.06 | 2 | 15.69 |
| 25 | 0 | 0 | 0.00 |
| 26 | 94.32 | 3 | 47.16 |
| 27 | 101 | 2 | 33.67 |
| 28 | 0 | | 0.00 |
| 38 | 0 | | 0.00 |
| 37 | 64.74 | 3 | 32.37 |
| 36 | 40.07 | 1 | 6.68 |
| 35 | 55.3 | 3 | 27.65 |
| 34 | 41.44 | 3 | 20.72 |
| 33 | 33.97 | 0 | 0.00 |
| 32 | 26.04 | 2 | 8.68 |
| 31 | 25.91 | 4 | 17.28 |
| 41 | 25.91 | 3 | 12.96 |
| 42 | 26.04 | 1 | 4.34 |
| 43 | 45.28 | 2 | 15.09 |
| 44 | 47.16 | 1 | 7.86 |
| 45 | 59.27 | 2 | 19.76 |
| 46 | 49.66 | 1 | 8.28 |
| 47 | 158.3 | 4 | 105.52 |
| 48 | 0 | | 0.00 |

-continued

| tooth | PESA | nr of sites with BOP | PISA (mm2) |
|---|---|---|---|
| Total Periodontal Epithelial Surface Area (mm2) | | | |
| 1384.7 | | | |
| Total Periodontal Inflamed Surface Area (mm2) | | | |
| 526.2 | | | |

TABLE 3

| Sample No. | PISA(mm2) |
|---|---|
| 1 | 477 |
| 2 | 20 |
| 3 | 215 |
| 4 | 250 |
| 5 | 167 |
| 6 | 77 |
| 7 | 161 |
| 8 | 318 |
| 9 | 180 |
| 10 | 1050 |
| 11 | 203 |
| 12 | 535 |
| 13 | 1154 |
| 14 | 1018 |
| 15 | 382 |
| 16 | 2814 |
| 17 | 1172 |
| 18 | 147 |
| 19 | 1570 |
| 20 | 1120 |
| 21 | 164 |
| 22 | 1205 |
| 23 | 1321 |
| 24 | 320 |
| 25 | 571 |
| 26 | 73 |
| 27 | 3775 |
| 28 | 2076 |
| 29 | 445 |
| 30 | 768 |
| 31 | 680 |
| 32 | 915 |
| 33 | 3335 |
| 34 | 2326 |
| 35 | 395 |
| 36 | 3420 |
| 37 | 1447 |
| 38 | 309 |
| 39 | 846 |
| 40 | 369 |
| 41 | 223 |
| 42 | 3735 |
| 43 | 52 |
| 44 | 100 |
| 45 | 597 |
| 46 | 526 |

Detection of Oral Bacteria in Saliva Sample
<Extraction of DNA from Saliva>
1-1 Bead Disruption To a 2-ml tube, 400 µl of the above saliva, 400 µl of sterilized water, and 0.4 g of 0.1-mm glass beads (#GB-01 manufactured by TOMY SEIKO CO., LTD.) were added, and the lid was tightly closed. Thereafter, bead disruption was performed for 5 minutes at 3200 rpm by setting the tube in Micro Smash (manufactured by TOMY SEIKO CO., LTD.). Then, the tube was set in a centrifuge to drop beads and the like, and lightly centrifuged at 1800 g for 5 minutes. The supernatant was dispensed in an amount of 400 µl into a new 1.5 ml tube.

1-2 Enzyme Treatment

The sample 1-1 was mixed with 90 µl of Buffer ATL from Qiagen, 10 µl of Proteinase K, and 100 µl of Buffer AL to adjust a total volume to 600 and the mixture was incubated at 56° C. for 1 hour.

1-3 Column Purification

After incubation, 120 µl of ethanol was added and vortexed. Then, using a QIAamp DNA Micro Kit (Qiagen), a total amount of 720 µl was put into the column of the kit, the mixture was centrifuged at 14000 rpm for 1 minute, and the eluate was discarded. Then, in accordance with the protocol of the kit, the column was washed with 500 µl of Buffer AW1 and 500 µl of Buffer AW2. Subsequently, after the column in an empty state was centrifuged at 14000 rpm for 1 minute, DNA was eluted with 20 µl of sterilized water. About 4 to 20 ng/µl of a DNA solution was obtained from each of the 46 samples.

<Amplification Reaction of Bacterial DNA>

The DNA solution was diluted to 20 pg/µl and used as a PCR template. In order to amplify the sequence of the detection target region of 16S rRNA of an oral bacterium in each sample, PCR was carried out under the reaction conditions with the reaction solution composition described below. PCR was performed using, as a PCR kit, Premix Ex Taq (trademark) Hot Start Version (manufactured by Takara Holdings Inc.) and the ProFlex (trademark) PCR System (manufactured by Thermo Fisher Scientific). As primers, primers having the following sequences were used. The forward primer used had the 5' end labeled with Cy5.

Forward Primer (for Bacterial Amplification):

(SEQ ID NO: 32)
5'-Cy5-TCCTACGGGAGGCAGCAGT-3'

Reveres Primer (for Bacterial Amplification):

(SEQ ID NO: 33)
5'-CAGGGTATCTAATCCTGTTTGCTACC-3'

Forward Primer (for Absolute Load Index Amplification):

(SEQ ID NO: 34)
5'-Cy5-GAGAAGCCTACACAAACGTAACGTC-3'

Reveres primer (for absolute load index amplification):

(SEQ ID NO: 35)
5'-CTCTAAAGACCGCTCTATCTCGG-3'

<Reaction Solution Composition>

| | |
|---|---|
| 2 × Premix Ex Taq (registered trademark) Hot Start Version | 10 µL |
| 4 µM forward primer (for bacterial amplification) | 1 µL |
| 4 µM reverse primer (for bacterial amplification) | 1 µL |
| 4 µM forward primer (for absolute load index amplification) | 1 µL |
| 4 µM reverse primer (for absolute load index amplification) | 1 µL |
| Template DNA | 5 µL |
| Absolute load index | 1 µL |
| Total | 20 µL |

<Reaction Conditions>

After heating at 95° C. for 1 minute, a total of 40 cycles of "dissociation: 98° C. (10 sec)→annealing: 55° C. (30 sec)→synthesis: 72° C. (20 sec)" were performed, and the mixture was cooled at 4° C., thereby obtaining an amplification product.

<DNA Chip: Production of DNA Chip for Detecting Oral Bacteria>

A through-hole type DNA chip was produced by a method similar to the method described in Example 1 of JP Patent Publication (Kokai) No. 2007-74950A (method for detecting methylated DNA and/or unmethylated DNA).

Note that as oligonucleotide probes mounted herein, probes having the sequence information shown in Table 4 were used.

TABLE 4

| SEQ ID NO | Sequence | Probe name |
|---|---|---|
| 1 | TTCAATGCAATACTCGTATC | Porphyromonas gingivalis |
| 2 | CACGTATCTCATTTTATTCCCCTGT | Tannerella forsythia |
| 3 | CCTCTTCTTCTTATTCTTCATCTGC | Treponema denticola |
| 4 | GCCTTCGCAATAGGTATT | Campylobacter gracilis |
| 5 | GTCATAATTCTTTCCCAAGA | Campylobacter rectus |
| 6 | CAATGGGTATTCTTCTTGAT | Campylobacter showae |
| 7 | TAGTTATACAGTTTCCAACG | Fusobacterium nucleatum subsp. vincentii |
| 8 | CCAGTACTCTAGTTACACA | Fusobacterium nucleatum subsp. polymorphum |
| 9 | TTTCTTTCTTCCCAACTGAA | Fusobacterium nucleatum subsp. animalis |
| 10 | TACATTCCGAAAAACGTCAT | Fusobacterium nucleatum subsp. nucleatum |
| 11 | TATGCAGTTTCCAACGCAA | Fusobacterium periodonticum |
| 12 | CGAAGGGTAAATGCAAAAAGGC | Prevotella intermedia |
| 13 | CTTTATTCCCACATAAAAGC | Prevotella nigrescens |
| 14 | AAGTACCGTCACTGTGTG | Streptococcus constellatus |
| 15 | GTCAATTTGGCATGCTATTAACACACC | Aggregatibacter actinomycetemcomitans |
| 16 | CCCAAGCAGTTCTATGGT | Campylobacter concisus |

TABLE 4-continued

| SEQ ID NO | Sequence | Probe name |
|---|---|---|
| 17 | TACACGTACACCTTATTCTT | Capnocytophaga gingivalis |
| 18 | CAACCATTCAAGACCAACA | Capnocytophaga ochracea |
| 19 | TCAAAGGCAGTTGCTTAGT | Capnocytophaga sputigena |
| 20 | CTCTAGCTATCCAGTTCAG | Eikenella corrodens |
| 21 | CACCCGTTCTTCTCTTACA | Streptococcus gordonii |
| 22 | ACAGTATGAACTTTCCATTCT | Streptococcus intermedius |
| 23 | TCTCCCCTCTTGCACTCA | Streptococcus mitis |
| 24 | TCCCCTCTTGCACTCAAGT | Streptococcus mitis bv 2 |
| 25 | AAGTCAGCCCGTACCCA | Actinomyces odontolyticus |
| 26 | TCCTTCTAACTGTTCGC | Veillonella parvula |
| 27 | CCACCCACAAGGAGCAG | Actinomyces naeslundii II |
| 28 | TTCGCATTAGGCACGTTC | Selenomonas noxia |
| 29 | CACACGTTCTTGACTTAC | Streptococcus mutans |
| 30 | CTATTCGACCAGCGATATCACTACGTAGGC | Control DNA |
| 31 | CGTATTACCGCGGCTGCTGGCAC | Total bacteria |

<Hybridization with DNA Chip>

A hybridization solution was prepared by mixing the respective solutions as described below.

| | |
|---|---|
| DNA amplification product obtained after PCR | 20 µL |
| 1M Tris-HCl | 48 µL |
| 1M NaCl | 48 µL |
| 0.5% Tween20 | 20 µL |
| Water | 65 µL |
| Total | 200 µL |

An automatic hybrid washing apparatus (type: AHF-200, manufactured by Mitsubishi Chemical Corporation) was used for hybridization and washing of the DNA chip.

The hybridization solution in an amount of 200 µL was brought into contact with the DNA chip, followed by hybridization at 50° C. for 16 hours.

After the hybridization, the DNA chip was washed under the following conditions. Washing with 1000 µL of 0.24 M Tris.HCl/0.24 M NaCl/0.05% Tween-20 solution for 220 seconds was repeated 12 times. Then, washing with 1000 µL of 0.24 M Tris.HCl/0.24 M NaCl for 220 seconds was repeated 4 times.

After the completion of washing, each chip was transferred to a 0.24M Tris.HCl/0.24M NaCl mixed solution at room temperature.

Detection

After the washing, the fluorescence intensity of each spot of the DNA chip was measured under the following conditions using Genopal Reader (type: GR-S1, manufactured by Mitsubishi Chemical Corporation).

Detection Conditions

Center excitation wavelength: 633 nm
Exposure time: 0.1, 1, 4, and 40 seconds

Results

The fluorescence intensity of a spot with a probe mounted thereon for a bacterium to be detected was divided by the background value (the median of the fluorescence intensities of spots without a probe), thereby calculating the SN ratio of the fluorescence intensity derived from hybridization (hereinafter referred to as "signal intensity").

Prediction of PISA Value Based on Bacterial Load

Correlation Analysis of PISA Value and Bacterial Load

First, the PISA value and the SN ratio data indicating the bacterial load of each bacterium were associated with each sample. The results are shown in Table 5.

TABLE 5

| Sample No. | PISA | Control DNA | Total bacteria | Porphyromonas gingivalis | Tannerella forsythia | Treponema denticola | Campylobacter gracilis | Campylobacter rectus | Campylobacter showae | Fusobacterium nucleatum subsp. vincentii | Fusobacterium nucleatum subsp. polymorphum | Fusobacterium nucleatum subsp. animalis | Fusobacterium nucleatum subsp. nucleatum | Fusobacterium periodonticum | Prevotella intermedia |
|---|---|---|---|---|---|---|---|---|---|---|---|---|---|---|---|
| 1 | 477 | 775.5 | 1818.7 | 1.5 | 1.4 | 1.3 | 1.6 | 1.2 | 1.0 | 1.1 | 1.2 | 1.4 | 1.1 | 1.0 | 1.0 |
| 2 | 20 | 576.4 | 1871.3 | 1.4 | 1.5 | 1.1 | 1.4 | 1.1 | 1.0 | 1.2 | 1.1 | 1.6 | 1.5 | 1.1 | 1.0 |
| 3 | 215 | 919.0 | 2089.9 | 1.4 | 2.6 | 3.0 | 1.5 | 1.5 | 1.0 | 3.8 | 1.5 | 4.7 | 9.1 | 1.9 | 1.2 |
| 4 | 250 | 940.1 | 2219.2 | 1.3 | 8.0 | 4.0 | 1.6 | 1.3 | 1.0 | 3.5 | 1.7 | 5.4 | 10.8 | 1.6 | 1.1 |
| 5 | 167 | 750.1 | 2246.7 | 1.4 | 1.3 | 1.3 | 1.5 | 1.2 | 1.0 | 1.3 | 1.2 | 2.0 | 2.0 | 1.1 | 1.0 |
| 6 | 77 | 865.9 | 2228.3 | 1.5 | 1.3 | 1.3 | 1.6 | 1.3 | 1.0 | 1.9 | 1.6 | 3.1 | 17.2 | 2.5 | 1.2 |
| 7 | 161 | 1200.6 | 1518.4 | 2.1 | 1.1 | 1.4 | 1.5 | 1.2 | 1.0 | 1.2 | 1.4 | 3.9 | 62.9 | 2.3 | 1.1 |
| 8 | 318 | 842.4 | 2473.2 | 1.3 | 1.1 | 1.7 | 1.6 | 1.2 | 1.0 | 1.2 | 1.2 | 1.8 | 3.8 | 1.2 | 1.0 |
| 9 | 180 | 664.5 | 2084.0 | 1.5 | 1.7 | 1.3 | 1.6 | 1.2 | 1.0 | 1.4 | 1.2 | 1.8 | 7.4 | 1.7 | 1.1 |
| 10 | 1050 | 1062.4 | 2002.4 | 1.6 | 13.5 | 9.8 | 1.5 | 6.0 | 1.1 | 12.3 | 1.8 | 42.4 | 30.1 | 3.5 | 1.0 |
| 11 | 203 | 657.2 | 2273.0 | 1.6 | 3.9 | 3.6 | 1.6 | 1.7 | 1.1 | 1.2 | 1.4 | 1.8 | 7.1 | 1.6 | 1.1 |
| 12 | 535 | 1143.7 | 1904.5 | 1.7 | 21.1 | 15.4 | 1.5 | | | | | | | | |
| 13 | 1154 | 1104.7 | 2201.8 | 1.4 | 13.8 | 33.7 | 1.6 | | | | | | | | |
| 14 | 1018 | 948.3 | 1994.4 | 5.0 | 19.2 | 35.8 | 1.5 | | | | | | | | |
| 15 | 382 | 831.9 | 2233.3 | 1.2 | 2.6 | 1.2 | 1.5 | | | | | | | | |
| 16 | 2814 | 1038.0 | 1743.3 | 2.1 | 70.4 | 112.8 | 1.5 | | | | | | | | |
| 17 | 1172 | 1174.1 | 1882.9 | 2.6 | 11.3 | 7.3 | 1.5 | | | | | | | | |
| 18 | 147 | 862.3 | 2340.0 | 1.4 | 3.2 | 1.3 | 1.6 | | | | | | | | |
| 19 | 1570 | 1381.4 | 2132.8 | 4.8 | 5.7 | 3.2 | 1.6 | | | | | | | | |
| 20 | 1120 | 941.6 | 2295.5 | 1.3 | 6.8 | 2.3 | 1.6 | | | | | | | | |
| 21 | 164 | 785.6 | 2202.2 | 1.3 | 1.1 | 1.2 | 1.6 | | | | | | | | |
| 22 | 1205 | 1445.7 | 1921.0 | 1.7 | 8.1 | 1.5 | 1.5 | | | | | | | | |
| 23 | 1321 | 1181.4 | 1999.4 | 2.7 | 13.1 | 23.8 | 1.6 | | | | | | | | |
| 24 | 320 | 871.8 | 2150.1 | 1.2 | 1.6 | 1.1 | 1.4 | | | | | | | | |
| 25 | 571 | 1179.3 | 1903.6 | 2.2 | 2.3 | 1.7 | 1.5 | | | | | | | | |
| 26 | 73 | 1379.4 | 2261.9 | 1.8 | 4.2 | 1.5 | 1.7 | | | | | | | | |
| 27 | 3775 | 183.8 | 1844.6 | 1.3 | 3.1 | 1.3 | 1.4 | | | | | | | | |
| 28 | 2076 | 698.7 | 1932.7 | 1.2 | 0.9 | 1.1 | 1.4 | | | | | | | | |
| 29 | 445 | 566.3 | 2003.9 | 1.1 | 4.2 | 1.2 | 1.4 | | | | | | | | |
| 30 | 768 | 536.4 | 2279.7 | 1.3 | 5.1 | 1.2 | 1.5 | | | | | | | | |
| 31 | 680 | 956.5 | 1266.5 | 2.6 | 60.1 | 42.1 | 1.2 | | | | | | | | |
| 32 | 915 | 909.3 | 2112.6 | 1.3 | 4.7 | 1.5 | 1.5 | | | | | | | | |
| 33 | 3335 | 1055.0 | 1969.3 | 7.8 | 72.5 | 223.0 | 1.5 | | | | | | | | |
| 34 | 2326 | 809.7 | 2230.9 | 1.5 | 4.5 | 12.1 | 1.5 | | | | | | | | |
| 35 | 395 | 824.3 | 2109.2 | 1.2 | 2.0 | 2.4 | 1.5 | | | | | | | | |
| 36 | 3420 | 1273.6 | 2402.9 | 3.7 | 45.5 | 54.7 | 1.7 | | | | | | | | |
| 37 | 1447 | 1180.0 | 2532.5 | 2.5 | 8.6 | 19.4 | 1.7 | | | | | | | | |
| 38 | 309 | 750.7 | 2378.4 | 1.9 | 1.9 | 2.7 | 1.6 | | | | | | | | |
| 39 | 846 | 846.1 | 2595.5 | 1.4 | 3.1 | 4.4 | 1.7 | | | | | | | | |
| 40 | 369 | 912.9 | 2340.5 | 1.3 | 4.0 | 15.3 | 1.5 | | | | | | | | |
| 41 | 223 | 896.4 | 2595.5 | 1.4 | 1.2 | 1.8 | 1.7 | | | | | | | | |
| 42 | 3735 | 1267.9 | 2913.9 | 7.1 | 95.4 | 253.9 | 1.7 | | | | | | | | |
| 43 | 52 | 827.2 | 2512.2 | 3.4 | 2.2 | 4.1 | 1.7 | | | | | | | | |
| 44 | 100 | 1023.3 | 2454.0 | 1.4 | 1.1 | 1.5 | 1.7 | | | | | | | | |
| 45 | 597 | 1105.6 | 2423.0 | 1.3 | 1.4 | 1.2 | 1.6 | | | | | | | | |
| 46 | 526 | 1034.7 | 2131.6 | 1.5 | 1.5 | 1.4 | 1.6 | | | | | | | | |

TABLE 5-continued

| | | | | | | | |
|---|---|---|---|---|---|---|---|
| 1.2 | 1.0 | 5.1 | 3.1 | 24.1 | 112.7 | 2.6 | 1.0 |
| 1.3 | 1.0 | 2.8 | 4.3 | 6.9 | 69.6 | 1.8 | 1.1 |
| 3.7 | 1.1 | 3.8 | 3.4 | 11.9 | 83.4 | 2.7 | 1.8 |
| 1.5 | 1.0 | 1.6 | 1.9 | 1.7 | 9.8 | 1.2 | 1.0 |
| 2.0 | 1.0 | 1.4 | 1.5 | 4.0 | 34.7 | 1.2 | 1.0 |
| 1.2 | 1.0 | 2.3 | 1.5 | 18.6 | 68.5 | 1.9 | 1.0 |
| 1.6 | 1.0 | 3.1 | 2.1 | 3.1 | 14.4 | 1.7 | 1.1 |
| 9.4 | 1.1 | 6.8 | 1.3 | 32.8 | 35.8 | 3.1 | 1.1 |
| 1.5 | 1.0 | 1.3 | 1.5 | 1.9 | 12.4 | 1.8 | 1.0 |
| 1.2 | 1.0 | 1.3 | 1.4 | 1.9 | 15.2 | 2.3 | 1.1 |
| 1.2 | 1.0 | 3.6 | 1.9 | 15.0 | 35.7 | 1.7 | 1.1 |
| 6.8 | 1.2 | 6.1 | 3.4 | 16.1 | 39.3 | 2.9 | 1.1 |
| 1.1 | 0.9 | 1.5 | 1.2 | 1.6 | 2.0 | 1.1 | 1.0 |
| 5.1 | 1.0 | 1.9 | 1.6 | 7.6 | 36.1 | 1.7 | 1.0 |
| 2.0 | 1.0 | 8.2 | 2.0 | 21.2 | 58.2 | 4.4 | 1.1 |
| 1.3 | 1.0 | 1.1 | 1.2 | 1.7 | 7.4 | 1.6 | 1.0 |
| 1.1 | 0.9 | 0.9 | 1.1 | 1.1 | 0.9 | 0.9 | 1.0 |
| 1.1 | 1.0 | 1.4 | 1.3 | 1.6 | 3.9 | 1.2 | 0.9 |
| 1.4 | 1.1 | 1.1 | 1.2 | 1.3 | 2.0 | 1.0 | 1.1 |
| 4.1 | 1.4 | 2.1 | 1.7 | 6.1 | 61.1 | 1.7 | 1.7 |
| 1.2 | 1.0 | 1.3 | 1.2 | 1.7 | 8.6 | 1.5 | 1.1 |
| 36.1 | 1.2 | 5.9 | 1.8 | 63.6 | 136.2 | 2.5 | 1.2 |
| 1.4 | 1.0 | 6.3 | 1.7 | 21.7 | 22.2 | 2.7 | 1.2 |
| 1.5 | 1.0 | 2.1 | 1.4 | 2.3 | 5.4 | 1.4 | 1.0 |
| 33.7 | 1.1 | 4.2 | 1.8 | 68.6 | 160.6 | 2.1 | 1.1 |
| 8.1 | 1.1 | 9.5 | 2.7 | 38.6 | 133.3 | 7.4 | 2.0 |
| 11.0 | 1.5 | 2.7 | 1.7 | 6.9 | 40.6 | 3.4 | 1.1 |
| 2.0 | 1.1 | 2.9 | 2.0 | 9.0 | 183.4 | 12.4 | 1.1 |
| 4.4 | 1.1 | 3.2 | 5.0 | 6.7 | 105.0 | 4.8 | 1.0 |
| 20.9 | 2.1 | 1.6 | 1.7 | 3.2 | 55.7 | 5.4 | 1.1 |
| 23.1 | 1.3 | 6.3 | 3.2 | 48.9 | 231.6 | 6.1 | 1.2 |
| 28.2 | 1.6 | 3.4 | 1.8 | 11.2 | 91.4 | 6.6 | 4.6 |
| 8.3 | 1.3 | 1.8 | 1.7 | 5.6 | 109.9 | 7.2 | 1.2 |
| 1.5 | 1.0 | 9.7 | 1.8 | 37.2 | 22.8 | 3.5 | 1.1 |
| 7.2 | 1.1 | 5.4 | 1.6 | 25.7 | 24.2 | 2.8 | 1.1 |

| Prevotella nigrescens | Streptococcus constellatus | Aggregatibacter actinomycetemcomitans | Campylobacter concisus | Capnocytophaga gingivalis | Capnocytophaga ochracea | Capnocytophaga sputigena | Eikenella corrodens |
|---|---|---|---|---|---|---|---|
| 1.0 | 1.4 | 1.5 | 1.6 | 1.1 | 1.1 | 1.0 | 0.9 |
| 1.1 | 1.1 | 2.0 | 1.0 | 1.0 | 1.0 | 1.0 | 1.0 |
| 1.0 | 1.7 | 1.8 | 1.1 | 1.2 | 1.1 | 1.0 | 1.1 |
| 1.0 | 2.7 | 1.4 | 1.5 | 1.1 | 1.1 | 1.0 | 1.1 |
| 0.9 | 6.9 | 1.4 | 1.0 | 1.1 | 1.1 | 1.1 | 1.0 |
| 1.0 | 2.9 | 1.4 | 1.8 | 1.1 | 1.5 | 1.6 | 1.0 |
| 1.0 | 6.5 | 2.1 | 2.7 | 1.5 | 1.1 | 1.7 | 1.1 |
| 0.9 | 7.9 | 1.5 | 1.1 | 1.2 | 1.1 | 1.2 | 1.0 |
| 1.0 | 2.1 | 2.2 | 1.1 | 1.1 | 1.1 | 1.2 | 1.1 |
| 1.2 | 17.9 | 1.1 | 1.2 | 3.0 | 1.2 | 1.1 | 1.0 |
| 1.0 | 2.3 | 1.4 | 1.1 | 1.3 | 1.1 | 1.4 | 1.1 |
| 1.0 | 3.8 | 1.2 | 2.3 | 1.8 | 2.0 | 2.2 | 1.1 |
| 1.0 | 2.7 | 1.2 | 1.0 | 1.2 | 1.6 | 1.6 | 1.1 |
| 1.0 | 3.2 | 1.1 | 1.7 | 2.1 | 1.0 | 1.6 | 1.1 |
| 1.0 | 2.1 | 1.6 | 1.2 | 1.3 | 1.0 | 1.0 | 1.0 |
| 1.0 | 6.1 | 1.2 | 1.0 | 1.2 | 1.9 | 2.4 | 1.1 |
| 1.0 | 3.5 | 1.3 | 1.8 | 1.1 | 1.1 | 1.9 | 1.0 |
| 1.1 | 1.9 | 1.4 | 1.4 | 1.7 | 1.3 | 2.7 | 1.3 |
| 0.9 | 1.8 | 7.9 | 2.0 | 1.4 | 1.1 | 1.2 | 1.0 |
| 1.0 | 1.3 | 1.5 | 1.4 | 1.3 | 1.1 | 1.1 | 1.0 |
| 1.0 | 1.2 | 1.3 | 1.0 | 1.1 | 1.1 | 1.2 | 1.0 |
| 1.0 | 5.9 | 1.2 | 1.0 | 1.0 | 1.0 | 1.0 | 0.9 |
| 1.1 | 1.5 | 2.1 | 3.6 | 5.9 | 1.1 | 3.4 | 1.2 |
| 0.9 | 1.2 | 1.2 | 1.1 | 1.2 | 1.1 | 1.0 | 1.0 |
| 1.0 | 2.6 | 5.7 | 2.3 | 1.3 | 1.5 | 2.1 | 1.1 |
| 1.1 | 6.9 | 1.9 | 3.8 | 1.7 | 1.5 | 2.2 | 1.1 |
| 1.0 | 2.0 | 1.1 | 1.0 | 1.6 | 1.0 | 2.5 | 1.0 |
| 0.9 | 1.4 | 1.2 | 1.1 | 1.0 | 1.0 | 1.1 | 1.0 |
| 1.1 | 3.5 | 1.8 | 0.9 | 0.9 | 1.0 | 1.0 | 0.9 |
| 1.0 | 1.2 | 1.4 | 1.1 | 1.4 | 1.1 | 1.3 | 1.0 |
| 1.2 | 3.6 | 0.9 | 0.8 | 0.8 | 1.1 | 1.6 | 0.9 |
| 1.0 | 1.2 | 1.2 | 1.4 | 1.6 | 1.0 | 1.2 | 1.0 |
| 1.0 | 1.6 | 1.5 | 2.1 | 1.3 | 1.7 | 2.6 | 1.0 |
| 1.4 | 5.9 | 1.5 | 1.7 | 1.4 | 1.0 | 1.6 | 1.1 |
| 1.0 | 1.4 | 1.2 | 1.0 | 4.0 | 1.4 | 2.8 | 1.0 |
| 1.2 | 1.7 | 5.9 | 1.6 | 1.4 | 2.2 | 3.0 | 1.5 |
| 1.1 | 4.4 | 1.9 | 6.5 | 1.1 | 1.6 | 2.8 | 1.4 |
| 1.4 | 1.2 | 1.2 | 2.5 | 20.5 | 1.3 | 7.3 | 2.3 |
| 1.1 | 1.6 | 1.4 | 3.5 | 1.8 | 2.2 | 3.1 | 1.0 |
| 1.0 | 1.8 | 1.2 | 2.5 | 1.1 | 1.2 | 1.1 | 1.1 |
| 1.0 | 1.5 | 1.4 | 7.5 | 1.3 | 1.4 | 4.7 | 1.0 |

TABLE 5-continued

| 1.0 | 2.1 | 1.3 | 1.2 | 5.7 | 1.4 | 4.9 | 1.1 |
|---|---|---|---|---|---|---|---|
| 1.3 | 2.7 | 4.0 | 9.0 | 11.9 | 2.4 | 6.4 | 1.4 |
| 1.4 | 1.3 | 1.4 | 5.8 | 1.7 | 1.2 | 2.7 | 1.1 |
| 1.6 | 4.6 | 1.5 | 2.6 | 1.6 | 1.8 | 1.6 | 1.6 |
| 1.7 | 5.5 | 1.4 | 7.1 | 2.5 | 1.4 | 2.9 | 2.7 |

| *Streptococcus gordonii* | *Streptococcus intermedius* | *Streptococcus mitis* | *Streptococcus mitis* bv 2 | *Actinomyces odontolyticus* | *Veillonella parvula* | *Actinomyces naeslundii* II | *Selenomonas noxia* | *Streptococcus mutans* |
|---|---|---|---|---|---|---|---|---|
| 21.9 | 1.2 | 2.6 | 13.1 | 58.4 | 1.1 | 98.7 | 1.1 | 22.3 |
| 11.5 | 1.1 | 2.3 | 13.8 | 152.3 | 1.0 | 5.1 | 1.0 | 12.2 |
| 8.8 | 2.4 | 3.2 | 17.1 | 104.0 | 1.1 | 3.5 | 1.0 | 14.3 |
| 11.3 | 3.0 | 3.3 | 12.6 | 41.3 | 1.1 | 2.0 | 1.3 | 6.3 |
| 19.2 | 12.6 | 80.2 | 168.0 | 46.3 | 1.1 | 3.6 | 1.1 | 1.3 |
| 15.5 | 3.6 | 36.1 | 80.7 | 42.1 | 1.1 | 6.0 | 1.2 | 15.9 |
| 96.9 | 1.2 | 2.8 | 5.1 | 8.1 | 1.1 | 10.0 | 1.0 | 5.6 |
| 30.0 | 3.8 | 157.5 | 337.6 | 60.1 | 1.1 | 7.4 | 1.0 | 4.6 |
| 16.1 | 7.3 | 106.3 | 236.0 | 176.8 | 1.1 | 3.0 | 1.1 | 7.3 |
| 42.7 | 3.7 | 9.7 | 23.3 | 14.4 | 1.3 | 3.4 | 2.1 | 0.9 |
| 18.5 | 3.2 | 70.0 | 146.5 | 39.4 | 1.1 | 3.6 | 1.1 | 5.8 |
| 39.1 | 26.1 | 2.8 | 5.7 | 7.0 | 1.2 | 11.8 | 2.5 | 14.8 |
| 67.9 | 12.8 | 18.7 | 38.1 | 7.9 | 1.2 | 24.5 | 1.4 | 3.3 |
| 83.0 | 11.2 | 10.5 | 21.6 | 5.0 | 1.1 | 15.2 | 1.4 | 2.6 |
| 28.6 | 13.5 | 121.0 | 249.6 | 89.6 | 1.0 | 4.4 | 1.1 | 6.2 |
| 66.2 | 5.0 | 2.3 | 4.3 | 5.6 | 1.6 | 3.6 | 2.2 | 7.1 |
| 31.1 | 4.0 | 1.4 | 2.1 | 4.7 | 1.1 | 1.5 | 1.9 | 10.4 |
| 30.1 | 4.5 | 8.5 | 22.0 | 23.5 | 1.2 | 15.6 | 1.1 | 31.8 |
| 162.8 | 4.1 | 8.6 | 15.9 | 6.7 | 1.2 | 11.8 | 2.0 | 5.4 |
| 29.8 | 3.3 | 38.4 | 82.6 | 52.8 | 1.1 | 9.6 | 1.0 | 9.1 |
| 9.5 | 1.3 | 31.3 | 73.4 | 29.0 | 1.1 | 2.5 | 1.1 | 18.1 |
| 22.4 | 1.1 | 4.3 | 10.8 | 9.9 | 1.0 | 1.6 | 1.0 | 4.8 |
| 84.8 | 13.8 | 15.7 | 30.4 | 9.8 | 1.2 | 6.0 | 1.0 | 10.2 |
| 23.3 | 11.1 | 42.9 | 90.0 | 23.7 | 1.0 | 7.1 | 1.0 | 26.3 |
| 74.0 | 2.7 | 6.0 | 11.6 | 3.5 | 1.1 | 48.2 | 1.5 | 4.7 |
| 33.5 | 5.4 | 19.5 | 36.4 | 9.5 | 1.4 | 41.2 | 2.0 | 13.5 |
| 29.3 | 3.6 | 1.5 | 2.0 | 4.0 | 1.1 | 5.1 | 1.0 | 1.2 |
| 41.3 | 7.2 | 109.1 | 215.8 | 19.7 | 1.0 | 54.5 | 0.9 | 5.2 |
| 10.9 | 4.2 | 60.8 | 158.3 | 131.9 | 1.0 | 6.3 | 1.0 | 22.0 |
| 17.5 | 3.8 | 26.6 | 75.1 | 45.4 | 1.1 | 3.8 | 1.0 | 5.3 |
| 37.1 | 4.1 | 2.0 | 3.8 | 2.5 | 1.1 | 13.9 | 2.1 | 2.2 |
| 37.3 | 4.6 | 24.6 | 51.1 | 19.5 | 1.0 | 6.8 | 1.1 | 6.6 |
| 51.5 | 13.1 | 1.6 | 3.0 | 2.9 | 1.6 | 1.5 | 1.8 | 1.2 |
| 37.7 | 10.1 | 10.9 | 22.8 | 12.8 | 1.7 | 6.1 | 1.3 | 4.6 |
| 20.0 | 3.1 | 60.4 | 124.7 | 20.5 | 1.1 | 4.3 | 1.0 | 7.1 |
| 41.6 | 18.6 | 1.6 | 2.2 | 2.2 | 1.4 | 6.0 | 14.8 | 1.9 |
| 22.7 | 5.0 | 8.5 | 17.7 | 12.4 | 1.9 | 27.1 | 1.7 | 6.0 |
| 11.1 | 4.4 | 24.8 | 50.3 | 12.6 | 1.1 | 7.1 | 1.9 | 1.7 |
| 12.5 | 1.4 | 28.1 | 53.7 | 21.0 | 1.2 | 2.7 | 1.3 | 5.5 |
| 32.1 | 2.1 | 63.3 | 125.8 | 11.7 | 1.1 | 27.9 | 1.0 | 4.8 |
| 16.0 | 1.2 | 52.7 | 105.2 | 31.9 | 1.1 | 1.9 | 1.1 | 8.5 |
| 21.3 | 2.6 | 5.7 | 10.6 | 7.5 | 2.0 | 5.5 | 0.9 | 2.5 |
| 31.9 | 12.2 | 14.1 | 30.0 | 10.1 | 1.2 | 5.7 | 1.6 | 10.0 |
| 17.8 | 1.6 | 39.6 | 76.4 | 21.1 | 1.2 | 4.5 | 1.1 | 2.7 |
| 53.1 | 5.1 | 10.5 | 22.7 | 7.8 | 2.0 | 25.9 | 2.4 | 9.0 |
| 62.1 | 17.0 | 5.6 | 11.2 | 9.0 | 2.7 | 33.3 | 2.5 | 15.3 |

After that, the correlation coefficient between PISA and the SN ratio of each bacterium was obtained by using "data analysis" of Excel, and summarized in Table 6.

TABLE 6

| | PISA |
|---|---|
| *Streptococcus mutans* | −0.41 |
| *Actinomyces odontolyticus* | −0.37 |
| *Streptococcus mitis* bv 2 | −0.31 |
| *Streptococcus mitis* | −0.30 |
| *Campylobacter concisus* | −0.19 |
| *Prevotella intermedia* | −0.09 |
| *Campylobacter showae* | −0.09 |
| *Prevotella nigrescens* | −0.07 |
| *Eikenella corrodens* | −0.07 |
| *Capnocytophaga gingivalis* | −0.06 |
| *Actinomyces naeslundii* II | −0.04 |
| *Streptococcus constellatus* | −0.02 |

TABLE 6-continued

| | PISA |
|---|---|
| Total bacteria | −0.01 |
| *Campylobacter gracilis* | −0.01 |
| *Fusobacterium periodonticum* | 0.01 |
| *Fusobacterium nucleatum* subsp. *polymorphum* | 0.09 |
| Control DNA | 0.12 |
| *Aggregatibacter actinomycetemcomitans* | 0.13 |
| *Capnocytophaga sputigena* | 0.14 |
| *Capnocytophaga ochracea* | 0.17 |
| *Streptococcus intermedius* | 0.18 |
| *Fusobacterium nucleatum* subsp. *vincentii* | 0.22 |
| *Streptococcus gordonii* | 0.23 |
| *Veillonella parvula* | 0.35 |
| *Selenomonas noxia* | 0.37 |
| *Fusobacterium nucleatum* subsp. *nucleatum* | 0.42 |
| *Campylobacter rectus* | 0.45 |
| *Porphyromonas gingivalis* | 0.57 |

TABLE 6-continued

| | PISA |
|---|---|
| *Fusobacterium nucleatum* subsp. *animalis* | 0.58 |
| *Tannerella forsythia* | 0.67 |
| *Treponema denticola* | 0.67 |

In the comparison of the SN ratio showing the bacterial load of each bacterium and the PISA value for the entire oral cavity, the correlation was as follows in descending order of correlation: *Treponema denticola, Tannerella forsythia, Fusobacterium nucleatum* subsp. *animalis, Porphyromonas gingivalis*, and *Campylobacter rectus*. These contained "Red Complex" and were considered to be indexes of the degree of inflammation of the entire oral cavity. Meanwhile, those showing the inverse correlation were *Streptococcus mutans, Actinomyces odontolyticus, Streptococcus mitis* bv 2, *Streptococcus mitis*, and *Campylobacter concisus*. These were considered to be indexes of the degree of health of the overall oral cavity.

Subsequently, a model for predicting the PISA value with a model tree was created using a machine learning technique based on the SN ratio of the bacterial load of each bacterium using the data shown in Table 5. Optimization by the "M5" method using the "caret" package of the statistical software "R" (R Development Core Team) was performed for analysis.

After the data in Table 5 were read as "bacteria," the following command was executed.

m←train(PISA~.,data=bacteria,method="M5")

This is a command for generating a model tree with PISA as an objective variable and explanatory variables as all types of bacteria in Table 5. All 46 sample data were used.

When the optimal model that was executed was output by entering the result output command "m$finalModel," the following prediction model was obtained. The results are shown in FIG. 1.

```
M5 unpruned model tree:
(using smoothed linear models)
Actinomyces.odontolyticus <= 20.1 :
|  Campylobacter.concisus <= 2.2 :
|  |  Capnocytophaga.sputigena <= 2.15 :
|  |  |  Tannerella.forsythia <= 6.9 :
|  |  |  |  Streptococcus.mutans <= 5.3 : LM1 (2/12.282%)
|  |  |  |  Streptococcus.mutans >  5.3 : LM2 (2/32.179%)
|  |  |  Tannerella.forsythia >  6.9 :
|  |  |  |  Streptococcus.mutans <= 2.95 : LM3 (3/16.447%)
|  |  |  |  Streptococcus.mutans >  2.95 : LM4 (3/2.075%)
|  |  Capnocytophaga.sputigena >  2.15 :
|  |  |  Streptococcus.gordonii <= 35.45 : LM5 (2/1.965%)
|  |  |  Streptococcus.gordonii >  35.45 : LM6 (3/26.323%)
|  Campylobacter.concisus >  2.2 :
|  |  Treponema.denticola <= 15.35 :
|  |  |  Fusobacterium.nucleatum.subsp..nucleatum <= 38.35 : LM7
(3/2.882%)
|  |  |  Fusobacterium.nucleatum.subsp..nucleatum >  38.35:
|  |  |  |  Actinomyces.odontolyticus <= 10.9 : LM8 (3/4.64%)
|  |  |  |  Actinomyces.odontolyticus >  10.9 : LM9 (2/2.948%)
|  |  Treponema.denticola >  15.35 : LM10 (3/39.648%)
Actinomyces.odontolyticus >  20.1 :
|  Tannerella.forsythia <= 2.85 :
|  |  Streptococcus.gordonii <= 19.6 :
|  |  |  Actinomyces.naeslundii.II <= 4.05 : LM11 (5/2.414%)
|  |  |  Actinomyces.naeslundii.II >  4.05 : LM12 (3/3.304%)
|  |  Streptococcus.gordonii >  19.6 :
|  |  |  Control.DNA <= 837.15 : LM13 (3/4.132%)
|  |  |  Control.DNA >  837.15 : LM14 (2/0.098%)
|  Tannerella.forsythia >  2.85 :
|  |  Streptococcus.constellatus <= 1.75 : LM15 (3/14.832%)
|  |  Streptococcus.constellatus >  1.75 :
|  |  |  Porphyromonas.gingivalis <= 1.35 : LM16 (2/9.58%)
|  |  |  Porphyromonas.gingivalis >  1.35 : LM17 (2/2.751%)
LM num: 1
  .outcome =
        5.9609 * Treponema.denticola
        + 2.719 * Streptococcus.gordonii
        - 2.4637 * Actinomyces.odontolyticus
        - 43.3698 * Streptococcus.mutans
        + 161.5714 * Capnocytophaga.sputigena
        - 0.4833 * Control.DNA
        + 3.734 * Tannerella.forsythia
        + 1510.5973
LM num: 2
  .outcome =
        5.9609 * Treponema.denticola
        + 2.719 * Streptococcus.gordonii
        - 2.4637 * Actinomyces.odontolyticus
        - 43.3698 * Streptococcus.mutans
        + 161.5714 * Capnocytophaga.sputigena
        - 0.4833 * Control.DNA
        + 3.734 * Tannerella.forsythia
        + 1507.5864
```

```
LM num: 3
   .outcome =
      5.9609 * Treponema.denticola
      + 2.719 * Streptococcus.gordonii
      - 2.4637 * Actinomyces.odontolyticus
      - 26.3717 * Streptococcus.mutans
      + 161.5714 * Capnocytophaga.sputigena
      - 0.4833 * Control.DNA
      + 3.9077 * Tannerella.forsythia
      + 1392.5945
LM num: 4
   .outcome =
      5.9609 * Treponema.denticola
      + 2.719 * Streptococcus.gordonii
      - 2.4637 * Actinomyces.odontolyticus
      - 26.3717 * Streptococcus.mutans
      + 161.5714* Capnocytophaga.sputigena
      - 0.4833 * Control.DNA
      + 3.9077 * Tannerella.forsythia
      + 1394.1708
LM num: 5
   .outcome =
      5.9609 * Treponema.denticola
      + 1.2546 * Streptococcus.gordonii
      - 2.4637 * Actinomyces.odontolyticus
      - 26.3717 * Streptococcus.mutans
      + 201.9643 * Capnocytophaga.sputigena
      - 0.4833 * Control.DNA
      + 5.5586 * Tannerella.forsythia
      + 1565.177
LM num: 6
   .outcome =
      5.9609 * Treponema.denticola
      + 1.336 * Streptococcus.gordonii
      - 2.4637 * Actinomyces.odontolyticus
      - 26.3717 * Streptococcus.mutans
      + 201.9643 * Capnocytophaga.sputigena
      - 0.4833 * Control.DNA
      + 5.5586 * Tannerella.forsythia
      + 1555.611
LM num: 7
   .outcome =
      13.3672 * Treponema.denticola
      + 2.719 * Streptococcus.gordonii
      - 2.4637 * Actinomyces.odontolyticus
      - 30.4289 * Streptococcus.mutans
      - 0.4833 * Control.DNA
      + 5.5586 * Tannerella.forsythia
      - 0.3524 * Fusobacterium.nucleatum.subsp..nucleatum
      + 1314.4003
LM num: 8
   .outcome =
      13.3672 * Treponema.denticola
      + 2.719 * Streptococcus.gordonii
      - 1.3817 * Actinomyces.odontolyticus
      - 30.4289 * Streptococcus.mutans
      - 0.4833 * Control.DNA
      + 5.5586 * Tannerella.forsythia
      - 0.3171 * Fusobacterium.nucleatum.subsp..nucleatum
      + 1293.9573
LM num: 9
   .outcome =
      13.3672 * Treponema.denticola
      + 2.719 * Streptococcus.gordonii
      - 1.3181 * Actinomyces.odontolyticus
      - 30.4289 * Streptococcus.mutans
      - 0.4833 * Control.DNA
      + 5.5586 * Tannerella.forsythia
      - 0.3171 * Fusobacterium.nucleatum.subsp..nucleatum
      + 1294.0756
LM num: 10
   .outcome =
      15.293 * Treponema.denticola
      + 2.719 * Streptococcus.gordonii
      - 2.4637 * Actinomyces.odontolyticus
      - 30.4289 * Streptococcus.mutans
      - 0.4833 * Control.DNA
      + 5.5586 * Tannerella.forsythia
      + 1320.5275
```

```
LM num: 11
.outcome =
    3.3786 * Treponema.denticola
    + 5.1956 * Streptococcus.gordonii
    - 2.8861 * Actinomyces.odontolyticus
    - 0.5662 * Control.DNA
    + 29.9183 * Tannerella.forsythia
    - 2.6289 * Actinomyces.naeslundii.II
    + 826.1665
LM num: 12
.outcome =
    3.3786 * Treponema.denticola
    + 5.1956 * Streptococcus.gordonii
    - 2.8861 * Actinomyces.odontolyticus
    - 0.5662 * Control.DNA
    + 29.9183 * Tannerella.forsythia
    - 2.9643 * Actinomyces.naeslundii.II
    + 825.1613
LM num: 13
.outcome =
    3.3786 * Treponema.denticola
    + 5.4972 * Streptococcus.gordonii
    - 2.8861 * Actinomyces.odontolyticus
    - 0.6637 * Control.DNA
    + 29.9183 * Tannerella.forsythia
    + 0.4481 * Actinomyces.naeslundii.II
    + 906.7614
LM num: 14
.outcome =
    3.3786 * Treponema.denticola
    + 5.4972 * Streptococcus.gordonii
    - 2.8861 * Actinomyces.odontolyticus
    - 0.6694 * Control.DNA
    + 29.9183 * Tannerella.forsythia
    + 0.4481 * Actinomyces.naeslundii.II
    + 910.6162
LM num: 15
.outcome =
    -215.5803 * Porphyromonas.gingivalis
    + 3.3786 * Treponema.denticola
    + 3.1851 * Streptococcus.gordonii
    - 2.8861 * Actinomyces.odontolyticus
    - 56.1926 * Streptococcus.constellatus
    - 0.5662 * Control.DNA
    + 36.302 * Tannerella.forsythia
    + 1327.7476
LM num: 16
.outcome =
    -221.29 * Porphyromonas.gingivalis
    + 3.3786 * Treponema.denticola
    + 3.1851 * Streptococcus.gordonii
    - 2.8861 * Actinomyces.odontolyticus
    - 53.2351 * Streptococcus.constellatus
    - 0.5662 * Control.DNA
    + 36.302 * Tannerella.forsythia
    + 1307.8776
LM num: 17
.outcome =
    -221.29 * Porphyromonas.gingivalis
    + 3.3786 * Treponema.denticola
    + 3.1851 * Streptococcus.gordonii
    - 2.8861 * Actinomyces.odontolyticus
    - 53.2351 * Streptococcus.constellatus
    - 0.5662 * Control.DNA
    + 36.302 * Tannerella.forsythia
    + 1307.1008
```

The command "p←predict(m, newdata=bacteria)" was entered, and the measured SN ratio data of the bacterial load of each bacterium for 46 samples were substituted into the created prediction model "m," thereby obtaining the predicted PISA values "p" corresponding to 46 samples.

Subsequently, the command cor(p,bacteria$PISA) was entered for calculating the correlation coefficient between the predicted PISA values "p" and the measured PISA values. As a result, The correlation coefficient was 0.8759666.

Figures 1, 2:
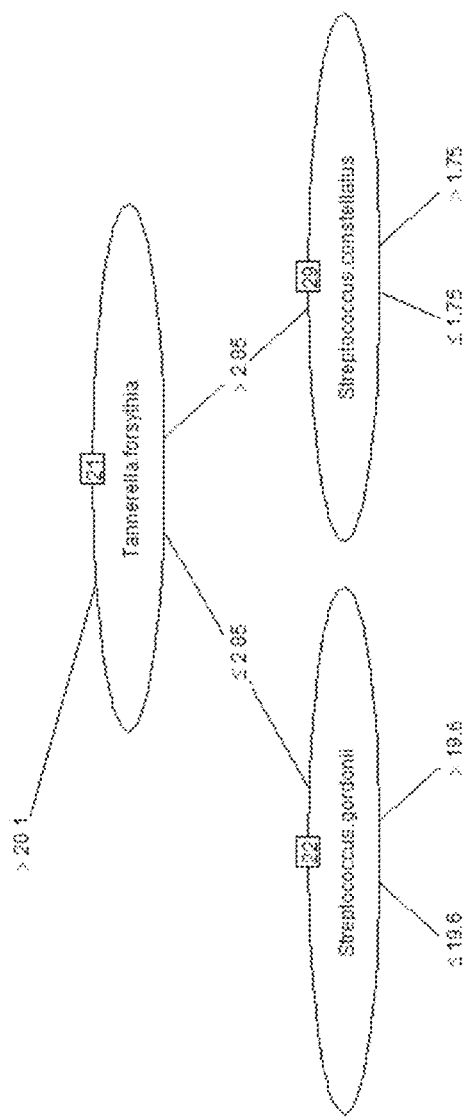
Figures 1, 2:
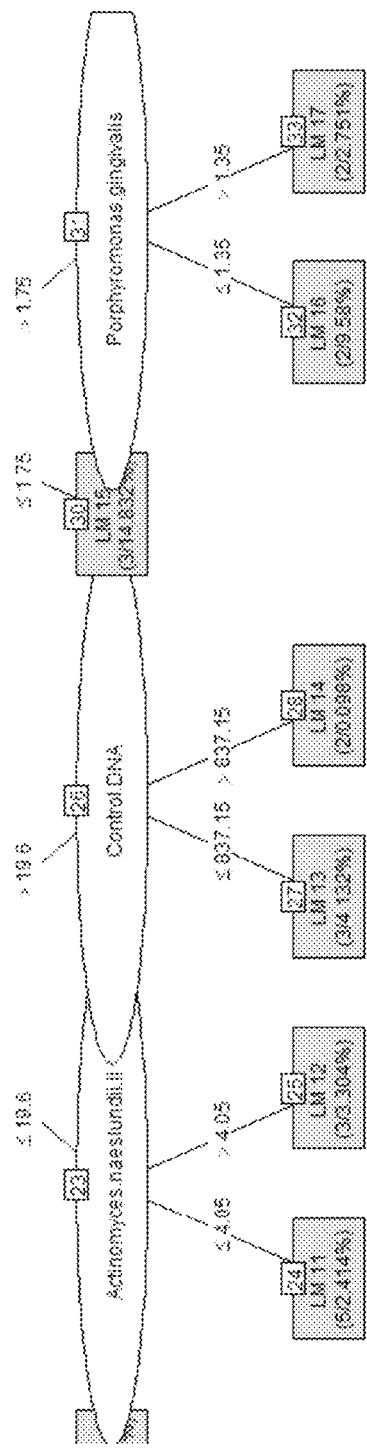
Figure 2:
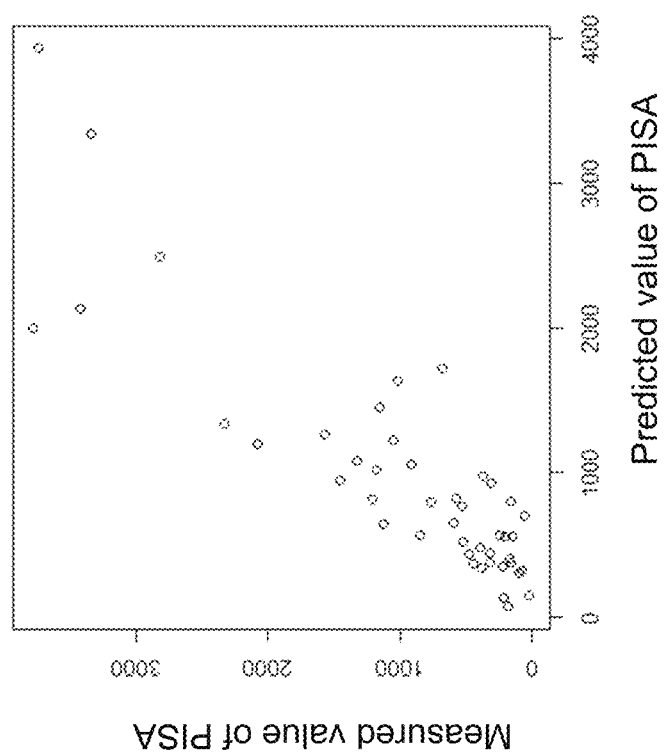

FIG. 2 shows a scatter diagram of the predicted PISA values "p" and the measured PISA values.

As shown in this model, it was found that the PISA value can be predicted from the SN ratio of the DNA chip.

In particular, in comparing the SN ratio showing the bacterial load of each bacterium shown in Table 6 with the PISA value of the entire oral cavity, it was shown that the PISA value can be predicted from the SN ratio of the bacterial group of *Streptococcus mutans, Actinomyces odontolyticus, Campylobacter concisus, Actinomyces. naeslundii*.

II, and *Streptococcus. constellatus* which has a negative correlation coefficient and the bacterial group of *Capnocytophaga sputigena, Tannerella forsythia, Streptococcus gordonii, Treponema denticola, Fusobacterium nucleatum* subsp. *nucleatum*, and *Porphyromonas gingivalis* which has a positive correlation coefficient.

Example 2

The same detection results as in Example 1 were used for predicting the PISA values based on the bacterial loads.

<Correlation Analysis of PISA Value and Bacterial Load>
First, the PISA value and the SN ratio data indicating the bacterial load of each bacterium were associated with each sample. Then, the median of the SN ratios of the absolute load index probes of all the samples was calculated, and the SN ratio of the absolute load index probe of each sample was divided by this median. This is specified as the interchip correction value. The interchip SN ratio data were then standardized by dividing the SN ratio data of all bacteria for each sample by the interchip correction value for each sample. The results are shown in Table 7.

TABLE 7

| PISA | Total bacteria | Porphyromonas gingivalis | Tannerella forsythia | Treponema denticola | Campylobacter gracilis | Campylobacter rectus | Campylobacter showae |
|---|---|---|---|---|---|---|---|
| 477 | 2148.1 | 1.8 | 1.7 | 1.5 | 1.9 | 1.4 | 1.2 |
| 20 | 2973.7 | 2.2 | 2.4 | 1.7 | 2.2 | 1.7 | 1.6 |
| 215 | 2083 | 1.4 | 2.6 | 3 | 1.5 | 1.5 | 1 |
| 250 | 2162.2 | 1.3 | 7.8 | 3.9 | 1.6 | 1.3 | 1 |
| 167 | 2743.5 | 1.7 | 1.6 | 1.6 | 1.8 | 1.5 | 1.2 |
| 77 | 2357.1 | 1.6 | 1.4 | 1.4 | 1.7 | 1.4 | 1.1 |
| 161 | 1158.4 | 1.6 | 0.8 | 1.1 | 1.1 | 0.9 | 0.8 |
| 318 | 2689.1 | 1.4 | 1.2 | 1.8 | 1.7 | 1.3 | 1.1 |
| 180 | 2872.6 | 2.1 | 2.3 | 1.8 | 2.2 | 1.7 | 1.4 |
| 1050 | 1726.4 | 1.4 | 11.6 | 8.4 | 1.3 | 5.2 | 0.9 |
| 203 | 3167.9 | 2.2 | 5.4 | 5 | 2.2 | 2.4 | 1.5 |
| 535 | 1525.2 | 1.4 | 16.9 | 12.3 | 1.2 | 1 | 0.8 |
| 1154 | 1825.6 | 1.2 | 11.4 | 27.9 | 1.3 | 1.1 | 0.8 |
| 1018 | 1926.4 | 4.8 | 18.5 | 34.6 | 1.4 | 3.6 | 1.1 |
| 382 | 2458.9 | 1.3 | 2.9 | 1.3 | 1.7 | 1.7 | 1.1 |
| 2814 | 1538.3 | 1.9 | 62.1 | 99.5 | 1.3 | 1.8 | 0.9 |
| 1172 | 1468.9 | 2 | 8.8 | 5.7 | 1.2 | 0.9 | 0.8 |
| 147 | 2485.6 | 1.5 | 3.4 | 1.4 | 1.7 | 1.7 | 1.1 |
| 1570 | 1414.2 | 3.2 | 3.8 | 2.1 | 1.1 | 6.2 | 0.7 |
| 1120 | 2233 | 1.3 | 6.6 | 2.2 | 1.6 | 1.5 | 1 |
| 164 | 2567.6 | 1.5 | 1.3 | 1.4 | 1.9 | 1.4 | 1.2 |
| 1205 | 1217.1 | 1.1 | 5.1 | 1 | 1 | 0.8 | 0.6 |
| 1321 | 1550.2 | 2.1 | 10.2 | 18.5 | 1.2 | 5.3 | 0.9 |
| 320 | 2259 | 1.3 | 1.7 | 1.2 | 1.5 | 1.2 | 0.9 |
| 571 | 1478.5 | 1.7 | 1.8 | 1.3 | 1.2 | 4 | 0.8 |
| 73 | 1501.9 | 1.2 | 2.8 | 1 | 1.1 | 1.3 | 0.7 |
| 3775 | 9192.4 | 6.5 | 15.4 | 6.5 | 7 | 6.5 | 5 |
| 2076 | 2533.6 | 1.6 | 1.2 | 1.4 | 1.8 | 1.4 | 1.2 |
| 445 | 3241.2 | 1.8 | 6.8 | 1.9 | 2.3 | 1.8 | 1.6 |
| 768 | 3892.8 | 2.2 | 8.7 | 2 | 2.6 | 2.4 | 1.9 |
| 680 | 1212.8 | 2.5 | 57.6 | 40.3 | 1.1 | 3.9 | 1.3 |
| 915 | 2128.1 | 1.3 | 4.7 | 1.5 | 1.5 | 1.2 | 1 |
| 3335 | 1709.7 | 6.8 | 62.9 | 193.6 | 1.3 | 31.3 | 1 |
| 2326 | 2523.6 | 1.7 | 5.1 | 13.7 | 1.7 | 1.6 | 1.1 |
| 395 | 2343.7 | 1.3 | 2.2 | 2.7 | 1.7 | 1.7 | 1.1 |
| 3420 | 1728.1 | 2.7 | 32.7 | 39.3 | 1.2 | 24.2 | 0.8 |
| 1447 | 1965.8 | 1.9 | 6.7 | 15.1 | 1.3 | 6.3 | 0.9 |
| 309 | 2902 | 2.3 | 2.3 | 3.3 | 2 | 13.4 | 1.8 |
| 846 | 2809.8 | 1.5 | 3.4 | 4.8 | 1.8 | 2.2 | 1.2 |
| 369 | 2348.3 | 1.3 | 4 | 15.4 | 1.5 | 4.4 | 1.1 |
| 223 | 2652.1 | 1.4 | 1.2 | 1.8 | 1.7 | 21.4 | 2.1 |
| 3735 | 2105 | 5.1 | 68.9 | 183.4 | 1.2 | 16.7 | 0.9 |
| 52 | 2781.7 | 3.8 | 2.4 | 4.5 | 1.9 | 31.2 | 1.8 |
| 100 | 2196.6 | 1.3 | 1 | 1.3 | 1.5 | 7.4 | 1.2 |
| 597 | 2007.4 | 1.1 | 1.2 | 1 | 1.3 | 1.2 | 0.8 |
| 526 | 1887 | 1.3 | 1.3 | 1.2 | 1.4 | 6.4 | 1 |

| Fusobacterium nucleatum subsp. vincentii | Fusobacterium nucleatum subsp. polymorphum | Fusobacterium nucleatum subsp. animalis | Fusobacterium nucleatum subsp. nucleatum | Fusobacterium periodonticum | Prevotella intermedia | Prevotella nigrescens | Streptococcus constellatus |
|---|---|---|---|---|---|---|---|
| 1.3 | 1.4 | 1.7 | 1.3 | 1.2 | 1.2 | 1.2 | 1.7 |
| 1.9 | 1.7 | 2.5 | 2.4 | 1.7 | 1.6 | 1.7 | 1.7 |
| 3.8 | 1.5 | 4.7 | 9.1 | 1.9 | 1.2 | 1 | 1.7 |
| 3.4 | 1.7 | 5.3 | 10.5 | 1.6 | 1.1 | 1 | 2.6 |
| 1.6 | 1.5 | 2.4 | 2.4 | 1.3 | 1.2 | 1.1 | 8.4 |
| 2 | 1.7 | 3.3 | 18.2 | 2.6 | 1.3 | 1.1 | 3.1 |
| 0.9 | 1.1 | 3 | 48 | 1.8 | 0.8 | 0.8 | 5 |
| 1.3 | 1.3 | 2 | 4.1 | 1.3 | 1.1 | 1 | 8.6 |
| 1.9 | 1.7 | 2.5 | 10.2 | 2.3 | 1.5 | 1.4 | 2.9 |
| 10.6 | 1.6 | 36.6 | 26 | 3 | 0.9 | 1 | 15.4 |
| 1.7 | 2 | 2.5 | 9.9 | 2.2 | 1.5 | 1.4 | 3.2 |

TABLE 7-continued

| | | | | | | | |
|---|---|---|---|---|---|---|---|
| 4.1 | 2.5 | 19.3 | 90.3 | 2.1 | 0.8 | 0.8 | 3 |
| 2.3 | 3.6 | 5.7 | 57.7 | 1.5 | 0.9 | 0.8 | 2.2 |
| 3.7 | 3.3 | 11.5 | 80.6 | 2.6 | 1.7 | 1 | 3.1 |
| 1.8 | 2.1 | 1.9 | 10.8 | 1.3 | 1.1 | 1.1 | 2.3 |
| 1.2 | 1.3 | 3.5 | 30.6 | 1.1 | 0.9 | 0.9 | 5.4 |
| 1.8 | 1.2 | 14.5 | 53.4 | 1.5 | 0.8 | 0.8 | 2.7 |
| 3.3 | 2.2 | 3.3 | 15.3 | 1.8 | 1.2 | 1.2 | 2 |
| 4.5 | 0.9 | 21.7 | 23.7 | 2.1 | 0.7 | 0.6 | 1.2 |
| 1.3 | 1.5 | 1.8 | 12.1 | 1.8 | 1 | 1 | 1.3 |
| 1.5 | 1.6 | 2.2 | 17.7 | 2.7 | 1.3 | 1.2 | 1.4 |
| 2.3 | 1.2 | 9.5 | 22.6 | 1.1 | 0.7 | 0.6 | 3.7 |
| 4.7 | 2.6 | 12.5 | 30.5 | 2.2 | 0.9 | 0.9 | 1.2 |
| 1.6 | 1.3 | 1.7 | 2.1 | 1.2 | 1.1 | 0.9 | 1.3 |
| 1.5 | 1.2 | 5.9 | 28 | 1.3 | 0.8 | 0.8 | 2 |
| 5.4 | 1.3 | 14.1 | 38.6 | 2.9 | 0.7 | 0.7 | 4.6 |
| 5.5 | 6 | 8.5 | 36.9 | 8 | 5 | 5 | 10 |
| 1.2 | 1.4 | 1.4 | 1.2 | 1.2 | 1.3 | 1.2 | 1.8 |
| 2.3 | 2.1 | 2.6 | 6.3 | 1.9 | 1.5 | 1.8 | 5.7 |
| 1.9 | 2 | 2.2 | 3.4 | 1.7 | 1.9 | 1.7 | 2 |
| 2 | 1.6 | 5.8 | 58.5 | 1.6 | 1.6 | 1.1 | 3.4 |
| 1.3 | 1.2 | 1.7 | 8.7 | 1.5 | 1.1 | 1 | 1.2 |
| 5.1 | 1.6 | 55.2 | 118.2 | 2.2 | 1 | 0.9 | 1.4 |
| 7.1 | 1.9 | 24.5 | 25.1 | 3.1 | 1.4 | 1.6 | 6.7 |
| 2.3 | 1.6 | 2.6 | 6 | 1.6 | 1.1 | 1.1 | 1.6 |
| 3 | 1.3 | 49.3 | 115.5 | 1.5 | 0.8 | 0.9 | 1.2 |
| 7.4 | 2.1 | 30 | 103.5 | 5.7 | 1.6 | 0.9 | 3.4 |
| 3.3 | 2.1 | 8.4 | 49.5 | 4.1 | 1.3 | 1.7 | 1.5 |
| 3.1 | 2.2 | 9.7 | 198.5 | 13.4 | 1.2 | 1.2 | 1.7 |
| 3.2 | 5 | 6.7 | 105.4 | 4.8 | 1 | 1 | 1.8 |
| 1.6 | 1.7 | 3.3 | 56.9 | 5.5 | 1.1 | 1 | 1.5 |
| 4.6 | 2.3 | 35.3 | 167.3 | 4.4 | 0.9 | 0.7 | 1.5 |
| 3.8 | 2 | 12.4 | 101.2 | 7.3 | 5.1 | 1.4 | 3 |
| 1.6 | 1.5 | 5 | 98.4 | 6.4 | 1.1 | 1.3 | 1.2 |
| 8 | 1.5 | 30.8 | 18.9 | 2.9 | 0.9 | 1.3 | 3.8 |
| 4.8 | 1.4 | 22.8 | 21.4 | 2.5 | 1 | 1.5 | 4.9 |

| Aggregatibacter actinomycetemcomitans | Campylobacter concisus | Capnocytophaga gingivalis | Capnocytophaga ochracea | Capnocytophaga sputigena | Eikenella corrodens | Streptococcus gordonii | Streptococcus intermedius |
|---|---|---|---|---|---|---|---|
| 1.8 | 1.9 | 1.3 | 1.3 | 1.2 | 1.1 | 25.9 | 1.4 |
| 3.2 | 1.6 | 1.6 | 1.6 | 1.6 | 1.6 | 18.3 | 1.7 |
| 1.8 | 1.1 | 1.2 | 1.1 | 1 | 1.1 | 8.8 | 2.4 |
| 1.4 | 1.5 | 1.1 | 1.1 | 1 | 1.1 | 11 | 2.9 |
| 1.7 | 1.2 | 1.3 | 1.3 | 1.3 | 1.2 | 23.4 | 15.4 |
| 1.5 | 1.9 | 1.2 | 1.6 | 1.7 | 1.1 | 16.4 | 3.8 |
| 1.6 | 2.1 | 1.1 | 0.8 | 1.3 | 0.8 | 73.9 | 0.9 |
| 1.6 | 1.2 | 1.3 | 1.2 | 1.3 | 1.1 | 32.6 | 4.1 |
| 3 | 1.5 | 1.5 | 1.5 | 1.7 | 1.5 | 22.2 | 10.1 |
| 0.9 | 1 | 2.6 | 1 | 0.9 | 0.9 | 36.8 | 3.2 |
| 2 | 1.5 | 1.8 | 1.5 | 2 | 1.5 | 25.8 | 4.5 |
| 1 | 1.8 | 1.4 | 1.6 | 1.8 | 0.9 | 31.3 | 20.9 |
| 1 | 0.8 | 1 | 1.3 | 1.3 | 0.9 | 56.3 | 10.6 |
| 1.1 | 1.6 | 2 | 1 | 1.5 | 1.1 | 80.2 | 10.8 |
| 1.8 | 1.3 | 1.4 | 1.1 | 1.1 | 1.1 | 31.5 | 14.9 |
| 1.1 | 0.9 | 1.1 | 1.7 | 2.1 | 1 | 58.4 | 4.4 |
| 1 | 1.4 | 0.9 | 0.9 | 1.5 | 0.8 | 24.3 | 3.1 |
| 1.5 | 1.5 | 1.8 | 1.4 | 2.9 | 1.4 | 32 | 4.8 |
| 5.2 | 1.3 | 0.9 | 0.7 | 0.8 | 0.7 | 107.9 | 2.7 |
| 1.5 | 1.4 | 1.3 | 1.1 | 1.1 | 1 | 29 | 3.2 |
| 1.5 | 1.2 | 1.3 | 1.3 | 1.4 | 1.2 | 11.1 | 1.5 |
| 0.8 | 0.6 | 0.6 | 0.6 | 0.6 | 0.6 | 14.2 | 0.7 |
| 1.6 | 2.8 | 4.6 | 0.9 | 2.6 | 0.9 | 65.7 | 10.7 |
| 1.3 | 1.2 | 1.3 | 1.2 | 1.1 | 1.1 | 24.5 | 11.7 |
| 4.4 | 1.8 | 1 | 1.2 | 1.6 | 0.9 | 57.5 | 2.1 |
| 1.3 | 2.5 | 1.1 | 1 | 1.5 | 0.7 | 22.2 | 3.6 |
| 5.5 | 5 | 8 | 5 | 12.5 | 5 | 146 | 17.9 |
| 1.6 | 1.4 | 1.3 | 1.3 | 1.4 | 1.3 | 54.1 | 9.4 |
| 2.9 | 1.5 | 1.5 | 1.6 | 1.6 | 1.5 | 17.6 | 6.8 |
| 2.4 | 1.9 | 2.4 | 1.9 | 2.2 | 1.7 | 29.9 | 6.5 |
| 0.9 | 0.8 | 0.8 | 1.1 | 1.5 | 0.9 | 35.5 | 3.9 |
| 1.2 | 1.4 | 1.6 | 1 | 1.2 | 1 | 37.6 | 4.6 |
| 1.3 | 1.8 | 1.1 | 1.5 | 2.3 | 0.9 | 44.7 | 11.4 |
| 1.7 | 1.9 | 1.6 | 1.1 | 1.8 | 1.2 | 42.6 | 11.4 |
| 1.3 | 1.1 | 4.4 | 1.6 | 3.1 | 1.1 | 22.2 | 3.4 |
| 4.2 | 1.2 | 1 | 1.6 | 2.2 | 1.1 | 29.9 | 13.4 |
| 1.5 | 5 | 0.9 | 1.2 | 2.2 | 1.1 | 17.6 | 3.9 |
| 1.5 | 3.1 | 25 | 1.6 | 8.9 | 2.8 | 13.5 | 5.4 |
| 1.5 | 3.8 | 1.9 | 2.4 | 3.4 | 1.1 | 13.5 | 1.5 |
| 1.2 | 2.5 | 1.1 | 1.2 | 1.1 | 1.1 | 32.2 | 2.1 |
| 1.4 | 7.7 | 1.3 | 1.4 | 4.8 | 1 | 16.3 | 1.2 |

TABLE 7-continued

| | | | | | | | |
|---|---|---|---|---|---|---|---|
| 0.9 | 0.9 | 4.1 | 1 | 3.5 | 0.8 | 15.4 | 1.9 |
| 4.4 | 10 | 13.2 | 2.7 | 7.1 | 1.6 | 35.3 | 13.5 |
| 1.3 | 5.2 | 1.5 | 1.1 | 2.4 | 1 | 15.9 | 1.4 |
| 1.2 | 2.2 | 1.3 | 1.5 | 1.3 | 1.3 | 44 | 4.2 |
| 1.2 | 6.3 | 2.2 | 1.2 | 2.6 | 2.4 | 55 | 15 |

| Streptococcus mitis | Streptococcus mitis bv 2 | Actinomyces odontolyticus | Veillonella parvula | Actinomyces naeslundii II | Selenomonas noxia | Streptococcus mutans |
|---|---|---|---|---|---|---|
| 3.1 | 15.5 | 69 | 1.3 | 116.6 | 1.3 | 26.3 |
| 3.7 | 21.9 | 242 | 1.6 | 8.1 | 1.6 | 19.4 |
| 3.2 | 17 | 103.7 | 1.1 | 3.5 | 1 | 14.3 |
| 3.2 | 12.3 | 40.2 | 1.1 | 1.9 | 1.3 | 6.1 |
| 97.9 | 205.1 | 56.5 | 1.3 | 4.4 | 1.3 | 1.6 |
| 38.2 | 85.4 | 44.5 | 1.2 | 6.3 | 1.3 | 16.8 |
| 2.1 | 3.9 | 6.2 | 0.8 | 7.6 | 0.8 | 4.3 |
| 171.3 | 367.1 | 65.3 | 1.2 | 8 | 1.1 | 5 |
| 146.5 | 325.3 | 243.7 | 1.5 | 4.1 | 1.5 | 10.1 |
| 8.4 | 20.1 | 12.4 | 1.1 | 2.9 | 1.8 | 0.8 |
| 97.6 | 204.2 | 54.9 | 1.5 | 5 | 1.5 | 8.1 |
| 2.2 | 4.6 | 5.6 | 1 | 9.5 | 2 | 11.9 |
| 15.5 | 31.6 | 6.6 | 1 | 20.3 | 1.2 | 2.7 |
| 10.1 | 20.9 | 4.8 | 1.1 | 14.7 | 1.4 | 2.5 |
| 133.2 | 274.8 | 98.7 | 1.1 | 4.8 | 1.2 | 6.8 |
| 2 | 3.8 | 4.9 | 1.4 | 3.2 | 1.9 | 6.3 |
| 1.1 | 1.6 | 3.7 | 0.9 | 1.2 | 1.5 | 8.1 |
| 9 | 23.4 | 25 | 1.3 | 16.6 | 1.2 | 33.8 |
| 5.7 | 10.5 | 4.4 | 0.8 | 7.8 | 1.3 | 3.6 |
| 37.4 | 80.3 | 51.4 | 1.1 | 9.3 | 1 | 8.9 |
| 36.5 | 85.6 | 33.8 | 1.3 | 2.9 | 1.3 | 21.1 |
| 2.7 | 6.8 | 6.3 | 0.6 | 1 | 0.6 | 3 |
| 12.2 | 23.6 | 7.6 | 0.9 | 4.7 | 0.8 | 7.9 |
| 45.1 | 94.6 | 24.9 | 1.1 | 7.5 | 1.1 | 27.6 |
| 4.7 | 9 | 2.7 | 0.9 | 37.4 | 1.2 | 3.7 |
| 12.9 | 24.2 | 6.3 | 0.9 | 27.4 | 1.3 | 9 |
| 7.5 | 10 | 19.9 | 5.5 | 25.4 | 5 | 6 |
| 143 | 282.9 | 25.8 | 1.3 | 71.4 | 1.2 | 6.8 |
| 98.3 | 256 | 213.3 | 1.6 | 10.2 | 1.6 | 35.6 |
| 45.4 | 128.2 | 77.5 | 1.9 | 6.5 | 1.7 | 9.1 |
| 1.9 | 3.6 | 2.4 | 1.1 | 13.3 | 2 | 2.1 |
| 24.8 | 51.5 | 19.6 | 1 | 6.8 | 1.1 | 6.6 |
| 1.4 | 2.6 | 2.5 | 1.4 | 1.3 | 1.6 | 1 |
| 12.3 | 25.8 | 14.5 | 1.9 | 6.9 | 1.5 | 5.2 |
| 67.1 | 138.6 | 22.8 | 1.2 | 4.8 | 1.1 | 7.9 |
| 1.2 | 1.6 | 1.6 | 1 | 4.3 | 10.6 | 1.4 |
| 6.6 | 13.7 | 9.6 | 1.5 | 21 | 1.3 | 4.7 |
| 30.3 | 61.4 | 15.4 | 1.3 | 8.7 | 2.3 | 2.1 |
| 30.4 | 58.1 | 22.7 | 1.3 | 2.9 | 1.4 | 6 |
| 63.5 | 126.2 | 11.7 | 1.1 | 28 | 1 | 4.8 |
| 53.8 | 107.5 | 32.6 | 1.1 | 1.9 | 1.1 | 8.7 |
| 4.1 | 7.7 | 5.4 | 1.4 | 4 | 0.7 | 1.8 |
| 15.6 | 33.2 | 11.2 | 1.3 | 6.3 | 1.8 | 11.1 |
| 35.4 | 68.4 | 18.9 | 1.1 | 4 | 1 | 2.4 |
| 8.7 | 18.8 | 6.5 | 1.7 | 21.5 | 2 | 7.5 |
| 5 | 9.9 | 8 | 2.4 | 29.5 | 2.2 | 13.5 |

After that, the correlation coefficient between PISA and the SN ratio of each bacterium was obtained by using "data analysis" of Excel, and summarized in Table 8.

TABLE 8

| | PISA |
|---|---|
| Streptococcus mutans | −0.38 |
| Actinomyces odontolyticus | −0.32 |
| Streptococcus mitis bv 2 | −0.28 |
| Streptococcus mitis | −0.26 |
| Campylobacter concisus | −0.12 |
| Capnocytophaga gingivalis | −0.01 |
| Actinomyces naeslundii II | 0.00 |
| Fusobacterium periodonticum | 0.09 |
| Streptococcus constellatus | 0.11 |
| Prevotella intermedia | 0.12 |
| Aggregatibacter actinomycetemcomitans | 0.20 |
| Eikenella corrodens | 0.20 |
| Campylobacter showae | 0.20 |

TABLE 8-continued

| | PISA |
|---|---|
| Total bacteria | 0.22 |
| Campylobacter gracilis | 0.24 |
| Prevotella nigrescens | 0.24 |
| Fusobacterium nucleatum subsp. polymorphum | 0.25 |
| Streptococcus intermedius | 0.26 |
| Capnocytophaga sputigena | 0.27 |
| Capnocytophaga ochracea | 0.29 |
| Fusobacterium nucleatum subsp. vincentii | 0.29 |
| Fusobacterium nucleatum subsp. nucleatum | 0.38 |
| Campylobacter rectus | 0.38 |
| Veillonella parvula | 0.39 |
| Streptococcus gordonii | 0.45 |
| Selenomonas noxia | 0.47 |
| Fusobacterium nucleatum subsp. animalis | 0.60 |
| Porphyromonas gingivalis | 0.65 |

TABLE 8-continued

|  | PISA |
|---|---|
| *Treponema denticola* | 0.68 |
| *Tannerella forsythia* | 0.68 |

In the comparison of the SN ratio showing the bacterial load of each bacterium and the PISA value for the entire oral cavity, the correlation was as follows in descending order of correlation: *Tannerella forsythia, Treponema denticola, Porphyromonas gingivalis, Fusobacterium nucleatum* subsp. *animalis, Selenomonas noxia, Streptococcus gordonii, Veillonella parvula, Campylobacter rectus*, and *Fusobacterium nucleatum* subsp. *nucleatum*. These contained "Red Complex" and were considered to be indexes of the degree of inflammation of the entire oral cavity. Meanwhile, those showing the inverse correlation were *Streptococcus mutans, Actinomyces odontolyticus, Streptococcus mitis* bv 2, *Streptococcus mitis*, and *Campylobacter concisus*. These were considered to be indexes of the degree of health of the overall oral cavity.

Subsequently, a model for predicting the PISA value with a model tree was created using a machine learning technique based on the SN ratio of the bacterial load of each bacterium using the data shown in Table 7. Next, optimization by the "M5" method using the "caret" package of the statistical software "R" (R Development Core Team) was performed.

After the data in Table 7 were read as "bacteria," the following command was executed.

m←train(PISA~.,data=bacteria,method="M5")

This is a command for generating a model tree with PISA as an objective variable and explanatory variables as all types of bacteria in Table 7. All 46 sample data were used.

When the optimal model that was executed was output by entering the result output command "m$finalModel," the following prediction model was obtained.

```
M5 unpruned model tree:
(using smoothed linear models)
Treponema.denticola <= 6.1 :
|   Campylobacter.concisus <= 1.45 :
|   |   Actinomyces.odontolyticus <= 53.95 :
|   |   |   Streptococcus.mutans <= 15 :
|   |   |   |   Tannerella.forsythia <= 4.9 :
|   |   |   |   |   Porphyromonas.gingivalis <= 1.45 : LM1 (2/25.547%)
|   |   |   |   |   Porphyromonas.gingivalis >  1.45 : LM2 (2/24.859%)
|   |   |   |   Tannerella.forsythia >   4.9 : LM3 (3/3.438%)
|   |   |   Streptococcus.mutans >  15 : LM4 (2/7.664%)
|   |   Actinomyces.odontolyticus >  53.95 :
|   |   |   Fusobacterium.nucleatum.subsp..animalis <= 2.2 : LM5 (2/3.144%)
|   |   |   Fusobacterium.nucleatum.subsp..animalis >  2.2 : LM6 (2/2.358%)
|   Campylobacter.concisus >  1.45 :
|   |   Capnocytophaga.ochracea <= 1.15 :
|   |   |   Fusobacterium.periodonticum <= 2.35 : LM7 (2/4.372%)
|   |   |   Fusobacterium.periodonticum >  2.35 : LM8 (2/1.326%)
|   |   Capnocytophaga.ochracea >  1.15 :
|   |   |   Total.bacteria <= 2252.6 : LM9 (4/4.488%)
|   |   |   Total.bacteria >   2252.6 :
|   |   |   |   Capnocytophaga.ochracea <= 1.55 : LM10 (4/2.777%)
|   |   |   |   Capnocytophaga.ochracea >  1.55 :
|   |   |   |   |   Tannerella.forsythia <= 2.9 :
|   |   |   |   |   |   Tannerella.forsythia <=2.35 : LM11 (2/11.398%)
|   |   |   |   |   |   Tannerella.forsythia >  2.35 : LM12 (2/1.572%)
|   |   |   |   |   Tannerella.forsythia >  2.9 : LM13 (3/17.057%)
Treponema.denticola >  6.1 :
|   Campylobacter.rectus <= 6.4 :
|   |   Veillonella.parvula <= 1.25 :
|   |   |   Streptococcus.gordonii <= 36.15 : LM14 (3/12.485%)
|   |   |   Streptococcus.gordonii >   36.15 :
|   |   |   |   Tannerella.forsythia <= 11.5 : LM15 (2/8.205%)
|   |   |   |   Tannerella.forsythia >  11.5 : LM16 (2/1.572%)
|   |   Veillonella.parvula >  1.25 : LM17 (3/55.578%)
|   Campylobacter.rectus >   6.4 :
|   |   Total.bacteria <= 1916.55 : LM18 (2/4.176%)
|   |   Total.bacteria >  1916.55 : LM19 (2/1.965%)
LM num: 1
.outcome =
        0.1154 * Total.bacteria
        - 87.6234 * Porphyromonas.gingivalis
        + 32.2177 * Tannerella.forsythia
        + 3.4246 * Treponema.denticola
        + 10.3816 * Fusobacterium.nucleatum.subsp..animalis
        + 4.5488 * Streptococcus.gordonii
        - 2.8479 * Actinomyces.odontolyticus
        - 4.1907 * Streptococcus.mutans
        + 353.0028
LM num: 2
.outcome =
        0.1154 * Total.bacteria
        - 87.6234 * Porphyromonas.gingivalis
        + 32.2177 * Tannerella.forsythia
        + 3.4246 * Treponema.denticola
        + 10.3816 * Fusobacterium.nucleatum.subsp..animalis
        + 4.5488 * Streptococcus.gordonii
```

− 2.8479 * Actinomyces.odontolyticus
− 4.1907 * Streptococcus.mutans
+ 354.0939

LM num: 3
.outcome =
0.1154 * Total.bacteria
− 87.6234 * Porphyromonas.gingivalis
+ 32.2177 * Tannerella.forsythia
+ 3.4246 * Treponema.denticola
+ 10.3816 * Fusobacterium.nucleatum.subsp..animalis
+ 4.5488 * Streptococcus.gordonii
− 2.8479 * Actinomyces.odontolyticus
− 4.1907 * Streptococcus.mutans
+ 353.0353

LM num: 4
.outcome =
0.1154 * Total.bacteria
− 87.6234 * Porphyromonas.gingivalis
+ 32.2177 * Tannerella.forsythia
+ 3.4246 * Treponema.denticola
+ 10.3816 * Fusobacterium.nucleatum.subsp..animalis
+ 4.5488 * Streptococcus.gordonii
− 2.8479 * Actinomyces.odontolyticus
− 5.4232 * Streptococcus.mutans
+ 347.5507

LM num: 5
.outcome =
0.1154 * Total.bacteria
− 87.6234 * Porphyromonas.gingivalis
+ 32.2177 * Tannerella.forsythia
+ 3.4246 * Treponema.denticola
+ 10.3816 * Fusobacterium.nucleatum.subsp..animalis
+ 4.5488 * Streptococcus.gordonii
− 3.3806 * Actinomyces.odontolyticus
+ 263.7849

LM num: 6
.outcome =
0.1154 * Total.bacteria
− 87.6234 * Porphyromonas.gingivalis
+ 32.2177 * Tannerella.forsythia
+ 3.4246 * Treponema.denticola
+ 10.3816 * Fusobacterium.nucleatum.subsp..animalis
+ 4.5488 * Streptococcus.gordonii
− 3.3806 * Actinomyces.odontolyticus
+ 262.54

LM num: 7
.outcome =
0.1154 * Total.bacteria
− 87.6234 * Porphyromonas.gingivalis
+ 27.5903 * Tannerella.forsythia
+ 3.4246 * Treponema.denticola
+ 10.3816 * Fusobacterium.nucleatum.subsp..animalis
+ 4.5488 * Streptococcus.gordonii
− 0.6784 * Actinomyces.odontolyticus
+ 33.5894

LM num: 8
.outcome =
0.1154 * Total.bacteria
− 87.6234 * Porphyromonas.gingivalis
+ 27.5903 * Tannerella.forsythia
+ 3.4246 * Treponema.denticola
+ 10.3816 * Fusobacterium.nucleatum.subsp..animalis
+ 4.5488 * Streptococcus.gordonii
− 0.6784 * Actinomyces.odontolyticus
+ 32.468

LM num: 9
.outcome =
0.0649 * Total.bacteria
− 87.6234 * Porphyromonas.gingivalis
+ 43.8294 * Tannerella.forsythia
+ 3.4246 * Treponema.denticola
+ 10.3816 * Fusobacterium.nucleatum.subsp..animalis
+ 4.5488 * Streptococcus.gordonii
− 0.6784 * Actinomyces.odontolyticus
+ 146.6484

LM num: 10
.outcome =
0.0785 * Total.bacteria
− 87.6234 * Porphyromonas.gingivalis + 44.0191 * Tannerella.forsythia
          + 3.4246 * Treponema.denticola
          + 10.3816 * Fusobacterium.nucleatum.subsp..animalis
          + 4.5488 * Streptococcus.gordonii
          − 0.6784 * Actinomyces.odontolyticus
          + 93.2371
LM num: 11
    .outcome =
          0.0785 * Total.bacteria
          − 87.6234 * Porphyromonas.gingivalis
          + 45.0694 * Tannerella.forsythia
          + 3.4246 * Treponema.denticola
          + 10.3816 * Fusobacterium.nucleatum.subsp..animalis
          + 4.5488 * Streptococcus.gordonii
          − 0.6784 * Actinomyces.odontolyticus
          + 91.1073
LM num: 12
    .outcome =
          0.0785 * Total.bacteria
          − 87.6234 * Porphyromonas.gingivalis
          + 45.0694 * Tannerella.forsythia
          + 3.4246 * Treponema.denticola
          + 10.3816 * Fusobacterium.nucleatum.subsp..animalis
          + 4.5488 * Streptococcus.gordonii
          − 0.6784 * Actinomyces.odontolyticus
          + 91.0077
LM num: 13
    .outcome =
          0.0785 * Total.bacteria
          − 87.6234 * Porphyromonas.gingivalis
          + 45.1623 * Tannerella.forsythia
          + 3.4246 * Treponema.denticola
          + 10.3816 * Fusobacterium.nucleatum.subsp..animalis
          + 4.5488 * Streptococcus.gordonii
          − 0.6784 * Actinomyces.odontolyticus
          + 93.4098
LM num: 14
    .outcome =
          −0.0279 * Total.bacteria
          − 142.0103 * Porphyromonas.gingivalis
          + 9.7177 * Tannerella.forsythia
          + 5.5503 * Treponema.denticola
          + 24.5588 * Campylobacter.rectus
          + 16.8253 * Fusobacterium.nucleatum.subsp..animalis
          + 10.5169 * Streptococcus.gordonii
          + 793.003 * Veillonella.parvula
          − 497.9287
LM num: 15
    .outcome =
          −0.0279 * Total.bacteria
          − 142.0103 * Porphyromonas.gingivalis
          + 9.7177 * Tannerella.forsythia
          + 5.5503 * Treponema.denticola
          + 24.5588 * Campylobacter.rectus
          + 16.8253 * Fusobacterium.nucleatum.subsp..animalis
          + 10.4819 * Streptococcus.gordonii
          + 793.003 * Veillonella.parvula
          − 489.1573
LM num: 16
    .outcome =
          −0.0279 * Total.bacteria
          − 142.0103 * Porphyromonas.gingivalis
          + 9.7177 * Tannerella.forsythia
          + 5.5503 * Treponema.denticola
          + 24.5588 * Campylobacter.rectus
          + 16.8253 * Fusobacterium.nucleatum.subsp..animalis
          + 10.4819 * Streptococcus.gordonii
          + 793.003 * Veillonella.parvula
          − 489.4669
LM num: 17
    .outcome =
          −0.0279 * Total.bacteria
          − 142.0103 * Porphyromonas.gingivalis
          + 9.7177 * Tannerella.forsythia
          + 5.5503 * Treponema.denticola
          + 24.5588 * Campylobacter.rectus
          + 16.8253 * Fusobacterium.nucleatum.subsp..animalis

```
        + 10.4024 * Streptococcus.gordonii
        + 853.2173 * Veillonella.parvula
        - 506.1734
LM num: 18
.outcome =
        -0.0958 * Total.bacteria
        - 142.0103 * Porphyromonas.gingivalis
        + 9.7177 * Tannerella.forsythia
        + 5.5503 * Treponema.denticola
        + 32.3143 * Campylobacter.rectus
        + 16.8253 * Fusobacterium.nucleatum.subsp..animalis
        + 7.3721 * Streptococcus.gordonii
        + 686.8925 * Veillonella.parvula
        + 139.0553
LM num: 19
.outcome =
        -0.0958 * Total.bacteria
        - 142.0103 * Porphyromonas.gingivalis
        + 9.7177 * Tannerella.forsythia
        + 5.5503 * Treponema.denticola
        + 32.3143 * Campylobacter.rectus
        + 16.8253 * Fusobacterium.nucleatum.subsp..animalis
        + 7.3721 * Streptococcus.gordonii
        + 686.8925 * Veillonella.parvula
        + 143.569
```

Number of Rules: 19

Subsequently, the command "p←predict(m, newdata=bacteria)" was entered, and the measured SN ratio data of the bacterial load of each bacterium for 46 samples were substituted into the created prediction model "m," thereby obtaining the predicted PISA values "p" corresponding to 46 samples.

Figure 3:
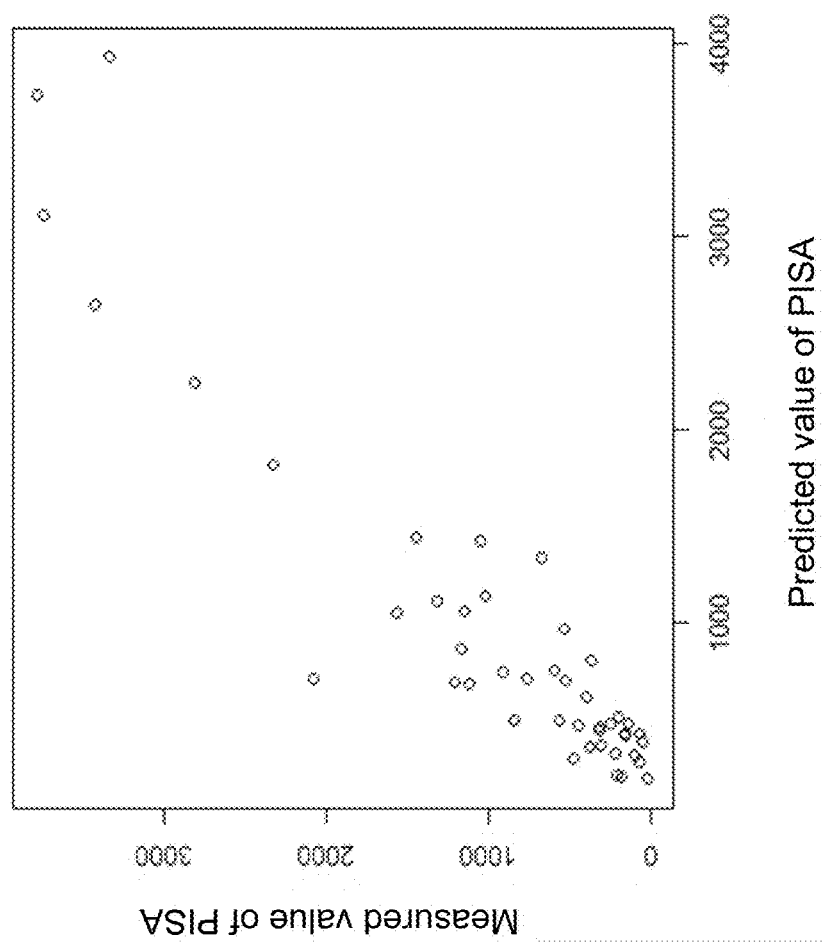
FIG. 3 is a figure showing a scatter diagram of PISA values (horizontal axis) predicted from a model tree created from the SN ratio of each bacterial load after interchip correction and PISA measurement values (vertical axis).

In order to calculate the correlation coefficient between the actual PISA values and the predicted PISA values, the command cor(p,bacteria$PISA) was executed for calculating the correlation coefficient between the predicted PISA values "p" and the measured PISA values. As a result, The correlation coefficient was 0.9291664. FIG. 3 shows a scatter diagram of the predicted PISA values "p" and the measured PISA values. As shown in this model, it was found that the PISA value can be predicted from the SN ratio of the DNA chip.

In particular, in comparing the SN ratio showing the bacterial load of each bacterium shown in Table 8 with the PISA value of the entire oral cavity, it was shown that the PISA value can be predicted from the SN ratio of the bacterial group of *Streptococcus mutans, Actinomyces odontolyticus*, and *Campylobacter concisus* which has a negative correlation coefficient and the bacterial group of *Tannerella forsythia, Treponema denticola, Porphyromonas gingivalis, Fusobacterium nucleatum* subsp. *animalis, Streptococcus gordonii, Veillonella parvula, Campylobacter rectus, Capnocytophaga ochracea*, and *Fusobacterium periodonticum* which has a positive correlation coefficient.

Example 3

A model for predicting the PISA value with a model tree was created using a machine learning technique based on the SN ratio of the bacterial load of each bacterium using the same data as in Table 7 described in Example 2. The "M5" method of the "caret" package of the statistical software "R" (R Development Core Team) was used for analysis.

In constructing the prediction model, 34 samples were randomly extracted from 46 samples and used for the cross-validation method. The ratio of model construction training data and verification data in the cross-validation method was 75:25, and the learning frequency was 10 times.

After the model construction, the remaining 12 samples of data that were not used for model construction were used as future unknown data and used for verification.

More specifically, after setting the table of Table 7 to the data frame name "bacteria," the following commands were executed.

fitControl←trainControl(method="CV",p=0.75, number=10)

train.index←sample(nrow(bacteria),nrow (bacteria)*0.75)

Modeling data set data.train←bacteria[train.index,]

Test data set data.test←bacteria[-train.index,]

data.m5←train(data.train[,-1],data.train$PISA, method="M5",trControl=fitControl)

(The ratio of model construction training data and verification data in the cross-validation method was 75:25, and the learning frequency was 10 times.)

data.m5$results #Display of construction model

Verification results with unknown data

PISA.pred←predict(data.m5,newdata=data.test[,-1])

Calculation of correlation coefficient cor(PISA.pred,data.test$PISA)

Output of scatter diagram plot(PISA.pred,data.test$PISA)

Results on training data

PISA.predtr←predict(data.m5,newdata=data.train[,-1])

Calculation of correlation coefficient cor(PISA.predtr,data.train$PISA)

Output of scatter diagram plot(PISA.predtr,data.train$PISA)

Figures 1, 4:
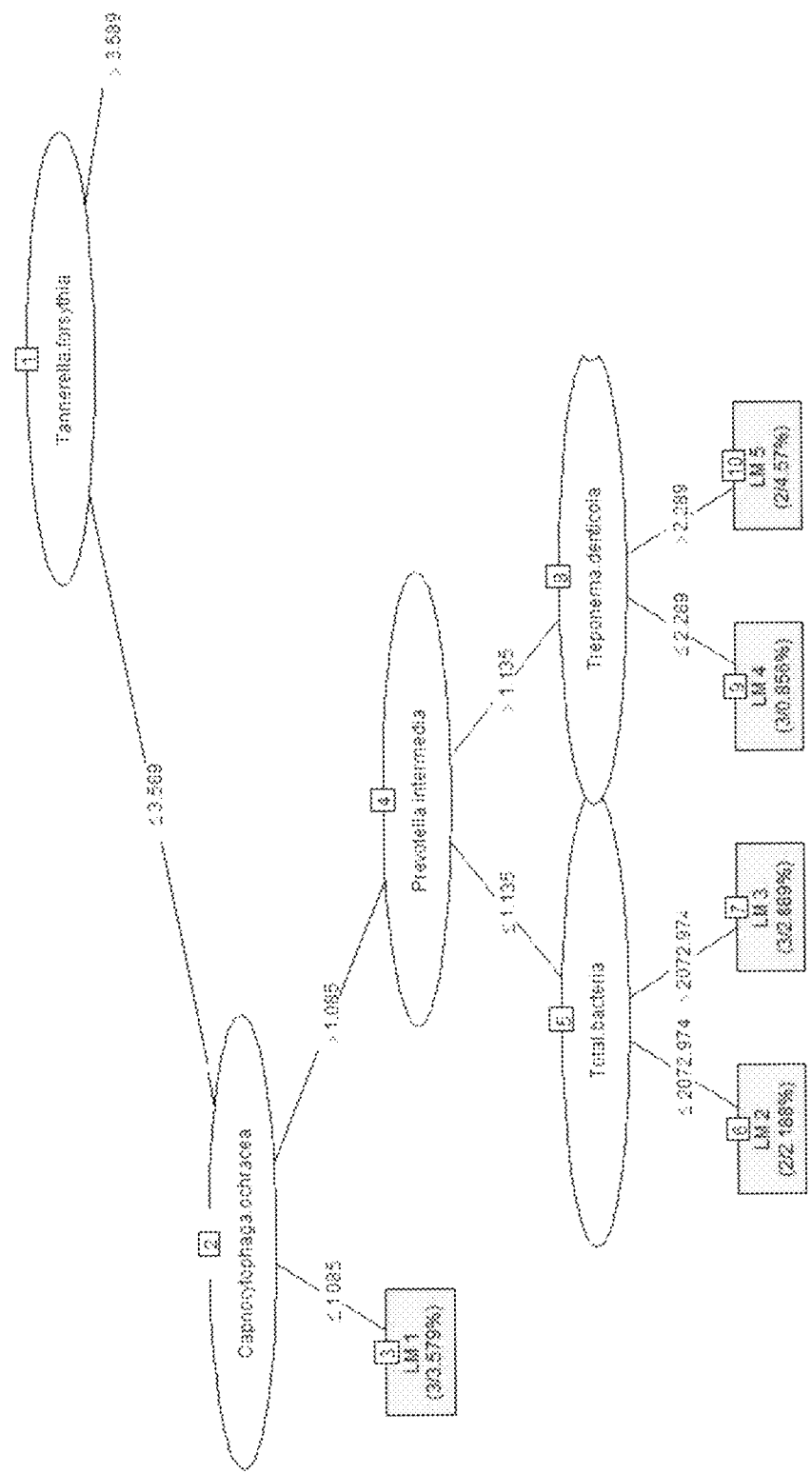
Figures 1, 4:
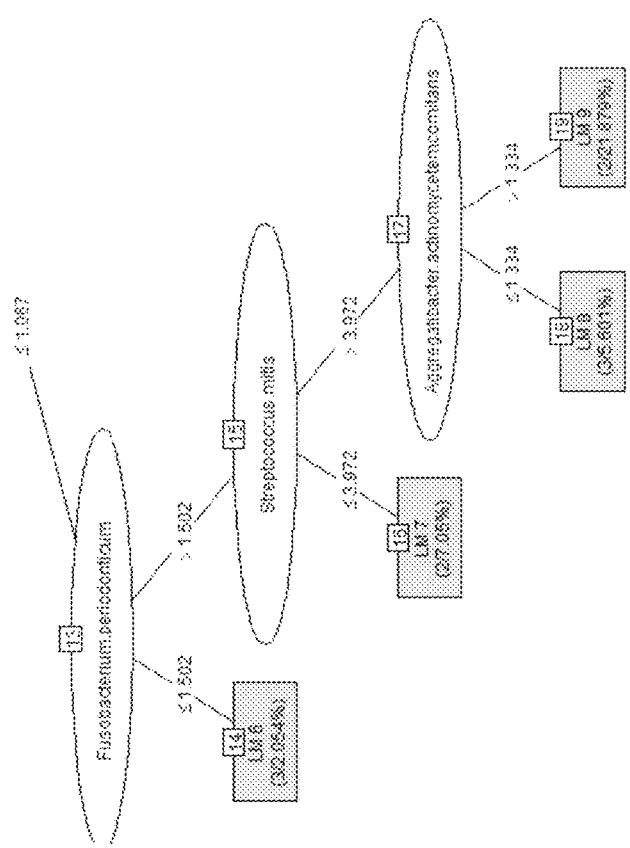
Figures 2, 4:
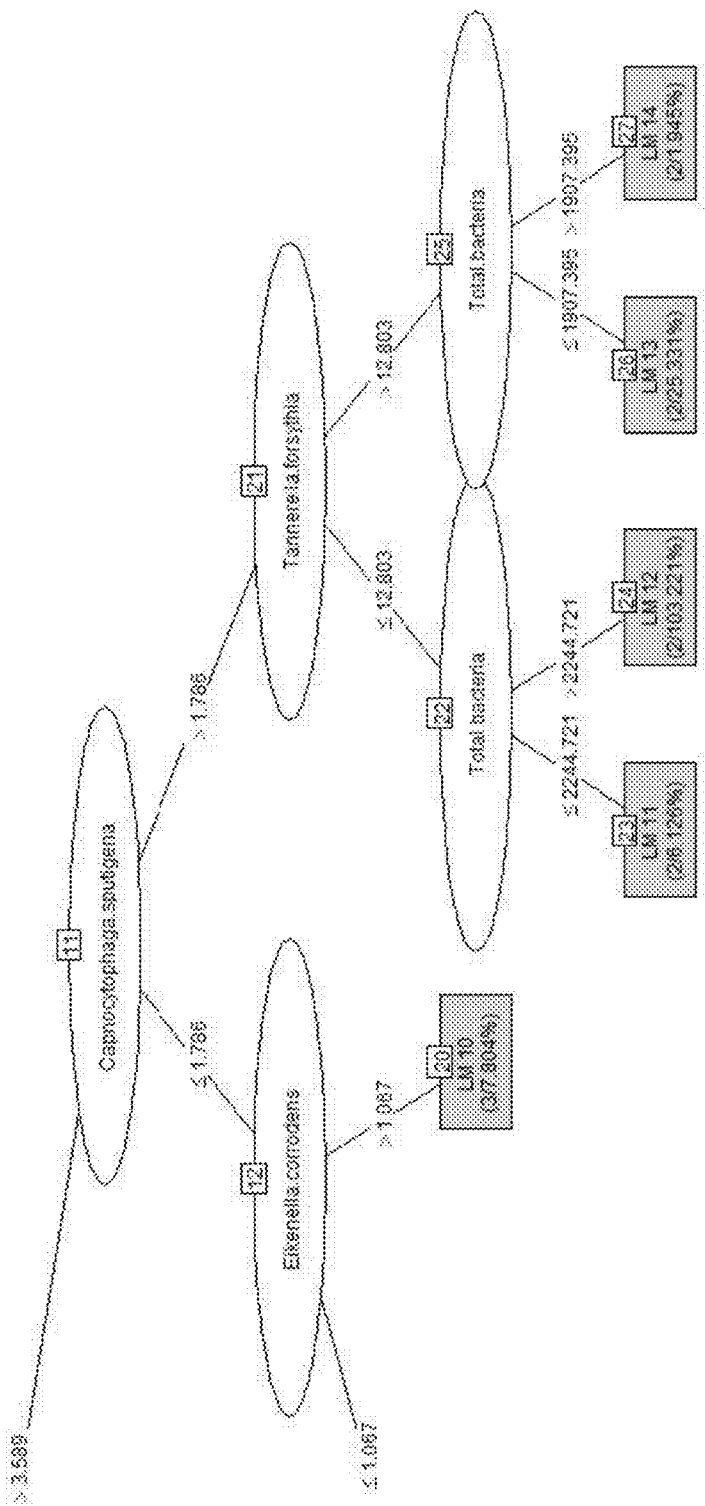

As a result, the following results were obtained for the construction model (FIG. 4).

M5 unpruned model tree:
(using smoothed linear models)
Tannerella.forsythia <= 3.589 :
|   Capnocytophaga.ochracea <= 1.085 : LM1 (3/3.579%)
|   Capnocytophaga.ochracea >  1.085 :
|   |   Prevotella.intermedia <= 1.135 :
|   |   |   Total.bacteria <= 2072.974 : LM2 (2/2.188%)
|   |   |   Total.bacteria >  2072.974 : LM3 (3/2.889%)
|   |   Prevotella.intermedia >  1.135:
|   |   |   Treponema.denticola <= 2.289 : LM4 (3/0.856%)
|   |   |   Treponema.denticola >  2.289 : LM5 (2/4.57%)
Tannerella.forsythia >  3.589 :
|   Capnocytophaga.sputigena <= 1.786 :
|   |   Eikenella.corrodens <= 1.067 :
|   |   |   Fusobacterium.periodonticum <= 1.502 : LM6 (3/2.054%)
|   |   |   Fusobacterium.periodonticum >  1.502 :
|   |   |   |   Streptococcus.mitis <= 3.972 : LM7 (2/7.05%)
|   |   |   |   Streptococcus.mitis >  3.972 :
|   |   |   |   |   Aggregatibacter.actinomycetemcomitans <= 1.334 : LM8 (3/5.601%)
|   |   |   |   |   Aggregatibacter.actinomycetemcomitans >  1.334 : LM9 (2/21.879%)
|   |   Eikenella.corrodens >  1.067 : LM10 (3/7.804%)
|   Capnocytophaga.sputigena >  1.786 :
|   |   Tannerella.forsythia <= 12.803 :
|   |   |   Total.bacteria <= 2244.721 : LM11 (2/6.126%)
|   |   |   Total.bacteria >  2244.721 : LM12 (2/103.221%)
|   |   Tannerella.forsythia >  12.803 :
|   |   |   Total.bacteria <= 1907.395 : LM13 (2/25.331%)
|   |   |   Total.bacteria >  1907.395 : LM14 (2/1.945%)
LM num: 1
.outcome =
        0.1964 * Total.bacteria
        + 8.473 * Treponema.denticola
        − 3.7524 * Streptococcus.mitis
        + 136.0844
LM num: 2
.outcome =
        0.1872 * Total.bacteria
        + 8.473 * Treponema.denticola
        − 102.9193 * Prevotella.intermedia
        − 3.7524 * Streptococcus.mitis
        + 297.6459
LM num: 3
.outcome =
        0.1877 * Total.bacteria
        + 8.473 * Treponema.denticola
        − 102.9193 * Prevotella.intermedia
        − 3.7524 * Streptococcus.mitis
        + 295.2116
LM num: 4
.outcome =
        0.1964 * Total.bacteria
        + 10.9568 * Treponema.denticola
        − 102.9193 * Prevotella.intermedia
        − 3.7524 * Streptococcus.mitis
        + 261.0986
LM num: 5
.outcome =
        0.1964 * Total.bacteria
        + 11.1029 * Treponema.denticola
        − 102.9193 * Prevotella.intermedia
        − 3.7524 * Streptococcus.mitis
        + 261.4416
LM num: 6
.outcome =
        0.1528 * Total.bacteria
        + 6.7947 * Tannerella.forsythia
        + 6.5901 * Treponema.denticola
        + 29.1856 * Aggregatibacter.actinomycetemcomitans
        + 74.536 * Capnocytophaga.sputigena
        − 197.1112 * Eikenella.corrodens
        − 5.6233 * Streptococcus.mitis
        + 637.0725
LM num: 7
.outcome =
        0.1528 * Total.bacteria
        + 6.7947 * Tannerella.forsythia
        + 6.5901 * Treponema.denticola
        + 32.1268 * Aggregatibacter.actinomycetemcomitans
        + 74.536 * Capnocytophaga.sputigena

```
            - 197.1112 * Eikenella.corrodens
            - 5.6233 * Streptococcus.mitis
            + 625.658
    LM num: 8
        .outcome =
            0.1528 * Total.bacteria
            + 6.7947 * Tannerella.forsythia
            + 6.5901 * Treponema.denticola
            + 32.301 * Aggregatibacter.actinomycetemcomitans
            + 74.536 * Capnocytophaga.sputigena
            - 197.1112 * Eikenella.corrodens
            - 5.6233 * Streptococcus.mitis
            + 627.695
    LM num: 9
        .outcome =
            0.1528 * Total.bacteria
            + 6.7947 * Tannerella.forsythia
            + 6.5901 * Treponema.denticola
            + 32.3574 * Aggregatibacter.actinomycetemcomitans
            + 74.536 * Capnocytophaga.sputigena
            - 197.1112 * Eikenella.corrodens
            - 5.6233 * Streptococcus.mitis
            + 627.9978
    LM num: 10
        .outcome =
            0.1528 * Total.bacteria
            + 6.7947 * Tannerella.forsythia
            + 6.5901 * Treponema.denticola
            + 22.9812 * Aggregatibacter.actinomycetemcomitans
            + 74.536 * Capnocytophaga.sputigena
            - 273.7656 * Eikenella.corrodens
            - 5.6233 * Streptococcus.mitis
            + 673.9955
    LM num: 11
        .outcome =
            0.1989 * Total.bacteria
            + 14.1331 * Tannerella.forsythia
            + 6.5901 * Treponema.denticola
            + 90.7394 * Capnocytophaga.sputigena
            - 6.2112 * Streptococcus.mitis
            + 410.322
    LM num: 12
        .outcome =
            0.1989 * Total.bacteria
            + 14.1331 * Tannerella.forsythia
            + 6.5901 * Treponema.denticola
            + 90.7394 * Capnocytophaga.sputigena
            - 6.2112 * Streptococcus.mitis
            + 409.7214
    LM num: 13
        .outcome =
            0.1989 * Total.bacteria
            + 14.1331 * Tannerella.forsythia
            + 6.5901 * Treponema.denticola
            + 90.7394 * Capnocytophaga.sputigena
            - 6.2112 * Streptococcus.mitis
            + 497.6085
    LM num: 14
        .outcome =
            0.1989 * Total.bacteria
            + 14.1331 * Tannerella.forsythia
            + 6.5901 * Treponema.denticola
            + 90.7394 * Capnocytophaga.sputigena
            - 6.2112 * Streptococcus.mitis
            + 501.0283
```

Number of Rules: 14

Figure 5:
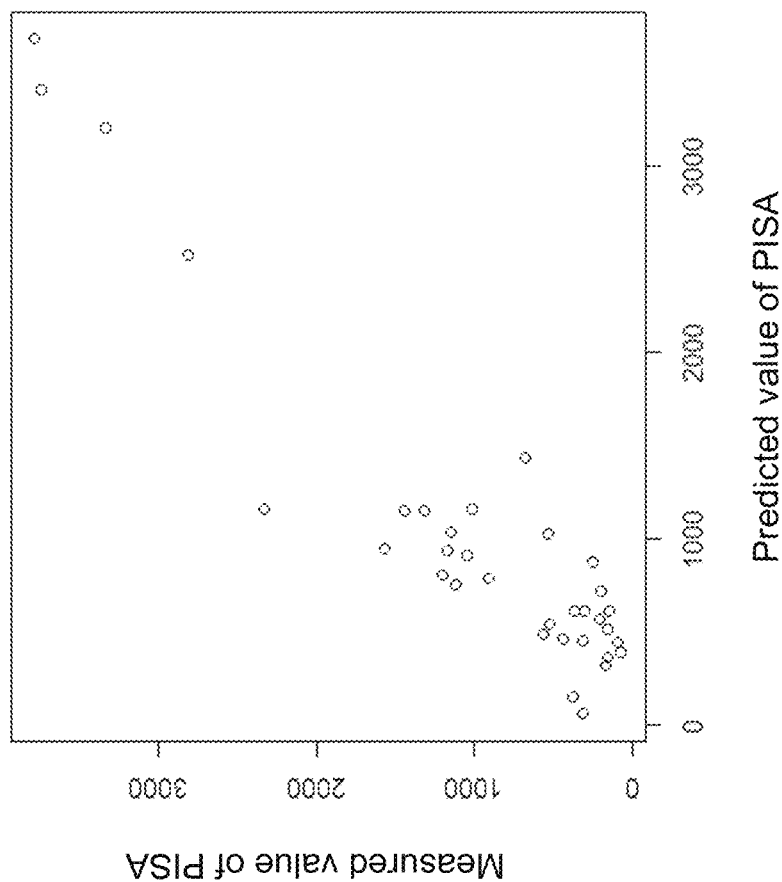
FIG. 5 is a figure showing a scatter diagram of PISA values (horizontal axis) predicted for 34 data used for creating the model tree in FIG. 4 and PISA measurement values (vertical axis).

As a result of inputting the training data to the constructed model, the correlation coefficient between the actual PISA value and the predicted value was 0.9318094. The results are shown in the scatter diagram of FIG. 5.

Figure 6:
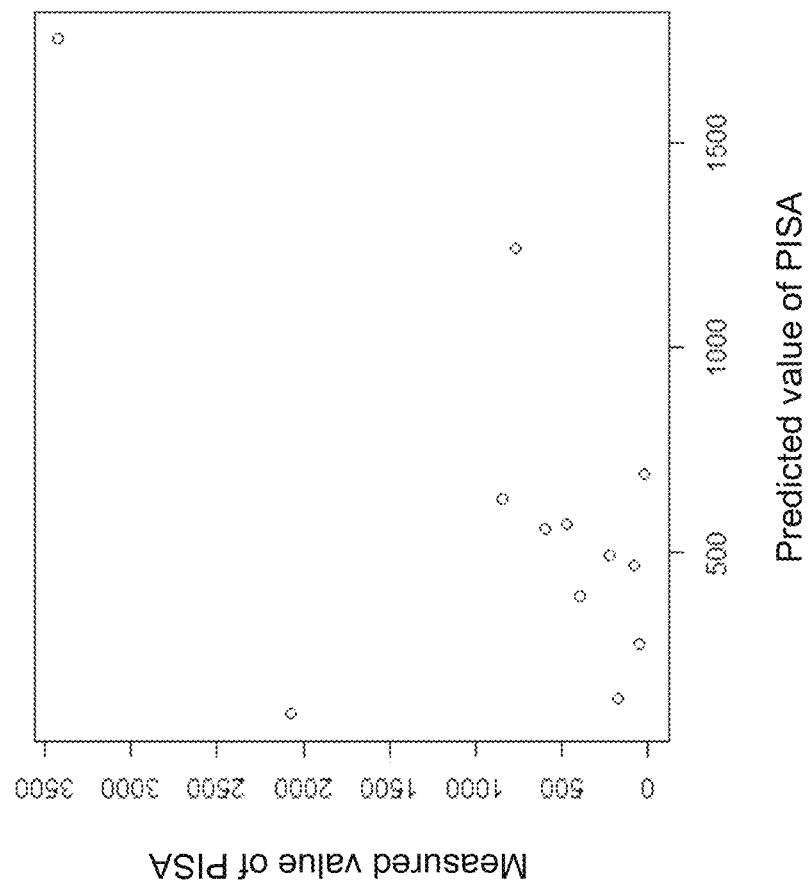
FIG. 6 is a figure showing a scatter diagram of PISA measurement values of the remaining 12 data not used for modeling out of 46 data in total (vertical axis) and PISA values (horizontal axis) predicted from the model tree in FIG. 4.

Meanwhile, in the verification results in which unknown data were input to the constructed model, the correlation coefficient between the actual PISA value and the predicted value was 0.5986115. The results are shown in the scatter diagram of FIG. 6.

The results showed that the PISA value can be predicted even for unknown data.

In particular, in comparing the SN ratio showing the bacterial load of each bacterium shown in Table 8 with the PISA value of the entire oral cavity, it was shown that the PISA value can be predicted from the SN ratio of the bacterial group of *Streptococcus mitis* which has a negative correlation coefficient and the bacterial group of *Tannerella forsythia, Treponema denticola, Capnocytophaga ochracea, Capnocytophaga sputigena, Eikenella corrodens, Aggre-* gatibacter actinomycetemcomitans, Prevotella intermedia, and Fusobacterium periodonticum which has a positive correlation coefficient.

Example 4

<Comparison with Existing Determination Methods>

Regarding the determination of the periodontal disease state using saliva as a sample, according to the "Clinical indicating the total bacterial load were calculated and designated as existing indexes. Based on these indexes, "mild," "moderate," and "severe" were determined.

Table 9 summarizes the determined results, the measured PISA values, the predicted PISA values based on the results of Example 3, the SN ratio of three bacteria, and the SN ratio of total bacteria.

TABLE 9

| PISA (measured value) | Total bacteria | *Porphyromonas gingivalis* | *Tannerella forsythia* | *Treponema denticola* | Sum of SN ratio of bacteria/Total bacterial SN ratio | Determination | Predicted value of PISA |
|---|---|---|---|---|---|---|---|
| 161 | 1158.4 | 1.6 | 0.8 | 1.1 | 0.3% | Moderate | 365 |
| 73 | 1501.9 | 1.2 | 2.8 | 1 | 0.3% | Moderate | 391 |
| 571 | 1478.5 | 1.7 | 1.8 | 1.3 | 0.3% | Moderate | 485 |
| 526 | 1887 | 1.3 | 1.3 | 1.2 | 0.2% | Moderate | 539 |
| 597 | 2007.4 | 1.1 | 1.2 | 1 | 0.2% | Moderate | 557 |
| 100 | 2196.6 | 1.3 | 1 | 1.3 | 0.2% | Moderate | 472 |
| 320 | 2259 | 1.3 | 1.7 | 1.2 | 0.2% | Moderate | 447 |
| 395 | 2343.7 | 1.3 | 2.2 | 2.7 | 0.3% | Moderate | 393 |
| 382 | 2458.9 | 1.3 | 2.9 | 1.3 | 0.2% | Moderate | 155 |
| 223 | 2652.1 | 1.4 | 1.2 | 1.8 | 0.2% | Moderate | 493 |
| 318 | 2689.1 | 1.4 | 1.2 | 1.8 | 0.2% | Moderate | 59 |
| 147 | 2485.6 | 1.5 | 3.4 | 1.4 | 0.3% | Moderate | 607 |
| 2076 | 2533.6 | 1.6 | 1.2 | 1.4 | 0.2% | Moderate | 104 |
| 164 | 2567.6 | 1.5 | 1.3 | 1.4 | 0.2% | Moderate | 510 |
| 77 | 2357.1 | 1.6 | 1.4 | 1.4 | 0.2% | Moderate | 462 |
| 477 | 2148.1 | 1.8 | 1.7 | 1.5 | 0.2% | Moderate | 564 |
| 167 | 2743.5 | 1.7 | 1.6 | 1.6 | 0.2% | Moderate | 327 |
| 20 | 2973.7 | 2.2 | 2.4 | 1.7 | 0.2% | Moderate | 685 |
| 180 | 2872.6 | 2.1 | 2.3 | 1.8 | 0.2% | Moderate | 141 |
| 215 | 2083 | 1.4 | 2.6 | 3 | 0.3% | Moderate | 568 |
| 309 | 2902 | 2.3 | 2.3 | 3.3 | 0.3% | Moderate | 621 |
| 52 | 2781.7 | 3.8 | 2.4 | 4.5 | 0.4% | Moderate | 274 |
| 846 | 2809.8 | 1.5 | 3.4 | 4.8 | 0.3% | Moderate | 629 |
| 1205 | 1217.1 | 1.1 | 5.1 | 1 | 0.6% | Severe | 799 |
| 1172 | 1468.9 | 2 | 8.8 | 5.7 | 1.1% | Severe | 936 |
| 1154 | 1825.6 | 1.2 | 11.4 | 27.9 | 2.2% | Severe | 1039 |
| 915 | 2128.1 | 1.3 | 4.7 | 1.5 | 0.4% | Moderate | 792 |
| 680 | 1212.8 | 2.5 | 57.6 | 40.3 | 8.3% | Severe | 1421 |
| 1050 | 1726.4 | 1.4 | 11.6 | 8.4 | 1.2% | Severe | 897 |
| 1120 | 2233 | 1.3 | 6.6 | 2.2 | 0.5% | Moderate | 752 |
| 1570 | 1414.2 | 3.2 | 3.8 | 2.1 | 0.6% | Severe | 942 |
| 250 | 2162.2 | 1.3 | 7.8 | 3.9 | 0.6% | Severe | 871 |
| 369 | 2348.3 | 1.3 | 4 | 15.4 | 0.9% | Severe | 613 |
| 1018 | 1926.4 | 4.8 | 18.5 | 34.6 | 3.0% | Severe | 1101 |
| 445 | 3241.2 | 1.8 | 6.8 | 1.9 | 0.3% | Moderate | 450 |
| 1321 | 1550.2 | 2.1 | 10.2 | 18.5 | 2.0% | Severe | 1145 |
| 1447 | 1965.8 | 1.9 | 6.7 | 15.1 | 1.2% | Severe | 1154 |
| 2326 | 2523.6 | 1.7 | 5.1 | 13.7 | 0.8% | Severe | 1161 |
| 203 | 3167.9 | 2.2 | 5.4 | 5 | 0.4% | Moderate | 724 |
| 768 | 3892.8 | 2.2 | 8.7 | 2 | 0.3% | Moderate | 1238 |
| 535 | 1525.2 | 1.4 | 16.9 | 12.3 | 2.0% | Severe | 1271 |
| 2814 | 1538.3 | 1.9 | 62.1 | 99.5 | 10.6% | Severe | 2515 |
| 3335 | 1709.7 | 6.8 | 62.9 | 193.6 | 15.4% | Severe | 3202 |
| 3420 | 1728.1 | 2.7 | 32.7 | 39.3 | 4.3% | Severe | 1755 |
| 3735 | 2105 | 5.1 | 68.9 | 183.4 | 12.2% | Severe | 3394 |
| 3775 | 9192.4 | 6.5 | 15.4 | 6.5 | 0.3% | Moderate | 3678 |

Guidelines for Antibacterial Therapy for Patients with Periodontal Disease (in Japanese) (edited by the Japanese Society of Periodontology), the state can be determined to be "mild" when the total bacterial count of three types of bacteria is less than 0.05% with respect to the total bacterial count, "moderate" when it is 0.05% or more and less than 0.5% with respect to the total bacterial count, and "severe" when it is 0.5% or more with respect to the total bacterial count.

Figure 7:
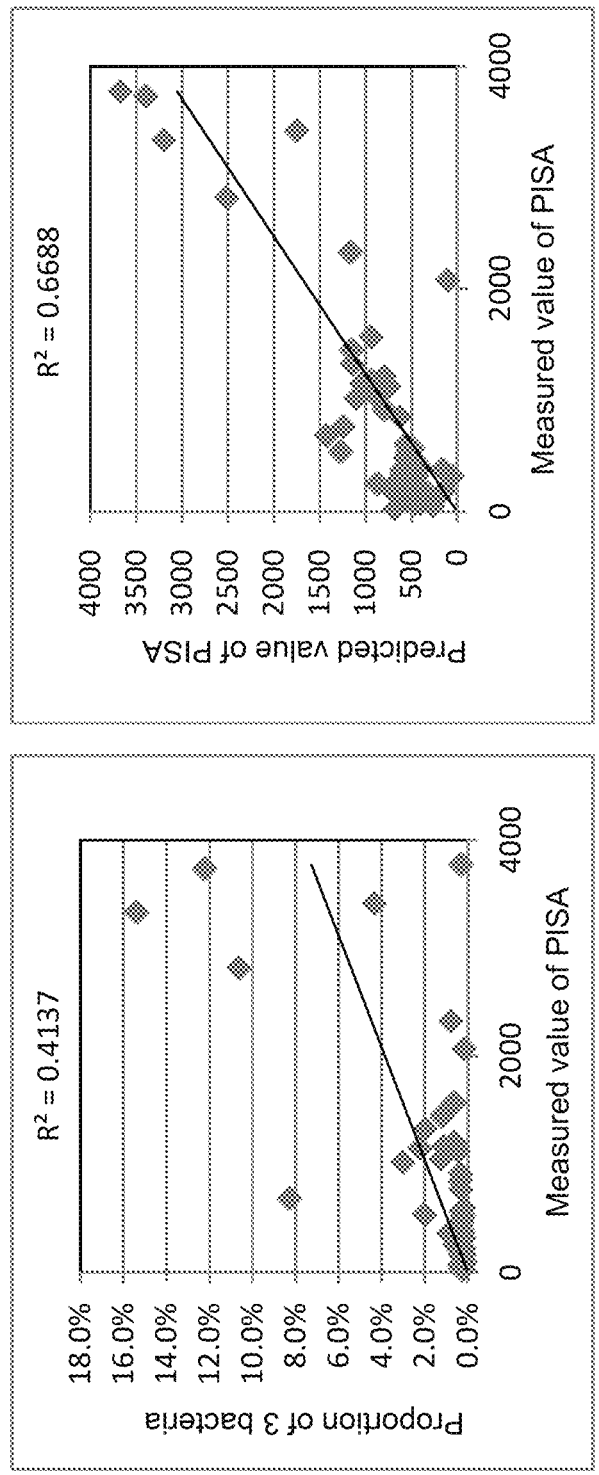
FIG. 7 is a figure showing a comparison of a scatter diagram (left) of PISA measurement values and "proportions of three bacteria with respect to the total bacterial load (known in the art)" and a scatter diagram (right) of PISA actual measurement values and PISA prediction values.

Therefore, among the SN ratios shown in Table 7, the total value of SN ratios of three types of red-complex bacteria, namely *Porphyromonas gingivalis*, *Tannerella forsythia*, and *Treponema denticola*, and the SN ratio of total bacteria A graph in which the X axis represents the measured PISA values shown in Table 9 and the Y axis represents the existing "ratio of three bacteria" is shown as the left graph of FIG. 7. Similarly, a graph in which the X axis represents the measured PISA values and the Y axis represents the predicted PISA values is shown as the right graph of FIG. 7. The coefficient of determination with the measured PISA value was about 0.41 for the existing method and about 0.66 for the method of the present invention, showing that the periodontal disease state can be predicted more accurately than the existing method. In addition, the average of "predicted PISA" values of the samples determined to be "severe" by the existing method was 1424, and the average of predicted PISA values of the samples determined to be "moderate" was 736, showing that the indexes of the present invention can be compared with the conventional indexes.

Example 5

Figure 8:
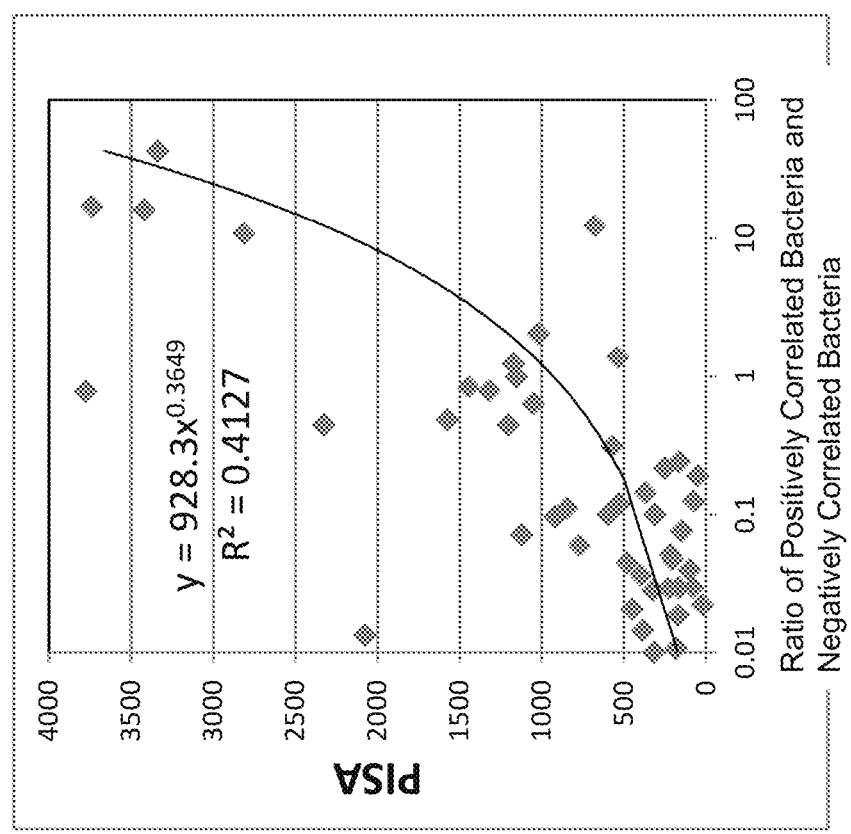
FIG. 8 is a figure showing a scatter diagram of PISA measurement values and ratios of bacteria showing a positive correlation and bacteria showing a negative correlation ("balance index").

Based on the data in Tables 7 and 8, the top three bacterial species (*Porphyromonas gingivalis*, *Treponema denticola*, and *Tannerella forsythia*) showing a "positive correlation" of the bacterial load and PISA and the top three bacterial species (*Streptococcus mutans*, *Actinomyces odontolyticus*, and *Streptococcus mitis* bv 2) showing a "negative correlation" of the bacterial load and PISA were selected. The total ratio of the SN ratios of the groups of three bacteria (the ratio of the bacteria showing a positive correlation and the bacteria showing a negative correlation: "balance index") was calculated.
A scatter diagram of the calculated values (X axis) and the PISA values (Y axis) is shown in FIG. 8. As a result, it was found that there is a relationship between X and Y with a coefficient of determination of about 0.41. That is, it was found that PISA can be estimated even when the balance index is used.

Example 6

In order to investigate bacterial species newly discussed in recent years, a DNA chip which is newly equipped with the bacterial probes shown in Table 10 was prepared in the same manner as in Example 1.

TABLE 10

| SEQ ID NO | Name | Probe sequence |
|---|---|---|
| 30 | Control DNA | CTATTCGACCAGCGATATCACTACGTAGGC |
| 31 | Total bacteria | CGTATTACCGCGGCTGCTGGCAC |
| 36 | *Eubacterium nodatum* probe | CCTACGCTTACTTAACCACCTA |
| 37 | *Parvimonas micra* probe | GTGCTTAATGAGGTTAAGCC |
| 38 | *Filifactor alocis* probe | CCCCTACTACAGAGTTTTACGA |
| 39 | *Streptococcus sobrinus* probe | TACACACGTTCTTCCCCTAC |
| 40 | *Porphyromonas pasteri* probe | ACACGTGACTCTTGTTATTC |
| 41 | *Veillonella atypica* probe | CGTCAAATCCTCGCACTATTC |
| 42 | *Haemophilus parainfluenzae* probe | AGTTAACGTCAATCACCTAG |
| 43 | *Alloprevotella* spp. (*A. rava*, OT 308) probe | TTCCCAACTAAAAGCAGTTTA |
| 44 | *Streptococcus parasanguinis* probe | CTGGTAAGTTACCGTCAC |
| 45 | *Actinomyces israelii* probe | GCGCTTCATAACCCGGCTAC |

TABLE 10-continued

| SEQ ID NO | Name | Probe sequence |
|---|---|---|
| 46 | *Prevotella pallens* probe | CACGTGCATCAAATTATTCTCG |
| 47 | *Prevotella loescheii* probe | CCTACTTTCAGCGCACTCAA |
| 48 | *Prevotella histicola* probe | CACGTGACTGACTTTATCCC |
| 49 | *Solobacterium moorei* probe | CCAACAATTTAACCACTTAC |
| 50 | *Prevotella melaninogenica* probe | AATAGGGACACGTCCCTAAC |
| 51 | *Selenomonas sputigena* probe | GTACCGTCACCCAAACTCAATA |
| 52 | *Rothia dentocariosa* probe | ACCCACTGCAAAACCAGGGT |
| 53 | *Rothia mucilaginosa* probe | TCTCTTCTTCCCTGCTAACA |
| 54 | *Veillonella rogosae* probe | ACCGTCAATTCCTCTAACTATT |
| 55 | *Peptostreptococcus stomatis* probe | ACCACCGACTTGAAGGACCA |
| 56 | *Prevotella denticola* probe | AGTCAGACGTTGGGCGCCTA |
| 57 | *Porphyromonas endodontalis* probe | TACATGCATCTCAGCTACACGT |
| 58 | *Streptococcus salivarius* probe | CACACTCGTTCTTGACTTAC |
| 59 | *Actinomyces graevenitzii* probe | AAAAAGCAGTGCCTTGTTCC |
| 60 | *Treponema medium* probe | GTCGATTACCGTCATCAGATG |
| 61 | *Treponema socranskii* probe | TTCCTCCAAAACTTATTCCT |
| 62 | *Gemella sanguinis* probe | CCGTCTCTACTGTATATAGT |
| 63 | *Porphyromonas catoniae* probe | GGTACATTCACTATGGTACACG |
| 64 | *Corynebacterium matruchotii* probe | TCTTAACAAAGGTACCGTCACC |
| 65 | *Eubacterium saphenum* probe | CCCTAGGACAGAGGCTTACA |
| 66 | *Neisseria flavescens* probe | AGCTGTCGATATTAGCAACAG |
| 67 | *Granulicatella adiacens* probe | GTCAAGGCGCTAACAGTTAC |

TABLE 10-continued

| SEQ ID NO | Name | Probe sequence |
|---|---|---|
| 68 | Eubacterium sulci probe | AAACCCTGCGCTTAAGGTGC |
| 69 | Megasphaera micronuciformis probe | TAACCACAAGATTATTCGTC |
| 70 | Prevotella shahii probe | ACGTGGGCTCTTTTATCCCC |
| 71 | SR1 sp. OT 345 probe | CGTCATTCGTCTTCTGCCAA |

PISA data were also collected for 56 samples that were partially collected in addition to the same samples as in Example 1, and fluorescence intensity data were acquired for these samples using the new DNA chip shown in Table 10. The experimental conditions at the time of acquisition were the same as in Example 1, but the following two points were changed.

The primers used for PCR were changed as follows.
R and Y represent mixed bases, R represents A and G, and Y represents C and T.
Forward Primer (for Bacterial Amplification):

(SEQ ID NO: 72)
5'-Cy5-TACGGGAGGCAGCAG-3'

Reverse Primer (for Bacterial Amplification):

(SEQ ID NO: 73)
5'-CRGGGTATCTAATCCYGTT-3'

Forward Primer (for Absolute Load Index Amplification):

(SEQ ID NO: 34)
5'-Cy5-GAGAAGCCTACACAAACGTAACGTC-3'

Reverse Primer (for Absolute Load Index Amplification):

(SEQ ID NO: 35)
5'-CTCTAAAGACCGCTCTATCTCGG-3'

The hybridization temperature and time were set to 50° C. for 16 hours. Subsequently, the obtained fluorescence intensity was processed as follows.

The fluorescence intensity of a spot with a probe mounted thereon for a bacterium to be detected was subtracted by the background value (the median of the fluorescence intensities of spots without a probe), thereby calculating the signal intensity derived from hybridization. At this time, when the signal intensity was below a certain threshold, it was determined to be noise and was set to "0." Here, as the threshold value, a value three times the standard deviation of 20 values excluding the upper and lower 5 values out of the fluorescence intensities of 30 spots without a probe was used.

Further, the relative ratio of each bacterium to the total bacteria was calculated by dividing the signal intensity of the probe for a detection target bacterium by the signal intensity of the probe for the total microbial load index. For the subsequent analysis, the value obtained by converting the relative ratio to the total bacterial load by log 10 was used. However, since the value "0" cannot be calculated, the value after log 10 conversion was replaced with −4. Thus, data were obtained for all 56 specimens. Table 11 summarizes the results and PISA for each specimen.

TABLE 11

| sample | PISA | control | Total bacteria | Eubacterium nodatum | Parvimonas micra | Filifactor alocis | Streptococcus sobrinus |
|---|---|---|---|---|---|---|---|
| S21-D-1 | 425.7 | −0.4041 | 0.0000 | −2.9683 | −2.6500 | −2.5172 | −3.1388 |
| S22-D-1 | 202.4 | −0.2117 | 0.0000 | −1.9637 | −2.5179 | −1.4308 | −3.1828 |
| S23-D-1 | 168.9 | −0.3855 | 0.0000 | −3.1033 | −1.5887 | −3.0227 | −3.2070 |
| S24-D-1 | 986.1 | 0.2100 | 0.0000 | −1.8923 | −2.6821 | −0.9415 | −3.0353 |
| S25-D-1 | 165.5 | −0.3962 | 0.0000 | −3.1174 | −2.0946 | −3.0340 | −3.1664 |
| S27-D-1 | 1038.7 | −0.4092 | 0.0000 | −2.0722 | −2.5980 | −0.9767 | −3.1170 |
| S29-D-1 | 517.4 | −0.4205 | 0.0000 | −1.8183 | −2.2273 | −0.8296 | −2.8578 |
| S30-D-1 | 842 | −0.1747 | 0.0000 | −2.0923 | −2.9067 | −0.5196 | −3.0649 |
| S31-D-1 | 375.6 | −0.4451 | 0.0000 | −2.9414 | −2.0677 | −1.6945 | −3.1806 |
| S32-D-1 | 2787.6 | −0.3766 | 0.0000 | −1.6477 | −2.3286 | −0.5893 | −2.9905 |
| S21-D-2 | 20.8 | −0.3665 | 0.0000 | −3.0521 | −2.8745 | −2.2106 | −3.1718 |
| S22-D-2 | 232.2 | −0.2838 | 0.0000 | −2.6253 | −2.5896 | −1.2442 | −3.1817 |
| S23-D-2 | 79.6 | −0.4439 | 0.0000 | −2.9023 | −2.5324 | −2.1456 | −3.2511 |
| S24-D-2 | 133.1 | −0.1888 | 0.0000 | −2.9760 | −3.1022 | −1.9866 | −3.2112 |
| S25-D-2 | 146.3 | −0.4493 | 0.0000 | −3.1358 | −2.4064 | −3.1955 | −3.2584 |
| S28-D-2 | 182.7 | −0.3839 | 0.0000 | −2.9588 | −1.8171 | −1.5686 | −3.2036 |
| S30-D-2 | 845.8 | −0.2814 | 0.0000 | −1.8058 | −2.4906 | −0.4954 | −2.9830 |
| S33-D-1 | 1114.7 | −0.4773 | 0.0000 | −2.1308 | −2.0347 | −1.0241 | −3.1309 |
| S34-D-1 | 1579.1 | −0.3212 | 0.0000 | −1.8323 | −2.7186 | −0.7213 | −2.8756 |
| S35-D-1 | 1114.5 | −0.2992 | 0.0000 | −2.8984 | −1.6078 | −1.8382 | −3.1712 |
| S36-D-1 | 1200.8 | −0.4286 | 0.0000 | −2.4481 | −1.9592 | −0.9394 | −3.0826 |
| S37-D-1 | 1224.3 | −0.2250 | 0.0000 | −2.5320 | −2.9796 | −0.9526 | −3.1160 |
| S38-D-1 | 546.9 | −0.3282 | 0.0000 | −2.7404 | −3.0769 | −1.5577 | −3.2493 |
| S39-D-1 | 3772.9 | −0.5547 | 0.0000 | −3.0937 | −1.8102 | −1.8031 | −3.2558 |
| S40-D-1 | 363.7 | −0.3681 | 0.0000 | −2.6247 | −2.2045 | −1.7012 | −3.2897 |
| S33-D-2 | 146.3 | −0.4434 | 0.0000 | −2.8416 | −2.7573 | −1.6321 | −3.2243 |
| S35-D-2 | 161.8 | −0.2903 | 0.0000 | −3.1390 | −3.1692 | −3.0497 | −3.2927 |
| S41-D-1 | 2044.1 | −0.2496 | 0.0000 | −3.0794 | −2.0890 | −3.0232 | −3.1872 |
| S42-D-1 | 446.5 | −0.1390 | 0.0000 | −2.5856 | −2.6911 | −2.1033 | −2.9256 |
| S43-D-1 | 776.1 | −0.4267 | 0.0000 | −3.1124 | −2.0334 | −2.4262 | −3.2673 |

TABLE 11-continued

| | | | | | | |
|---|---|---|---|---|---|---|
| S44-D-1 | 912.4 | −0.3480 | 0.0000 | −1.7858 | −2.1845 | −1.0993 | −3.1443 |
| S45-D-1 | 890.8 | −0.6629 | 0.0000 | −2.8862 | −2.1416 | −1.5709 | −3.1344 |
| S46-D-1 | 646.6 | −0.3367 | 0.0000 | −1.5777 | −2.6398 | −0.5950 | −3.0034 |
| S47-D-1 | 803 | −0.3496 | 0.0000 | −2.9024 | −1.9560 | −1.8176 | −3.1875 |
| S48-D-1 | 3334.8 | −0.2703 | 0.0000 | −1.9902 | −2.4634 | −0.2961 | −2.9813 |
| S49-D-1 | 1876.5 | −0.4199 | 0.0000 | −2.6332 | −2.1929 | −1.3293 | −3.0881 |
| S50-D-1 | 361.5 | −0.5875 | 0.0000 | −3.0613 | −2.2416 | −2.4477 | −3.3172 |
| S51-D-1 | 3377.4 | −0.1896 | 0.0000 | −1.8236 | −2.3475 | −0.5848 | −3.0905 |
| S37-D-2 | 277.7 | −0.2221 | 0.0000 | −3.0045 | −2.3901 | −2.8793 | −3.2224 |
| S38-D-2 | 70.9 | −0.3526 | 0.0000 | −2.8874 | −2.8699 | −1.7492 | −3.2152 |
| S55-D-1 | 478.2 | −0.7278 | 0.0000 | −3.1306 | −1.9955 | −2.1856 | −3.3932 |
| S56-D-1 | 251.7 | −0.6150 | 0.0000 | −3.1476 | −2.4952 | −2.3903 | −3.4383 |
| S57-D-1 | 171 | −0.3423 | 0.0000 | −3.1615 | −2.5984 | −3.3032 | −3.4125 |
| S58-D-1 | 686.4 | −0.6548 | 0.0000 | −3.2505 | −3.2316 | −2.4917 | −3.4788 |
| S59-D-1 | 365 | −0.7328 | 0.0000 | −3.2749 | −2.1765 | −2.6648 | −3.4504 |
| S60-D-1 | 3702.8 | −0.4387 | 0.0000 | −2.5621 | −2.3331 | −1.0153 | −3.3760 |
| S40-D-2 | 0 | −0.4462 | 0.0000 | −3.1535 | −2.7634 | −3.0900 | −3.3706 |
| S73-D-2 | 95.8 | −0.6657 | 0.0000 | −3.2201 | −3.2242 | −2.9253 | −3.3901 |
| S52-D-2 | 1436.2 | −0.5495 | 0.0000 | −2.6666 | −2.7815 | −1.4491 | −3.3358 |
| S56-D-2 | 503.4 | −0.6792 | 0.0000 | −3.1778 | −2.6095 | −2.2246 | −3.4541 |
| S59-D-2 | 228.1 | −0.9631 | 0.0000 | −3.2568 | −2.2626 | −3.1281 | −3.3909 |
| S72-D-1 | 729.1 | −0.6859 | 0.0000 | −3.1303 | −2.1138 | −1.4160 | −4.0000 |
| S72-D-2 | 52.4 | −0.5090 | 0.0000 | −2.9165 | −2.7704 | −1.5378 | −3.3496 |
| S73-D-1 | 139.5 | −0.3953 | 0.0000 | −3.1864 | −2.9573 | −2.4445 | −3.3583 |
| S74-D-1 | 489.4 | −0.4760 | 0.0000 | −3.1565 | −2.6150 | −3.2928 | −3.3710 |
| S74-D-2 | 509.4 | −0.6355 | 0.0000 | −3.1240 | −2.7799 | −3.3183 | −3.4044 |

| Porphyromonas pasteri | Veillonella atypica | Haemophilus parainfluenzae | Alloprevotella spp. (A. rava.OT 308) | Streptococcus parasanguinis | Actinomyces israelii | Prevotella pallens |
|---|---|---|---|---|---|---|
| −2.9668 | −1.8821 | −2.1762 | −3.0607 | −0.7277 | −3.0711 | −3.1171 |
| −3.1701 | −2.0487 | −2.3899 | −2.9118 | −1.0366 | −2.6934 | −2.4242 |
| −1.9922 | −2.5321 | −1.6311 | −3.0471 | −1.5073 | −3.0962 | −2.7775 |
| −2.5822 | −2.2165 | −1.4038 | −2.9472 | −1.4053 | −2.5734 | −3.0476 |
| −2.8110 | −2.7334 | −2.3972 | −2.8863 | −1.5704 | −2.8231 | −2.9567 |
| −2.7311 | −1.5192 | −2.5069 | −3.1244 | −2.1189 | −2.8351 | −2.2768 |
| −3.1444 | −1.7414 | −2.3271 | −3.2513 | −1.2296 | −2.5948 | −3.2679 |
| −2.8874 | −3.1872 | −2.1318 | −3.0527 | −1.6186 | −2.9367 | −3.2028 |
| −2.0778 | −2.8170 | −1.8976 | −3.1238 | −1.6882 | −3.0717 | −2.7410 |
| −2.2792 | −3.0341 | −1.7463 | −3.1621 | −1.6914 | −2.9288 | −3.1572 |
| −3.1544 | −2.0861 | −2.3871 | −2.9441 | −0.6218 | −3.1601 | −2.8548 |
| −3.1990 | −2.6512 | −3.0512 | −3.0704 | −1.0049 | −2.9518 | −2.5744 |
| −2.5231 | −1.9928 | −1.8202 | −3.0567 | −1.3445 | −3.2046 | −2.0449 |
| −2.8732 | −1.7094 | −0.8061 | −2.8250 | −1.5565 | −3.0050 | −2.4743 |
| −1.6170 | −2.6094 | −2.1690 | −3.0181 | −1.3639 | −3.2445 | −2.2350 |
| −2.5150 | −1.9178 | −1.8890 | −3.0653 | −1.7285 | −2.9871 | −2.5429 |
| −2.9169 | −3.1286 | −1.5783 | −3.0814 | −1.9216 | −2.8077 | −3.1991 |
| −2.5569 | −2.0295 | −1.9898 | −2.8601 | −1.5360 | −3.0024 | −2.4915 |
| −2.9082 | −2.0450 | −1.5386 | −3.0268 | −1.2059 | −2.8011 | −3.1362 |
| −1.5516 | −3.0622 | −1.9368 | −3.0759 | −1.0786 | −2.9634 | −2.7571 |
| −2.8119 | −2.7348 | −1.8331 | −3.0740 | −1.2621 | −2.8166 | −3.0635 |
| −2.3963 | −1.6904 | −0.7032 | −2.8162 | −1.4271 | −2.6523 | −2.9558 |
| −2.8050 | −2.0032 | −1.0772 | −3.1502 | −1.9445 | −3.0397 | −3.1289 |
| −1.8963 | −3.1410 | −1.6995 | −3.0669 | −2.5565 | −3.1787 | −3.2049 |
| −2.2095 | −2.3109 | −2.5090 | −3.1961 | −1.6167 | −3.2010 | −2.6926 |
| −3.0146 | −1.4880 | −1.8614 | −3.0901 | −1.3766 | −3.1280 | −2.0478 |
| −1.9794 | −2.0257 | −1.3506 | −3.1875 | −1.3149 | −3.2422 | −2.3229 |
| −2.7593 | −3.0975 | −1.8300 | −3.0588 | −1.0304 | −2.7202 | −3.1452 |
| −2.6189 | −2.4579 | −2.9264 | −3.0795 | −1.2936 | −2.9756 | −2.0974 |
| −2.0233 | −2.5378 | −1.8815 | −3.1907 | −1.2263 | −3.1630 | −2.3968 |
| −2.8673 | −2.2669 | −1.4653 | −3.1397 | −1.2770 | −2.2168 | −3.2124 |
| −2.3855 | −2.9538 | −2.0681 | −3.1423 | −1.4800 | −2.8005 | −2.9758 |
| −2.7432 | −1.4766 | −1.0111 | −3.0583 | −1.1259 | −2.7657 | −3.0607 |
| −2.2591 | −1.7829 | −1.6919 | −2.9230 | −1.4528 | −2.9930 | −1.9533 |
| −2.7487 | −2.5910 | −2.1884 | −3.0231 | −1.8099 | −2.9302 | −3.1270 |
| −2.2408 | −1.3168 | −1.1684 | −2.6125 | −1.8164 | −2.9804 | −2.0967 |
| −1.8428 | −2.6992 | −1.7738 | −2.7390 | −1.8763 | −3.2035 | −2.5349 |
| −3.1286 | −2.0611 | −2.2949 | −3.1607 | −1.5457 | −2.6296 | −2.6828 |
| −2.5478 | −2.6060 | −2.1827 | −3.1383 | −0.9690 | −2.4917 | −3.1743 |
| −3.0198 | −1.8054 | −1.3818 | −3.0751 | −1.9448 | −2.7774 | −3.1286 |
| −2.4615 | −1.9934 | −1.8663 | −2.5575 | −1.8219 | −3.2454 | −1.7447 |
| −2.4123 | −3.1333 | −1.5113 | −2.5565 | −2.0334 | −2.9232 | −1.9557 |
| −1.7152 | −2.6184 | −1.2355 | −3.2947 | −1.6676 | −3.1758 | −2.4195 |
| −1.9126 | −1.6708 | −1.5011 | −2.8998 | −2.7789 | −3.3596 | −3.4280 |
| −1.6227 | −3.3682 | −2.1455 | −2.9410 | −1.9524 | −3.3361 | −2.4180 |
| −1.9958 | −3.3760 | −1.5075 | −2.6845 | −2.6423 | −3.1850 | −3.3049 |
| −2.1916 | −2.2703 | −1.0904 | −1.9866 | −2.1990 | −3.1481 | −1.9479 |
| −2.0651 | −1.9992 | −0.7118 | −2.4599 | −2.4247 | −3.3551 | −2.1016 |
| −3.2280 | −1.7105 | −0.9517 | −2.5167 | −2.0390 | −2.9646 | −1.9555 |

TABLE 11-continued

| | | | | | | |
|---|---|---|---|---|---|---|
| −2.7564 | −2.0536 | −1.5702 | −2.3090 | −1.8188 | −2.6595 | −1.9767 |
| −1.5260 | −3.3402 | −0.9948 | −3.0124 | −2.0499 | −3.3951 | −3.2389 |
| −1.7328 | −3.1251 | −1.4806 | −1.9022 | −2.7673 | −3.3034 | −2.1938 |
| −2.1380 | −2.6548 | −1.0988 | −1.9272 | −1.9561 | −3.0010 | −2.2287 |
| −2.1083 | −2.0000 | −1.3869 | −2.4757 | −2.1461 | −3.2456 | −2.1213 |
| −2.1162 | −2.2881 | −1.3099 | −1.9485 | −1.7618 | −2.9067 | −1.4817 |
| −2.5220 | −2.0396 | −1.4300 | −2.8226 | −1.9823 | −2.9219 | −1.4193 |

| *Prevotella loescheii* | *Prevotella histicola* | *Solobacterium moorei* | *Prevotella melaninogenica* | *Selenomonas sputigena* | *Rothia dentocariosa* | *Rothia mucilaginosa* |
|---|---|---|---|---|---|---|
| −3.1523 | −2.7245 | −3.1535 | −3.1832 | −3.1808 | −2.1131 | −0.2316 |
| −3.2039 | −2.9244 | −3.2108 | −3.0411 | −3.1893 | −2.5821 | −0.5975 |
| −3.2732 | −3.0673 | −3.2977 | −2.6159 | −3.1597 | −2.5633 | −0.8997 |
| −3.0975 | −3.0513 | −3.1248 | −3.0141 | −2.8157 | −2.7091 | −0.4358 |
| −3.2696 | −2.8734 | −3.2890 | −3.1156 | −3.2890 | −2.3721 | −0.6113 |
| −3.2791 | −3.0362 | −3.3319 | −2.0170 | −2.0266 | −2.1546 | −1.0044 |
| −3.2607 | −2.5463 | −3.3111 | −2.9281 | −2.3887 | −2.5827 | −0.4464 |
| −3.2228 | −3.1415 | −3.2559 | −2.9549 | −2.6974 | −2.5012 | −0.3441 |
| −3.1782 | −2.8424 | −3.2004 | −2.4610 | −3.0176 | −2.5743 | −0.3258 |
| −3.1512 | −3.1177 | −3.2088 | −2.9972 | −2.6785 | −2.4154 | −1.0825 |
| −3.1390 | −2.1382 | −3.1601 | −3.0635 | −3.1869 | −2.5814 | −0.3344 |
| −3.2247 | −2.5214 | −3.2294 | −3.1080 | −2.8141 | −2.9881 | −0.7092 |
| −3.2383 | −1.9848 | −3.2673 | −1.9814 | −2.4209 | −2.4156 | −0.5836 |
| −3.1757 | −2.6136 | −3.2032 | −3.0101 | −3.2160 | −2.5945 | −0.2358 |
| −3.2295 | −2.1036 | −3.2600 | −2.0176 | −3.2354 | −2.7441 | −0.4095 |
| −3.2099 | −2.9407 | −3.2083 | −2.5981 | −3.1884 | −2.9160 | −0.3579 |
| −3.2087 | −3.0008 | −3.2543 | −3.1183 | −2.2862 | −3.0919 | −0.3216 |
| −3.1625 | −2.4945 | −3.1935 | −2.9049 | −2.6746 | −2.4110 | −0.5961 |
| −3.1645 | −3.0356 | −3.2197 | −3.0527 | −2.9845 | −2.4955 | −0.2739 |
| −3.1529 | −3.0429 | −3.1861 | −2.6530 | −3.1046 | −2.7145 | −0.4680 |
| −3.1741 | −2.9661 | −3.1905 | −2.9257 | −3.0116 | −2.2591 | −0.2717 |
| −3.1269 | −2.4735 | −3.1509 | −2.5234 | −2.5307 | −2.8843 | −0.2998 |
| −3.2521 | −3.1036 | −3.2821 | −3.0288 | −3.1216 | −1.8478 | −0.5362 |
| −3.2489 | −3.0053 | −3.2263 | −2.7471 | −2.9458 | −3.0834 | −0.5381 |
| −3.2647 | −2.7550 | −3.2690 | −3.0064 | −3.1081 | −3.1031 | −0.5240 |
| −3.1884 | −1.5166 | −3.2198 | −2.6941 | −2.3839 | −2.5499 | −0.5609 |
| −3.2435 | −2.7120 | −3.2810 | −2.4394 | −2.9770 | −3.0565 | −0.3553 |
| −3.1915 | −3.1401 | −3.1774 | −2.9416 | −3.1887 | −2.6397 | −0.1681 |
| −3.1410 | −2.2269 | −3.1817 | −2.1908 | −2.9756 | −3.0947 | −0.2507 |
| −3.2316 | −2.9686 | −3.2374 | −1.8786 | −3.1439 | −3.0871 | −0.1347 |
| −3.1745 | −2.8156 | −3.2334 | −3.1339 | −2.1563 | −2.4771 | −0.3480 |
| −3.1791 | −2.7968 | −3.1981 | −2.6136 | −3.0148 | −2.4408 | −0.0900 |
| −3.0607 | −2.9769 | −3.1183 | −2.8207 | −2.7218 | −2.4093 | −0.2847 |
| −3.1644 | −2.1068 | −3.1964 | −2.3942 | −3.1005 | −2.7393 | −0.5617 |
| −3.2166 | −2.8409 | −3.2867 | −2.8115 | −2.3703 | −2.7586 | −1.1183 |
| −3.1439 | −2.3472 | −3.1841 | −2.4439 | −3.0223 | −2.8787 | −0.9181 |
| −3.2697 | −3.0588 | −3.3084 | −2.1281 | −3.1685 | −3.0831 | −0.2925 |
| −3.1595 | −2.9803 | −3.2636 | −2.4641 | −2.3579 | −2.8549 | −1.0267 |
| −3.1907 | −2.9815 | −3.1893 | −3.1508 | −3.2048 | −3.1611 | −0.1383 |
| −3.2165 | −2.7518 | −3.2381 | −2.6846 | −2.5712 | −2.4892 | −0.1204 |
| −3.3599 | −2.4165 | −3.3721 | −1.9538 | −3.2393 | −3.1290 | −1.1040 |
| −3.3020 | −3.1650 | −3.4335 | −2.3103 | −2.2028 | −3.0068 | −0.7930 |
| −3.3537 | −2.0416 | −3.4157 | −2.5846 | −3.3649 | −2.8339 | −0.5294 |
| −3.4353 | −2.8804 | −3.4550 | −1.8944 | −3.1953 | −3.2553 | −0.8793 |
| −3.3780 | −3.2967 | −3.4043 | −2.2492 | −3.0907 | −2.7606 | −0.7538 |
| −3.3914 | −2.6672 | −3.4576 | −2.7962 | −2.8006 | −3.0875 | −1.5759 |
| −3.2860 | −2.1825 | −3.3632 | −2.1978 | −3.0212 | −3.1067 | −1.2517 |
| −3.3332 | −2.8956 | −3.3901 | −2.8340 | −3.3722 | −2.2744 | −1.0071 |
| −3.3218 | −2.8201 | −3.3683 | −1.9017 | −2.9016 | −2.8374 | −1.1101 |
| −3.4209 | −2.9378 | −3.4452 | −2.5135 | −1.8233 | −3.1770 | −0.9486 |
| −3.3694 | −3.3452 | −3.4136 | −2.5794 | −2.9350 | −3.1162 | −1.0660 |
| −3.4202 | −2.4282 | −3.4173 | −2.0868 | −2.8530 | −3.3067 | −1.4362 |
| −3.2660 | −2.8410 | −3.3799 | −2.1398 | −2.4097 | −3.1442 | −1.2464 |
| −3.3284 | −2.9464 | −3.3553 | −2.1586 | −3.3342 | −2.6394 | −0.6222 |
| −3.3582 | −1.8012 | −3.3873 | −2.7910 | −3.0916 | −2.3881 | −1.2078 |
| −3.3513 | −1.7480 | −3.4208 | −2.8416 | −2.9310 | −2.3159 | −1.1645 |

| *Veillonella rogosae* | *Peptostreptococcus stomatis* | *Prevotella denticola* | *Porphyromonas endodontalis* | *Streptococcus salivarius* | *Actinomyces graevenitzii* | *Treponema medium* |
|---|---|---|---|---|---|---|
| −3.1257 | −3.1759 | −2.8166 | −3.0935 | −0.8860 | −1.9862 | −3.1894 |
| −3.1999 | −2.4419 | −3.1216 | −2.0009 | −0.5899 | −2.9258 | −2.6097 |
| −2.4449 | −2.3812 | −3.1795 | −3.0124 | −2.0441 | −2.7801 | −3.3120 |
| −2.2807 | −2.0259 | −3.1045 | −2.3059 | −1.6714 | −2.5869 | −2.3592 |
| −3.0897 | −2.1341 | −3.1942 | −2.3026 | −1.0891 | −1.9855 | −3.1059 |
| −3.3161 | −2.3700 | −3.0744 | −1.4214 | −2.5234 | −1.8188 | −2.5221 |
| −3.2286 | −2.3610 | −3.2341 | −1.7975 | −1.2296 | −1.4165 | −2.4631 |
| −2.8880 | −1.8506 | −3.0123 | −1.6050 | −1.7065 | −2.1290 | −2.3537 |
| −2.5862 | −1.8055 | −3.0793 | −2.3615 | −1.7470 | −1.7597 | −2.8641 |

TABLE 11-continued

| | | | | | | |
|---|---|---|---|---|---|---|
| −2.0384 | −2.0084 | −3.1393 | −1.3400 | −2.0169 | −2.1380 | −2.0907 |
| −3.1255 | −3.1659 | −2.3781 | −2.8928 | −0.9345 | −1.3501 | −3.1962 |
| −3.2139 | −2.5557 | −2.9260 | −2.1322 | −1.1951 | −1.8457 | −2.9739 |
| −2.6816 | −2.5467 | −2.8593 | −2.4317 | −1.0665 | −2.1406 | −3.2673 |
| −2.1543 | −1.9598 | −3.1267 | −2.9053 | −1.1448 | −1.9312 | −2.8784 |
| −3.0781 | −2.7125 | −2.9504 | −2.7403 | −1.3874 | −3.2445 | −3.2962 |
| −1.6619 | −2.0756 | −3.1608 | −2.4317 | −1.5943 | −2.4918 | −2.7971 |
| −2.5017 | −1.8021 | −3.1206 | −1.6408 | −1.8152 | −2.5547 | −1.9879 |
| −2.8879 | −2.1646 | −3.0602 | −1.8220 | −1.2282 | −1.7972 | −2.6260 |
| −3.0376 | −2.3386 | −3.1387 | −1.4879 | −1.0311 | −2.6180 | −2.2718 |
| −2.8443 | −1.7971 | −3.1366 | −2.0953 | −1.5105 | −1.9476 | −2.6745 |
| −2.5983 | −2.0102 | −3.1674 | −1.3333 | −1.4048 | −1.8453 | −2.5637 |
| −2.0804 | −2.6618 | −3.0717 | −1.7327 | −1.2231 | −3.0305 | −1.9865 |
| −1.8660 | −3.0126 | −3.2507 | −2.5145 | −1.6390 | −2.1492 | −3.0047 |
| −1.2608 | −1.8525 | −3.1952 | −1.1961 | −2.7113 | −3.1988 | −2.5833 |
| −2.4433 | −1.5641 | −3.0905 | −1.6278 | −1.5236 | −2.1024 | −2.8418 |
| −2.9107 | −2.6647 | −2.5982 | −2.1817 | −0.9274 | −1.7289 | −2.8901 |
| −2.3804 | −2.5369 | −2.9872 | −3.0556 | −1.0366 | −1.2896 | −3.1453 |
| −2.9036 | −2.3106 | −3.1623 | −3.1788 | −1.6616 | −3.0940 | −3.1732 |
| −3.0960 | −1.9683 | −2.9796 | −3.0255 | −1.0483 | −2.6215 | −3.2094 |
| −1.4264 | −1.9202 | −3.1393 | −2.6375 | −1.4045 | −2.1968 | −3.1920 |
| −2.5190 | −1.9771 | −3.1096 | −1.9534 | −1.4017 | −2.8178 | −2.0553 |
| −2.9364 | −1.9271 | −3.1562 | −2.8401 | −2.2202 | −2.5433 | −2.7689 |
| −2.5501 | −1.9663 | −3.0766 | −2.6264 | −1.1646 | −2.4285 | −2.1084 |
| −2.0733 | −1.5424 | −2.9341 | −2.7112 | −1.3207 | −3.1469 | −2.7863 |
| −2.8383 | −2.3061 | −3.1250 | −1.6595 | −1.4513 | −2.3673 | −2.0808 |
| −2.5078 | −2.6427 | −2.6503 | −2.0662 | −1.4796 | −2.3074 | −2.5611 |
| −1.8340 | −2.4751 | −3.2046 | −2.8934 | −1.9635 | −2.6281 | −2.6251 |
| −2.0419 | −1.9151 | −3.0967 | −1.5728 | −1.8558 | −1.4326 | −1.9564 |
| −3.1838 | −2.4783 | −3.1977 | −2.7606 | −0.9086 | −3.1508 | −3.2361 |
| −1.9908 | −2.9569 | −3.1107 | −2.2503 | −1.6504 | −1.6411 | −2.9128 |
| −1.7250 | −2.0715 | −2.8828 | −2.6734 | −1.8598 | −2.1908 | −3.2622 |
| −1.5881 | −2.0602 | −2.7975 | −2.2971 | −2.6913 | −2.1123 | −2.0826 |
| −2.1723 | −2.6232 | −3.1115 | −3.0432 | −1.7158 | −1.9927 | −2.7408 |
| −1.6939 | −3.2243 | −3.1057 | −2.6677 | −2.7828 | −2.1339 | −3.0757 |
| −2.3657 | −1.9927 | −3.1329 | −1.4731 | −2.4926 | −1.5206 | −2.9951 |
| −1.9261 | −2.2030 | −3.2449 | −1.2937 | −2.3992 | −2.1305 | −2.0898 |
| −2.0292 | −2.6663 | −3.0823 | −2.7768 | −1.8435 | −1.4027 | −2.7848 |
| −1.4993 | −3.1173 | −3.0883 | −3.0690 | −2.3825 | −3.0416 | −2.8003 |
| −1.6602 | −2.3487 | −3.0821 | −2.3867 | −1.8291 | −1.7837 | −2.4450 |
| −1.9614 | −2.5429 | −2.4459 | −2.5934 | −1.6577 | −2.0516 | −2.0145 |
| −2.1199 | −2.7547 | −3.2199 | −2.5402 | −1.3852 | −2.1961 | −2.1900 |
| −1.8202 | −1.7844 | −3.0246 | −1.3692 | −2.7195 | −3.2957 | −1.8481 |
| −1.5619 | −1.9628 | −2.8828 | −2.4663 | −1.6387 | −3.2038 | −1.9133 |
| −1.9243 | −3.0295 | −3.2292 | −3.1812 | −2.0316 | −2.5032 | −2.7238 |
| −2.6102 | −2.4840 | −2.7505 | −3.3769 | −2.1787 | −2.5522 | −3.2183 |
| −3.2099 | −3.1887 | −2.5859 | −3.3717 | −1.6968 | −2.6746 | −3.3673 |

| Treponema socranskii | Gemella sanguinis | Porphyromonas catoniae | Corynebacterium matruchotii | Eubacterium saphenum | Neisseria flavescens | Granulicatella adiacens |
|---|---|---|---|---|---|---|
| −3.1795 | −1.5614 | −3.1970 | −2.7110 | −3.0561 | −2.4256 | −0.6794 |
| −3.2481 | −1.5807 | −3.2526 | −2.4813 | −1.2420 | −2.6400 | −1.0283 |
| −3.2653 | −1.4454 | −3.2894 | −2.8315 | −2.9775 | −2.2433 | −0.5363 |
| −3.1174 | −1.9073 | −3.0798 | −2.3373 | −3.0933 | −1.2615 | −0.9932 |
| −3.2877 | −1.5089 | −3.2997 | −2.8535 | −3.1595 | −2.6174 | −0.9092 |
| −3.3292 | −1.4364 | −3.3226 | −2.7144 | −2.2250 | −2.0230 | −1.3821 |
| −3.2826 | −2.0265 | −3.3274 | −2.3654 | −1.2664 | −2.1614 | −0.8544 |
| −3.0991 | −2.0915 | −3.2532 | −2.6417 | −0.9539 | −2.2156 | −1.0559 |
| −3.1698 | −1.2831 | −3.1992 | −2.6575 | −3.1175 | −2.5320 | −0.9112 |
| −3.1980 | −1.5062 | −3.1289 | −2.1786 | −1.0620 | −1.1319 | −1.0510 |
| −3.1915 | −1.7911 | −3.2009 | −2.7123 | −3.1418 | −2.4806 | −0.8415 |
| −3.2487 | −1.7299 | −3.2536 | −2.5056 | −2.3600 | −2.8141 | −1.3736 |
| −3.2673 | −1.3667 | −3.2673 | −2.4330 | −3.1881 | −2.1050 | −0.9035 |
| −3.2112 | −1.9845 | −3.2226 | −2.6562 | −3.0850 | −0.9772 | −0.8517 |
| −3.2696 | −1.6750 | −3.2827 | −2.7613 | −3.1848 | −2.5996 | −0.9741 |
| −3.2162 | −1.4243 | −3.2178 | −2.8051 | −2.8313 | −2.3232 | −0.6534 |
| −3.2331 | −2.2892 | −3.2590 | −2.7242 | −1.4782 | −2.3109 | −1.0835 |
| −3.1981 | −1.6219 | −3.1785 | −2.5041 | −2.0722 | −1.8069 | −0.8449 |
| −3.2034 | −1.4608 | −3.2063 | −2.3709 | −1.7270 | −1.5989 | −0.9729 |
| −3.1646 | −1.0501 | −3.1847 | −2.8223 | −2.4296 | −2.3020 | −0.5791 |
| −3.1877 | −1.6047 | −3.1989 | −2.7671 | −0.9411 | −2.2344 | −0.6419 |
| −3.0305 | −1.4626 | −3.1763 | −2.5010 | −2.3014 | −1.6175 | −0.8647 |
| −3.2836 | −1.7845 | −3.2821 | −2.9545 | −3.2331 | −1.9474 | −0.9332 |
| −3.2251 | −2.1046 | −3.2698 | −2.6823 | −3.0317 | −0.7100 | −0.7726 |
| −3.2763 | −1.4769 | −3.3162 | −2.5689 | −2.4542 | −2.0383 | −0.7167 |
| −3.2349 | −2.1641 | −3.2334 | −1.8687 | −2.3585 | −1.9065 | −0.9671 |
| −3.2810 | −1.3169 | −3.3002 | −2.4301 | −3.1659 | −2.3266 | −1.1283 |
| −3.1312 | −1.1493 | −3.2002 | −2.8178 | −3.2032 | −1.6322 | −0.1792 |
| −3.0517 | −1.7080 | −3.1468 | −2.7772 | −2.1377 | −2.3728 | −0.7166 |

TABLE 11-continued

| | | | | | | |
|---|---|---|---|---|---|---|
| −3.2506 | −1.5015 | −3.2536 | −2.9821 | −3.0851 | −2.2778 | −0.6414 |
| −3.1420 | −1.7323 | −3.2392 | −2.5434 | −1.5350 | −1.0559 | −0.7195 |
| −3.1841 | −1.6168 | −3.0604 | −2.8939 | −3.1766 | −2.3695 | −0.6698 |
| −2.5828 | −1.8392 | −3.1351 | −2.1684 | −3.0173 | −2.3936 | −0.7300 |
| −3.1788 | −1.4937 | −3.0995 | −2.8723 | −2.0544 | −1.9228 | −0.6667 |
| −3.2570 | −2.0894 | −3.1960 | −2.5486 | −1.1921 | −2.0270 | −1.1512 |
| −3.1047 | −1.5722 | −3.0345 | −2.8165 | −1.7974 | −1.0766 | −0.7679 |
| −3.3099 | −1.4868 | −3.3261 | −2.8868 | −3.2605 | −2.3724 | −0.7803 |
| −3.2247 | −1.9738 | −3.2459 | −2.3032 | −2.9230 | −2.3057 | −0.6593 |
| −3.1166 | −0.9540 | −3.2224 | −2.9297 | −3.1322 | −2.0627 | −0.1868 |
| −3.1233 | −1.8103 | −3.2696 | −2.6343 | −3.1703 | −1.9200 | −0.8054 |
| −3.3626 | −1.9388 | −3.3735 | −2.8404 | −3.2622 | −1.9256 | −1.0397 |
| −3.4242 | −1.9918 | −3.3562 | −2.7753 | −2.9471 | −1.6346 | −0.9150 |
| −3.2923 | −1.8281 | −3.4318 | −2.9681 | −3.2343 | −1.1838 | −0.8989 |
| −3.4237 | −1.7510 | −3.4772 | −2.7818 | −3.2825 | −1.2298 | −1.0420 |
| −3.3738 | −1.3505 | −3.4073 | −3.1744 | −3.3322 | −1.4644 | −0.8744 |
| −2.7360 | −2.4786 | −3.3545 | −2.8678 | −2.0927 | −1.6942 | −1.5111 |
| −3.3676 | −2.1312 | −3.2740 | −2.8704 | −3.2787 | −1.5831 | −1.0482 |
| −3.3825 | −1.6676 | −3.3931 | −3.2099 | −3.2305 | −1.1442 | −0.8334 |
| −3.3246 | −1.8666 | −3.3288 | −2.6209 | −2.8111 | −1.9726 | −0.9557 |
| −3.4467 | −2.0609 | −3.4663 | −2.7169 | −3.3785 | −2.5963 | −1.0244 |
| −3.4136 | −1.6677 | −4.0000 | −2.9614 | −3.3655 | −0.5568 | −1.0826 |
| −3.4144 | −1.6708 | −3.3879 | −2.9524 | −2.6392 | −1.2910 | −1.0180 |
| −3.3372 | −1.8551 | −3.3580 | −2.6461 | −2.4876 | −1.7159 | −1.1664 |
| −3.3491 | −1.6886 | −3.3662 | −2.9129 | −2.8695 | −1.1598 | −0.7664 |
| −3.3949 | −2.3363 | −3.2880 | −2.7109 | −3.3696 | −1.4094 | −1.0031 |
| −3.3996 | −2.7510 | −3.3442 | −2.5001 | −3.3628 | −1.9728 | −1.0960 |

| Eubacterium sulci | Megasphaera micronuciformis | Prevotella shahii | SR1 sp. OT 345 |
|---|---|---|---|
| −2.4121 | −2.6029 | −3.1857 | −3.1616 |
| −2.1996 | −2.8909 | −3.2436 | −3.2727 |
| −1.1907 | −2.8747 | −3.1597 | −1.8571 |
| −2.8193 | −3.0947 | −3.1263 | −1.6704 |
| −1.5071 | −3.2094 | −3.2343 | −0.9922 |
| −2.2329 | −3.0472 | −3.3305 | −3.3266 |
| −2.4683 | −2.9988 | −3.3330 | −2.2647 |
| −2.1430 | −3.2437 | −3.1447 | −1.2060 |
| −1.5550 | −2.8244 | −3.0452 | −1.4940 |
| −2.5118 | −3.2034 | −3.0734 | −1.5360 |
| −2.5520 | −2.4629 | −3.1915 | −3.2106 |
| −1.6851 | −2.9411 | −3.2373 | −3.2438 |
| −2.0023 | −2.9823 | −3.1627 | −2.3708 |
| −2.2126 | −2.8107 | −3.1954 | −1.7889 |
| −1.5940 | −2.8017 | −2.7914 | −2.2594 |
| −1.6725 | −2.9796 | −2.9323 | −1.0625 |
| −2.1826 | −3.2482 | −3.2528 | −0.9876 |
| −2.0977 | −2.9729 | −3.1770 | −0.6772 |
| −2.5153 | −3.0579 | −3.1948 | −2.8783 |
| −1.8384 | −3.1739 | −2.7316 | −1.7972 |
| −2.0119 | −3.1443 | −3.2075 | −2.1996 |
| −2.1211 | −2.4765 | −3.1221 | −3.1776 |
| −2.7736 | −3.0705 | −3.2881 | −2.7699 |
| −2.0726 | −3.2785 | −2.9848 | −1.3943 |
| −1.5791 | −3.2330 | −3.2060 | −1.5050 |
| −2.0808 | −2.4283 | −3.2258 | −2.0089 |
| −2.0212 | −3.0750 | −3.2824 | −3.2897 |
| −3.1081 | −3.1543 | −3.2152 | −3.2032 |
| −2.0787 | −3.1269 | −3.1708 | −1.8968 |
| −1.7492 | −3.2403 | −3.1006 | −2.2676 |
| −2.6962 | −3.2057 | −3.2097 | −2.4182 |
| −2.2406 | −3.1981 | −2.7753 | −2.4488 |
| −2.8058 | −2.5330 | −3.1170 | −2.3627 |
| −1.6332 | −2.7348 | −2.8275 | −1.4269 |
| −2.5204 | −3.1563 | −3.2489 | −1.2029 |
| −1.9606 | −2.4033 | −3.1798 | −1.3838 |
| −2.0776 | −3.0840 | −2.9938 | −1.0833 |
| −2.5800 | −2.5738 | −3.2416 | −1.6790 |
| −2.6716 | −3.1261 | −3.2270 | −3.0100 |
| −2.5668 | −2.9483 | −3.2593 | −3.2637 |
| −1.9523 | −2.1290 | −3.2527 | −2.0127 |
| −1.8247 | −2.7259 | −2.2596 | −1.4928 |
| −1.8019 | −2.6176 | −2.8457 | −1.9778 |
| −3.2662 | −2.8833 | −3.4707 | −3.4707 |
| −1.7018 | −2.8275 | −2.6257 | −1.2317 |
| −2.2886 | −3.3871 | −2.7767 | −1.1799 |
| −1.8004 | −2.3365 | −2.5000 | −1.6383 |
| −2.4499 | −3.2336 | −2.9909 | −1.3615 |
| −1.9119 | −3.0798 | −3.3218 | −2.3540 |

TABLE 11-continued

| | | | |
|---|---|---|---|
| −2.2350 | −2.0147 | −3.0325 | −1.4018 |
| −2.0684 | −3.1842 | −2.9851 | −1.8125 |
| −1.8976 | −3.4457 | −2.7072 | −1.2601 |
| −2.1698 | −3.3070 | −2.5226 | −1.8028 |
| −2.5893 | −3.1761 | −3.0504 | −1.7048 |
| −1.7742 | −2.1735 | −3.3949 | −3.4090 |
| −2.3614 | −2.0427 | −3.3778 | −3.4012 |

The correlation coefficient of PISA and the value of log 10 (relative ratio to the total bacterial load) of each bacterium was calculated for all 36 types of bacteria, and further, the bacterial species having an absolute value of the correlation coefficient larger than 0.2 were selected. Bacteria having a positive correlation coefficient and bacteria having a negative correlation coefficient are shown below (Table 12).

TABLE 12

| Probe | Correlation |
|---|---|
| *Prevotella pallens* | −0.3564 |
| *Streptococcus salivarius* | −0.2738 |
| *Eubacterium sulci* | −0.2659 |
| *Rothia mucilaginosa* | −0.2556 |
| *Prevotella denticola* | −0.2330 |
| *Veillonella atypica* | −0.2261 |
| *Prevotella histicola* | −0.2255 |
| *Megasphaera micronuciformis* | −0.2176 |
| *Streptococcus parasanguinis* | −0.2106 |
| SR1 sp. OT 345 | 0.2053 |
| *Porphyromonas catoniae* | 0.2278 |
| *Selenomonas sputigena* | 0.2281 |
| *Neisseria flavescens* | 0.2301 |
| *Streptococcus sobrinus* | 0.2500 |
| *Parvimonas micra* | 0.2560 |
| *Peptostreptococcus stomatis* | 0.2860 |
| *Treponema socranskii* | 0.3357 |
| *Eubacterium saphenum* | 0.3647 |
| *Eubacterium nodatum* | 0.4170 |
| *Treponema medium* | 0.4386 |
| *Filifactor alocis* | 0.4983 |
| *Porphyromonas endodontalis* | 0.5607 |

The bacterial group having a negative correlation coefficient was determined to include the following 9 bacterial species: *Prevotella pallens, Streptococcus salivarius, Eubacterium sulci, Rothia mucilaginosa, Prevotella denticola, Veillonella atypica, Prevotella histicola, Megasphaera micronuciformis,* and *Streptococcus parasanguinis.*

The bacterial group showing a positive correlation coefficient was determined to include the following 13 bacterial species: SR1 sp. OT 345, *Porphyromonas catoniae, Selenomonas sputigena, Neisseria flavescens, Streptococcus sobrinus, Parvimonas micra, Peptostreptococcus stomatis, Treponema socranskii, Eubacterium saphenum, Eubacterium nodatum, Treponema medium, Filifactor alocis,* and *Porphyromonas endodontalis.*

Subsequently, a model for prediction by multiple regression analysis with the numerical values after the log 10 conversion of the above 22 bacterial species as explanatory variables and the PISA values as objective variables was created. For analysis, statistical software "R" (R Development Core Team) was used, and the analysis was performed using the "lm" function.

The following command was executed after reading PISA in Table 11 and the data of the bacteria (22 types, data of 56 samples) as "data01."

res1←lm(PISA~.,data=data01)

(Command to perform multiple regression analysis on data of 56 samples with PISA values as objective variables and 22 types of bacteria as explanatory variables)

Figure 9:
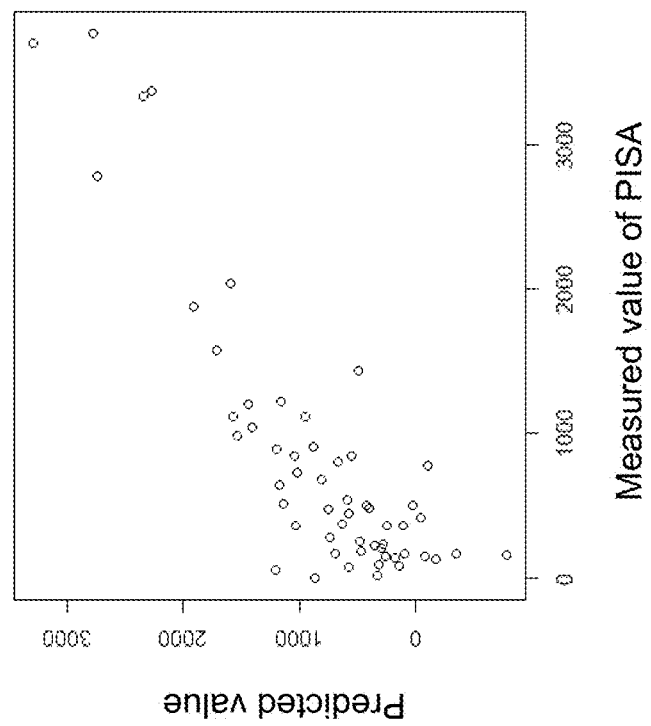
FIG. 9 is a figure showing a scatter diagram obtained by conducting a test with 56 samples, using the bacterial load of bacterial species that had a statistically significant correlation with PISA values (horizontal axis) as an explanatory variable, and creating a prediction model formula by multiple regression analysis to predict PISA values (vertical axis).

The correlation coefficient between the predicted PISA value obtained by substituting the data of each bacterial load into the executed prediction model formula res1 and the actual PISA was 0.8618542. This scatter diagram is shown in FIG. 9.

Sequence Listing Free Text
SEQ ID NOS: 1 to 74: Synthetic DNAs
Sequence Listing

The invention claimed is:

1. A method for determining a degree of periodontal pocket inflammation in an oral cavity of a subject, the method comprising:
   collecting a saliva sample from a subject with an unknown degree of periodontal pocket inflammation;
   adding an absolute load index to the saliva sample;
   detecting a species of bacteria in the saliva sample using a probe or DNA chip;
   quantifying a bacterial load of each species of bacteria detected by calculating a SN ratio;
   calculating a correlation coefficient from the SN ratio of each species of bacteria detected, wherein the SN ratio is corrected by a signal intensity of the absolute load index; and
   determining the degree of periodontal pocket inflammation in the oral cavity based on the value of the correlation coefficient obtained for each species of bacteria,
   wherein the correlation coefficient is calculated from the SN ratio of each species of bacteria detected and the degree of periodontal pocket inflammation,
   wherein the species of bacteria to be detected include:
   a bacterium having a positive correlation between a bacterial load of the bacterium and the degree of periodontal pocket inflammation in the oral cavity; and
   a bacterium having a negative correlation between a bacterial load of the bacterium and the degree of periodontal pocket inflammation in the oral cavity.

2. The method according to claim 1, wherein the periodontal pocket inflammation area is represented by a periodontal inflamed surface area (PISA) or a concealed area in periodontal pocket of a tooth root surface (CAPRS) value.

3. The method according to claim 1, wherein the bacterium having the positive correlation is at least one selected from the group consisting of *Treponema denticola, Tannerella forsythia, Fusobacterium nucleatum* subsp. *animalis, Porphyromonas gingivalis, Campylobacter rectus, Fusobacterium nucleatum* subsp. *nucleatum, Selenomonas noxia, Veillonella parvula, Streptococcus gordonii, Fusobacterium nucleatum* subsp. *vincentii, Streptococcus intermedius, Capnocytophaga ochracea, Capnocytophaga sputigena, Aggregatibacter actinomycetemcomitans, Fusobacterium nucleatum* subsp. *polymorphum, Fusobacterium periodonticum,* SR1 sp. OT 345, *Porphyromonas catoniae, Selenomonas sputigena, Neisseria flavescens, Streptococcus sobrinus, Parvimonas micra, Peptostreptococcus stomatis, Treponema socranskii, Eubacterium saphenum, Eubacterium nodatum, Treponema* medium, *Filifactor alocis*, and *Porphyromonas endodontalis*.

4. The method according to claim 1, wherein the bacterium having the negative correlation is at least one selected from the group consisting of *Streptococcus mutans, Actinomyces odontolyticus, Streptococcus mitis* bv 2, *Streptococcus mitis, Campylobacter concisus, Capnocytophaga gingivalis, Prevotella pallens, Streptococcus salivarius, Eubacterium sulci, Rothia mucilaginosa, Prevotella denticola, Veillonella atypica, Prevotella histicola, Megasphaera micronuciformis*, and *Streptococcus parasanguinis*.

5. The method according to claim 1, further comprising:
   detecting the bacterial load of a species of bacteria in a saliva sample from a subject with a known degree of periodontal pocket inflammation;
   pairing the correlation coefficient of each species of bacteria with a degree of periodontal pocket inflammation unique to each species; and
   constructing a relational expression model between the bacterial load of each species of bacteria and the degree of periodontal pocket inflammation.

6. The method according to claim 5, wherein a method for creating the prediction model is a method using one selected from among machine learning algorithms of linear regression, regression tree, model tree, neural network, support vector machine, bagging, boosting, and random forest.

7. The method of claim 1, wherein an absolute value of the correlation coefficient for the species of bacteria is at least 0.1 when the number of measurements is at least 40.

* * * * *

```
                    SEQUENCE LISTING

<160> NUMBER OF SEQ ID NOS: 74

<210> SEQ ID NO 1
<211> LENGTH: 20
<212> TYPE: DNA
<213> ORGANISM: Artificial
<220> FEATURE:
<223> OTHER INFORMATION: Synthetic DNA

<400> SEQUENCE: 1
ttcaatgcaa tactcgtatc                                            20

<210> SEQ ID NO 2
<211> LENGTH: 25
<212> TYPE: DNA
<213> ORGANISM: Artificial
<220> FEATURE:
<223> OTHER INFORMATION: Synthetic DNA

<400> SEQUENCE: 2
```
cacgtatctc attttattcc cctgt                                              25

<210> SEQ ID NO 3
<211> LENGTH: 25
<212> TYPE: DNA
<213> ORGANISM: Artificial
<220> FEATURE:
<223> OTHER INFORMATION: Synthetic DNA

<400> SEQUENCE: 3
cctcttcttc ttattcttca tctgc                                              25

<210> SEQ ID NO 4
<211> LENGTH: 18
<212> TYPE: DNA
<213> ORGANISM: Artificial
<220> FEATURE:
<223> OTHER INFORMATION: Synthetic DNA

<400> SEQUENCE: 4
gccttcgcaa taggtatt                                                      18

<210> SEQ ID NO 5
<211> LENGTH: 20
<212> TYPE: DNA
<213> ORGANISM: Artificial
<220> FEATURE:
<223> OTHER INFORMATION: Synthetic DNA

<400> SEQUENCE: 5
gtcataattc tttcccaaga                                                    20

<210> SEQ ID NO 6
<211> LENGTH: 20
<212> TYPE: DNA
<213> ORGANISM: Artificial
<220> FEATURE:
<223> OTHER INFORMATION: Synthetic DNA

<400> SEQUENCE: 6
caatgggtat tcttcttgat                                                    20

<210> SEQ ID NO 7
<211> LENGTH: 20
<212> TYPE: DNA
<213> ORGANISM: Artificial
<220> FEATURE:
<223> OTHER INFORMATION: Synthetic DNA

<400> SEQUENCE: 7
tagttataca gtttccaacg                                                    20

<210> SEQ ID NO 8
<211> LENGTH: 19
<212> TYPE: DNA
<213> ORGANISM: Artificial
<220> FEATURE:
<223> OTHER INFORMATION: Synthetic DNA

<400> SEQUENCE: 8
ccagtactct agttacaca                                                     19

<210> SEQ ID NO 9
<211> LENGTH: 20
<212> TYPE: DNA
<213> ORGANISM: Artificial

<220> FEATURE:
<223> OTHER INFORMATION: Synthetic DNA

<400> SEQUENCE: 9
tttctttctt cccaactgaa                                          20

<210> SEQ ID NO 10
<211> LENGTH: 20
<212> TYPE: DNA
<213> ORGANISM: Artificial
<220> FEATURE:
<223> OTHER INFORMATION: Synthetic DNA

<400> SEQUENCE: 10
tacattccga aaaacgtcat                                          20

<210> SEQ ID NO 11
<211> LENGTH: 19
<212> TYPE: DNA
<213> ORGANISM: Artificial
<220> FEATURE:
<223> OTHER INFORMATION: Synthetic DNA

<400> SEQUENCE: 11
tatgcagttt ccaacgcaa                                           19

<210> SEQ ID NO 12
<211> LENGTH: 22
<212> TYPE: DNA
<213> ORGANISM: Artificial
<220> FEATURE:
<223> OTHER INFORMATION: Synthetic DNA

<400> SEQUENCE: 12
cgaagggtaa atgcaaaaag gc                                       22

<210> SEQ ID NO 13
<211> LENGTH: 20
<212> TYPE: DNA
<213> ORGANISM: Artificial
<220> FEATURE:
<223> OTHER INFORMATION: Synthetic DNA

<400> SEQUENCE: 13
ctttattccc acataaaagc                                          20

<210> SEQ ID NO 14
<211> LENGTH: 18
<212> TYPE: DNA
<213> ORGANISM: Artificial
<220> FEATURE:
<223> OTHER INFORMATION: Synthetic DNA

<400> SEQUENCE: 14
aagtaccgtc actgtgtg                                            18

<210> SEQ ID NO 15
<211> LENGTH: 27
<212> TYPE: DNA
<213> ORGANISM: Artificial
<220> FEATURE:
<223> OTHER INFORMATION: Synthetic DNA

<400> SEQUENCE: 15
gtcaatttgg catgctatta acacacc                                  27

```
<210> SEQ ID NO 16
<211> LENGTH: 18
<212> TYPE: DNA
<213> ORGANISM: Artificial
<220> FEATURE:
<223> OTHER INFORMATION: Synthetic DNA

<400> SEQUENCE: 16
cccaagcagt tctatggt                                                   18

<210> SEQ ID NO 17
<211> LENGTH: 20
<212> TYPE: DNA
<213> ORGANISM: Artificial
<220> FEATURE:
<223> OTHER INFORMATION: Synthetic DNA

<400> SEQUENCE: 17
tacacgtaca ccttattctt                                                 20

<210> SEQ ID NO 18
<211> LENGTH: 19
<212> TYPE: DNA
<213> ORGANISM: Artificial
<220> FEATURE:
<223> OTHER INFORMATION: Synthetic DNA

<400> SEQUENCE: 18
caaccattca agaccaaca                                                  19

<210> SEQ ID NO 19
<211> LENGTH: 19
<212> TYPE: DNA
<213> ORGANISM: Artificial
<220> FEATURE:
<223> OTHER INFORMATION: Synthetic DNA

<400> SEQUENCE: 19
tcaaaggcag ttgcttagt                                                  19

<210> SEQ ID NO 20
<211> LENGTH: 19
<212> TYPE: DNA
<213> ORGANISM: Artificial
<220> FEATURE:
<223> OTHER INFORMATION: Synthetic DNA

<400> SEQUENCE: 20
ctctagctat ccagttcag                                                  19

<210> SEQ ID NO 21
<211> LENGTH: 19
<212> TYPE: DNA
<213> ORGANISM: Artificial
<220> FEATURE:
<223> OTHER INFORMATION: Synthetic DNA

<400> SEQUENCE: 21
cacccgttct tctcttaca                                                  19

<210> SEQ ID NO 22
<211> LENGTH: 21
<212> TYPE: DNA
<213> ORGANISM: Artificial
<220> FEATURE:
<223> OTHER INFORMATION: Synthetic DNA
```

<400> SEQUENCE: 22
acagtatgaa ctttccattc t					21

<210> SEQ ID NO 23
<211> LENGTH: 18
<212> TYPE: DNA
<213> ORGANISM: Artificial
<220> FEATURE:
<223> OTHER INFORMATION: Synthetic DNA

<400> SEQUENCE: 23
tctcccctct tgcactca					18

<210> SEQ ID NO 24
<211> LENGTH: 19
<212> TYPE: DNA
<213> ORGANISM: Artificial
<220> FEATURE:
<223> OTHER INFORMATION: Synthetic DNA

<400> SEQUENCE: 24
tcccctcttg cactcaagt					19

<210> SEQ ID NO 25
<211> LENGTH: 17
<212> TYPE: DNA
<213> ORGANISM: Artificial
<220> FEATURE:
<223> OTHER INFORMATION: Synthetic DNA

<400> SEQUENCE: 25
aagtcagccc gtaccca					17

<210> SEQ ID NO 26
<211> LENGTH: 17
<212> TYPE: DNA
<213> ORGANISM: Artificial
<220> FEATURE:
<223> OTHER INFORMATION: Synthetic DNA

<400> SEQUENCE: 26
tccttctaac tgttcgc					17

<210> SEQ ID NO 27
<211> LENGTH: 17
<212> TYPE: DNA
<213> ORGANISM: Artificial
<220> FEATURE:
<223> OTHER INFORMATION: Synthetic DNA

<400> SEQUENCE: 27
ccacccacaa ggagcag					17

<210> SEQ ID NO 28
<211> LENGTH: 18
<212> TYPE: DNA
<213> ORGANISM: Artificial
<220> FEATURE:
<223> OTHER INFORMATION: Synthetic DNA

<400> SEQUENCE: 28
ttcgcattag gcacgttc					18

<210> SEQ ID NO 29

```
<211> LENGTH: 18
<212> TYPE: DNA
<213> ORGANISM: Artificial
<220> FEATURE:
<223> OTHER INFORMATION: Synthetic DNA

<400> SEQUENCE: 29
cacacgttct tgacttac                                                    18

<210> SEQ ID NO 30
<211> LENGTH: 30
<212> TYPE: DNA
<213> ORGANISM: Artificial
<220> FEATURE:
<223> OTHER INFORMATION: Synthetic DNA

<400> SEQUENCE: 30
ctattcgacc agcgatatca ctacgtaggc                                       30

<210> SEQ ID NO 31
<211> LENGTH: 23
<212> TYPE: DNA
<213> ORGANISM: Artificial
<220> FEATURE:
<223> OTHER INFORMATION: Synthetic DNA

<400> SEQUENCE: 31
cgtattaccg cggctgctgg cac                                              23

<210> SEQ ID NO 32
<211> LENGTH: 19
<212> TYPE: DNA
<213> ORGANISM: Artificial
<220> FEATURE:
<223> OTHER INFORMATION: Synthetic DNA

<400> SEQUENCE: 32
tcctacggga ggcagcagt                                                   19

<210> SEQ ID NO 33
<211> LENGTH: 26
<212> TYPE: DNA
<213> ORGANISM: Artificial
<220> FEATURE:
<223> OTHER INFORMATION: Synthetic DNA

<400> SEQUENCE: 33
cagggtatct aatcctgttt gctacc                                           26

<210> SEQ ID NO 34
<211> LENGTH: 25
<212> TYPE: DNA
<213> ORGANISM: Artificial
<220> FEATURE:
<223> OTHER INFORMATION: Synthetic DNA

<400> SEQUENCE: 34
gagaagccta cacaaacgta acgtc                                            25

<210> SEQ ID NO 35
<211> LENGTH: 23
<212> TYPE: DNA
<213> ORGANISM: Artificial
<220> FEATURE:
<223> OTHER INFORMATION: Synthetic DNA

<400> SEQUENCE: 35
```
ctctaaagac cgctctatct cgg                                              23

<210> SEQ ID NO 36
<211> LENGTH: 22
<212> TYPE: DNA
<213> ORGANISM: Artificial
<220> FEATURE:
<223> OTHER INFORMATION: Synthetic DNA

<400> SEQUENCE: 36
cctacgctta cttaaccacc ta                                               22

<210> SEQ ID NO 37
<211> LENGTH: 20
<212> TYPE: DNA
<213> ORGANISM: Artificial
<220> FEATURE:
<223> OTHER INFORMATION: Synthetic DNA

<400> SEQUENCE: 37
gtgcttaatg aggttaagcc                                                  20

<210> SEQ ID NO 38
<211> LENGTH: 22
<212> TYPE: DNA
<213> ORGANISM: Artificial
<220> FEATURE:
<223> OTHER INFORMATION: Synthetic DNA

<400> SEQUENCE: 38
cccctactac agagttttac ga                                               22

<210> SEQ ID NO 39
<211> LENGTH: 20
<212> TYPE: DNA
<213> ORGANISM: Artificial
<220> FEATURE:
<223> OTHER INFORMATION: Synthetic DNA

<400> SEQUENCE: 39
tacacacgtt cttcccctac                                                  20

<210> SEQ ID NO 40
<211> LENGTH: 20
<212> TYPE: DNA
<213> ORGANISM: Artificial
<220> FEATURE:
<223> OTHER INFORMATION: Synthetic DNA

<400> SEQUENCE: 40
acacgtgact cttgttattc                                                  20

<210> SEQ ID NO 41
<211> LENGTH: 21
<212> TYPE: DNA
<213> ORGANISM: Artificial
<220> FEATURE:
<223> OTHER INFORMATION: Synthetic DNA

<400> SEQUENCE: 41
cgtcaaatcc tcgcactatt c                                                21

<210> SEQ ID NO 42
<211> LENGTH: 20
<212> TYPE: DNA

```
<213> ORGANISM: Artificial
<220> FEATURE:
<223> OTHER INFORMATION: Synthetic DNA

<400> SEQUENCE: 42
agttaacgtc aatcacctag                                              20

<210> SEQ ID NO 43
<211> LENGTH: 21
<212> TYPE: DNA
<213> ORGANISM: Artificial
<220> FEATURE:
<223> OTHER INFORMATION: Synthetic DNA

<400> SEQUENCE: 43
ttcccaacta aaagcagttt a                                            21

<210> SEQ ID NO 44
<211> LENGTH: 18
<212> TYPE: DNA
<213> ORGANISM: Artificial
<220> FEATURE:
<223> OTHER INFORMATION: Synthetic DNA

<400> SEQUENCE: 44
ctggtaagtt accgtcac                                                18

<210> SEQ ID NO 45
<211> LENGTH: 20
<212> TYPE: DNA
<213> ORGANISM: Artificial
<220> FEATURE:
<223> OTHER INFORMATION: Synthetic DNA

<400> SEQUENCE: 45
gcgcttcata acccggctac                                              20

<210> SEQ ID NO 46
<211> LENGTH: 22
<212> TYPE: DNA
<213> ORGANISM: Artificial
<220> FEATURE:
<223> OTHER INFORMATION: Synthetic DNA

<400> SEQUENCE: 46
cacgtgcatc aaattattct cg                                           22

<210> SEQ ID NO 47
<211> LENGTH: 20
<212> TYPE: DNA
<213> ORGANISM: Artificial
<220> FEATURE:
<223> OTHER INFORMATION: Synthetic DNA

<400> SEQUENCE: 47
cctactttca gcgcactcaa                                              20

<210> SEQ ID NO 48
<211> LENGTH: 20
<212> TYPE: DNA
<213> ORGANISM: Artificial
<220> FEATURE:
<223> OTHER INFORMATION: Synthetic DNA

<400> SEQUENCE: 48
cacgtgactg actttatccc                                              20
```

<210> SEQ ID NO 49
<211> LENGTH: 20
<212> TYPE: DNA
<213> ORGANISM: Artificial
<220> FEATURE:
<223> OTHER INFORMATION: Synthetic DNA

<400> SEQUENCE: 49
ccaacaattt aaccacttac                                                   20

<210> SEQ ID NO 50
<211> LENGTH: 20
<212> TYPE: DNA
<213> ORGANISM: Artificial
<220> FEATURE:
<223> OTHER INFORMATION: Synthetic DNA

<400> SEQUENCE: 50
aatagggaca cgtccctaac                                                   20

<210> SEQ ID NO 51
<211> LENGTH: 22
<212> TYPE: DNA
<213> ORGANISM: Artificial
<220> FEATURE:
<223> OTHER INFORMATION: Synthetic DNA

<400> SEQUENCE: 51
gtaccgtcac ccaaactcaa ta                                                22

<210> SEQ ID NO 52
<211> LENGTH: 20
<212> TYPE: DNA
<213> ORGANISM: Artificial
<220> FEATURE:
<223> OTHER INFORMATION: Synthetic DNA

<400> SEQUENCE: 52
acccactgca aaaccagggt                                                   20

<210> SEQ ID NO 53
<211> LENGTH: 20
<212> TYPE: DNA
<213> ORGANISM: Artificial
<220> FEATURE:
<223> OTHER INFORMATION: Synthetic DNA

<400> SEQUENCE: 53
tctcttcttc cctgctaaca                                                   20

<210> SEQ ID NO 54
<211> LENGTH: 22
<212> TYPE: DNA
<213> ORGANISM: Artificial
<220> FEATURE:
<223> OTHER INFORMATION: Synthetic DNA

<400> SEQUENCE: 54
accgtcaatt cctctaacta tt                                                22

<210> SEQ ID NO 55
<211> LENGTH: 20
<212> TYPE: DNA
<213> ORGANISM: Artificial
<220> FEATURE:

<223> OTHER INFORMATION: Synthetic DNA

<400> SEQUENCE: 55
accaccgact tgaaggacca                                                    20

<210> SEQ ID NO 56
<211> LENGTH: 20
<212> TYPE: DNA
<213> ORGANISM: Artificial
<220> FEATURE:
<223> OTHER INFORMATION: Synthetic DNA

<400> SEQUENCE: 56
agtcagacgt tgggcgccta                                                    20

<210> SEQ ID NO 57
<211> LENGTH: 22
<212> TYPE: DNA
<213> ORGANISM: Artificial
<220> FEATURE:
<223> OTHER INFORMATION: Synthetic DNA

<400> SEQUENCE: 57
tacatgcatc tcagctacac gt                                                 22

<210> SEQ ID NO 58
<211> LENGTH: 20
<212> TYPE: DNA
<213> ORGANISM: Artificial
<220> FEATURE:
<223> OTHER INFORMATION: Synthetic DNA

<400> SEQUENCE: 58
cacactcgtt cttgacttac                                                    20

<210> SEQ ID NO 59
<211> LENGTH: 20
<212> TYPE: DNA
<213> ORGANISM: Artificial
<220> FEATURE:
<223> OTHER INFORMATION: Synthetic DNA

<400> SEQUENCE: 59
aaaaagcagt gccttgttcc                                                    20

<210> SEQ ID NO 60
<211> LENGTH: 21
<212> TYPE: DNA
<213> ORGANISM: Artificial
<220> FEATURE:
<223> OTHER INFORMATION: Synthetic DNA

<400> SEQUENCE: 60
gtcgattacc gtcatcagat g                                                  21

<210> SEQ ID NO 61
<211> LENGTH: 20
<212> TYPE: DNA
<213> ORGANISM: Artificial
<220> FEATURE:
<223> OTHER INFORMATION: Synthetic DNA

<400> SEQUENCE: 61
ttcctccaaa acttattcct                                                    20

```
<210> SEQ ID NO 62
<211> LENGTH: 20
<212> TYPE: DNA
<213> ORGANISM: Artificial
<220> FEATURE:
<223> OTHER INFORMATION: Synthetic DNA

<400> SEQUENCE: 62
ccgtctctac tgtatatagt                                               20

<210> SEQ ID NO 63
<211> LENGTH: 22
<212> TYPE: DNA
<213> ORGANISM: Artificial
<220> FEATURE:
<223> OTHER INFORMATION: Synthetic DNA

<400> SEQUENCE: 63
ggtacattca ctatggtaca cg                                            22

<210> SEQ ID NO 64
<211> LENGTH: 22
<212> TYPE: DNA
<213> ORGANISM: Artificial
<220> FEATURE:
<223> OTHER INFORMATION: Synthetic DNA

<400> SEQUENCE: 64
tcttaacaaa ggtaccgtca cc                                            22

<210> SEQ ID NO 65
<211> LENGTH: 20
<212> TYPE: DNA
<213> ORGANISM: Artificial
<220> FEATURE:
<223> OTHER INFORMATION: Synthetic DNA

<400> SEQUENCE: 65
ccctaggaca gaggcttaca                                               20

<210> SEQ ID NO 66
<211> LENGTH: 21
<212> TYPE: DNA
<213> ORGANISM: Artificial
<220> FEATURE:
<223> OTHER INFORMATION: Synthetic DNA

<400> SEQUENCE: 66
agctgtcgat attagcaaca g                                             21

<210> SEQ ID NO 67
<211> LENGTH: 20
<212> TYPE: DNA
<213> ORGANISM: Artificial
<220> FEATURE:
<223> OTHER INFORMATION: Synthetic DNA

<400> SEQUENCE: 67
gtcaaggcgc taacagttac                                               20

<210> SEQ ID NO 68
<211> LENGTH: 20
<212> TYPE: DNA
<213> ORGANISM: Artificial
<220> FEATURE:
<223> OTHER INFORMATION: Synthetic DNA
```

```
<400> SEQUENCE: 68
aaaccctgcg cttaaggtgc                                          20

<210> SEQ ID NO 69
<211> LENGTH: 20
<212> TYPE: DNA
<213> ORGANISM: Artificial
<220> FEATURE:
<223> OTHER INFORMATION: Synthetic DNA

<400> SEQUENCE: 69
taaccacaag attattcgtc                                          20

<210> SEQ ID NO 70
<211> LENGTH: 20
<212> TYPE: DNA
<213> ORGANISM: Artificial
<220> FEATURE:
<223> OTHER INFORMATION: Synthetic DNA

<400> SEQUENCE: 70
acgtgggctc ttttatcccc                                          20

<210> SEQ ID NO 71
<211> LENGTH: 20
<212> TYPE: DNA
<213> ORGANISM: Artificial
<220> FEATURE:
<223> OTHER INFORMATION: Synthetic DNA

<400> SEQUENCE: 71
cgtcattcgt cttctgccaa                                          20

<210> SEQ ID NO 72
<211> LENGTH: 15
<212> TYPE: DNA
<213> ORGANISM: Artificial
<220> FEATURE:
<223> OTHER INFORMATION: Synthetic DNA

<400> SEQUENCE: 72
tacgggaggc agcag                                               15

<210> SEQ ID NO 73
<211> LENGTH: 19
<212> TYPE: DNA
<213> ORGANISM: Artificial
<220> FEATURE:
<223> OTHER INFORMATION: Synthetic DNA

<400> SEQUENCE: 73
crgggtatct aatccygtt                                           19

<210> SEQ ID NO 74
<211> LENGTH: 488
<212> TYPE: DNA
<213> ORGANISM: Artificial
<220> FEATURE:
<223> OTHER INFORMATION: Synthetic DNA

<400> SEQUENCE: 74
gtgagaagcc tacacaaacg taacgtcagg gctaagacaa acgctaacgg tacaccctag   60
atgggagctt gtagctagat cgctaagtcc taccgacatg taggcatact cacgaaggca  120
attccctgaa agcctcgtct tatcccgaac ttggcatctg ctgatacgtc aggttgaacg  180
```

```
                                            -continued cgtacattta cctgtcatgc gtgggccttc tccgaatagc ctacgtagtg atatcgctgg        240
tcgaataggc ggattgctca taaatgcaca ttggctaagg cccacggaac acgaatcacg        300
tgagatcact tactattcga cggaactact atacgcaccg ggacatgcaa gtagcgtccc        360
acaagcataa ggaactctat actcgccatc tacgcagcta caggggatac acgtatgagc        420
ggttacgaag taaagccgag atagagcggt ctttagagaa aaaacaggat tagataccct        480
ggtagtcc                                                                488
```